(12) United States Patent
Brogdon et al.

(10) Patent No.: US 11,542,488 B2
(45) Date of Patent: Jan. 3, 2023

(54) SORTASE SYNTHESIZED CHIMERIC ANTIGEN RECEPTORS

(71) Applicants: Novartis AG, Basel (CH); The Trustees of the University of Pennsylvania, Philadelphia, PA (US)

(72) Inventors: Jennifer Brogdon, Cambridge, MA (US); Carla Guimaraes, Cambridge, MA (US); John Hastewell, Cambridge, MA (US); Andreas Loew, Cambridge, MA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/327,778

(22) PCT Filed: Jul. 21, 2015

(86) PCT No.: PCT/US2015/041363
§ 371 (c)(1),
(2) Date: Jan. 20, 2017

(87) PCT Pub. No.: WO2016/014553
PCT Pub. Date: Jan. 28, 2016

(65) Prior Publication Data
US 2017/0211055 A1    Jul. 27, 2017

(30) Foreign Application Priority Data

Jul. 21, 2014    (WO) ............... PCT/CN2014/082600
Nov. 6, 2014    (WO) ............... PCT/CN2014/090503

(51) Int. Cl.
*C12N 9/52*    (2006.01)
*C12N 5/10*    (2006.01)
*C07K 16/00*    (2006.01)

(52) U.S. Cl.
CPC ............... *C12N 9/52* (2013.01); *C07K 16/00* (2013.01); *C12N 5/10* (2013.01); *C07K 2319/00* (2013.01);
(Continued)

(58) Field of Classification Search
None
See application file for complete search history.

(56) References Cited

U.S. PATENT DOCUMENTS 5,359,046 A    10/1994    Capon et al.
5,686,281 A    11/1997    Roberts
(Continued)

FOREIGN PATENT DOCUMENTS

EP    0574512 A1    12/1993
EP    0871495 A1    10/1998
(Continued)

OTHER PUBLICATIONS

McCluskey et al., "Receptor-directed chimeric toxins created by sortase-mediated protein fusion", Molecular Cancer Therapeutics, vol. 12, No. 10, pp. 2273-2281, published online Aug. 14, 2013 (Year: 2013).*
(Continued)

*Primary Examiner* — Richard C Ekstrom
(74) *Attorney, Agent, or Firm* — Saul Ewing LLP; Kathryn Doyle

(57) ABSTRACT

Sortase molecules and methods described herein allow for the construction of a CAR or CAR member, e.g., in situ, on a CARX, e.g., CART, cell. For example, sortase mediated transfer of an antigen binding domain, e.g., a scFv, onto a CAR member having a sortase acceptor motif in place of an antigen binding domain can provide for a complete CAR
(Continued)

member on a cell wherein the cell does not comprise nucleic acid that encodes the complete CAR member.

14 Claims, 15 Drawing Sheets

Specification includes a Sequence Listing.

(52) U.S. Cl.
CPC ...... *C07K 2319/02* (2013.01); *C07K 2319/03* (2013.01); *C07K 2319/30* (2013.01); *C07K 2319/70* (2013.01)

(56) References Cited

U.S. PATENT DOCUMENTS

| | | |
|---|---|---|
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0257994 A1 | 10/2009 | Jensen |
| 2011/0052554 A1 | 3/2011 | Zakrzewski et al. |
| 2011/0321183 A1 | 12/2011 | Ploegh et al. |
| 2012/0148552 A1 | 6/2012 | Jensen |
| 2012/0282670 A1* | 11/2012 | Rossomando ......... C07K 19/00 435/188 |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0122043 A1 | 5/2013 | Guimaraes et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0030697 A1 | 1/2014 | Ploegh et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0122707 A1 | 5/2016 | Swee et al. |
| 2016/0185861 A1 | 6/2016 | Bedoya et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |

(56) References Cited

U.S. PATENT DOCUMENTS

| | | | |
|---|---|---|---|
| 2020/0085869 | A1 | 3/2020 | Schuster et al. |
| 2020/0087376 | A1 | 3/2020 | Fraietta et al. |
| 2020/0113941 | A1 | 4/2020 | Brannetti et al. |
| 2020/0179511 | A1 | 6/2020 | Daley et al. |
| 2020/0215171 | A1 | 7/2020 | Brogdon et al. |
| 2020/0281973 | A1 | 9/2020 | Dranoff |
| 2020/0283729 | A1 | 9/2020 | Loew et al. |
| 2020/0291354 | A1 | 9/2020 | Johnson et al. |
| 2020/0339704 | A1 | 10/2020 | Bradner et al. |

FOREIGN PATENT DOCUMENTS

| | | | |
|---|---|---|---|
| EP | 1226244 | A2 | 7/2002 |
| WO | 1992015322 | A1 | 9/1992 |
| WO | 199530014 | A1 | 11/1995 |
| WO | 9623814 | A1 | 8/1996 |
| WO | 9624671 | A1 | 8/1996 |
| WO | 1997015669 | A1 | 5/1997 |
| WO | 9723613 | A2 | 7/1997 |
| WO | 9818809 | A1 | 5/1998 |
| WO | 9900494 | A2 | 1/1999 |
| WO | 9957268 | A1 | 11/1999 |
| WO | 0014257 | A1 | 3/2000 |
| WO | 2002033101 | A1 | 4/2002 |
| WO | 02077029 | A2 | 10/2002 |
| WO | 02088334 | A1 | 11/2002 |
| WO | 2003057171 | A2 | 7/2003 |
| WO | 2005019429 | A2 | 3/2005 |
| WO | 2005044996 | A2 | 5/2005 |
| WO | 2005/118788 | A2 | 12/2005 |
| WO | 2006060878 | A1 | 6/2006 |
| WO | 2008045437 | A2 | 4/2008 |
| WO | 2010085660 | A2 | 7/2010 |
| WO | 2011059836 | A2 | 5/2011 |
| WO | 2011097477 | A1 | 8/2011 |
| WO | 2012056911 | A1 | 5/2012 |
| WO | 2012058460 | A2 | 5/2012 |
| WO | 2012079000 | A1 | 6/2012 |
| WO | 2012082841 | A2 | 6/2012 |
| WO | 2012/099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138858 | A1 | 10/2012 |
| WO | 2013019615 | A2 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013/126712 | A1 | 8/2013 |
| WO | 2013126729 | A1 | 8/2013 |
| WO | 2013126733 | A1 | 8/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |
| WO | 2014039513 | A2 | 3/2014 |
| WO | 2014/055442 | A2 | 4/2014 |
| WO | 2014055657 | A1 | 4/2014 |
| WO | 2014070865 | A1 | 5/2014 |
| WO | 2014130635 | A1 | 8/2014 |
| WO | 2014/145252 | A2 | 9/2014 |
| WO | 2014183066 | A2 | 11/2014 |
| WO | 2015013169 | A2 | 1/2015 |
| WO | 2015042393 | A2 | 3/2015 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2015157252 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |

OTHER PUBLICATIONS

Levary et al., "Protein-protein fusion catalyzed by sortase A", PLoS ONE, 6(4): e18342 doi:10.1371/journal/pone.0018342 (2011) (Year: 2011).*

Baeksgaard & Sorensen, "Acute tumor lysis syndrome in solid tumors—a case report and review of the literature" Cancer Chemotherapy Pharmacology (2003) vol. 51 pp. 187-192.

Bondanza et al. "Suicide gene therapy of graft-versus-host disease induced by central memory human T lymphocytes" Blood (2006) vol. 107 No. 5 pp. 1828-1836.

Brentjens et al. "Genetically Targeted T Cells Eradicate Systemic Acute Lymphoblastic Leukemia Xenografts", Clinical Cancer Research(2007) vol. 13, No. 18, pp. 5426-5435.

Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.

Brentjens et al., "A Phase 1 Trial for the Treatment of chemo-Refractory Chronic Lymphocytic Leukemia with CD19-Targeted Autologous T Cells" Molecular Therapy (2008) vol. 16 Suppl 1 p. S15.

Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).

Brentjens et al., "Eradication of systemic B-cell tumors by genetically targeted human T lymphocytes co-stimulated by CD80 and interleukin-15" Nature Medicine (2003) vol. 9 No. 3 pp. 279-286.

Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.

Brocker and Karjalainen, "Signals through T Cell Receptor—Chain alone Are Insufficient to Prime Resting T Lymphocytes" J. Exp. Med. (1995) vol. 181 pp. 1653-1659.

Call & Wucherpfennig, "The T Cell Receptor: Critical Role of the Membrane Environment in Receptor Assembly and Function" Annu. Rev. Immunol. (2005) vol. 23 pp. 101-125.

Carpenito et al. "Control of large, established tumor xenografts with genetically retargeted human T cells containing CD28 and CD137 domains", Proc Natl Acad Sci USA (2009) vol. 106 pp. 3360-3365.

Davila et al. "B Cell Aplasia In a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.

Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.

Dorr "Reprogramming the specificity of sortase enzymes" PNAS (2014) vol. 111, No. 37, pp. 13343-13348.

Dropulic and June, "Gene-Based Immunotherapy for Human Immunodeficiency Virus Infection and Acquired Immunodeficiency Syndrome" Human Gene Therapy (2006) vol. 17 pp. 577-588.

Dull et al, "A Third-Generation Lentivirus Vector with a Conditional Packaging System" Journal of Virology (1998) vol. 72 No. 11 pp. 8463-8471.

Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).

Finney et al., "Activation of resting human primary T cells with chimeric receptors: costimulation from CD28, inducible costimula-

(56) References Cited

OTHER PUBLICATIONS tor, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093(2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Guimaraes et al. "Identification of host cell factors required for intoxication through use of modified cholera toxin" The Journal of Cell Biology (2011) vol. 195, No. 5, pp. 751-764.
Guimaraes et al. "Site-specific C-terminal internal loop labeling of proteins using sortase-mediated reactions" Nature Protocols (2013) vol. 8, No. 9, pp. 1787-1799.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-SPECIFIC SCFV:~-Chimera" Int J. Cancer (1996) vol. 68 pp. 232-238.
Hess et al. "An M13 bacteriophage display framework that allows sortasemediated modification of surface-accessible phage proteins" Bioconjug. Chem. (2012) vol. 23, No. 7, pp. 1478-1487.
Hess et al. "Orthogonal labeling of M13 minor capsid proteins with DNA to self-assemble end-to-end multi-phage structures" ASC Synth Biol. (2013) vol. 2, No. 9, pp. 490-496.
Hirakawa et al. "Design of Ca2+-independent *Staphylococcus aureus* sortase A mutants" Biotechnology and Bioengineering (2012) DOI: 10.1002/bit.24585.
Ho et al., "Adoptive immunotherapy: Engineering T cell responses as biological weapons for tumor mass destruction" Cancer Cell (2003) vol. 3 pp. 431-437.

Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International application No. PCT/CN2014/090503, dated Apr. 22, 2015.
International Search Report and Written Opinion for International Application No. PCT/US2015/041293 dated Sep. 11, 2015.
International Search Report and Written Opinion for International Application No. PCT/US2015/041363 dated Nov. 11, 2015.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin

(56) References Cited

OTHER PUBLICATIONS lymphoma following CD34+-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
MacAllan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Policarpo et al., "Flow-Based Enzymatic Ligation by Sortase A" Angewandte Chemie (2014) vol. 53, pp. 9203-9208.
Popp et al. "Sortaggin: a versatile method for protein labeling" Nature Chemical Biology (2007) vol. 3, No. 11, pp. 707-708.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Swee et al. "Sortase-mediated modification of ?DEC205 affords optimization of antigen presentation and immunization against a set of viral epitopes" PNAS (2013) vol. 110, No. 4, pp. 1428-1433.
Theile et al. "Site-specific N-terminal labeling of proteins using sortasemediated reactions" Nature Protocols (2013) vol. 8, No. 9, pp. 1800-1807.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Wagner et al. "Bispecific antibody generated with sortase and click chemistry has broad antiinfuenza virus activity" PNAS (2014) vol. 111, No. 47, pp. 16820-16825.
Willemsen et al., "Genetic Engineering of T Cell Specificity for Immunotherapy of Cancer" Human Immunology (2003) vol. 64 pp. 56-68.
Witte et al. "Production of unnaturally linked chimeric proteins using a combination of sortase-catalyzed transpeptidation and click chemistry" Nature Protocols (2013) vol. 8, No. 9, pp. 1808-1819.
Witte et al. "Site-specific protein modification using immobilized sortase in batch and continuous-flow systems" Nature Protocols (2015) vol. 10, No. 3, pp. 508-516.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.

(56) References Cited

OTHER PUBLICATIONS

Popp et al. "Sortaggin: a versatile method for protein labeling" Nature Chemical Biology (2007) vol. 3, No. 11, Supplemental Material.
Soding et al. "Protein homology detection by HMM-HMM comparison" Bioinformatics (2005) vol. 21, No. 7, pp. 951-960.
Ton-That et al. "Purification and characterization of sortase, the transpeptidase that cleaves surface proteins of *Staphylococcus aureus* at the LPXTG motif" PNAS (1999) vol. 96, No. 22, pp. 12424-12429.
Burnett et al., "Conditional macrophage ablation in transgenic mice expressing a Fas-based suicide gene," Journal of Leukocyte Biology (2004) vol. 75, pp. 612-623.
Comfort et al., "A Comparative Genome Analysis Identifies Distinct Sorting Pathways in Gram-Positive Bacteria," Infection and Immunity (2004) vol. 72, No. 5, pp. 2710-2722.
Guimaraes et al., "Site-specific C-terminal internal loop labeling of proteins using sortase-mediated reactions," Nat Protoc (2013) vol. 8, No. 9, pp. 1787-1799.
Spirig et al., "Sortase enzymes in Gram-positive bacteria," Molecular Microbiology (2011) vol. 82, No. 5, pp. 1044-1059.

\* cited by examiner

SORTASE SYNTHESIZED CHIMERIC ANTIGEN RECEPTORS

This application is a national stage application under 35 U.S.C. § 371 of International Application No. PCT/US2015/041363, filed Jul. 21, 2015, published as International Publication No. WO2016/014553 on Jan. 28, 2016, which claims priority to International Application PCT/CN2014/082600 filed Jul. 21, 2014, and International Application PCT/CN2014/090503 filed Nov. 6, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 21, 2015, is named N2067-7054WO3_SL.txt and is 380,675 bytes in size.

FIELD OF THE INVENTION

The invention relates generally to a Chimeric Antigen Receptors (CARS) and cells expressing CARs, as well as sortase-based method of making and using the same, e.g., to target and inactivate or kill target cells, e.g., cancer cells.

BACKGROUND

Adoptive cell transfer (ACT) therapy with autologous T-cells, especially with T-cells transduced with Chimeric Antigen Receptors (CARs), are useful in treating cancer.

SUMMARY

Sortase molecules and methods described herein allow for the construction of a CAR or CAR member, e.g., in situ, on a CARX, e.g., CART, cell. E.g., sortase mediated transfer of an antigen binding domain, e.g., a scFv, onto a CAR member having a sortase acceptor motif in place of an antigen binding domain can provide for a complete CAR member on a cell wherein the cell does not comprise nucleic acid that encodes the complete CAR member. Because the gene encoding the antigen binding domain is not comprised in the genome of a CARX cell, the number of antigen binding domain comprising CAR members attached to the CARX surface will decrease over time, e.g., due to each cell division or membrane protein turnover. This imposes a time limit to the activity of CARXs, e.g., CARTs. Thus, sortase mediated transfer can be used to couple an extracellular domain, herein provide for inclusion of a "safety mechanism" in CARX cells, e.g., CART cells.

In one aspect, a sortase acceptor member described herein comprises:
  (i) a sortase acceptor motif;
  (ii) a transmembrane domain; and optionally
  (iii) an intracellular signaling domain or (iv) a switch domain.

In an embodiment, the components of the sortase acceptor member, in order of N terminal to C terminal, is (i), (ii), and (iii) or (iv).

In an embodiment, the sortase acceptor member comprises an intracellular signaling domain.

In an embodiment, the sortase acceptor member comprises a switch domain.

In an embodiment, the sortase acceptor member comprises a moiety, e.g., an amino acid residue, e.g., a Gly or Ala residue, which accepts transfer of a moiety by a sortase.

In an embodiment, the sortase acceptor member comprises a moiety, e.g., an amino acid residue, e.g., a Gly or Ala residue, which accepts transfer of a moiety mediated by nucleophilic attack.

In an embodiment, the sortase acceptor motif comprises, consists of, or consists essentially of, Gly-, Gly-Gly-, Gly-Gly-Gly-, Gly-Gly-Gly-Gly- (SEQ ID NO: 31), or Gly-Gly-Gly-Gly-Gly- (SEQ ID ON: 32). In an embodiment, the sortase acceptor motif comprises, Gly-, Gly-Gly-, Gly-Gly-Gly-, Gly-Gly-Gly-Gly- (SEQ ID NO: 31), or Gly-Gly-Gly-Gly-Gly- (SEQ ID NO: 32). In an embodiment, the sortase acceptor motif comprises, Gly-.

In an embodiment, the sortase acceptor motif comprises, consists of, or consists essentially of, Ala-, Ala-Ala-, Ala-Ala-Ala-, Ala-Ala-Ala-Ala- (SEQ ID NO: 33), Ala-Ala-Ala-Ala-Ala- (SEQ ID NO: 34). In an embodiment, the sortase acceptor motif comprises Ala-, Ala-Ala-, Ala-Ala-Ala-, Ala-Ala-Ala-Ala- (SEQ ID NO: 33), Ala-Ala-Ala-Ala-Ala- (SEQ ID NO: 34). In an embodiment, the sortase acceptor motif comprises, Ala-.

As is discussed herein, a sortase acceptor member can provide a substrate useful, e.g., for making CARs, e.g., as substrate for the in situ formation of a CAR on an immune effector cell. In an embodiment a sortase acceptor member comprises the transmembrane and intracellular elements of a CAR.

In an embodiment, the sortase acceptor member comprises, e.g., in the N terminal to C terminal direction:
  (i) a sortase acceptor motif;
  (ii) a transmembrane domain; and
  (iii) an intracellular signaling domain.

As is discussed herein, embodiments of a sortase acceptor member can comprise one or more intracellular signaling domains. Embodiments of such members, and intracellular signaling domains, are described in the section following immediately hereafter, sometimes referred to herein as the Intracellular Signaling domain Module.

In an embodiment, the intracellular signaling domain comprises a primary intracellular signaling domain, selected, e.g., from the list in Table 8. In an embodiment, the primary intracellular signaling domain comprises a CD3zeta domain.

In an embodiment, the intracellular signaling domain comprises a costimulatory signaling domain, e.g., selected from the list in Table 9. In an embodiment, the intracellular signaling domain comprises a 4-1BB domain.

In an embodiment, the intracellular signaling domain comprises a domain from Table 13.

In an embodiment, the sortase acceptor member comprises a second intracellular signaling domain. In an embodiment, the second intracellular signaling domain comprises a primary intracellular signaling domain, e.g., selected from the list in Table 8. In an embodiment, the second intracellular signaling domain comprises a costimulatory domain, e.g., selected from the list in Table 9.

In an embodiment, a first and second intracellular signaling domains comprise: a primary intracellular signaling domain and a costimulatory signaling domain. In an embodiment, a first and second intracellular signaling domains comprise: a 4-1BB domain and a CD3zeta domain. In an embodiment, a first and second intracellular signaling domains comprise: a CD28 domain and a 4-1BB domain.

In an embodiment, the sortase acceptor member comprises a third intracellular signaling domain. In an embodiment, the third intracellular signaling domain comprises a primary intracellular signaling domain, e.g., selected from the list in Table 8. In an embodiment, the third intracellular signaling domain comprises a costimulatory domain, e.g., selected from the list in Table 9.

In an embodiment, one of the first, second and third intracellular signaling domain comprises a primary intracellular signaling domain, e.g., selected from the list in Table 8, and the other two comprise costimulatory domains, e.g., selected from, Table 9.

In an embodiment, two of the first, second and third intracellular signaling domains comprise primary intracellular signaling domains, e.g., selected from the list in Table 8, and the other comprises a costimulatory domain, e.g., selected from, Table 9.

In an embodiment, each of the first, second and third intracellular signaling domains is a primary intracellular signaling domain, e.g., selected from the list in Table 8.

In an embodiment, each of the first, second and third intracellular signaling domains comprises a costimulatory signaling domain, e.g., selected from the list in Table 9.

In an embodiment, the first, second, and third intracellular signaling domains comprise: a CD28 domain; a 4-1BB domain, and a CD3zeta domain.

In an embodiment, the sortase acceptor member comprises a fourth intracellular signaling domain. In an embodiment, the fourth intracellular signaling domain is a primary intracellular signaling domain, e.g., selected from the list in Table 8. In an embodiment, the fourth intracellular signaling domain is a costimulatory domain, e.g., selected from the list in Table 9. In an embodiment, one of the first, second, third and fourth intracellular signaling domain is a primary intracellular signaling domain, e.g., selected from the list in Table 8 and the other three are costimulatory domains, e.g., selected from the list in Table 9. In an embodiment, two of the first, second, third, and fourth intracellular signaling domains are primary intracellular signaling domains, e.g., selected from the list in Table 8, and the other two are costimulatory domain, e.g., selected from the list in Table 9. In an embodiment, three of the first, second, third, and fourth intracellular signaling domains comprise re primary intracellular signaling domains, e.g., selected from the list in Table 8, and the other is a costimulatory domain, e.g., selected from the list in Table 9. In an embodiment, each of the first, second, third, and fourth intracellular signaling domains is a primary intracellular signaling domain, e.g., selected from the list in Table 8. In an embodiment, each of the first, second, third, and fourth intracellular signaling domains is a costimulatory signaling domain, e.g., selected from the list in Table 9.

In embodiments, the intracellular signaling domain of the isolated CAR molecule comprises a costimulatory domain. In embodiments, the intracellular signaling domain of the isolated CAR molecule comprises a primary signaling domain. In embodiments, the intracellular signaling domain of the isolated CAR molecule comprises a costimulatory domain and a primary signaling domain.

In one embodiment, the isolated nucleic acid molecule further comprises a sequence encoding a costimulatory domain, e.g., a costimulatory domain described herein. In embodiments, the intracellular signaling domain comprises a costimulatory domain. In embodiments, the intracellular signaling domain comprises a primary signaling domain. In embodiments, the intracellular signaling domain comprises a costimulatory domain and a primary signaling domain.

In one embodiment, the costimulatory domain comprises a functional signaling domain of a protein selected from the group consisting of an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In embodiments, the costimulatory domain comprises 4-1BB, CD27, CD28, or ICOS. In one embodiment, the costimulatory domain comprises a sequence of SEQ ID NO:2. In one embodiment, the costimulatory domain comprises an amino acid sequence having at least one, two or three modifications (e.g., substitutions) but not more than 20, 10 or 5 modifications (e.g., substitutions) of an amino acid sequence of SEQ ID NO:2, or a sequence with 95-99% identity to an amino acid sequence of SEQ ID NO:2.

In embodiments, the primary signaling domain comprises a functional signaling domain of CD3 zeta. In embodiments, the functional signaling domain of CD3 zeta comprises SEQ ID NO: 3 (mutant CD3 zeta) or SEQ ID NO: 251 (wild type human CD3 zeta), or a sequence with 95-99% identity thereof.

In one embodiment, the encoded costimulatory domain of 4-1BB comprises the sequence of SEQ ID NO:2. In one embodiment, the encoded costimulatory domain comprises an amino acid sequence having at least one, two or three modifications but not more than 20, 10 or 5 modifications of an amino acid sequence of SEQ ID NO:2, or a sequence with 95-99% identity to an amino acid sequence of SEQ ID NO:2. In one embodiment, the nucleic acid sequence encoding the costimulatory domain encoding SEQ ID NO: 2, or a sequence with 95-99% identity thereof. In another embodiment, the encoded costimulatory domain of CD28 comprises the amino acid sequence of SEQ ID NO:261. In one embodiment, the encoded costimulatory domain comprises an amino acid sequence having at least one, two or three modifications but not more than 20, 10 or 5 modifications of an amino acid sequence of SEQ ID NO:261, or a sequence with 95-99% identity to an amino acid sequence of SEQ ID NO:261. In one embodiment, the nucleic acid sequence encoding the costimulatory domain of CD28 comprises the nucleotide sequence of SEQ ID NO:262, or a sequence with 95-99% identity thereof. In another embodiment, the encoded costimulatory domain of CD27 comprises the amino acid sequence of SEQ ID NO:271. In one embodiment, the encoded costimulatory domain comprises an amino acid sequence having at least one, two or three modifications but not more than 20, 10 or 5 modifications of an amino acid sequence of SEQ ID NO:271, or a sequence with 95-99% identity to an amino acid sequence of SEQ ID NO:271. In one embodiment, the nucleic acid sequence encoding the costimulatory domain of CD27 comprises the nucleotide sequence of SEQ ID NO:272, or a sequence with 95-99% identity thereof. In another embodiment, the encoded costimulatory domain of ICOS comprises the amino acid sequence of SEQ ID NO:263. In one embodiment, the encoded costimulatory domain of ICOS comprises an amino acid sequence having at least one, two or three modifications but not more than 20, 10 or 5 modifications of an amino acid sequence of SEQ ID NO:263, or a sequence with 95-99% identity to an amino acid sequence of SEQ ID NO:263. In one embodiment, the nucleic acid sequence encoding the costimulatory domain of ICOS comprises the nucleotide sequence of SEQ ID NO:264, or a sequence with 95-99% identity thereof.

In one embodiment, the intracellular signaling domain comprises a functional signaling domain of CD27 and/or a functional signaling domain of CD3 zeta. In one embodiment, the intracellular signaling domain comprises a functional signaling domain of CD28 and/or a functional signaling domain of CD3 zeta. In one embodiment, the intracellular signaling domain comprises a functional signaling domain of ICOS and/or a functional signaling domain of CD3 zeta. In one embodiment, the intracellular signaling domain comprises a functional signaling domain of 4-1BB and/or a functional signaling domain of CD3 zeta.

As is discussed herein, a sortase acceptor member can provide a substrate for various applications, e.g., for making RCARs.

In an embodiment, the sortase acceptor member comprises:
  (i) a sortase acceptor motif;
  (ii) a transmembrane domain; and
  (iii) a switch domain.

As is discussed herein, embodiments of a sortase acceptor member that serves as a substrate for making the antigen binding member of an RCAR can comprise any of a variety of switch domains. In an embodiment, the switch domain on the antigen binding member, together with the switch domain on the intracellular signaling member form a dimerization switch. As is discussed herein, the sortase acceptor member can include a switch domain that is a component of any of a variety of dimerization switches, e.g., a dimerization switch described in the section entitled Dimerization Switch.

In an embodiment, the switch domain is a component of a heterodimerization switch. In an embodiment, the switch domain is a component of a homodimerization switch.

In an embodiment, the switch domain is intracellular. In an embodiment, the switch domain is extracellular.

In an embodiment the switch domain is a component of a FKBP-FRP based switch, e.g., together with the switch domain of another element of the RCAR, e.g., an intracellular signaling member, the switch domain forms a FKBP-FRP based switch.

In an embodiment, the switch domain comprises a rapamycin analog binding sequence having at least 80, 85, 90, 95, 98, or 99% identity with FKBP.

In an embodiment, the switch domain comprises a rapamycin analog binding sequence binding sequence having at least 80, 85, 90, 95, 98, or 99% identity with FRP.

In an embodiment, the switch domain comprises a rapamycin analog binding sequence that differs by no more than 10, 9, 8, 7, 6, 5, 4, 3, 2, or 1 amino acid residues from the corresponding sequence of FKBP.

In an embodiment, the switch domain comprises a rapamycin analog binding sequence that differs by no more than 10, 9, 8, 7, 6, 5, 4, 3, 2, or 1 amino acid residues from the corresponding sequence of FRP.

In an embodiment, the switch domain comprises a rapamycin, or rapamycin analog, binding sequence from FRP, e.g., a sequence comprising a lysine at residue 2098 or a sequence comprising a leucine at residue 2098.

In an embodiment, the switch domain comprises a rapamycin analog binding sequence from FRP, e.g., a sequence comprising a lysine at residue 2098 or a sequence comprising a leucine at residue 2098.

In an embodiment, the switch domain comprises an AP21967 binding sequence from FKBP.

In an embodiment, the switch domain comprises an AP21967 binding sequence from FRP, e.g., a sequence comprising a lysine at residue 2098 or a sequence comprising a leucine at residue 2098.

In an embodiment, the switch domain is a component of a GyrB-GyrB based switch, e.g., together with the switch domain of another element of the RCAR, e.g., an intracellular signaling member, the switch domain forms a GyrB-GyrB based switch.

In an embodiment, the switch domain comprises a GyrB-GyrB based switch domain.

In an embodiment, the switch domain comprises a coumermycin binding sequence having at least 80, 85, 90, 95, 98, or 99% identity with the 24 K Da amino terminal sub-domain of GyrB. In an embodiment, the switch domain comprises a coumermycin binding sequence that differs by no more than 10, 9, 8, 7, 6, 5, 4, 3, 2, or 1 amino acid residues from the corresponding sequence of 24 K Da amino terminal sub-domain of GyrB. In an embodiment, the switch domain comprises a coumermycin binding sequence from the 24 K Da amino terminal sub-domain of GyrB. In an embodiment, the switch domain comprises the 24 K Da amino terminal sub-domain of GyrB.

In an embodiment, the switch domain is a component of a GAI-GID1 based switch, e.g., together with the switch domain of another element of the RCAR, e.g., an intracellular signaling member, the switch domain forms a GAI-GID1 based switch.

In an embodiment, the switch domain comprises a gibberellin, or gibberellin analog, e.g., $GA_3$, binding sequence having at least 80, 85, 90, 95, 98, or 99% identity with GID1. In an embodiment, the switch domain comprises a GAI switch domain having at least 80, 85, 90, 95, 98, or 99% identity with GAI. In an embodiment, the switch domain comprises a gibberellin, or gibberellin analog, e.g., $GA_3$, binding sequence that differs by no more than 10, 9, 8, 7, 6, 5, 4, 3, 2, or 1 amino acid residues from the corresponding sequence of FKBP. In an embodiment, the switch domain comprises a gibberellin, or gibberellin analog, e.g., GA3, binding sequence that differs by no more than 10, 9, 8, 7, 6, 5, 4, 3, 2, or 1 amino acid residues from the corresponding sequence of GID1. In an embodiment, the switch domain comprises a GAI switch domain that differs by no more than 10, 9, 8, 7, 6, 5, 4, 3, 2, or 1 amino acid residues from the corresponding sequence of GAI.

In an embodiment, the switch domain is a component of a Halo-tag/SNAP-tag based switch, e.g., together with the switch domain of another element of the RCAR, e.g., an intracellular signaling member, the switch domain forms a Halo-tag/SNAP-tag based switch. In an embodiment, the switch domain comprises a Halotag switch domain comprising at least 80, 85, 90, 95, 98, or 99% identity with SEQ ID NO 9. In an embodiment, the switch domain comprises a SNAP-tag switch domain having at least 80, 85, 90, 95, 98, or 99% identity with SEQ ID NO 10. In an embodiment, the switch domain comprises a Halo-tag switch domain that differs by no more than 10, 9, 8, 7, 6, 5, 4, 3, 2, or 1 amino acid residues from SEQ ID NO 9. In an embodiment, the switch domain comprises a SNAP-tag switch domain that differs by no more than 10, 9, 8, 7, 6, 5, 4, 3, 2, or 1 amino acid residues from SEQ ID 10.

In an embodiment, the dimerization molecule is a non-covalent dimerization molecule. In an embodiment, the dimerization molecule is covalent dimerization molecule. In an embodiment, the dimerization switch, e.g., a homodimerization switch, e.g., an extracellular homodimerization switch, comprises switch domains that comprise tag molecules, e.g., a c-myc peptide tag, flag peptide tag, HA peptide tag or V5 peptide tag, and the dimerization switch comprises polypeptides with affinity for the switch domains, e.g., antibody molecules and non-antibody scaffold.

In an embodiment, the sortase acceptor member further comprises a second order dimerization switch.

In an embodiment, the dimerization molecule has a valency of greater than two, e.g., it is multi-valent, and binds, and thus clusters or dimerizes, more than two switch domains.

In an aspect, a nucleic acid, e.g., an isolated nucleic acid, or a vector, e.g., a lentiviral vector, as described herein, encodes a sortase acceptor member described herein. In an embodiment, the sortase acceptor member comprises an intracellular signaling domain and, e.g., is suitable for the formation of an uCAR. In an embodiment, the sortase acceptor member comprises an intracellular signaling domain and, e.g., is suitable for the formation of an iCAR. In an embodiment, the sortase acceptor member comprises a switch domain and, e.g., is suitable for the formation of a RCAR. In an embodiment, the sequence encoding the sortase acceptor member, e.g., a sortase acceptor member that comprises a switch domain and, e.g., is suitable for the formation of a RCAR, and sequence encoding an intracellular signaling member are present in a single nucleic acid molecule, a vector, e.g., a lentiviral vector. In an embodiment, the sequence encoding the sortase acceptor member that comprises a switch domain is operatively linked to a first control region and sequence encoding the intracellular signaling member is operatively linked to a second control region. In an embodiment, the sequence encoding the sortase acceptor member that comprises a switch domain is translated as a first RNA and sequence encoding intracellular signaling member is translated as a second RNA. In an embodiment, the sequence encoding the sortase acceptor member that comprises a switch domain and sequence encoding intracellular signaling member are translated as a single RNA. In an embodiment, the sequence encoding the sortase acceptor member that comprises a switch domain is present on a first nucleic acid molecule and sequence encoding intracellular signaling member is present on a second nucleic acid molecule. In an embodiment, the nucleic acid further comprises a sequence encoding a shRNA targeting a coinhibitory domain.

In an aspect, a cell, or preparation of cells, is described herein, comprising a nucleic acid encoding a sortase acceptor member as described herein. In an embodiment, the cell is a T cell. In an embodiment, the cell is an NK cell.

In an aspect, a cell, or preparation of cells, is described herein, comprising a sortase acceptor member as described herein. In an embodiment, the sortase acceptor member is inserted into the membrane of the cell. In an embodiment, the cell is a T cell. In an embodiment, the cell is an NK cell.

In an embodiment, the cell comprises a sortase acceptor member comprising:
 (i) a sortase acceptor motif;
 (ii) a transmembrane domain; and
 (iii) an intracellular signaling domain.

In an embodiment, the cell comprises a sortase acceptor member comprising:
 (i) a sortase acceptor motif;
 (ii) a transmembrane domain; and
 (iii) a switch domain, In an embodiment, the cell further comprises an intracellular binding member. In an embodiment, the cell further comprises a shRNA targeting a coinhibitory domain.

In an aspect, a CAR member is described herein, comprising, e.g., in order of N terminal to C terminal:
 (i) an antigen binding domain, an extracellular domain (ECD) of an inhibitory molecule, or a costimulatory ECD domain;
 (ii) a sortase transfer signature;
 (iii) a transmembrane domain; and optionally,
 (iv) an intracellular signaling domain or (v) a switch domain.

In an embodiment, the sequence of the components of the CAR member, in order of N terminal to C terminal, is (i), (ii), (iii), (iv) or (v).

In an embodiment, (i) comprises an antigen binding domain. In an embodiment, (i) comprises an extracellular domain (ECD) of an inhibitory molecule. In an embodiment, (i) comprises a costimulatory ECD domain.

In an embodiment, the CAR member comprises an intracellular signaling domain.

In an embodiment, the CAR member comprises a switch domain.

In an embodiment, the sortase transfer signature comprises an amino acid residue from a sortase recognition motif. In an embodiment, the sortase transfer signature comprises an amino acid residue, e.g., an $X_1$ amino acid residue, from a sortase recognition motif from any of Tables 1-6.

In an embodiment, the sortase transfer signature comprises an amino acid residue from a sortase acceptor motif. In an embodiment, the sortase transfer signature comprises a G residue from a sortase acceptor motif. In an embodiment, the sortase transfer signature comprises an A residue from a sortase acceptor motif.

In an embodiment, the sortase transfer signature comprises (i) an amino acid residue, e.g., an $X_1$ amino acid residue, from a sortase recognition motif, e.g., from a sortase recognition motif of any of Tables 1-6; and (ii) an amino acid residue a sortase acceptor motif, e.g., an A or a G residue. In an embodiment, (i) and (ii) are adjacent one another.

In an embodiment, the sortase transfer signature comprises an amino acid residue from the sequence LPXT (SEQ ID NO: 30), wherein X is any amino acid.

In an embodiment, the sortase transfer signature comprises 2, 3, or 4 an amino acid residues from the sequence LPXT (SEQ ID NO: 30), wherein X is any amino acid.

In an embodiment, the sortase transfer signature comprises an amino acid residue of a sortase acceptor motif, e.g., it comprises, 2, 3, 4, or 5 amino acid residues of a sortase acceptor motif. In an embodiment, the sortase transfer signature comprises a Gly residue. In an embodiment, the sortase transfer signature comprises 2, 3, 4 or 5 Gly residues. In an embodiment, the sortase transfer signature comprises an Ala residue. In an embodiment, the sortase transfer signature comprises 2, 3, 4 or 5 Ala residues.

In an embodiment, the sortase transfer signature comprises Y amino acid residues, including TG, from LPXTGGG (SEQ ID NO: 28) wherein Y is 2, 3, 4, 5, 6 or 7, wherein X is any amino acid. In an embodiment, Y is 2. In an embodiment, Y is 7.

In an embodiment, the sortase transfer signature comprises Y amino acid residues, including TA, from LPXTAAA (SEQ IN NO: 29), wherein Y is 2, 3, 4, 5, 6 or 7, wherein X is any amino acid. In an embodiment, Y is 2. In an embodiment, Y is 7.

As is discussed herein, a sortase can be used to attach an extracellular domain, e.g., an antigen binding domain, to other components of a CAR or RCAR. In embodiments the CAR or RCAR will comprise a sortase transfer signature.

In an embodiment, the CAR member described herein comprises:
(i) an antigen binding domain, an extracellular domain (ECD) of an inhibitory molecule, or a costimulatory ECD domain;
(ii) a sortase transfer signature;
(iii) a transmembrane domain; and
(iv) an intracellular signaling domain.

In an embodiment, (i) comprises an antigen binding domain. In an embodiment, (i) comprises an extracellular domain (ECD) of an inhibitory molecule. In an embodiment, (i) comprises a costimulatory ECD domain.

In an aspect, a cell, or preparation of cells, is described herein, comprising a CAR member comprising a sortase transfer signature, e.g., comprising a CAR member described herein. In an embodiment, the CAR is inserted into the membrane of the cell. In an embodiment, the cell is a T cell. In an embodiment, the cell is an NK cell.

In an embodiment, the CAR comprises:
an antigen binding domain;
a sortase transfer signature;
a transmembrane domain; and
an intracellular signaling domain.

In an embodiment, the CAR comprises:
an antigen binding domain;
a sortase transfer signature;
a transmembrane domain; and
a switch domain,
and, optionally, the cell comprises an intracellular binding member.

As is discussed herein, embodiments of a CAR can comprise one or more intracellular signaling domains. Embodiments of such members, and intracellular signaling domains, are described in the section following immediately hereafter, sometimes referred to herein as the Intracellular Signaling domain Module.

As is discussed herein, a sortase can be used to attach an extracellular domain, e.g., an antigen binding domain, to a RCAR member.

In an embodiment, the CAR member of claim 97, comprising:
(i) an antigen binding domain, an extracellular domain (ECD) of an inhibitory molecule, or a costimulatory ECD domain;
(ii) a sortase transfer signature; (e.g., -Xxx-Xxx-Xxx-Xxx-Gly-Gly-Gly-);
(iii) a transmembrane domain; and
(iv) a switch domain.

In an embodiment, (i) comprises an antigen binding domain. In an embodiment, (i) comprises an extracellular domain (ECD) of an inhibitory molecule. In an embodiment, (i) comprises a costimulatory ECD domain.

As is discussed herein, an embodiment of a RCAR member can comprises a switch domain. In an embodiment, the switch domain on the antigen binding member, together with the switch domain on an intracellular signaling member, form a dimerization switch. As is discussed herein, a RCAR member comprising can include a switch domain that is a component of any of a variety of dimerization switches, e.g., a dimerization switch described herein, e.g., in the Dimerization Switch Module.

In an aspect, a method of providing a cell comprising a CAR member is described herein, comprising an antigen binding domain, an extracellular domain (ECD) of an inhibitory molecule, or a costimulatory ECD domain, a transmembrane domain, and an intracellular signaling domain or a switch domain, comprising:
a) providing a precursor cell comprising a sortase acceptor member comprising:
(i) a sortase acceptor motif;
(ii) a transmembrane domain; and
(iii) an intracellular signaling domain or (iv) a switch domain
b) contacting the precursor cell with
(i) a sortase molecule and a polypeptide comprising an antigen binding domain, an extracellular domain (ECD) of an inhibitory molecule, or a costimulatory ECD domain and a sortase recognition motif; or
(ii) a complex comprising a polypeptide comprising an antigen binding domain, an extracellular domain (ECD) of an inhibitory molecule, or a costimulatory ECD domain, a cleaved sortase recognition site, and a sortase;
under conditions sufficient to allow transfer of the polypeptide comprising an antigen binding domain, an extracellular domain (ECD) of an inhibitory molecule, or a costimulatory ECD domain and a cleaved sortase recognition motif to the sortase acceptor motif on the sortase acceptor member, thereby providing the cell.

In an embodiment, the method comprises contacting the precursor cell with a sortase molecule and a polypeptide comprising an antigen binding domain, an extracellular domain (ECD) of an inhibitory molecule, or a costimulatory ECD domain and a sortase recognition motif.

In an embodiment, the method comprises contacting the precursor cell with a complex comprising a polypeptide comprising an antigen binding domain, an extracellular domain (ECD) of an inhibitory molecule, or a costimulatory ECD domain; a cleaved sortase recognition site, and a sortase.

In an embodiment, the sortase is a calcium independent sortase. In an embodiment, the sortase is a sortase A. In an embodiment, the sortase is a *Staphylococcus aureus* sortase.

In an embodiment, the sortase acceptor member comprises, e.g., in the N terminal to C terminal direction:
(i) a sortase acceptor motif (e.g., Gly-Gly-Gly-);
(ii) a transmembrane domain; and
(iii) an intracellular signaling domain.

In an embodiment, the sortase acceptor member comprises
(i) a sortase acceptor motif (e.g., Gly-Gly-Gly-);
(ii) a transmembrane domain; and
(iii) a switch domain.

In an embodiment, the cell further comprises an intracellular signaling member.

In an embodiment, polypeptide comprises an antigen binding domain.

In an embodiment, the polypeptide comprises an extracellular domain (ECD) of an inhibitory molecule.

In an embodiment, the polypeptide comprises a costimulatory ECD domain.

In an aspect, a polypeptide is described herein, comprising an antigen binding domain, an extracellular domain (ECD) of an inhibitory molecule, or a costimulatory ECD domain, attached, e.g., as a chimeric polypeptide, to a sortase recognition motif. In an embodiment, the polypeptide comprises an antigen binding domain. In an embodiment, the polypeptide comprises an extracellular domain (ECD) of an inhibitory molecule. In an embodiment, the polypeptide comprises a costimulatory ECD domain.

In an aspect, a reaction mixture is described herein, comprising a polypeptide comprising an antigen binding domain, an extracellular domain (ECD) of an inhibitory molecule, or a costimulatory ECD domain, and a sortase recognition motif. In an embodiment, the reaction mixture further comprises a sortase. In an embodiment, the reaction mixture further comprises a precursor cell comprising a sortase acceptor member. In an embodiment, the polypeptide comprises an antigen binding domain. In an embodiment, the polypeptide comprises an extracellular domain (ECD) of an inhibitory molecule. In an embodiment, the polypeptide comprises a costimulatory ECD domain. In an embodiment, the reaction mixture further comprises a sortase and a precursor cell comprising a sortase acceptor member. In an embodiment, the polypeptide comprises an antigen binding domain. In an embodiment, the polypeptide comprises an extracellular domain (ECD) of an inhibitory molecule. In an embodiment, the polypeptide comprises a costimulatory ECD domain.

In an aspect, a reaction mixture is described herein, comprising:
a complex comprising an antigen binding domain, an extracellular domain (ECD) of an inhibitory molecule, or a costimulatory ECD domain, a cleaved sortase recognition motif, and a sortase. In an embodiment, the reaction mixture further comprises a precursor cell comprising a sortase acceptor member.

In an aspect, a reaction mixture is described herein, comprising:
a sortase; and
a cell comprising a CAR member comprising an antigen binding domain, an extracellular domain (ECD) of an inhibitory molecule, or a costimulatory ECD domain, a sortase transfer signature, a transmembrane domain, and an intracellular signaling domain or switch domain. In an embodiment, the polypeptide comprises an antigen binding domain. In an embodiment, the polypeptide comprises an extracellular domain (ECD) of an inhibitory molecule. In an embodiment, the polypeptide comprises a costimulatory ECD domain.

In an aspect, a method of providing a cell having a first conjugate and a second conjugate attached thereto is described herein, comprising
a) providing a first sortase acceptor member disposed in or on a precursor cell,
b) providing a second sortase acceptor member disposed in or on the precursor cell;
c) contacting the precursor cell with:
  (i) a first sortase molecule and a first moiety coupled to a first sortase recognition motif, or
  (ii) a complex comprising the first moiety coupled to a cleaved first sortase recognition motif and a second sortase molecule; and
d) contacting the precursor cells with:
  (iii) a second sortase molecule and a second moiety coupled to a second sortase recognition motif; or
  (iv) a complex comprising the second moiety coupled to a cleaved second sortase recognition motif and a second sortase molecule;
under conditions sufficient to allow transfer of a first moiety coupled to a cleaved first sortase recognition motif to the first sortase acceptor member to generate a first conjugate, and transfer of a second moiety coupled to a cleaved second sortase recognition motif to the second sortase acceptor member to generate a second conjugate, thereby providing the cell having a first conjugate and a second conjugate attached thereto, e.g., wherein the first conjugate comprises the first moiety and the third moiety, and the second conjugate comprises the second moiety and the fourth moiety. In an embodiment, steps a) and b) are performed simultaneously. In an embodiment, steps a) and c) are performed before steps b) and d). In an embodiment, steps b) and d) are performed before steps a) and c). In an embodiment, steps a), b), c) and c) are performed simultaneously. In an embodiment, steps a), b), c) and d) are performed simultaneously.

In an embodiment, the first sortase molecule and the second sortase molecule are different. In an embodiment, the first sortase molecule and the second sortase molecule are the same. In an embodiment, the first sortase molecule is a sortase molecule described herein, and the second sortase molecule is a wild-type sortase A, e.g., from *S. aureus, S. pyogenes, Actionomyces naeslundii, Bacillus anthracis, Bacillus cereus, Bacillus halodurans, Bacillus subtilis, Bifidobacterium longum, Clostridium botunlinum, Clostridium difficile, Corynebacterium diphtheriae, Corynebacterium efficiens, Corynebacterium glutamicum, Enterococcus faecium, Geobacillus* sp., *Listeria innocua, Listeria monocytogenes, Oceanobacillus iheyensis, Ruminococcus albus, Streptomyces avermitilis, Streptomyces coelicolor, Streptomyces griseus, Staphylococcus epidermis, Streptococcus agalactiae, Streptococcus equi, Streptococcus gordonii, Streptococcus pyogenes, Thermobifida fusca,* or *Tropheryma wipplei*.

In an embodiment, the structures of the first sortase acceptor member and the second sortase acceptor member are the same. In an embodiment, the structures of the first sortase acceptor member and the second sortase acceptor member are different.

In an embodiment, the structures of the first moiety and the second moiety are the same. In an embodiment, the structures of the first moiety and the second moiety are different. In an embodiment, the first moiety comprises an antigen binding domain, an extracellular domain (ECD) of an inhibitory molecule, or a costimulatory ECD domain. In an embodiment, the first moiety comprises an antigen binding domain, an extracellular domain (ECD) of an inhibitory molecule, or a costimulatory ECD domain target binding molecule and the second moiety comprises an antigen binding domain, an extracellular domain (ECD) of an inhibitory molecule, or a costimulatory ECD domain.

In an embodiment, the first moiety and the second moiety bind the same target. In an embodiment, the first moiety and the second moiety bind the same target with different affinities. In an embodiment, the first moiety and the second moiety bind different targets. In an embodiment, the first moiety or the second moiety comprises a marker, e.g., a luciferase, dye, or fluorophore.

In an aspect, a method of providing a cell comprising a CAR member is described herein, comprising an antigen binding domain, a sortase transfer signature, a transmembrane domain, and an intracellular signaling domain or a switch domain comprising:
providing a mixture comprising (i) a cell comprising a CAR member comprising an antigen binding domain, an extracellular domain (ECD) of an inhibitory molecule, or a costimulatory ECD domain, a sortase transfer signature, a transmembrane domain, and an intracellular signaling domain or a switch domain; and (ii) a sortase; and
separating the sortase from the cell, thereby providing a cell comprising a CAR member comprising an antigen binding domain, an extracellular domain (ECD) of an inhibitory molecule, or a costimulatory ECD domain, a sortase transfer signature, a transmembrane domain, and an intracellular signaling domain or a switch domain.

In an embodiment, the CAR member comprises an antigen binding domain. In an embodiment, the CAR member comprises an extracellular domain (ECD) of an inhibitory molecule. In an embodiment, the CAR member comprises a costimulatory ECD domain.

In an aspect, a cell, or a preparation of cells, made by any of the methods described herein is provided herein.

In an aspect, a cell, or a preparation of cells, is described herein, comprising a CAR member comprising an antigen binding domain, an extracellular domain (ECD) of an inhibitory molecule, or a costimulatory ECD domain, a sortase transfer signature, a transmembrane domain, and an intracellular signaling domain or switch domain, which is substantially free of sortase.

In an aspect, a method of treating a subject, e.g., a mammal, e.g., a method of providing an anti-tumor immunity in a subject is described herein, comprising administering to the subject, an effective amount of a CARX cell comprising a sortase transfer signature described herein, e.g., a cell described herein, or a cell comprising a CAR member described herein. In an embodiment, the cell is an autologous T cell. In an embodiment, the cell is an allogeneic T cell. In an embodiment, the cell is an autologous NK cell. In an embodiment, the cell is an allogeneic NK cell. In an embodiment, the subject is a human.

In an embodiment, the method further comprises evaluating said human for a side effect of said treatment. In an embodiment, said side effect comprises acute respiratory distress syndrome, febrile neutropenia, hypotension, encephalopathy, hepatic transaminitis, seizure, or macrophage activation syndrome. In an embodiment, the method further comprises treating said human having a side effect with an anti-cytokine agent, e.g., a tumor necrosis factor antagonist, e.g., a TNF-Ig fusion, e.g., etanercept, an IL-6 antagonist, e.g., an IL-6 receptor antagonist, e.g., an anti-IL6 receptor antibody, e.g., tocilizumab, or a corticosteroid. In an embodiment, said treating comprises administering an anti-IL6 receptor antibody to said human.

In an embodiment, the method described herein further comprises treating a mammal, e.g., a human, having a disease associated with expression of EGFRvIII. In an embodiment, the disease associated with EGFRvIII expression is a proliferative disease, cancer, a precancerous condition, or a non-cancer related indication associated with expression of EGFRvIII. In an embodiment, the proliferative disease is a glioblastoma. In an embodiment, the cancer is selected from glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal and bladder carcinoma.

In an embodiment, the proliferative disease is chronic lymphocytic leukemia (CLL). In an embodiment, the proliferative disease is CLL and the antigen binding domain of the CAR targets CD19.

In an embodiment, the method further comprises administering to the subject a low, immune enhancing, dose of an mTOR inhibitor, e.g., RAD001 or rapamycin. In an embodiment, the dose comprises an allosteric, a catalytic mTOR inhibitor, or both. In an embodiment, the mTOR inhibitor is a RAD001. In an embodiment, the mTOR inhibitor is administered for an amount of time sufficient to decrease the proportion of PD-1 positive T cells, increase the proportion of PD-1 negative T cells, or increase the ratio of PD-1 negative T cells/PD-1 positive T cells, in the peripheral blood of the subject, or in a preparation of T cells isolated from the subject.

In an embodiment, the low, immune enhancing, dose of an mTOR inhibitor is administered prior to administration of immune effector cells, e.g., T cells to be engineered to express a CAR, (e.g., prior to or after harvest of the immune effector cells) for an amount of time sufficient for one or more of the following to occur:

i) a decrease in the number of PD-1 positive immune effector cells;
ii) an increase in the number of PD-1 negative immune effector cells;
iii) an increase in the ratio of PD-1 negative immune effector cells/PD-1 positive immune effector cells;
iv) an increase in the number of naive T cells;
v) an increase in the expression of one or more of the following markers: $CD62L^{high}$, $CD127^{high}$ $CD27^+$, and BCL2, e.g., on memory T cells, e.g., memory T cell precursors;
vi) a decrease in the expression of KLRG1, e.g., on memory T cells, e.g., memory T cell precursors; or
vii) an increase in the number of memory T cell precursors, e.g., cells with any one or combination of the following characteristics: increased $CD62L^{high}$ increased $CD127^{high}$ increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the low, immune enhancing, dose of an mTOR inhibitor is administered prior to harvest of immune effector cells, e.g., T cells to be engineered to express an CAR, for an amount of time sufficient for one or more of the following to occur, e.g., to occur in the harvested cells or in the engineered cells (or in non-harvested cells, or in both):

i) a decrease in the number of PD-1 positive immune effector cells;
ii) an increase in the number of PD-1 negative immune effector cells;
iii) an increase in the ratio of PD-1 negative immune effector cells/PD-1 positive immune effector cells;
iv) an increase in the number of naive T cells;
v) an increase in the expression of one or more of the following markers: $CD62L^{high}$, $CD127^{high}$ $CD27^+$, and BCL2, e.g., on memory T cells, e.g., memory T cell precursors;
vi) a decrease in the expression of KLRG1, e.g., on memory T cells, e.g., memory T cell precursors; or
vii) an increase in the number of memory T cell precursors, e.g., cells with any one or combination of the following characteristics: increased $CD62L^{high}$ increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the immune effector cell, e.g., T cell, to be engineered to express a CAR, e.g., an RCAR, is harvested at least 5, 10, 15, 20, 25, 30, 35, 40, 45, 50, 55, or 60 days after initiation, or completion, of dosing with the low, immune enhancing, dose of an mTOR inhibitor.

In an embodiment, the low, immune enhancing, dose of an mTOR inhibitor is administered after harvest of immune effector cells, e.g., T cells to be engineered to express a CAR, for an amount of time sufficient for one or more of the following to occur:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$ $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$ increased $CD127^{high}$, increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the low, immune enhancing, dose of an mTOR inhibitor is administered after administration of immune effector cells, e.g., T cells to be engineered to express a CAR, e.g., an RCAR, for an amount of time sufficient for one or more of the following to occur:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$ $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$ increased $CD127^{high}$ increased $CD27^+$, decreased KLRG1, and increased BCL2;

and wherein i), ii), iii), iv), v), vi), or vii) occurs e.g., at least transiently, e.g., as compared to a non-treated subject.

In an embodiment, the low, immune enhancing, dose of an mTOR inhibitor is administered to immune effector cells, e.g., T cells, which have, or will be engineered to express a CAR, ex vivo for an amount of time sufficient for one or more of the following to occur:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$ $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$ increased $CD27^+$, decreased KLRG1, and increased BCL2;

and wherein i), ii), iii), iv), v), vi), or vii) occurs e.g., at least transiently, e.g., as compared to a non-treated cell.

In an embodiment, the dose of an mTOR inhibitor is associated with mTOR inhibition of at least 5 but no more than 90%, e.g., as measured by p70 S6K inhibition. In an embodiment, the dose of an mTOR inhibitor is associated with mTOR inhibition of at least 10% but no more than 40%, e.g., as measured by p70 S6K inhibition.

In an embodiment, administering comprises administering, e.g., once per week, e.g., in an immediate release dosage form, 0.1 to 20, 0.5 to 10, 2.5 to 7.5, 3 to 6, or about 5, mgs of RAD001, or an amount of a mTOR inhibitor other than RAD001 that is bioequivalent to a once per week, immediate release dosage form of 0.1 to 20, 0.5 to 10, 2.5 to 7.5, 3 to 6, or about 5, mgs of RAD001.

In an embodiment, administering comprises administering, e.g., once per week, e.g., in a sustained release dosage form, 0.3 to 60, 1.5 to 30, 7.5 to 22.5, 9 to 18, or about 15 mgs of RAD001, or an amount of a mTOR inhibitor other than RAD001 that is bioequivalent to a once per week, sustained release dosage form of 0.3 to 60, 1.5 to 30, 7.5 to 22.5, 9 to 18, or about 15 mgs of RAD001.

In an embodiment, administering comprises administering, e.g., once per day, e.g., in an immediate release dosage form, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001, or an amount of a mTOR inhibitor other than RAD001 that is bioequivalent to a once per day, immediate release dosage form of 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001.

In an embodiment, administering comprises administering, e.g., once per day, e.g., in a sustained release dosage form, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001, or an amount of a mTOR inhibitor other than RAD001 that is bioequivalent to a once per day, sustained release dosage form of 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001.

In an embodiment, the CARX cell comprises an RCAR that comprise an FKBP-FRP based switch, the method comprises administering a dimerization molecule comprising an allosteric mTOR inhibitor, e.g., rapamycin or a rapalog, e.g., RAD001. In an embodiment, the method comprises administering a dimerization molecule comprising an allosteric mTOR inhibitor, e.g., RAD001, described in the section herein for a low, immune enhancing, dose of an allosteric mTOR inhibitor, e.g., RAD001. In an embodiment, the method comprises administering a dimerization molecule comprising RAD001. In an embodiment, the method comprises administering 0.1 to 20, 0.5 to 10, 2.5 to 7.5, 3 to 6, or about 5, mgs of RAD001 per week, e.g., delivered once per week. In an embodiment, the method comprises administering, 0.3 to 60, 1.5 to 30, 7.5 to 22.5, 9 to 18, or about 15 mgs of RAD001 in a sustained release formulation, per week, e.g., delivered once per week. In an embodiment, the method comprises administering, 0.005 to 1.5, 0.01 to 1.5, 0.1 to 1.5, 0.2 to 1.5, 0.3 to 1.5, 0.4 to 1.5, 0.5 to 1.5, 0.6 to 1.5, 0.7 to 1.5, 0.8 to 1.5, 1.0 to 1.5, 0.3 to 0.6, or about 0.5 mgs of RAD001 per day, e.g., delivered once per day. In an embodiment, the method comprises administering, 0.015 to 4.5, 0.03 to 4.5, 0.3 to 4.5, 0.6 to 4.5, 0.9 to 4.5, 1.2 to 4.5, 1.5 to 4.5, 1.8 to 4.5, 2.1 to 4.5, 2.4 to 4.5, 3.0 to 4.5, 0.9 to 1.8, or about 1.5 mgs of RAD001 in a sustained release formulation, per day, e.g., delivered once per day. In an embodiment, the method comprises administering, 0.1 to 30, 0.2 to 30, 2 to 30, 4 to 30, 6 to 30, 8 to 30, 10 to 30, 1.2 to 30, 14 to 30, 16 to 30, 20 to 30, 6 to 12, or about 10 mgs of RAD001 in a sustained release formulation, per week, e.g., delivered once per week.

In an aspect, a method of providing a cell comprising a sortase acceptor member or a sortase transfer signature is described herein, comprising:

providing an immune effector cell, e.g., a T cell from a human, to an entity, e.g., a laboratory or hospital; and receiving from said entity, a cell comprising a CAR that comprises a) a sortase acceptor member; or b) a sortase transfer signature, made from said immune effector cell, or a daughter cell thereof.

In an embodiment, the cell comprises a sortase acceptor member.

In an embodiment, the cell comprises a sortase transfer signature.

In an embodiment, said entity inserted a nucleic acid encoding the sortase acceptor member into said immune effector cell or a daughter cell thereof. In an embodiment, said entity performed a sortase mediated attachment of an antigen binding domain, an extracellular domain (ECD) of an inhibitory molecule, or a costimulatory ECD domain, to the sortase acceptor member.

In an embodiment, after receipt of an immune effector cell comprising a sortase acceptor member, attaching an antigen binding domain to the sortase acceptor member.

In some embodiments, the methods disclosed herein further comprise contacting the population of immune effector cells with a nucleic acid encoding a telomerase subunit, e.g., hTERT. The nucleic acid encoding the telomerase subunit can be DNA.

In some embodiments, the methods disclosed herein further comprise culturing the population of immune effector cells in serum comprising 2% hAB serum.

In an embodiment, the method further comprises administering said cell to a subject.

In an aspect, a method of providing a cell comprising a sortase acceptor member is described herein, comprising:

receiving from an entity, e.g., a health care provider, an immune effector cell, e.g., a T cell, from a human;

inserting a nucleic acid encoding a sortase acceptor member into said immune effector cell, or a daughter cell thereof, to form a cell comprising a sortase acceptor member; and, optionally, providing said CARX cell to said entity.

In an aspect, a nucleic acid is described herein, for use as a medicament.

In an aspect, a nucleic acid is described herein, for use in the treatment of a disease, characterized by the need of an enhanced immune response. In an embodiment, said disease is characterized by unwanted expression of EGFRvIII. In an embodiment, said disease characterized by unwanted expression of EGFRvIII is a proliferative disease, cancer, a precancerous condition, or a non-cancer related indication associated with expression of EGFRvIII. In an embodiment, said disease is characterized by sub-optimal anti-tumor immunity. In an embodiment, said disease is cancer. In an embodiment, said disease is glioblastoma. In an embodiment, said disease is glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

In an aspect, a vector system is described herein for use as a medicament.

In an aspect, a vector system described herein, for use in the treatment of a disease, characterized by the need of an enhanced immune response. In an embodiment, said disease is characterized by unwanted expression of EGFRvIII. In an embodiment, said disease characterized by unwanted expression of EGFRvIII is a proliferative disease, cancer, a precancerous condition, or a non-cancer related indication associated with expression of EGFRvIII. In an embodiment, said disease is characterized by sub-optimal anti-tumor immunity. In an embodiment, said disease is cancer. In an embodiment, said disease is glioblastoma. In an embodiment, said disease is glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

In an aspect, a CAR, e.g., an RCAR, is described herein, for use as a medicament.

In an aspect, a CAR described herein, e.g., an RCAR, for use in the treatment of a disease, characterized by the need of an enhanced immune response. In an embodiment, said disease is characterized by unwanted expression of EGFRvIII. In an embodiment, said disease characterized by unwanted expression of EGFRvIII is a proliferative disease, cancer, a precancerous condition, or a non-cancer related indication associated with expression of EGFRvIII. In an embodiment, said disease is characterized by sub-optimal anti-tumor immunity. In an embodiment, said disease is cancer. In an embodiment, said disease is glioblastoma. In an embodiment, said disease is glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

In an aspect, a CARX cell is described herein, for use as a medicament.

In an aspect, a CARX cell is described herein, for use in the treatment of a disease, characterized by the need of an enhanced immune response. In an embodiment, said disease is characterized by unwanted expression of EGFRvIII. In an embodiment, said disease characterized by unwanted expression of EGFRvIII is a proliferative disease, cancer, a precancerous condition, or a non-cancer related indication associated with expression of EGFRvIII. In an embodiment, said disease is characterized by sub-optimal anti-tumor immunity. In an embodiment, said disease is cancer. In an embodiment, said disease is glioblastoma. In an embodiment, said disease is glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal or bladder carcinoma.

Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 9B: FACS staining showing that cells transduced with CG13 and CART19 constructs display similar levels of scFV19 at their surface, based on biotinylated proteinL followed by detection with streptavidin PE.

FIG. 10A shows a schematic representation of the functionalization mechanism of engineered T cells at their surface using sortase A-mediated chemoenzymatic reactions and a LPETG peptide (SEQ ID NO: 112) decorated with a TAMRA fluorophore (red star). FIG. 10B shows FACS analysis of 2×10$^5$ Jurkat cells either not transduced (JNL) or transduced with construct CG11 ($G_3$MycpseudoCART, FIG. 6) and incubated with 40 μM mutant sortase A and either 1 μM or 5 μM (TAMRA) KLPETGG peptide (SEQ ID NO: 27), for 30 min at 37° C. in RPMI media supplemented with 1% FBS. Cells were washed three times with cold MACS buffer containing BSA before FACS analysis. The number of TAMRA positive cells (PE+) is indicated. The Figure discloses "LPETG$_3$" as SEQ ID NO: 25.

FIG. 14A shows day 0 PK following the first dose of RAD001. FIG. 14B shows Day 14 PK following the final RAD001 dose. Diamonds denote the 10 mg/kg dose of RAD001; squares denote the 1 mg/kg dose of RAD001; triangles denote the 3 mg/kg dose of RAD001; and x's denote the 10 mg/kg dose of RAD001.

FIG. 13A shows CD4+ CAR T cells; FIG. 13B shows CD8+ CAR T cells. Circles denote PBS; squares denote huCTL019; triangles denote huCTL019 with 3 mg/kg RAD001; inverted triangles denote huCTL019 with 0.3 mg/kg RAD001; diamonds denote huCTL019 with 0.03 mg/kg RAD001; and circles denote huCTL019 with 0.003 mg/kg RAD001.

DETAILED DESCRIPTION

Definitions

Figure 1:
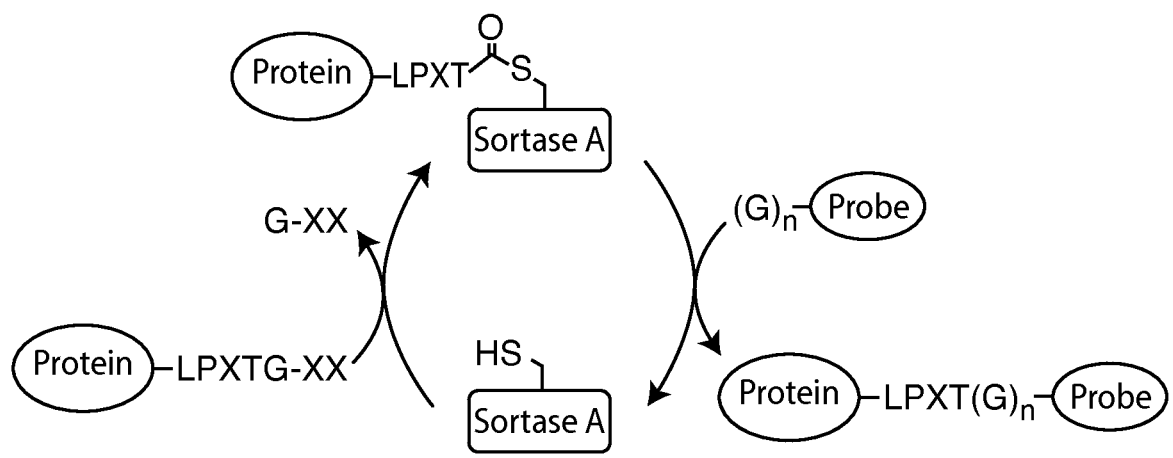
FIG. 1 is a schematic representation of C-terminal labeling of proteins. A protein modified at its C terminus with the LPXTG (SEQ ID NO: 109) sortase-recognition motif followed by a handle (e.g., His6 (SEQ ID NO: 110)) is incubated with S. aureus Sortase A. Sortase cleaves the threonine-glycine bond and via its active site cysteine residue forming an acyl intermediate with threonine in the protein. Addition of a peptide probe comprising a series of N-terminal glycine residues and a functional moiety of choice resolves the intermediate, thus regenerating the active site cysteine (HS) on sortase and ligating the peptide probe to the C terminus of the protein (Guimaraes et al., 2013). The Figure discloses "LPXT" as SEQ ID NO: 30.

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

As used herein, the term "about" in reference to a dose of mTOR inhibitor refers to up to a +/−10% variability in the amount of mTOR inhibitor, but can include no variability around the stated dose.

"Allogeneic" as the term is used herein refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. In an embodiment a CARX cell is allogeneic to a subject. In an embodiment a CARX cell is from the subject, and is autologous.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, "an apheresis sample" refers to a sample obtained using apheresis.

"Autologous" as the term is used herein refers to any material derived from the same individual to whom it is later to be re-introduced.

An "antigen binding domain" as the term is used herein, refers to a molecule that has affinity for a target antigen, typically an antigen on a target cell, e.g., a cancer cell. An exemplary antigen binding domain comprises a polypeptide, e.g., an antibody molecule (which includes an antibody, and antigen binding fragments thereof, e.g., a immunoglobulin, single domain antibody (sdAb), and an scFv), or a non-antibody scaffold, e.g., a fibronectin, and the like. In embodiments, the antigen binding domain is a single polypeptide. In embodiments, the antigen binding domain comprises, one, two, or more, polypeptides. In embodiments the antigen binding domain comprises a fragment of an antibody, that is sufficient to confer recognition and specific binding to the target antigen. Examples of an antibody fragment include, but are not limited to, an Fab, Fab', F(ab')$_2$, or Fv fragment, an scFv antibody fragment, a linear antibody, single domain antibody such as an sdAb (either VL or VH), a camelid VHH domain, and multi-specific antibodies formed from antibody fragments. In an embodiment, the antigen binding domain is a "scFv,"—which can comprise a fusion protein comprising a VL chain and a VH chain of an antibody, where the VH and VL are linked via a short flexible polypeptide linker. The scFv is capable of being expressed as a single chain polypeptide and retains the specificity of the intact antibody from which it is derived. Moreover, the VL and VH variable chains can be linked in either order, e.g., with respect to the N-terminal and C-terminal ends of the polypeptide, the scFv may comprise VL-linker-VH or may comprise VH-linker-VL. In embodiments, the antigen binding domain comprises a non antibody scaffold, e.g., a fibronectin, ankyrin, domain antibody, lipocalin, small modular immuno-pharmaceutical, maxybody, Protein A, or affilin. The non antibody scaffold has the ability to bind to target antigen on a cell. In embodiments, the antigen binding domain is a polypeptide or fragment thereof of a naturally occurring protein expressed on a cell. In an embodiment, the antigen binding domain binds a growth factor or hormone receptor. While not wishing to be bound by theory, the antigen binding domain serves to provide specificity for target cells, and in embodiments, optimize and immune effector function by coupling antigen binding to generation of a signal by an intracellular signaling domain on an intracellular signaling member.

As used herein, the term "antibody molecule" refers to a protein, e.g., an immunoglobulin chain or fragment thereof, comprising at least one immunoglobulin variable domain sequence. The term "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The terms "complementarity determining region" or "CDR," as used herein, refer to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR of the invention comprising an antibody or antibody fragment thereof may exist in a variety of forms, for example, where the antigen binding domain is expressed as part of a polypeptide chain including, for example, a single domain antibody fragment (sdAb), a single chain antibody (scFv), or e.g., a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), or a combination thereof.

"Antigen binding member," as that term is used herein, comprises an antigen binding domain, and a transmembrane domain or a membrane anchor. Antigen binding members are typically a member of an RCAR. An antigen binding member can also comprise a switch domain. In embodiments the switch domain on the antigen binding member can form a dimerization switch with a switch domain on an intracellular signaling member. The dimerization switch formed by these two switch domains can couple antigen binding to intracellular signal generation, and thereby optimize an immune effector function of the cell. In embodiments, the antigen binding member comprises an antigen binding domain which is other than the native extracellular domain of a molecule from which an intracellular signaling domain on the intracellular signaling member is derived. In embodiments, the antigen binding member comprises an antigen binding domain which binds an antigen which is not the ligand of the native extracellular domain of a molecule from which an intracellular signaling domain on the intracellular signaling member is derived. In an embodiment an antigen binding member comprises a sortase transfer signature. In an embodiment an antigen binding member comprises a sortase transfer signature disposed between two elements that have been coupled by sortase mediated transfer.

"Auxiliary antigen binding member," as that term is used herein, refers to a molecule comprising an antigen binding domain that binds an antigen other than the antigen bound by another antigen binding domain of the CAR, e.g., other than the antigen binding domain of the antigen binding member. In embodiments it comprises a transmembrane domain or membrane anchoring domain. In an embodiment an auxiliary antigen binding member comprises a sortase transfer signature. In an embodiment an auxiliary antigen binding member comprises a sortase transfer signature disposed between two elements that have been coupled by sortase mediated transfer.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

"Cancer" as the term is used herein, refers to a disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The terms "cancer associated antigen" or "tumor marker" interchangeably refers to a molecule (typically protein, carbohydrate or lipid) that is preferentially expressed on the surface of a cancer cell, either entirely or as a fragment (e.g., MHC/peptide), in comparison to a normal cell, and which is useful for the preferential targeting of a pharmacological agent to the cancer cell. In some embodiments, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a cancer-associated antigen is a cell surface molecule that is inappropriately synthesized in the cancer cell, for instance, a molecule that contains deletions, additions or mutations in comparison to the molecule expressed on a normal cell. In some embodiments, a cancer-associated antigen will be expressed exclusively on the cell surface of a cancer cell, entirely or as a fragment (e.g., MHC/peptide), and not synthesized or expressed on the surface of a normal cell.

"Costimulatory signaling domain," as that term is used herein, refers to a molecule, e.g., an endogenous molecule, of the CARX cell that, upon binding to its cognate counter ligand on a target cell, enhance, e.g., increases, an immune effector response.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

The term "chimeric antigen receptor", or "CAR" as that term is used herein, refers to a polypeptide, or in the case of RCARs, polypeptides, comprising a receptor, e.g., an antigen binding domain, a transmembrane domain, and an intracellular signaling domain. CARs include unitary CARs, or uCARs, and regulatable CARs, or RCARs. A CAR can comprise an inhibitory CAR, or iCAR. A single polypeptide component of a CAR is sometimes referred to as a CAR member. Domains or other functional or structural sequence on a member, e.g., a transmembrane domain or intracellular signaling domain, is referred to as an element. In an embodiment a CAR member comprises a sortase transfer signature. In an embodiment a CAR member comprises a sortase transfer signature disposed between two elements that have been coupled by sortase mediated transfer.

In one embodiment, the stimulatory molecule of the CAR is the zeta chain associated with the T cell receptor complex. In one embodiment, the cytoplasmic signaling domain comprises a primary signaling domain (e.g., a primary signaling domain of CD3-zeta). In one embodiment, the cytoplasmic signaling domain further comprises one or more functional signaling domains derived from at least one costimulatory molecule as defined below. In one embodiment, the costimulatory molecule is chosen from 4 1BB (i.e., CD137), ICOS, CD27 and/or CD28. In one embodiment, the CAR comprises a chimeric fusion protein comprising an extracellular antigen binding domain, a transmembrane domain and an intracellular signaling domain comprising a functional signaling domain derived from a stimulatory molecule. In one embodiment, the CAR comprises a chimeric fusion protein comprising an extracellular antigen binding domain, a transmembrane domain and an intracellular signaling domain comprising a functional signaling domain derived from a co-stimulatory molecule and a functional signaling domain derived from a stimulatory molecule. In one embodiment, the CAR comprises a chimeric fusion protein comprising an extracellular antigen binding domain, a transmembrane domain and an intracellular signaling domain comprising two functional signaling domains derived from one or more co-stimulatory molecule(s) and a functional signaling domain derived from a stimulatory molecule. In one embodiment, the CAR comprises a chimeric fusion protein comprising an extracellular antigen binding domain, a transmembrane domain and an intracellular signaling domain comprising at least two functional signaling domains derived from one or more co-stimulatory molecule(s) and a functional signaling domain derived from a stimulatory molecule. In one embodiment, the CAR comprises an optional leader sequence at the amino-terminus (N-ter) of the CAR fusion protein. In one embodiment, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane. In an embodiment a CAR comprises an antigen binding domain. In an embodiment, a CAR comprises an extracellular ligand domain specific for a counter ligand.

A CAR that comprises an antigen binding domain (e.g., a scFv, a single domain antibody, or TCR (e.g., a TCR alpha binding domain or TCR beta binding domain)) that targets a specific tumor marker X, such as those described herein, is referred to as XCAR. For example, a CAR that comprises an antigen binding domain that targets CD19 is referred to as CD19CAR. The CAR can be expressed in any cell, e.g., an immune effector cell as described herein (e.g., a T cell or an NK cell).

As used herein, the term "CD19" refers to the Cluster of Differentiation 19 protein, which is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding of the human CD19 can be found at Accession No. NM_001178098. As used herein, "CD19" includes proteins comprising mutations, e.g., point mutations, fragments, insertions, deletions and splice variants of full length wild-type CD19. CD19 is expressed on most B lineage cancers, including, e.g., acute lymphoblastic leukaemia, chronic lymphocyte leukaemia and non-Hodgkin lymphoma. Other cells with express CD19 are provided below in the definition of "disease associated with expression of CD19." It is also an early marker of B cell progenitors. See, e.g., Nicholson et al. Mol. Immun. 34 (16-17): 1157-1165 (1997). In one aspect the antigen-binding portion of the CARX, e.g., CART, recognizes and binds an antigen within the extracellular domain of the CD19 protein. In one aspect, the CD19 protein is expressed on a cancer cell.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

"Dimerization molecule," as that term is used herein, refers to a molecule that promotes the association of a first switch domain with a second switch domain in an RCAR. In embodiments, e.g., where the dimerization switch is disposed intracellulary, the dimerization molecule can cross the plasma membrane. In embodiments, e.g., where the dimerization switch is disposed extracellulary, the dimerization molecule need not cross the plasma membrane. In embodiments, the dimerization molecule does not naturally occur in the subject, or does not occur in concentrations that would result in significant dimerization. In embodiments, the dimerization molecule is a small molecule, e.g., rapamycin or a rapalogue. In embodiments, the dimerization molecule is a polypeptide. In embodiments, the dimerization molecule is an antibody molecule, e.g., antibody or antigen-binding fragment thereof. In embodiments, the first and second switch domains of a homodimerization switch or heterodimerization switch associate together in the presence of small molecule dimerization molecule e.g., rapamycin or a rapalogue. In embodiments, the first and second switch domains of a homodimerization switch or heterodimerization switch associate together in the presence of polypeptide dimerization molecule. In embodiments, the first and second switch domains of a homodimerization switch or heterodimerization switch associate together in the presence of a multimeric peptide dimerization molecule. In embodiments, the first and second switch domains of a homodimerization switch or heterodimerization switch associate together in the presence of an antibody molecule dimerization molecule. In embodiments, the antibody molecule comprises a monospecific antibody molecule. In embodiments, the antibody molecule is a dual specific antibody molecule.

Generally, a dimerization molecule will promote the association of at least two switch molecules (and thereby the association of intracellular domains linked to the switch domains). In embodiments the dimerization molecule has a valency of greater than two, e.g., it is multi-valent, and binds, and thus clusters or dimerizes, more than two switch domains. E.g., a dimerization molecule can comprise a plurality, e.g., at least 2, 3, 4, 5, 6, 7, 8, 9 or 10, binding domains, each of which can bind a switch domain.

The phrase "disease associated with expression of a tumor marker as described herein" includes, but is not limited to, a disease associated with a cell that expresses of a tumor marker as described herein or condition associated with a cell which expresses, or at any time expressed, a tumor marker as described herein including, e.g., proliferative diseases such as a cancer or malignancy or a precancerous condition such as a myelodysplasia, a myelodysplastic syndrome or a preleukemia; or a noncancer related indication associated with a cell which expresses a tumor marker as described herein. In one aspect, a cancer associated with expression of a tumor marker as described herein is a hematological cancer. In one aspect, a cancer associated with expression of a tumor marker as described herein is a solid cancer. Further diseases associated with expression of a tumor marker as described herein include, but not limited to, e.g., atypical and/or non-classical cancers, malignancies, precancerous conditions or proliferative diseases associated with expression of a tumor marker as described herein. Non-cancer related indications associated with expression of a tumor marker as described herein include, but are not limited to, e.g., autoimmune disease, (e.g., lupus), inflammatory disorders (allergy and asthma) and transplantation. In some embodiments, the tumor antigen-expressing cell expresses, or at any time expressed, mRNA encoding the tumor antigen. In an embodiment, the tumor antigen-expressing cell produces the tumor antigen protein (e.g., wild-type or mutant), and the tumor antigen protein may be present at normal levels or reduced levels. In an embodiment, the tumor antigen-expressing cell produced detectable levels of a tumor antigen protein at one point, and subsequently produced substantially no detectable tumor antigen protein.

The phrase "disease associated with expression of CD19" includes, but is not limited to, a disease associated with expression of CD19 or condition associated with cells which express, or at any time expressed, CD19 including, e.g., proliferative diseases such as a cancer or malignancy or a precancerous condition such as a myelodysplasia, a myelodysplastic syndrome or a preleukemia; or a noncancer related indication associated with cells which express CD19. For the avoidance of doubt, a disease associated with expression of CD19 may include a condition associated with cells which do not presently express CD19, e.g., because CD19 expression has been downregulated, e.g., due to treatment with a molecule targeting CD19, e.g., a CD19 CAR, but which at one time expressed CD19. In one aspect, a cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., B-cell acute Lymphoid Leukemia (BALL), T-cell acute Lymphoid Leukemia (TALL), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma (MCL), Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further diseases associated with expression of CD19 expression include, but not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

"dsRNA," as that term is used herein, refers to a nucleic acid molecule, having at least a region of duplexed structure, that is capable of mediating sequence specific inhibition of the expression of a target gene. dsRNAs comprise short interfering RNA (siRNA) and short hairpin RNA (shRNA). In embodiments, shRNA is similar in structure to an siRNA but includes a moiety, typically one or more RNA monomers, that connect a duplex region of sense and an antisense sequence. In an embodiment the shRNA, after intracellular processing (e.g., by Dicer), results in a 19-23 nucleotide duplex siRNA with 2 nucleotide 3' overhangs.

"Endogenous" as that term is used herein, refers to any material, e.g., a polypeptide, from or produced inside an organism, cell, tissue or system.

"Exogenous" as that term is used herein, refers to any material, e.g., a polypeptide, or dimerization molecule, introduced from or produced outside an organism, cell, tissue or system.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes. A CAR can be formed on an immune effector cell, e.g., by sortase mediated transfer of an extra cellular domain, e.g., an antigen binding domain, to turn it into a CARX cell, e.g., a CAR can be formed on a T cell, e.g., by sortase mediated transfer of an extra cellular domain, e.g., an antigen binding domain, to make a CARX, e.g., CART cell.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and costimulation are examples of immune effector function or response. An immune effector function or response can be promoted by the action of a CAR, and can, e.g., result in a CARX cell that is more effective at proliferation, cytokine production, cytotoxicity or upregulation of cell surface markers such as CD25, CD69, CD107a.

The term "effector function" refers to a specialized function of a cell. Effector function of a T cell, for example, may be cytolytic activity or helper activity including the secretion of cytokines.

The term "immunosenescence" refers to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems, e.g., in the aged population. Age-dependent biological changes such as depletion of hematopoietic stem cells, decline in the total number of phagocytes and NK cells and a decline in humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naïve CD4 and/or CD8 T cells, T cell repertoire, or response to vaccination in a subject greater than or equal to 65 years of age.

The term "impaired immune response" refers to a state in which a subject does not have an appropriate immune response, e.g., to cancer, vaccination, pathogen infection, among others. In some embodiments, a subject having an impaired immune response is predicted not to get protective antibody titer levels following prophylactic vaccination, or in which a subject does not have a decrease in disease burden after therapeutic vaccination. A subject can also have an impaired immune response if the subject is a member of a population known to have decreased immune function or that has a history of decreased immune function such as the elderly, subjects undergoing chemotherapy treatment, asplenic subjects, immunocompromised subjects, or subjects having HIV/AIDS. Methods described herein allow for the treatment of an impaired immune response by administration of a low, immune enhancing, dose of an mTOR inhibitor, e.g., an allosteric mTOR inhibitor, such as RAD001.

An inhibitory CAR (iCAR), as that term is used herein, is a CAR that recognizes an antigen on a non-target cell and produces a inhibitory signal, minimizing the activation of the cell. The extracellular domain of an iCAR can be added by sortase mediated transfer.

An "inhibitory extracellular domain," as that term is used herein, refers to polypeptide comprising an extracellular domain of an inhibitory molecule. Normally, binding to its conterligand has an inhibitory effect on the generation of an immune effector response. When linked, e.g., fused, or coupled by a dimerization switch, to an intracellular signaling domain, it redirects an interaction that normally inhibits the generation of an immune effector response into one that promotes an immune effector response.

"Inhibitory binding member," as that term is used herein, refers to a polypeptide that comprises an inhibitory extracellular domain, a transmembrane domain, and a switch domain.

"Inhibitory molecule," as that term is used herein, refers to a molecule, e.g., an endogenous molecule, of CARX cell, e.g., a CART cell that, upon binding to its cognate counter ligand on a target cell, minimizes, e.g., suppresses or inhibits, an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

"Intracellular signaling domain," as the term is used herein, refers to an intracellular portion of a molecule. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise cytoplasmic sequences of the T cell receptor, and a costimulatory intracellular signaling domain can comprise cytoplasmic sequence from co-receptor or costimulatory molecule.

Primary intracellular signaling domains can comprise signaling motifs which are known as immunoreceptor tyrosine-based activation motifs or ITAMs. Examples of ITAM containing primary cytoplasmic signaling sequences include those derived from CD3 zeta, FcR gamma, common FcR gamma (FCER1G), Fc gamma RIIa, FcR beta (Fc Epsilon Rib), CD3 gamma, CD3 delta, CD3 epsilon, CD5, CD22, CD79a, CD79b, CD278 (also known as "ICOS"), FcεRI, DAP10, DAP12, and CD66d. Further examples of molecules containing a primary intracellular signaling domain that are of particular use in the invention include those of DAP10, DAP12, and CD32.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

"Intracellular signaling member," as that term is used herein, refers to a polypeptide comprising an intracellular signaling domain and a switch domain. Typically an intracellular signaling member is a member of a RCAR. In embodiments it comprises a primary intracellular signal domain, and, optionally, a costimulatory signaling domain. In embodiments with more than one intracellular signaling domain, such domains may be linked to each other in a random or specified order. Optionally, a short oligo- or polypeptide linker, for example, between 2 and 10 amino acids in length, may be disposed between intracellular signaling domains. A glycine-serine doublet provides a particularly suitable linker.

In an embodiment, the intracellular signaling member comprises the signaling domain of CD3-zeta and the signaling domain of CD28. In an embodiment, the intracellular signaling member comprises the signaling domain of CD3-zeta and the signaling domain of 4-1BB. In an embodiment, the intracellular signaling domain of 4-1BB is a signaling domain from SEQ ID NO: 2. The amino acid sequence of a 4-1BB intracellular signaling domain is as follows:

(SEQ ID NO: 2)
KRGRKKLLYIFKQPFMRPVQTTQEEDGCSCRFPEEEEGGCEL

In an embodiment, the signaling domain of CD3-zeta is a signaling domain from SEQ ID NO: 3. The amino acid sequence of a CD3-zeta intracellular signaling domain is as follows:

(SEQ ID NO: 3)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

In an embodiment, the signaling domain of CD3-zeta is a signaling domain from SEQ ID NO: 251, as follows:

(SEQ ID NO: 251)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

In an embodiment, the signaling domain of CD28 is a signaling domain from SEQ ID NO: 261, as follows:

(SEQ ID NO: 261)
RSKRSRLLHSDYMNMTPRRPGPTRKHYQPYAPPRDFAAYRS

In an embodiment, the signaling domain of CD28 is encoded by a nucleotide sequence of SEQ ID NO: 262, as follows:

(SEQ ID NO: 262)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

In an embodiment, the signaling domain of ICOS is a signaling domain from SEQ ID NO: 263, as follows:

(SEQ ID NO: 263)
T K K K Y S S S V H D P N G E Y M F M R A V N T A

K K S R L T D V T L

In an embodiment, the signaling domain of ICOS is encoded by a nucleotide sequence of SEQ ID NO: 264, as follows:

(SEQ ID NO: 264)
ACAAAAAAGAAGTATTCATCCAGTGTGCACGACCCTAACGGTGAATACAT

GTTCATGAGAGCAGTGAACACAGCCAAAAAATCCAGACTCACAGATGTGA

CCCTA

In an embodiment, the signaling domain of CD27 is a signaling domain from SEQ ID NO: 271, as follows:

(SEQ ID NO: 271)
QRRKYRSNKGESPVEPAEPCRYSCPREEEGSTIPIQEDYRKPEPACSP

In an embodiment, the signaling domain of CD27 is encoded by a nucleotide sequence of SEQ ID NO: 272, as follows:

(SEQ ID NO: 272)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

"Isolated" as that term is used herein refers to a nucleic acid or polypeptide means separated from at least one contaminating compound. With regard to a nucleic acid or polypeptide that exists in nature, it means free of a compound with which it occurs in nature, wherein in embodiments, the contaminating compound is a polynucleotide or polypeptide. With regard to a nucleic acid or polypeptide that is made synthetically, it means free of a side reactant or compound used in its preparation, e.g., a solvent or starting reactant. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells.

"Membrane anchor," as that term is used herein, refers to a polypeptide sufficient to anchor an extracellular domain to the plasma membrane.

"Nucleic acid-based inhibitor," as that term is used herein, refers to a nucleic acid molecule that can inhibit expression of a target gene, e.g., an inhibitory molecule. It comprises double stranded RNA (dsRNA), including short hairpin RNA (shRNA) and short interfering RNA (siRNA), antisense RNA, and microRNA (miRNA). In an embodiment, the nucleic-acid based inhibitor binds to the target mRNA and inhibits the production of protein therefrom, e.g., by cleavage of the target mRNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or RNA may also include introns to the extent that the nucleotide sequence encoding the protein may in some version contain an intron(s).

"Regulatable chimeric antigen receptor (RCAR)," as that term is used herein, refers to a set of polypeptides, or members, typically two in the simplest embodiments, which when in a RCARX cell, provides the RCARX cell with specificity for a target cell, typically a cancer cell, and with regulatable intracellular signal generation, which can optimize an immune effector property of the RCARX cell. An RCARX cell relies at least in part, on an antigen binding domain to provide specificity to a target cell that comprises the antigen bound by the antigen binding domain. The RCAR includes a dimerization switch that, upon the presence of a dimerization molecule, can couple an intracellular signaling domain to an extracellular recognition element. An extracellular recognition element can be an antigen binding domain, an inhibitory counter ligand binding domain, or costimulatory ECD domain. In an embodiment an RCAR member comprises a sortase transfer signature, e.g., disposed between and extracellular domain and a transmembrane domain.

"CARX cell," as that term is used herein, refers to a cell comprising CAR. Any cell that is engineered to express a CAR can be used as a CARX cell. In an embodiment the CARX cell is a T cell, and is referred to as a CART cell. In an embodiment the CARX cell is an NK cell, and is referred to as a CARN cell. In an embodiment the CARX cell is autologous to the patient. In an embodiment the CARX is allogeneic to the patient. In an embodiment, a patient receives more than one kind of CARX cell, e.g., the patient receives a CART cell and a CARN cell. In an embodiment a CARX cell, e.g., a CART cell, comprises a CAR member comprising a sortase transfer signature, e.g., disposed between and extracellular domain and a transmembrane domain.

"Sortase," as that term is used herein, refers to an enzyme which catalyzes a transpeptidation reaction between a sortase recognition motif and a sortase acceptor motif. Various sortases from prokaryotic organisms have been identified. In an embodiment, the sortase molecule catalyzes a reaction to conjugate the C-terminus of a first moiety containing a sortase recognition motif to the N-terminus of a second moiety containing a sortase acceptor motif by a peptide bond.
In an embodiment, the sortase molecule catalyzes a reaction to couple a first moiety to a second moiety by a peptide bond.

In an embodiment, sortase mediated transfer is used to couple the N terminus of a first polypeptide, e.g., an extracellular binding domain, e.g., an antigen binding domain, to the N terminus of a second polypeptide, e.g., a transmembrane polypeptide, having an extracellular N terminus. In such embodiments, sortase mediated transfer is used to attach a coupling moiety, e.g., a "click" handle, to the N terminus of each polypeptide, wherein the coupling moieties mediate coupling of the polypeptides. In an embodiment the first polypeptide is an extracellular binding domain, e.g., an antigen binding domain, comprising a sortase acceptor motif, and the second polypeptide is a transmembrane polypeptide comprising an extracellular N terminal sortase acceptor motif, a transmembrane domain, and an intracellular signaling domain. Sortase mediated transfer is used to attach a coupling moiety, e.g., a click handle, to each polypeptide.

"Sortase acceptor member," as that term is used herein, refers to a molecule comprising a sortase acceptor motif. In an embodiment, the molecule is a polypeptide and further comprises a transmembrane domain, and optionally, an intracellular signaling domain, or a switch domain, or any combination thereof. In an embodiment, sortase mediated transfer of an element, e.g., an antigen binding domain, to a sortase acceptor member, from a completed CAR member.

"Sortase acceptor motif," as that term is used herein, refers to a moiety that acts as an acceptor for the sortase-mediated transfer of a polypeptide, from the sortase, to the sortase acceptor motif. In an embodiment the sortase acceptor motif is located at the N terminus of a polypeptide. In an embodiment the transferred polypeptide is linked by a peptide bond at its C terminus to the N terminal residue of the sortase acceptor motif. N-terminal acceptor motifs include Gly-[Gly]$_n$- (SEQ ID NO: 113), wherein n=0-5 and Ala-[Ala]$_n$- (SEQ ID NO: 114), wherein n=0-5.

"Sortase recognition motif," as that term is used herein, refers to polypeptide which, upon cleavage by a sortase molecule, e.g., a, forms a thioester bond with the sortase molecule. In an embodiment, the sortase recognition motif comprises a sequence from any of Tables 1-6. In an embodiment, sortase cleavage occurs between T and G/A. In an embodiment the peptide bond between T and G/A is replaced with an ester bond to the sortase molecule.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the primary cytoplasmic signaling sequence(s) that regulate primary activation of the immune cell in a stimulatory way for at least some aspect of the immune cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from CD3 zeta, common FcR gamma (FCER1G), FcR beta (Fc Epsilon Rib), CD3 gamma, CD3 delta, CD3 epsilon, CD5, CD22, CD79a, CD79b, DAP10, DAP12, CD278 (also known as "ICOS"), FcεRI, CD66d, DAP10, and DAP12. In a specific CAR of the invention, the intracellular signaling domain in any one or more CARs of the invention comprises an intracellular signaling sequence, e.g., a primary signaling sequence of CD3-zeta. In a specific CAR of the invention, the primary signaling sequence of CD3-zeta is the sequence provided as SEQ ID NO:3, or the equivalent residues from a non-human species, e.g., mouse, rodent, monkey, ape and the like. In a specific CAR of the invention, the primary signaling sequence of CD3-zeta is the sequence as provided in SEQ ID NO:251, or the equivalent residues from a non-human species, e.g., mouse, rodent, monkey, ape and the like.

"Sortase transfer signature," as that term is used herein, refers to the portion of a sortase recognition motif and the portion of a sortase acceptor motif remaining after the reaction that couples the former to the latter. In an embodiment, wherein the sortase recognition motif is LPXTG/A and wherein the sortase acceptor motif is GG, the resultant sortase transfer signature after sortase-mediated reaction comprises LPXTGG (SEQ ID NO: 115).

"Switch domain," as that term is used herein, refers to an entity, typically a polypeptide-based entity, that, in the presence of a dimerization molecule, associates with another switch domain. Switch domains are elements of an RCAR. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequence, and are referred to collectively as a heterodimerization switch. In an embodiment, the switch is intracellular. In embodiments, the switch is extracellular. In embodiments, the switch domain is a polypeptide-based entity, e.g., FKBP-FRB, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Transmembrane domain," as that term is used herein, refers to a polypeptide that spans the plasma membrane. In an embodiment it links an extracellular sequence, e.g., a switch domain, an extracellular recognition element, e.g., an antigen binding domain, an inhibitory counter ligand binding domain, or costimulatory ECD domain, to an intracellular sequence, e.g., to a switch domain or an intracellular signaling domain. A transmembrane domain of particular use in this invention may include at least the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C.

"Unitary CAR," or uCAR, as that term is used herein, refers to a CAR having a receptor, e.g., an antigen binding domain, a transmembrane domain, and an intracellular signaling domain on a single polypeptide.

"Unswitched auxiliary antigen binding member," as the term is used herein, refers to a polypeptide that comprises: an antigen binding domain which binds an antigen other than the antigen bound by another antigen binding domain of the CAR; a transmembrane domain; and an intracellular signaling domain, e.g., a primary intracellular signaling domain. Typically, it does not comprise a switch domain that can form a dimerization switch with a switch domain on another component of the RCAR.

"Unit dosage form" as the term is used herein refers to a dosage for suitable one administration. By way of example a unit dosage form can be a tablet, a capsule, or an amount of therapeutic disposed in a delivery device, e.g., a syringe or intravenous drip bag. In an embodiment a unit dosage form is administered in a single administration. In an embodiment more than one unit dosage form, e.g., two tablets, can be administered simultaneously.

"Xenogeneic" as the term is used herein refers to a graft derived from an animal of a different species.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or a "relapse" as used herein refers to the reappearance of a disease (e.g., cancer) or the signs and symptoms of a disease such as cancer after a period of improvement or responsiveness, e.g., after prior treatment of a therapy, e.g., cancer therapy. For example, the period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Sortases

The sortases are a family of enzymes that, in nature, play a role in the formation of the bacterial cell wall by covalently linking specific surface proteins to a peptidoglycan. The sortase enzyme recognizes a sortase recognition motif in a substrate protein and carries out a transpeptidation reaction. In the first step of the reaction, the sortase cleaves a peptide bond in the sortase recognition motif, forming an acyl intermediate with the cleaved sortase recognition motif. In the second step, the sortase binds to an acceptor protein or precursor cell wall component bearing a sortase acceptor motif and transfers the acyl intermediate to this N-terminus. The end result is formation of a new peptide bond between the C-terminus of the protein and the N-terminus of the acceptor protein or precursor of the cell wall component.

Sortase transpeptidation, also known as "sortase labeling" or "sortagging," can be used for bioconjugation of two proteins.

Sortases have been classified into 4 classes by sequence alignment and phylogenetic analysis of sortases from gram-positive bacterial genomes: Sortase A, Sortase B, Sortase C, and Sortase D (Dramsi, et al., *Res Microbiol.,* 156(3):289-97, 2005). Each class also comprises subfamilies, as follows: Sortase A (Subfamily 1), Sortase B (Subfamily 2), Sortase C (Subfamily 3), Sortase D (Subfamily 4 and Subfamily 5) (Comfort and Clubb, *Infect Immun.,* 72(5): 2710-22, 2004). Spirig et al. recently identified two additional classes by sequence analysis, Sortase E and Sortase F (Spirig et al., *Mol Microbiol.,* 2011). The skilled artisan would readily be able to assign an identified sortase to the correct class and/or subfamily based on its sequence or functional characteristics (e.g., transpeptidation activity).

Methods compositions disclosed herein can use or include a sortase from any bacterial species or strain, e.g., a sortase A, a sortase B, a sortase C, a sortase D, a sortase E, a sortase F, or a sortase from a yet unidentified class of sortase enzymes. All gram-positive bacteria examined to date possess at least one major housekeeping sortase (e.g., sortase A) (Barnett et al., *J Bacteriology* 2004). The methods described herein can be used to evaluate candidate sortases.

The amino acid sequences of many sortases and the nucleotide sequences that encode them are known to those of skill in the art and are disclosed in many of the references cited herein. The amino acid sequence of full-length, wild-type *S. aureus* Sortase A is as follows:

```
                                         SEQ ID NO: 1)
MKKWTNRLMTIAGVVLILVAAYLFAKPHIDNYLHDKDKDEKIEQYDKNVK

EQASKDNKQQAKPQIPKDKSKVAGYIEIPDADIKEPVYPGPATPEQLNRG

VSFAEENESLDDQNISIAGHTFIDRPNYQFTNLKAAKKGSMVYFKVGNET

RKYKMTSIRDVKPTDVEVLDEQKGKDKQLTLITCDDYNEKTGVWEKRKIF

VATEVK
```

The amino acid sequences of *S. aureus* sortase A and sortase B are homologous and share, for example, 22% sequence identity.

Other sortases with transamidase activity can be identified by sequence comparison and analysis. Newly identified sortases are also contemplated in the methods described herein. For example, a transamidase with 10%, 20%, 30%, 40%, or 50% or more sequence identity with an *S. pyogenes, S. aureus, A. neslundii, S. mutans, E. faecalis,* or *B. subtilis* open reading frame encoding a sortase can be used in the methods described herein. Sortases identified and displaying comparable transamidase activity to that of sortase A or sortase B from *S. aureus* can be utilized. As used herein, comparable transamidase activity refers to at least 10%, at least 15%, at least 20%, at least 25%, at least 30%, at least 40%, or at least 50% activity with respect to the activity of *S. aureus* sortase A.

Sortase Recognition Motifs

In the first step of a sortase-mediated transamidation reaction, the sortase recognizes a substrate with a sortase recognition motif. A sortase class may recognize a sortase recognition motif that may be different from another sortase class. Alternatively, a sortase class may recognize the same sortase recognition motif as another sortase class.

A first moiety to be coupled to a second moiety can first be coupled to a sortase recognition motif. A sortase can then be used to couple the first moiety to a second moiety coupled to a sortase acceptor motif.

In an embodiment, a sortase recognition motif has the structure $X_4-X_3-X_2-X_1-|-X_0$, wherein the sortase typically cleaves the bond between $X_1$ and $X_0$ to form an acyl intermediate. Examples of sortase recognition motifs are provided below.

A Sortase A recognition motif can have the following structure:

$$X_4-X_3-X_2-X_1-|-X_0$$

Wherein (SEQ ID NO: 39):
$X_4$=L or I
$X_3$=P or G
$X_2$=X
$X_1$=T or A
$X_0$=X,
and wherein X is any amino acid.

In an embodiment, the motif comprises (SEQ ID NO: 116):
$X_4$=L
$X_3$=P
$X_2$=X
$X_1$=T
$X_0$=X;
wherein X is any amino acid.

In an embodiment, the motif comprises (SEQ ID NO: 41):
$X_4$=L or I
$X_3$=P or G
$X_2$=K, A, N, E, or Q
$X_1$=T or A
$X_0$=A or G In an embodiment, the motif comprises (SEQ ID NO: 42):
$X_4$=L
$X_3$=P
$X_2$=K, A, N, E, or Q
$X_1$=T
$X_0$=X;
wherein X is any amino acid.

In an embodiment, the motif comprises (SEQ ID NO: 43):
$X_4$=L
$X_3$=P
$X_2$=K, A, N, E, or Q
$X_1$=T
$X_0$=G In an embodiment, the motif comprises (SEQ ID NO: 44):
$X_4$=L
$X_3$=P
$X_2$=K
$X_1$=T
$X_0$=G In an embodiment, the motif comprises (SEQ ID NO: 45):
$X_4$=L
$X_3$=P
$X_2$=A
$X_1$=T
$X_0$=G In an embodiment, the motif comprises (SEQ ID NO: 46):
$X_4$=L
$X_3$=P
$X_2$=N
$X_1$=T
$X_0$=G In an embodiment, the motif comprises (SEQ ID NO: 47):
$X_4$=L
$X_3$=P
$X_2$=E
$X_1$=T
$X_0$=G In an embodiment, the motif comprises (SEQ ID NO: 48):
$X_4$=L
$X_3$=P
$X_2$=X
$X_1$=A
$X_0$=G;
wherein X is any amino acid.
In an embodiment, the motif comprises (SEQ ID NO: 49):
$X_4$=L
$X_3$=P
$X_2$=N
$X_1$=A
$X_0$=G
In an embodiment, the motif comprises (SEQ ID NO: 50):
$X_4$=L
$X_3$=P
$X_2$=X
$X_1$=T
$X_0$=A;
wherein X is any amino acid.
In an embodiment, the motif comprises (SEQ ID NO: 51):
$X_4$=L
$X_3$=P
$X_2$=N
$X_1$=T
$X_0$=A
In an embodiment, the motif comprises (SEQ ID NO: 52):
$X_4$=L
$X_3$=G
$X_2$=X
$X_1$=T
$X_0$=G;
wherein X is any amino acid.
In an embodiment, the motif comprises (SEQ ID NO: 53):
$X_4$=L
$X_3$=G
$X_2$=A
$X_1$=T
$X_0$=G
In an embodiment, the motif comprises (SEQ ID NO: 54):
$X_4$=I
$X_3$=P
$X_2$=X
$X_1$=T
$X_0$=G;
wherein X is any amino acid.
In an embodiment, the motif comprises (SEQ ID NO: 55):
$X_4$=I
$X_3$=P
$X_2$=N
$X_1$=T
$X_0$=G
In an embodiment, the motif comprises (SEQ ID NO: 56):
$X_4$=I
$X_3$=P
$X_2$=E
$X_1$=T
$X_0$=G

TABLE 1

Sortase A Recognition Motifs

| Sortase A Recognition Motif Structure | wherein | SEQ ID NO: |
|---|---|---|
| $X_4$-$X_3$-$X_2$-$X_1$-\|-$X_0$ | $X_4$ = L or I; $X_3$ = P or G; $X_2$ = X; $X_1$ = T or A; $X_0$ = X; and X is any amino acid. | 39 |
| | $X_4$ = L; $X_3$ = P; $X_2$ = X; $X_1$ = T; and X is any amino acid. | 40 |
| | $X_4$ = L or I; $X_3$ = P or G; $X_2$ = K, A, N, E, or Q; $X_1$ = T or A; and $X_0$ = A or G. | 41 |
| | $X_4$ = L; $X_3$ = P; $X_2$ = K, A, N, E, or Q; $X_1$ = T; $X_0$ = X; and X is any amino acid. | 42 |
| | $X_4$ = L; $X_3$ = P; $X_2$ = K, A, N, E, or Q; $X_1$ = T; and $X_0$ = G. | 43 |
| | $X_4$ = L; $X_3$ = P; $X_2$ = K; $X_1$ = T; and $X_0$ = G. | 44 |
| | $X_4$ = L; $X_3$ = P; $X_2$ = A; $X_1$ = T; and $X_0$ = G. | 45 |
| | $X_4$ = L; $X_3$ = P; $X_2$ = N; $X_1$ = T; and $X_0$ = G. | 46 |
| | $X_4$ = L; $X_3$ = P; $X_2$ = E; $X_1$ = T; and $X_0$ = G. | 47 |
| | $X_4$ = L; $X_3$ = P; $X_2$ = X; $X_1$ = A; $X_0$ = G; and X is any amino acid. | 48 |
| | $X_4$ = L; $X_3$ = P; $X_2$ = N; $X_1$ = A; and $X_0$ = G. | 49 |
| | $X_4$ = L; $X_3$ = P; $X_2$ = X; $X_1$ = T; $X_0$ = A; and X is any amino acid. | 50 |
| | $X_4$ = L; $X_3$ = P; $X_2$ = N; $X_1$ = T; and $X_0$ = A. | 51 |
| | $X_4$ = L; $X_3$ = G; $X_2$ = X; $X_1$ = T; $X_0$ = G; and X is any amino acid. | 52 |
| | $X_4$ = L; $X_3$ = G; $X_2$ = A; $X_1$ = T; and $X_0$ = G | 53 |
| | $X_4$ = I; $X_3$ = P; $X_2$ = X; $X_1$ = T; $X_0$ = G; and X is any amino acid. | 54 |
| | $X_4$ = I; $X_3$ = P; $X_2$ = N; $X_1$ = T; and $X_0$ = G. | 55 |
| | $X_4$ = I; $X_3$ = P; $X_2$ = E; $X_1$ = T; and $X_0$ = G. | 56 |

A Sortase B recognition motif can have the following structure:

$X_4$-$X_3$-$X_2$-$X_1$-|-$X_0$

Wherein (SEQ ID NO: 57)
$X_4$=N
$X_3$=P, A, or S
$X_2$=X
$X_1$=T or S
$X_0$=X;
and wherein X is any amino acid.
In an embodiment, the motif comprises (SEQ ID NO: 58):
$X_4$=N
$X_3$=P, S or A
$X_2$=Q or K
$X_1$=T or S
$X_0$=A, H, N, G, or S
In an embodiment, the motif comprises (SEQ ID NO: 59):
$X_4$=N
$X_3$=P
$X_2$=X
$X_1$=T
$X_0$=X;
wherein X is any amino acid.

In an embodiment, the motif comprises (SEQ ID NO: 60):
$X_4$=N
$X_3$=P
$X_2$=Q or K
$X_1$=T
$X_0$=H, N, G, or S
In an embodiment, the motif comprises (SEQ ID NO: 61):
$X_4$=N
$X_3$=P
$X_2$=Q
$X_1$=T
$X_0$=N
In an embodiment, the motif comprises (SEQ ID NO: 62):
$X_4$=N
$X_3$=P
$X_2$=K
$X_1$=T
$X_0$=G
In an embodiment, the motif comprises (SEQ ID NO: 63):
$X_4$=N
$X_3$=S
$X_2$=K
$X_1$=T
$X_0$=A
In an embodiment, the motif comprises (SEQ ID NO: 64):
$X_4$=N
$X_3$=P
$X_2$=Q
$X_1$=T
$X_0$=G
In an embodiment, the motif comprises (SEQ ID NO: 65):
$X_4$=N
$X_3$=A
$X_2$=K
$X_1$=T
$X_0$=N
In an embodiment, the motif comprises (SEQ ID NO: 66):
$X_4$=N
$X_3$=P
$X_2$=Q
$X_1$=S
$X_0$=S

TABLE 2

Sortase B Recognition Motifs

| Sortase B Recognition Motif Structure | Wherein | SEQ ID NO: |
|---|---|---|
| $X_4$--$X_3$--$X_2$--$X_1$-\|-$X_0$ | $X_4$ = N; $X_3$ = P, A, or S; $X_2$ = X; $X_1$ = T or S; $X_0$ = X; and X is any amino acid. | 57 |
| | $X_4$ = N; $X_3$ = P, S or A; $X_2$ = Q or K; $X_1$ = T or S; and $X_0$ = A, H, N, G, or S. | 58 |
| | $X_4$ = N; $X_3$ = P; $X_2$ = X; $X_1$ = T; $X_0$ = X, and X is any amino acid. | 59 |
| | $X_4$ = N; $X_3$ = P; $X_2$ = Q or K; $X_1$ = T; and $X_0$ = H, N, G, or S. | 60 |
| | $X_4$ = N; $X_3$ = P; $X_2$ = Q; $X_1$ = T; and $X_0$ = N. | 61 |
| | $X_4$ = N; $X_3$ = P; $X_2$ = K; $X_1$ = T; and $X_0$ = G. | 62 |
| | $X_4$ = N; $X_3$ = S; $X_2$ = K; $X_1$ = T; and $X_0$ = A. | 63 |
| | $X_4$ = N; $X_3$ = P; $X_2$ = Q; $X_1$ = T; and $X_0$ = G. | 64 |
| | $X_4$ = N; $X_3$ = A; $X_2$ = K; $X_1$ = T; and $X_0$ = N. | 65 |
| | $X_4$ = N; $X_3$ = P; $X_2$ = Q; $X_1$ = S; and $X_0$ = S. | 66 |

A Sortase C recognition motif can have the following structure:

$$X_4\text{-}X_3\text{-}X_2\text{-}X_1\text{-}|\text{-}X_0$$

Wherein (SEQ ID NO: 67)
$X_4$=L
$X_3$=P
$X_2$=X
$X_1$=T
$X_0$=X;
and wherein X is any amino acid.
In an embodiment, the motif comprises (SEQ ID NO: 68):
$X_4$=L
$X_3$=P
$X_2$=K, S, E, L, A or N,
$X_1$=T
$X_0$=G.

TABLE 3

Sortase C Recognition Motifs

| Sortase C Recognition Motif Structure | Wherein | SEQ ID NO: |
|---|---|---|
| $X_4$--$X_3$--$X_2$--$X_1$-\|-$X_0$ | $X_4$ = L; $X_3$ = P; $X_2$ = X; $X_1$ = T; $X_0$ = X; and X is any amino acid. | 67 |
| | $X_4$ = L; $X_3$ = P; $X_2$ = K, S, E, L, A or N; $X_1$ = T; and $X_0$ = G. | 68 |

A Sortase D recognition motif can have the following structure:

$$X_4\text{-}X_3\text{-}X_2\text{-}X_1\text{-}|\text{-}X_0$$

Wherein (SEQ ID NO: 69)
$X_4$=L or N
$X_3$=P or A
$X_2$=X
$X_1$=T
$X_0$=G or A;
and wherein X is any amino acid.
In an embodiment, the motif comprises (SEQ ID NO: 70):
$X_4$=N
$X_3$=A
$X_2$=E, A, S, or H
$X_1$=T
$X_0$=G
In an embodiment, the motif comprises (SEQ ID NO: 71):
$X_4$=L
$X_3$=P
$X_2$=X
$X_1$=T
$X_0$=A;
wherein X is any amino acid.
In an embodiment, the motif comprises (SEQ ID NO: 72):
$X_4$=L
$X_3$=P
$X_2$=N $X_1$=T
$X_0$=A
In an embodiment, the motif comprises (SEQ ID NO: 73):
$X_4$=L
$X_3$=A
$X_2$=X
$X_1$=T
$X_0$=G;
wherein X is any amino acid.

TABLE 4

Sortase D Recognition Motifs

| Sortase D Recognition Motif Structure | Wherein | SEQ ID NO: |
|---|---|---|
| $X_4$--$X_3$--$X_2$--$X_1$-│-$X_0$ | $X_4$ = L or N; $X_3$ = P or A; $X_2$ = X; $X_1$ = T; $X_0$ = G or A; and X is any amino acid. | 69 |
| | $X_4$ = N; $X_3$ = A; $X_2$ = E, A, S, or H; $X_1$ = T; and $X_0$ = G. | 70 |
| | $X_4$ = L; $X_3$ = P; $X_2$ = X; $X_1$ = T; $X_0$ = A; and X is any amino acid. | 71 |
| | $X_4$ = L; $X_3$ = P; $X_2$ = N; $X_1$ = T; and $X_0$ = A. | 72 |
| | $X_4$ = L; $X_3$ = A; $X_2$ = X; $X_1$ = T; $X_0$ = G; and X is any amino acid. | 73 |

TABLE 5

Other Sortase Recognition Motifs

| Other Sortase Recognition Motif Structure | Wherein | SEQ ID NO: |
|---|---|---|
| $X_4$--$X_3$--$X_2$--$X_1$-│-$X_0$ | $X_4$ = L; $X_3$ = P; $X_2$ = X; $X_1$ = T; $X_0$ = X; and X is any amino acid. | 74 |
| | $X_4$ = L; $X_3$ = P; $X_2$ = K; $X_1$ = T; and $X_0$ = G. | 75 |
| | $X_4$ = L; $X_3$ = P; $X_2$ = I; $X_1$ = T; and $X_0$ = G. | 76 |
| | $X_4$ = L; $X_3$ = P; $X_2$ = D; $X_1$ = T; and $X_0$ = A. | 77 |
| | $X_4$ = L; $X_3$ = P; $X_2$ = L; $X_1$ = T; and $X_0$ = G. | 78 |
| | $X_4$ = L; $X_3$ = P; $X_2$ = E; $X_1$ = T; and $X_0$ = G. | 79 |
| | $X_4$ = L; $X_3$ = P; $X_2$ = M; $X_1$ = T; and $X_0$ = G. | 80 |
| | $X_4$ = L; $X_3$ = P; $X_2$ = Q; $X_1$ = T; and $X_0$ = S. | 81 |
| | $X_4$ = L; $X_3$ = A; $X_2$ = X; $X_1$ = T; $X_0$ = X; and X is any amino acid. | 82 |
| | $X_4$ = L; $X_3$ = A; $X_2$ = E; $X_1$ = T; and $X_0$ = G. | 83 |
| | $X_4$ = L; $X_3$ = A; $X_2$ = A; $X_1$ = T; and $X_0$ = G. | 84 |
| | $X_4$ = L; $X_3$ = A; $X_2$ = H; $X_1$ = T; and $X_0$ = G. | 85 |
| | $X_4$ = L; $X_3$ = A; $X_2$ = S; $X_1$ = T; and $X_0$ = G. | 86 |
| | $X_4$ = L; $X_3$ = A; $X_2$ = F; $X_1$ = T; and $X_0$ = G. | 87 |
| | $X_4$ = L; $X_3$ = P; $X_2$ = X; $X_1$ = A; $X_0$ = X; and X is any amino acid. | 88 |
| | $X_4$ = L; $X_3$ = A; $X_2$ = X; $X_1$ = T; $X_0$ = X; and X is any amino acid. | 89 |
| | $X_4$ = L; $X_3$ = G; $X_2$ = X; $X_1$ = T; $X_0$ = X; and X is any amino acid. | 90 |
| | $X_4$ = I; $X_3$ = P; $X_2$ = X; $X_1$ = T; $X_0$ = X; and X is any amino acid. | 91 |
| | $X_4$ = I; $X_3$ = P; $X_2$ = Q; $X_1$ = T; and $X_0$ = G. | 92 |

TABLE 5-continued

Other Sortase Recognition Motifs

| Other Sortase Recognition Motif Structure | Wherein | SEQ ID NO: |
|---|---|---|
| | $X_4$ = N; $X_3$ = P; $X_2$ = X; $X_1$ = T; $X_0$ = X; and X is any amino acid. | 93 |
| | $X_4$ = L; $X_3$ = P; $X_2$ = S; $X_1$ = T; $X_0$ = X; and X is any amino acid. | 94 |
| | $X_4$ = L; $X_3$ = P; $X_2$ = I; $X_1$ = T; $X_0$ = X; and X is any amino acid. | 95 |
| | $X_4$ = L; $X_3$ = A; $X_2$ = E; $X_1$ = T; $X_0$ = X; and X is any amino acid. | 96 |
| | $X_4$ = N; $X_3$ = P; $X_2$ = Q; $X_1$ = S; $X_0$ = X; and X is any amino acid. | 97 |
| | $X_4$ = N; $X_3$ = S; $X_2$ = K; $X_1$ = T; $X_0$ = X; and X is any amino acid. | 98 |
| | $X_4$ = N; $X_3$ = P; $X_2$ = Q; $X_1$ = T; $X_0$ = X; and X is any amino acid. | 99 |
| | $X_4$ = N; $X_3$ = A; $X_2$ = K; $X_1$ = T; $X_0$ = X; and X is any amino acid. | 100 |
| | $X_4$ = N; $X_3$ = P; $X_2$ = Q; $X_1$ = S; $X_0$ = X; and X is any amino acid. | 101 |
| | $X_4$ = L; $X_3$ = S; $X_2$ = R; $X_1$ = T; and $X_0$ = G. | 102 |
| | $X_4$ = S; $X_3$ = P; $X_2$ = K; $X_1$ = T; and $X_0$ = G. | 103 |
| | $X_4$ = L; $X_3$ = S; $X_2$ = R; $X_1$ = T; and $X_0$ = G. | 104 |
| | $X_4$ = V; $X_3$ = P; $X_2$ = D; $X_1$ = T; and $X_0$ = G. | 105 |
| | $X_4$ = Y; $X_3$ = P; $X_2$ = R; $X_1$ = R; and $X_0$ = G. | 106 |
| | $X_4$ = Q; $X_3$ = V; $X_2$ = P; $X_1$ = T; and $X_0$ = G. | 107 |

Table 6 below provides a general sortase recognition motif.

TABLE 6

General Sortase Recognition Motif

| Other Sortase Recognition Motif Structure | Wherein | SEQ ID NO: |
|---|---|---|
| $X_4$--$X_3$--$X_2$--$X_1$-│-$X_0$ | $X_4$ = L, N, I, Y, Q, V, or S; $X_3$ = P, G, A, S, or V; $X_2$ = $X_a$; $X_1$ = T, A, S, or R; $X_0$ = $X_b$; and wherein $X_a$ and $X_b$ can be any amino acid. In some embodiments, Xa and Xb are different amino acids. In some embodiments, $X_a$ and $X_b$ are the same amino acid. | 108 |

Sortase Mutants

Mutant sortase molecules can be used to form CAR members, e.g., in situ on immune effector cells that comprise a sortase acceptor motif. An exemplary sortase mutant, which is efficient, and not dependent on non-physiological reaction conditions, is *S. aureus* Sortase A mutant [P94R/E105K/E108Q/D160N/D165A/K190E/K196T]. It lacks the N-terminal 59 amino acids of *S. aureus* sortase A and includes mutations that render the enzyme calcium independent and which make the enzyme faster. (The number of residues herein begin with residue the first residue at the N terminal end of non-truncated *S. aureus* Sortase A.). The primary amino acid sequence is provided below. Mutations are in bold. The underlined residue is E in this embodiment but can be any amino acid, e.g., a conservative substitution.

The primary amino acid sequence of Sortase A mutant [P94R/E105K/E108Q/D160N/D165A/K190E/K196T] is as follows:

```
                                              (SEQ ID NO: 4)
MQAKPQIPKD KSKVAGYIEI PDADIKEPVY PGPATREQLN

RGVSFAKENQ SLDDQNISIA GHTFIDRPNY QFTNLKAAKK

GSMVYFKVGN ETRKYKMTSI RNVKPTAVEV LDEQKGKDKQ

LTLITCDDYN EETGVWETRK IFVATEVKLE HHHHHH
```

CARs

A chimeric antigen receptor, or CAR, typically includes an extracellular domain, e.g., an antigen binding domain, a transmembrane domain, and one or more intracellular signaling domains, typically a costimulatory signaling domain and a primary stimulatory signaling domain. In an embodiment, engagement of the extracellular domain, e.g., antigen binding domain, with an antigen on a target cell results in activation of the immune effector cell in which the CAR is disposed, typically a T cell or an NK cell. Activation allows for CAR cell mediated attack on the cell that is engaged.

uCARs

In some embodiments an antigen binding domain, a transmembrane domain, and one or more intracellular signaling domains, typically a costimulatory signaling domain and a primary stimulatory signaling domain is disposed on a single polypeptide. Such embodiments are referred to herein as unitary CARs, or uCARS. In an embodiment a uCAR comprises a sortase transfer signature.

RCARs

A CAR molecule can be partitioned such that the "binding domain" and a "signaling domain" are each linked to two separate "switch domains." In such embodiments, activation of signaling through the CAR only occurs when the switch domains, and hence the binding domain and the signaling domain, are brought together by a dimerization molecule, i.e. to switch "on" signaling through the CAR. Such CARs are referred to as regulatable CARs or RCARs. The use of a dimerization switch that turns "on" the activation of a signal to allow external, e.g., temporal, control over the immune effector response mediated by a cell containing a RCAR. As discussed in more detail below, in embodiments, the RCAR includes a dimerization switch that, upon the presence of a dimerization molecule, can couple an intracellular signaling domain to an extracellular recognition element, e.g., an antigen binding domain, an inhibitory counter ligand binding domain, or costimulatory ECD domain. Sortase molecules can be used to attach elements of an RCAR member, e.g., to attach an extracellular domain to a transmembrane containing RCAR member. In an embodiment a RCAR member comprises a sortase transfer signature, e.g., disposed between an extracellular domain and a transmembrane domain.

iCARs

An inhibitory CAR (iCAR) is a CAR that recognizes an antigen on a non-target cell and produces an inhibitory signal, minimizing the activation of the cell. The extracellular domain of an iCAR can be added by sortase mediated transfer. In an embodiment the iCAR comprises a sortase transfer signature, e.g., disposed between an extracellular domain and a transmembrane domain.

Antigen Binding Domain

The CARs described herein, e.g., RCARs or uCARs, typically include an antigen binding domain in the extracellular region. In an embodiment, the antigen binding domain can be attached other elements of a CAR member by sortase molecule mediated transfer.

The choice of an antigen binding domain can depend upon the type and number of ligands or receptors that define the surface of a target cell. For example, the antigen binding domain may be chosen to recognize an antigen that acts as a cell surface marker on target cells associated with a particular disease state. Examples of cell surface markers that may act as ligands or receptors include a cell surface marker associated with a particular disease state, e.g., cell surface makers for viral diseases, bacterial diseases parasitic infections, autoimmune diseases and disorders associated with unwanted cell proliferation, e.g., a cancer, e.g., a cancer described herein.

In the context of the present disclosure, "tumor antigen" or "proliferative disorder antigen" or "antigen associated with a proliferative disorder" refers to antigens that are common to specific proliferative disorders. In certain aspects, the proliferative disorder antigens of the present invention are derived from, cancers including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer and adenocarcinomas such as breast cancer, prostate cancer, ovarian cancer, pancreatic cancer, colon cancer and the like. In some embodiments, the cancer is B-cell acute lymphoid leukemia ("BALL"), T-cell acute lymphoid leukemia ("TALL"), acute lymphoid leukemia (ALL), acute myelogenous leukemia (AML); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia. Other related conditions include myelodysplastic syndromes (MDS, formerly known as "preleukemia") which are a diverse collection of hematological conditions united by ineffective production (or dysplasia) of myeloid blood cells and risk of transformation to AML.

In one embodiment, the tumor antigen comprises one or more antigenic cancer epitopes immunologically recognized by tumor infiltrating lymphocytes (TIL) derived from a cancer tumor of a mammal.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), EGFRvIII, IL-11Ra, IL-13Ra, EGFR, FAP, B7H3, Kit, CA-IX, CS-1, MUC1, BCMA, bcr-abl, HER2, β-human chorionic gonadotropin, alphafetoprotein (AFP), ALK, CD19, CD123, cyclin B1, lectin-reactive AFP, Fos-related antigen 1, ADRB3, thyroglobulin, EphA2, RAGE-1, RU1, RU2, SSX2, AKAP-4, LCK, OY-TES1, PAX5, SART3, CLL-1, fucosyl GM1, GloboH, MN-CA IX, EPCAM, EVT6-AML, TGS5, human telomerase reverse transcriptase, plysialic acid, PLAC1, RU1, RU2 (AS), intestinal carboxyl esterase, lewisY, sLe, LY6K, mut hsp70-2, M-CSF, MYCN, RhoC, TRP-2, CYP1B1, BORIS, prostase, prostate-specific antigen (PSA), PAX3, PAP, NY-ESO-1, LAGE-1a, LMP2, NCAM, p53, p53 mutant, Ras mutant, gp100, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART1, XAGE1, ELF2M, ERG (TMPRSS2 ETS fusion gene), NA17, neutrophil elastase, sarcoma translocation breakpoints, NY-BR-1, ephrinB2, CD20, CD22, CD24, CD30, CD33, CD38, CD44v6, CD97, CD171, CD179a, androgen receptor, FAP, insulin growth factor (IGF)-I, IGF-II, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUC1, HER2, and any combination thereof.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target antigens include transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

Non-limiting examples of tumor antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Depending on the desired antigen to be targeted, the RCAR of the invention can be engineered to include the appropriate antigen bind domain that is specific to the desired antigen target.

A CAR as described herein includes a CAR comprising an antigen binding domain (e.g., antibody or antibody fragment) that binds to a MHC presented-peptide. Normally, peptides derived from endogenous proteins fill the pockets of Major Histocompatability Complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Bood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library. Accordingly, the present invention provides a CAR, e.g., a RCAR described herein, that comprises an antigen binding domain that binds to a MHC presented peptide of a molecule selected from any tumor antigen described above that is expressed intracellularly, e.g., p53, BCR-Abl, Ras, K-ras, and c-met.

Antigen Binding Domains Derived from an Antibody Molecule

The antigen binding domain can be derived from an antibody molecule, e.g., one or more of monoclonal antibodies, polyclonal antibodies, recombinant antibodies, human antibodies, humanized antibodies, single-domain antibodies e.g., a heavy chain variable domain (VH), a light chain variable domain (VL) and a variable domain (VHH) from, e.g., human or camelid origin. In some instances, it is beneficial for the antigen binding domain to be derived from the same species in which the RCAR will ultimately be used in, e.g., for use in humans, it may be beneficial for the antigen binding domain of the CAR, e.g., the RCAR, e.g., described herein, to comprise a human or a humanized antigen binding domain. Antibodies can be obtained using known techniques known in the art.

The term "antibody," as used herein, refers to an immunoglobulin molecule which specifically binds with a target antigen. An antibody can be intact immunoglobulin derived from natural sources or from recombinant sources and can be an immunoreactive portion of intact immunoglobulin. Antibodies are typically tetramers of immunoglobulin molecules. The antibody molecule described herein may exist in a variety of forms where the antigen binding portion of the antibody is expressed as part of a contiguous polypeptide chain including, for example, a single domain antibody fragment (sdAb), a single chain antibody (scFv) and a humanized or human antibody, e.g., as described herein.

The term "antibody fragment" refers to a portion of an intact antibody and refers to the antigenic determining variable regions of an intact antibody. Examples of antibody fragments include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific molecules formed from antibody fragments such as a bivalent fragment comprising two or more, e.g., two Fab fragments linked by a disulfide bridge at the hinge region, or two or more, e.g., two isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody molecule which is generated using recombinant DNA technology, such as, for example, an antibody molecule expressed by a bacteriophage as described herein. The term should also be construed to mean an antibody molecule which has been generated by the synthesis of a DNA molecule encoding the antibody molecule and which DNA molecule expresses an antibody protein, or an amino acid sequence specifying the antibody, wherein the DNA or amino acid sequence has been obtained using synthetic DNA or amino acid sequence technology which is available and well known in the art.

In embodiments, the antigen binding domain comprises a fragment of an antibody that is sufficient to confer recognition and specific binding to the target antigen. Examples of an antibody fragment include, but are not limited to, an Fab, Fab', F(ab')$_2$, or Fv fragment, an scFv antibody fragment, a linear antibody, single domain antibody such as an sdAb (either VL or VH), a camelid VHH domain, and multi-specific antibodies formed from antibody fragments.

In an embodiment, the antigen binding domain is a "scFv," which can comprise a fusion protein comprising a VL chain and a VH chain of an antibody, where the VH and VL are, e.g., linked via a short flexible polypeptide linker, e.g., a linker described herein. The scFv is capable of being expressed as a single chain polypeptide and retains the specificity of the intact antibody from which it is derived. Moreover, the VL and VH variable chains can be linked in either order, e.g., with respect to the N-terminal and C-terminal ends of the polypeptide, the scFv may comprise VL-linker-VH or may comprise VH-linker-VL. An scFv can be prepared, e.g., according to methods known in the art (see, for example, Bird et al., (1988) Science 242:423-426 and Huston et al., (1988) Proc. Natl. Acad. Sci. USA 85:5879-5883).

As described above and elsewhere, scFv molecules can be produced by linking VH and VL chains together using flexible polypeptide linkers. In some embodiments, the scFv molecules comprise flexible polypeptide linker with an optimized length and/or amino acid composition. The flexible polypeptide linker length can greatly affect how the variable regions of a scFv fold and interact. In fact, if a short polypeptide linker is employed (e.g., between 5-10 amino acids, intrachain folding is prevented. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference. In one embodiment, the peptide linker of the scFv consists of amino acids such as glycine and/or serine residues used alone or in combination, to link variable heavy and variable light chain regions together. In one embodiment, the flexible polypeptide linker is a Gly/Ser linker and, e.g., comprises the amino acid sequence (Gly-Gly-Gly-Ser)n, where n is a positive integer equal to or greater than 1. For example, n=1, n=2, n=3, n=4, n=5 and n=6, n=7, n=8, n=9 and n=10 (SEQ ID NO: 35). In one embodiment, the flexible polypeptide linkers include, but are not limited to, (Gly$_4$ Ser)$_4$ (SEQ ID NO: 36) or (Gly4 Ser)$_3$ (SEQ ID NO: 37). In another embodiment, the linkers include multiple repeats of (Gly$_2$Ser), (GlySer) or (Gly$_3$Ser) (SEQ ID NO: 38).

In some embodiments, the antigen binding domain is a single domain antigen binding (SDAB) molecules. A SDAB molecule includes molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies (e.g., described in more detail below). SDAB molecules may be any of the art, or any future single domain molecules. SDAB molecules may be derived from any species including, but not limited to mouse, human, camel, llama, fish, shark, goat, rabbit, and bovine. This term also includes naturally occurring single domain antibody molecules from species other than *Camelidae* and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

According to another aspect, an SDAB molecule is a naturally occurring single domain antigen binding molecule known as a heavy chain devoid of light chains. Such single domain molecules are disclosed in WO 9404678 and Hamers-Casterman, C. et al. (1993) *Nature* 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from *Camelidae* species, for example in camel, llama, dromedary, alpaca and guanaco. Other species besides *Camelidae* may produce heavy chain molecules naturally devoid of light chain; such VHHs are within the scope of the invention.

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans et al., (2004) J Biol Chem 279:1256-1261; Dumoulin et al., (2003) Nature 424:783-788; Pleschberger et al., (2003) Bioconjugate Chem 14:440-448; Cortez-Retamozo et al., (2002) Int J Cancer 89:456-62; and Lauwereys et al., (1998) EMBO J 17:3512-3520. Engineered libraries of camelid antibodies and antibody fragments are commercially available, for example, from Ablynx, Ghent, Belgium (e.g., US20060115470; Domantis (US20070065440, US20090148434). As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

An antigen binding domain can comprise a camelid antibody or nanobody, or an antigen binding fragment thereof. Such antibodies can have high affinity for its cognate antigen. In certain embodiments herein, the camelid antibody or nanobody is naturally produced in the camelid animal, i.e., is produced by the camelid following immunization with antigen or a peptide fragment thereof. Alternatively, the camelid nanobody is engineered, i.e., produced by selection for example from a library of phage displaying appropriately mutagenized camelid nanobody proteins using panning procedures with the target antigen. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

In certain embodiments, the SDAB molecule is a single chain fusion polypeptide comprising one or more single domain molecules (e.g., nanobodies), devoid of a complementary variable domain or an immunoglobulin constant, e.g., Fc, region, that binds to one or more target antigens.

The SDAB molecules can be recombinant, CDR-grafted, humanized, camelized, de-immunized and/or in vitro generated (e.g., selected by phage display).

In one embodiment, the antigen biding domain portion comprises a human antibody or a fragment thereof.

In some embodiments, a non-human antibody is humanized, where specific sequences or regions of the antibody are modified to increase similarity to an antibody naturally produced in a human. In an embodiment, the antigen binding domain is humanized.

Non human antibodies can be humanized using a variety of techniques known in the art, e.g., CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., 2002, J. Immunol., 169:1119-25; Caldas et al., 2000, Protein Eng., 13(5):353-60; Morea et al., 2000, Methods, 20:267-79; Baca et al., 1997, J. Biol. Chem., 272:10678-84; Roguska et al., 1996, Protein Eng., 9(10):895-904; Couto et al., 1995, Cancer Res., 55:5973s-5977; Couto et al., 1995, Cancer Res., 55(8):1717-22; Sandhu 1994 Gene, 150(2):409-10; and Pedersen et al., 1994, J. Mol. Biol., 235(3):959-73, each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332: 323, which are incorporated herein by reference in their entireties.). In preferred embodiments, the humanized antibody molecule comprises a sequence described herein, e.g., a variable light chain and/or a variable heavy chain described herein, e.g., a humanized variable light chain and/or variable heavy chain described in Table 7.

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some embodiments, the antibody of the invention is further prepared using an antibody having one or more of the VH and/or VL sequences disclosed herein can be used as starting material to engineer a modified antibody, which modified antibody may have altered properties as compared to the starting antibody. In various embodiments, the antibody is engineered by modifying one or more amino acids within one or both variable regions (i.e., VH and/or VL), for example within one or more CDR regions and/or within one or more framework regions.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellular, however, a fragment of such antigen (peptide) is presented on the surface of the cancer cells by MHC.

An antigen binding domain can comprise a sequence from Table 7.

TABLE 7

Exemplary Antigen Binding Domains

| Target Antigen | Name | Amino Acid Sequence | SEQ ID NO: |
|---|---|---|---|
| CD19 | huscFv1 | EIVMTQSPATLSLSPGERATLSCRASQDISKYLNWYQQK PGQAPRLLIYHTSRLHSGIPARFSGSGSGTDYTLTISSL QPEDFAVYFCQQGNTLPYTFGQGTKLEIKGGGGSGGGGS GGGGSQVQLQESGPGLVKPSETLSLTCTVSGVSLPDYGV SWIRQPPGKGLEWIGVIWGSETTYYSSSLKSRVTISKDN SKNQVSLKLSSVTAADTAVYYCAKHYYYGGSYAMDYWGQ GTLVTVSS | 117 |
| CD19 | huscFv2 | Eivmtqspatlslspgeratlscrasqdiskylnwyqqkpgqaprl liyhtsrlhsgiparfsgsgsgtdytltisslqpedfavyfcqqgn tlpytfgqgtkleikggggsggggsggggsqvqlqesgpglvkpse tlsltctvsgvslpdygvswirqppgkglewigviwgsettyyqss lksrvtiskdnsknqvslklssvtaadtavyycakhyyyggsyamd ywgqgtlvtvss | 118 |
| CD19 | huscFv3 | Qvqlqesgpglvkpsetlsltctvsgvslpdygvswirqppgkgle wigviwgsettyyssslksrvtiskdnsknqvslklssvtaadtav yycakhyyyggsyamdywgqgtlvtvssggggsggggsggggseiv mtqspatlslspgeratlscrasqdiskylnwyqqkpgqaprlliy htsrlhsgiparfsgsgsgtdytltisslqpedfavyfcqqgntlp ytfgqgtkleik | 119 |
| CD19 | huscFv4 | Qvqlqesgpglvkpsetlsltctvsgvslpdygvswirqppgkgle wigviwgsettyyqsslksrvtiskdnsknqvslklssvtaadtav yycakhyyyggsyamdywgqgtlvtvssggggsggggsggggseiv mtqspatlslspgeratlscrasqdiskylnwyqqkpgqaprlliy htsrlhsgiparfsgsgsgtdytltisslqpedfavyfcqqgntlp ytfgqgtkleik | 120 |
| CD19 | huscFv5 | Eivmtqspatlslspgeratlscrasqdiskylnwyqqkpgqaprl liyhtsrlhsgiparfsgsgsgtdytltisslqpedfavyfcqqgn tlpytfgqgtkleikggggsggggsggggsggggsqvqlqesgpgl vkpsetlsltctvsgvslpdygvswirqppgkglewigviwgsett yyssslksrvtiskdnsknqvslklssvtaadtavyycakhyyygg syamdywgqgtlvtvss | 121 |
| CD19 | huscFv6 | Eivmtqspatlslspgeratlscrasqdiskylnwyqqkpgqaprl liyhtsrlhsgiparfsgsgsgtdytltisslqpedfavyfcqqgn tlpytfgqgtkleikggggsggggsggggsggggsqvqlqesgpgl vkpsetlsltctvsgvslpdygvswirqppgkglewigviwgsett yyqsslksrvtiskdnsknqvslklssvtaadtavyycakhyyygg syamdywgqgtlvtvss | 122 |

TABLE 7-continued

Exemplary Antigen Binding Domains

| Target Antigen | Name | Amino Acid Sequence | SEQ ID NO: |
|---|---|---|---|
| CD19 | huscFv7 | Qvqlqesgpglvkpsetlsltctvsgvslpdygvswirqppgkgle wigviwgsettyyssslksrvtiskdnsknqvslklssvtaadtav yycakhyyyggsyamdywgqgtlvtvssggggsggggsggggsggg gseivmtqspatlslspgeratlscrasqdiskylnwyqqkpgqap rlliyhtsrlhsgiparfsgsgsgtdytltisslqpedfavyfcqq gntlpytfgqgtkleik | 123 |
| CD19 | huscFv8 | Qvqlqesgpglvkpsetlsltctvsgvslpdygvswirqppgkgle wigviwgsettyyqsslksrvtiskdnsknqvslklssvtaadtav yycakhyyyggsyamdywgqgtlvtvssggggsggggsggggsggg gseivmtqspatlslspgeratlscrasqdiskylnwyqqkpgqap rlliyhtsrlhsgiparfsgsgsgtdytltisslqpedfavyfcqq gntlpytfgqgtkleik | 124 |
| CD19 | huscFv9 | Eivmtqspatlslspgeratlscrasqdiskylnwyqqkpgqaprl liyhtsrlhsgiparfsgsgsgtdytltisslqpedfavyfcqqgn tlpytfgqgtkleikggggsggggsggggsggggsqvqlqesgpgl vkpsetlsltctvsgvslpdygvswirqppgkglewigviwgsett yynsslksrvtiskdnsknqvslklssvtaadtavyycakhyyygg syamdywgqgtlvtvss | 125 |
| CD19 | HuscFv10 | Qvqlqesgpglvkpsetlsltctvsgvslpdygvswirqppgkgle wigviwgsettyynsslksrvtiskdnsknqvslklssvtaadtav yycakhyyyggsyamdywgqgtlvtvssggggsggggsggggsggg gseivmtqspatlslspgeratlscrasqdiskylnwyqqkpgqap rlliyhtsrlhsgiparfsgsgsgtdytltisslqpedfavyfcqq gntlpytfgqgtkleik | 126 |
| CD19 | HuscFv11 | Eivmtqspatlslspgeratlscrasqdiskylnwyqqkpgqaprl liyhtsrlhsgiparfsgsgsgtdytltisslqpedfavyfcqqgn tlpytfgqgtkleikggggsggggsggggsggggsqvqlqesgpglvkpse tlsltctvsgvslpdygvswirqppgkglewigviwgsettyynss lksrvtiskdnsknqvslklssvtaadtavyycakhyyyggsyamd ywgqgtlvtvss | 127 |
| CD19 | HuscFv12 | Qvqlqesgpglvkpsetlsltctvsgvslpdygvswirqppgkgle wigviwgsettyynsslksrvtiskdnsknqvslklssvtaadtav yycakhyyyggsyamdywgqgtlvtvssggggsggggsggggseiv mtqspatlslspgeratlscrasqdiskylnwyqqkpgqaprlliy htsrlhsgiparfsgsgsgtdytltisslqpedfavyfcqqgntlp ytfgqgtkleik | 128 |
| CD19 | muCTL019 | Diqmtqttsslsaslgdrvtiscrasqdiskylnwyqqkpdgtvkl liyhtsrlhsgvpsrfsgsgsgtdysltisnleqediatyfcqqgn tlpytfgggtkleitggggsggggsggggsevklqesgpglvapsq slsvtctvsgvslpdygvswirqpprkglewlgviwgsettyynsa lksrltiikdnsksqvflkmnslqtddtaiyycakhyyyggsyamd ywgqgtsvtvss | 129 |
| CD123 | Mu1172 | DIVLTQSPASLAVSLGQRATISC<u>RASESVDNYGNTFMH</u>WYQQ KPGQPPKLLIY<u>RASNLES</u>GIPARFSGSGSRTDFTLTINPVEADD VATYYC<u>QQSNEDPPT</u>FGAGTKLELKGGGGSGGGGSSGGGSQI QLVQSGPELKKPGETVKISCKASGYIFT<u>NYGMN</u>WVKQAPGKS FKWMG<u>WINTYTGESTYSADFKG</u>RFAFSLETSASTAYLHINDL KNEDTATYFCARS<u>GGYDPMDY</u>WGQGTSVTVSS | 130 |
| CD123 | Mu1176 | DVQITQSPSYLAASPGETITINC<u>RASKSISKDLA</u>WYQEKPGKTN KLLIY<u>SGSTLQS</u>GIPSRFSGSGSGTDFTLTISSLEPEDFAMYYC<u>Q QHNKYPYT</u>FGGGTKLEIKGGGGSGGGGSSGGGSQVQLQQPG AELVRPGASVKLSCKASGYTFT<u>SYWMN</u>WVKQRPDQGLEWIG <u>RIDPYDSETHYNQKFKD</u>KAILTVDKSSSTAYMQLSSLTSEDSA VYYCAR<u>GNWDD</u>YWGQGTTLTVSS | 131 |
| CD123 | huscFv1 | Divltqspdslavslgeratincrasesvdnygntfmhwyqqkpgqppklliyrasnlesgvpd rfsgsgsrtdftltisslqaedvavyycqqsnedpptfgqgtkleikggggsggggsggggsggg gsqiqlvqsgselkkpgasvkvsckasgyiftnygmnwvrqapgqglewmgwintytgest ysadfkgrfvfsldtsvstaylqinalkaedtavyycarsggydpmdywgqgtvtvss | 132 |
| CD123 | huscFv2 | Divltqspdslavslgeratincrasesvdnygntfmhwyqqkpgqppklliyrasnlesgvpd rfsgsgsrtdftltisslqaedvavyycqqsnedpptfgqgtkleikggggsggggsggggsggg gsqiqlvqsgaevkkpgasvkvsckasgyiftnygmnwvrqapgqrlewmgwintytgest ysadfkgrvtitldtsastaymelsslrsedtavyycarsggydpmdywgqgtvtvss | 133 |

TABLE 7-continued

Exemplary Antigen Binding Domains

| Target Antigen | Name | Amino Acid Sequence | SEQ ID NO: |
|---|---|---|---|
| CD123 | huscFv3 | Eivltqspatlslspgeratlscrasesvdnygntfmhwyqqkpgqaprlliyrasnlesgiparf sgsgsrtdftltisslepedvavyycqqsnedpptfgqgtkleikggggsggggsggggsgggg sqiqlvqsgselkkpgasvkvsckasgyiftnygmnwvrqapgqglewmgwintytgesty sadfkgrfvfsldtsvstaylqinalkaedtavyycarsggydpmdywgqgttvtvss | 134 |
| CD123 | huscFv4 | Eivltqspatlslspgeratlscrasesvdnygntfmhwyqqkpgqaprlliyrasnlesgiparf sgsgsrtdftltisslepedvavyycqqsnedpptfgqgtkleikggggsggggsggggsgggg sqiqlvqsgaevkkpgasvkvsckasgyiftnygmnwvrqapgqrlewmgwintytgesty sadfkgrvtitldtsastaymelsslrsedtavyycarsggydpmdywgqgttvtvss | 135 |
| CD123 | huscFv5 | Qiqlvqsgselkkpgasvkvsckasgyiftnygmnwvrqapgqglewmgwintytgesty sadfkgrfvfsldtsvstaylqinalkaedtavyycarsggydpmdywgqgttvtvssggggsg gggsggggsggggsdivltqspdslavslgeratincrasesvdnygntfmhwyqqkpgqpp klliyrasnlesgvpdrfsgsgsrtdftltisslqaedvavyycqqsnedpptfgqgtkleik | 136 |
| CD123 | huscFv6 | Qiqlvqsgselkkpgasvkvsckasgyiftnygmnwvrqapgqglewmgwintytgesty sadfkgrfvfsldtsvstaylqinalkaedtavyycarsggydpmdywgqgttvtvssggggsg gggsggggsggggseivltqspatlslspgeratlscrasesvdnygntfmhwyqqkpgqaprl liyrasnlesgiparfsgsgsrtdftltisslepedvavyycqqsnedpptfgqgtkleik | 137 |
| CD123 | huscFv7 | Qiqlvqsgaevkkpgasvkvsckasgyiftnygmnwvrqapgqrlewmgwintytgesty sadfkgrvtitldtsastaymelsslrsedtavyycarsggydpmdywgqgttvtvssggggsg gggsggggsggggsdivltqspdslavslgeratincrasesvdnygntfmhwyqqkpgqpp klliyrasnlesgvpdrfsgsgsrtdftltisslqaedvavyycqqsnedpptfgqgtkleik | 138 |
| CD123 | huscFv8 | Qiqlvqsgaevkkpgasvkvsckasgyiftnygmnwvrqapgqrlewmgwintytgesty sadfkgrvtitldtsastaymelsslrsedtavyycarsggydpmdywgqgttvtvssggggsg gggsggggsggggseivltqspatlslspgeratlscrasesvdnygntfmhwyqqkpgqaprl liyrasnlesgiparfsgsgsrtdftltisslepedvavyycqqsnedpptfgqgtkleik | 139 |
| EGFR vIII | huscFv1 | Eiqlvqsgaevkkpgatvkisckgsgfniedyyihwvqqapgkglewmgridpendetkyg pifqgrvtitadtstntvymelsslrsedtavyycafrggvywgqgttvtvssggggsggggsgg ggsggggsdvvmtqspdslavslgeratinckssqslldsdgktylnwlqqkpgqppkrlislv skldsgvpdrfsgsgsgtdftltisslqaedvavyycwqgthfpgtfgggtkveik | 140 |
| EGFR vIII | huscFv2 | Dvvmtqspdslavslgeratinckssqslldsdgktylnwlqqkpgqppkrlislvskldsgvp drfsgsgsgtdftltisslqaedvavyycwqgthfpgtfgggtkveikggggsggggsggggsg gggseiqlvqsgaevkkpgatvkisckgsgfniedyyihwvqqapgkglewmgridpende tkygpifqgrvtitadtstntvymelsslrsedtavyycafrggvywgqgttvtvss | 141 |
| EGFR vIII | huscFv3 | Eiqlvqsgaevkkpgeslrisckgsgfniedyyihwvrqmpgkglewmgridpendetkyg pifqghvtisadtsintvylqwsslkasdtamyycafrggvywgqgttvtvssggggsggggs ggggsggggsdvvmtqsplslpvtlgqpasisckssqslldsdgktylnwlqqrpgqsprrlisl vskldsgvpdrfsgsgsgtdftlkisrveaedvgvyycwqgthfpgtfgggtkveik | 142 |
| EGFR vIII | huscFv4 | Dvvmtqsplslpvtlgqpasisckssqslldsdgktylnwlqqrpgqsprrlislvskldsgvpd rfsgsgsgtdftlkisrveaedvgvyycwqgthfpgtfgggtkveikggggsggggsggggsg ggseiqlvqsgaevkkpgeslrisckgsgfniedyyihwvrqmpgkglewmgridpende tkygpifqghvtisadtsintvylqwsslkasdtamyycafrggvywgqgttvtvss | 143 |
| EGFR vIII | huscFv5 | Eiqlvqsgaevkkpgatvkisckgsgfniedyyihwvqqapgkglewmgridpendetkyg pifqgrvtitadtstntvymelsslrsedtavyycafrggvywgqgttvtvssggggsggggsgg ggsggggsdvvmtqsplslpvtlgqpasisckssqslldsdgktylnwlqqrpgqsprrlislvs kldsgvpdrfsgsgsgtdftlkisrveaedvgvyycwqgthfpgtfgggtkveik | 144 |
| EGFR vIII | huscFv6 | Eiqlvqsgaevkkpgeslrisckgsgfniedyyihwvrqmpgkglewmgridpendetkyg pifqghvtisadtsintvylqwsslkasdtamyycafrggvywgqgttvtvssggggsggggs ggggsggggsdvvmtqspdslavslgeratinckssqslldsdgktylnwlqqkpgqppkrlis lvskldsgvpdrfsgsgsgtdftltisslqaedvavyycwqgthfpgtfgggtkveik | 145 |
| EGFR vIII | huscFv7 | Dvvmtqspdslavslgeratinckssqslldsdgktylnwlqqkpgqppkrlislvskldsgvp drfsgsgsgtdftltisslqaedvavyycwqgthfpgtfgggtkveikggggsggggsggggsg gggseiqlvqsgaevkkpgeslrisckgsgfniedyyihwvrqmpgkglewmgridpende tkygpifqghvtisadtsintvylqwsslkasdtamyycafrggvywgqgttvtvss | 146 |
| EGFR vIII | huscFv8 | Dvvmtqsplslpvtlgqpasisckssqslldsdgktylnwlqqrpgqsprrlislvskldsgvpd rfsgsgsgtdftlkisrveaedvgvyycwqgthfpgtfgggtkveikggggsggggsggggsg gggseiqlvqsgaevkkpgatvkisckgsgfniedyyihwvqqapgkglewmgridpende tkygpifqgrvtitadtstntvymelsslrsedtavyycafrggvywgqgttvtvss | 147 |
| EGFR vIII | Mu310C | eiqlqqsgaelvkpgasvklsctgsgfniedyyihwvkqrteqglewigridpendetkygpif qgratitadtssntvylqlssltsedtavyycafrggvywgpgttltvssggggsggggsggggsh mdvvmtqspltlsvaigqsasisckssqslldsdgktylnwllqrpgqspkrlislvskldsgvp drftgsgsgtdftlrisrveaedlgiyycwqgthfpgtfgggtkleik | 148 |

TABLE 7-continued

Exemplary Antigen Binding Domains

| Target Antigen | Name | Amino Acid Sequence | SEQ ID NO: |
|---|---|---|---|
| mesothelin | ss1 (mu) | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSSGGGGSGGGGSGGGGSDIELTQSPAIMSASPGEKVTMTCSASSSVSYMHWYQQKSGTSPKRWIYDTSKLASGVPGRFSGSGSGNSYSLTISSVEADDATYYCQQWSGYPLTFGAGTKLEI | 149 |
| mesothelin | M1 (human) | QVQLQQSGAEVKKPGASVKVSCKAS<u>GYTFTGYYMH</u>WVRQAPGQGLEWMG<u>RINPNSGGTNYAQKFQG</u>RVTMTRDTSISTAYMELSRLRSEDTAVYYCAR<u>GRYYGMDV</u>WGQGTMVTVSSGGGGSGGGGSGGGGSGGGGSEIVLTQSPATLSLSPGERATISC<u>RASQSVSSNFA</u>WYQQRPGQAPRLLIY<u>DASNRAT</u>GIPPRFSGSGSGTDFTLTISSLEPEDFAAYYC<u>HQRSNWLYT</u>FGQGTKVDIK | 150 |
| mesothelin | M2 (human) | QVQLVQSGAEVKKPGASVKVSCKAS<u>GYTFTGYYMH</u>WVRQAPGQGLEWMG<u>WINPNSGGTNYAQKFQG</u>RVTMTRDTSISTAYMELSRLRSDDTAVYYCARD<u>LRRTVVTPRAYYGMDV</u>WGQGTTVTVSSGGGGSGGGGSGGGGSGGGGSDIQLTQSPSTLSASVGDRVTITC<u>QASQDISNSLN</u>WYQQKAGKAPKLLIY<u>DASTLET</u>GVPSRFSGSGSGTDFSFTISSLQPEDIATYYC<u>QQHDNLPLT</u>FGQGTKVEIK | 151 |
| mesothelin | M3 (human) | QVQLVQSGAEVKKPGAPVKVSCKAS<u>GYTFTGYYMH</u>WVRQAPGQGLEWMG<u>WINPNSGGTNYAQKFQG</u>RVTMTRDTSISTAYMELSRLRSDDTAVYYCARG<u>EWDGSYYYDY</u>WGQGTLVTVSSGGGGSGGGGSGGGGSGGGGSDIVLTQTPSSLSASVGDRVTITC<u>RASQSINTYLN</u>WYQHKPGKAPKLLIY<u>AASSLQS</u>GVPSRFSGSGSGTDFTLTISSLQPEDFATYYC<u>QQSFSPLT</u>FGGGTKLEIK | 152 |
| mesothelin | M4 (human) | QVQLVESGGGLVQPGGSLRLSCAAS<u>GFTFSSYWMH</u>WVRQVPGKGLVWVS<u>RINTDGSTTTYADSVEG</u>RFTISRDNAKNTLYLQMNSLRDDDTAVYYCVG<u>GHWAV</u>WGQGTTVTVSSGGGGSGGGGSGGGGSGGGGSDIQMTQSPSTLSASVGDRVTITC<u>RASQSISDRLA</u>WYQQKPGKAPKLLIYK<u>ASSLES</u>GVPSRFSGSGSGTEFTLTISSLQPDDFAVYYC<u>QQYGHLPMYT</u>FGQGTKVEIK | 153 |
| mesothelin | M5 (human) | QVQLVQSGAEVEKPGASVKVSCKAS<u>GYTFTDYYMH</u>WVRQAPGQGLEWMG<u>WINPNSGGTNYAQKFQG</u>RVTMTRDTSISTAYMELSRLRSDDTAVYYCAS<u>GWDFDY</u>WGQGTLVTVSSGGGGSGGGGSGGGGSGGGGSDIVMTQSPSSLSASVGDRVTITCR<u>ASQSIRYYLS</u>WYQQKPGKAPKLLIY<u>TASILQN</u>GVPSRFSGSGSGTDFTLTISSLQPEDFATYYC<u>LQTYTTPPD</u>FGPGTKVEIK | 154 |
| mesothelin | M6 (human) | QVQLVQSGAEVKKPGASVKVSCKAS<u>GYTFTSYYMH</u>WVRQAPGQGLEWMGI<u>INPSGGSTSYAQKFQG</u>RVTMTRDTSTSTVYMELSSLRSEDTAVYYCAR<u>YRLIAVAGDYYYYGMDV</u>WGQGTMVTVSSGGGGSGGGGSGGGGSGGGGSDIQMTQSPSSVSASVGDRVTITC<u>RASQGVGRWLA</u>WYQQKPGTAPKLLIY<u>AASTLQS</u>GVPSRFSGSGSGTDFTLTINNLQPEDFATYYC<u>QQANSFPLT</u>FGGGTRLEIK | 155 |
| mesothelin | M7 (human) | QVQLVQSGGGVVQPGRSLRLSCAAS<u>GFTFSSYAMH</u>WVRQAPGKGLEWVA<u>VISYDGSNKYYADSVKG</u>RFTISRDNSKNTLYLQMNSLRAEDTAVYYCAR<u>WKVSSSSPAFDY</u>WGQGTLVTVSSGGGGSGGGGSGGGGSGGGGSEIVLTQSPATLSLSPGERAILSC<u>RASQSVYTKYLG</u>WYQQKPGQAPRLLIY<u>DASTRAT</u>GIPDRFSGSGSGTDFTLTINRLEPEDFAVYYC<u>QHYGGSPLIT</u>FGQGTRLEIK | 156 |
| mesothelin | M8 (human) | QVQLQQSGAEVKKPGASVKVSCKTS<u>GYPFTGYSLH</u>WVRQAPGQGLEWMG<u>WINPNSGGTNYAQKFQG</u>RVTMTRDTSISTAYMELSRLRSDDTAVYYCARD<u>HYGGNSLFY</u>WGQGTLVTVSSGGGGSGGGGSGGGGSGGGGSDIQLTQSPSSISASVGDTVSITC<u>RASQDSGTWLA</u>WYQQKPGKAPNLLMY<u>DASTLED</u>GVPSRFSGSASGTEFTLTVNRLQPEDSATYYC<u>QQYNSYPLT</u>FGGGTKVDIK | 157 |

TABLE 7-continued

Exemplary Antigen Binding Domains

| Target Antigen | Name | Amino Acid Sequence | SEQ ID NO: |
|---|---|---|---|
| mesothelin (human) | M9 | QVQLVQSGAEVKKPGASVEVSCKAS<u>GYTFTSYYMH</u>WVRQAPGQGLE WMG<u>IINPSGGSTGYAQKFQG</u>RVTMTRDTSTSTVHMELSSLRSEDTA VYYCAR<u>GGYSSSSDAFDI</u>WGQGTMVTVSSGGGGSGGGGSGGGGSGG GGSDIQMTQSPPSLSASVGDRVTITC<u>RASQDISSALA</u>WYQQKPGTP PKLLIY<u>DASSLES</u>GVPSRFSGSGSGTDFTLTISSLQPEDFATYYC<u>Q QFSSYPLT</u>FGGGTRLEIK | 158 |
| mesothelin (human) | M10 | QVQLVQSGAEVKKPGASVKVSCKAS<u>GYTFTSYGIS</u>WVRQAPGQGLE WMG<u>WISAYNGNTNYAQKLQ</u>GRVTMTDTSTSTAYMELRSLRSDDTA VYYCARV<u>AGGIYYYYGMDV</u>WGQGTTITVSSGGGGSGGGGSGGGGSG GGGSDIVMTQTPDSLAVSLGERATISC<u>KSSHSVLYNRNNKNYLA</u>WY QQKPGQPPKLLFY<u>WASTRKS</u>GVPDRFSGSGSGTDFTLTISSLQPED FATYFC<u>QQTQTFPLT</u>FGQGTRLEIN | 159 |
| mesothelin (human) | M11 | QVQLQQSGAEVKKPGASVKVSCKAS<u>GYTFTGYYMH</u>WVRQAPGQGLE WMG<u>WINPNSGGTNYAQNFQG</u>RVTMTRDTSISTAYMELRRLRSDDTA VYYCAS<u>GWDFDY</u>WGQGTLVTVSSGGGGSGGGGSGGGGSGGGGSDIR MTQSPSSLSASVGDRVTITC<u>RASQSIRYYLS</u>WYQQKPGKAPKLLIY <u>TASILQN</u>GVPSRFSGSGSGTDFTLTISSLQPEDFATYYC<u>LQTYTTP DFGPGTKVEIK</u> | 160 |
| mesothelin (human) | | QVQLVQSGAEVKKPGASVKVSCKAS<u>GYTFTGYYMH</u>WVRQAPGQGLE WMG<u>RINPNSGGTNYAQKFQG</u>RVTMTTDTSTSTAYMELRSLRSDDTA VYYCAR<u>TTTSYAFDI</u>WGQGTMVTVSSGGGGSGGGGSGGGGSGGGGS DIQLTQSPSTLSASVGDRVTITC<u>RASQSISTWLA</u>WYQQKPGKAPNL LIY<u>KASTLES</u>GVPSRFSGSGSGTEFTLTISSLQPDDFATYYC<u>QQYN TYSPYT</u>FGQGTKLEIK | 161 |
| mesothelin (human) | M13 | QVQLVQSGGGLVKPGGSLRLSCEAS<u>GFIFSDYYMG</u>WIRQAPGKGLE WVS<u>YIGRSGSSMYYADSVKG</u>RFTFSRDNAKNSLYLQMNSLRAEDTA VYYCAAS<u>PVVAATEDFQH</u>WGQGTLVTVSSGGGGSGGGGSGGGGSGG GGSDIVMTQTPATLSLSPGERATLSC<u>RASQSVTSNYLA</u>WYQQKPGQ APRLLLF<u>GASTRAT</u>GIPDRFSGSGSGTDFTLTINRLEPEDFAMYYC <u>QQYGSAPVT</u>FGQGTKLEIK | 162 |
| mesothelin (human) | M14 | QVQLVQSGAEVRAPGASVKISCKAS<u>GFTFRGYYIH</u>WVRQAPGQGLE WMG<u>IINPSGGSRAYAQKFQG</u>RVTMTRDTSTSTVYMELSSLRSDDTA MYYCAR<u>TASCGGDCYYLDY</u>WGQGTLVTVSSGGGGSGGGGSGGGGSG GGGSDIQMTQSPPTLSASVGDRVTITC<u>RASENVNIWLA</u>WYQQKPGK APKLLIY<u>KSSSLAS</u>GPSRFSGSGSGAEFTLTISSLQPDDFATYYC <u>QQYQSYPLT</u>FGGGTKVDIK | 163 |
| mesothelin (human) | M15 | QVQLVQSGGGLVQPGRSLRLSCAAS<u>GFTFDDYAMH</u>WVRQAPGKGLE WVS<u>GISWNSGSIGYADSVKG</u>RFTISRDNAKNSLYLQMNSLRAEDTA VYYCAK<u>DGSSSWSWGYFDY</u>WGQGTLVTVSSGGGGSGGGGSGGGGSS SELTQDPAVSVALGQTVRTTC<u>QGDALRSYYAS</u>WYQQKPGQAPMLVI YG<u>KNNRPS</u>GIPDRFSGSDSGDTASLTITGAQAEDEADYYC<u>NSRDSS GYPV</u>FGTGTKVTVL | 164 |
| mesothelin (human) | M16 | EVQLVESGGGLVQPGRSLRLSCAAS<u>GFTFDDYAMH</u>WVRQAPGKGLE WVS<u>GISWNSGSTGYADSVKG</u>RFTISRDNAKNSLYLQMNSLRAEDTA LYYCAK<u>DSSSWYGGGSAFDI</u>WGQGTMVTVSSGGGGSGGGGSGGGGS SSELTQEPAVSVALGQTVRITC<u>QGDSLRSYYAS</u>WYQQKPGQAPVLV IFG<u>RSRRPS</u>GIPDRFSGSSSGNTASLIITGAQAEDEADYYC<u>NSRDN TANHYV</u>FGTGTKLTVL | 165 |
| mesothelin (human) | M17 | EVQLVESGGGLVQPGRSLRLSCAAS<u>GFTFDDYAMH</u>WVRQAPGKGLE WVS<u>GISWNSGSTGYADSVKG</u>RFTISRDNAKNSLYLQMNSLRAEDTA LYYCAK<u>DSSSWYGGGSAFDI</u>WGQGTMVTVSSGGGGSGGGGSGGGGS SSELTQDPAVSVALGQTVRITC<u>QGDSLRSYYAS</u>WYQQKPGQAPVLV IYG<u>KNNRPS</u>GIPDRFSGSSSGNTASLTITGAQAEDEADYYC<u>NSRGS SGNHYV</u>FGTGTKVTVL | 166 |
| mesothelin (human) | M18 | QVQLVQSGGGLVQPGGSLRLSCAAS<u>GFTFSSYWMH</u>WVRQAPGKGLV WVS<u>RINSDGSSTSYADSVKG</u>RFTISRDNAKNTLYLQMNSLRAEDTA VYYCVR<u>TGWVGSYYYYMDV</u>WGKGTTVTVSSGGGGSGGGGSGGGGSG GGGSEIVLTQSPGTLSLSPGERATLSC<u>RASQSVSSNYLA</u>WYQQKPG QPPRLLIY<u>DVSTRAT</u>GIPARFSGGGSGTDFTLTISSLEPEDFAVYY C<u>QQRSNWPPWT</u>FGQGTKVEIK | 167 |

TABLE 7-continued

Exemplary Antigen Binding Domains

| Target Antigen | Name | Amino Acid Sequence | SEQ ID NO: |
|---|---|---|---|
| mesothelin | M19 (human) | QVQLVQSGGGVVQPGRSLRLSCAASGFTFSSYGMHWVRQAPGKGLE WVAVISYDGSNKYYADSVKGRFTISRDNSKNTLYLQMNSLRAEDTA VYYCAKGYSRYYYYGMDVWGQGTTVTVSSGGGGSGGGGSGGGGSGG GGSEIVMTQSPATLSLSPGERAILSCRASQSVYTKYLGWYQQKPGQ APRLLIYDASTRATGIPDRFSGSGSGTDFTLTINRLEPEDFAVYYC QHYGGSPLITFGQGTKVDIK | 168 |
| mesothelin | M20 (human) | QVQLVQSGGGLVQPGGSLRLSCAASGFTFSSYAMSWVRQAPGKGLE WVSAISGSGGSTYYADSVKGRFTISRDNSKNTLYLQMNSLRAEDTA VYYCAKREAAAGHDWYFDLWGRGTLVTVSSGGGGSGGGGSGGGGSG GGGSDIRVTQSPSSLSASVGDRVTITCRASQSISSYLNWYQQKPGK APKLLIYAASSLQSGVPSRFSGSGSGTDFTLTISSLQPEDFATYYC QQSYSIPLTFGQGTKVEIK | 169 |
| mesothelin | M21 (human) | QVQLVQSWAEVKKPGASVKVSCKASGYTFTSYYMHWVRQAPGQGLE WMGIINPSGGSTSYAQKFQGRVTMTRDTSTSTVYMELSNLRSEDTA VYYCARSPRVTTGYFDYWGQGTLVTVSSGGGGSGGGGSGGGGSGGG GSDIQLTQSPSTLSASVGDRVTITCRASQSISSWLAWYQQKPGKAP KLLIYKASSLESGVPSRFSGSGSGTEFTLTISSLQPDDFATYYCQQ YSSYPLTFGGGTRLEIK | 170 |
| mesothelin | M22 (human) | QVQLVQSGAEVRRPGASVKISCRASGDTSTRHYIHWLRQAPGQGPE WMGVINPTTGPATGSPAYAQMLQGRVTMTRDTSTRTVYMELRSLRF EDTAVYYCARSVVGRSAPYYFDYWGQGTLVTVSSGGGGSGGGGSGG GGSGGGGSDIQMTQSPSSLSASVGDRVTITCRASQGISDYSAWYQQ KPGKAPKLLIYAASTLQSGVPSRFSGSGSGTDFTLTISYLQSEDFA TYYCQQYYSYPLTFGGGTKVDIK | 171 |
| mesothelin | M23 (human) | QVQLQQSGAEVKKPGASVKVSCKASGYTFTNYYMHWVRQAPGQGLE WMGIINPSGGYTTYAQKFQGRLTMTRDTSTSTVYMELSSLRSEDTA VYYCARIRSCGGDCYYFDNWGQGTLVTVSSGGGGSGGGGSGGGGSG GGGSDIQLTQSPSTLSASVGDRVTITCRASENVNIWLAWYQQKPGK APKLLIYKSSSLASGVPSRFSGSGSGAEFTLTISSLQPDDFATYYC QQYQSYPLTFGGGTKVDIK | 172 |
| mesothelin | M24 (human) | QITLKESGPALVKPTQTLTLTCTFSGFSLSTAGVHVGWIRQPPGKA LEWLALISWADDKRYRPSLRSRLDITRVTSKDQVVLSMTNMQPEDT ATYYCALQGFDGYEANWGPGTLVTVSSGGGGSGGGGSGGGGSGGGG SDIVMTQSPSSLSASAGDRVTITCRASRGISSALAWYQQKPGKPPK LLIYDASSLESGVPSRFSGSGSGTDFTLTIDSLEPEDFATYYCQQS YSTPWTFGQGTKVDIK | 173 |
| CLL-1 | 139115 (human) | EVQLQQSGAEVKKPGSSVKVSCKASGGTFSSYAISWVRQAPGQGLEWMGGII PIFGTANYAQKFQGRVTITADESTSTAYMELSSLRSEDTAVYYCARDLEMAT IMGGYWGQGTLVTVSSGGGGSGGGGSGGGGSQSALTQPASVSGSPGQSITIS CTGTSSDVGGYNYVSWYQQHPGKAPKLMIYDVSNRPSGVSNRFSGSKSGNTA SLTISGLQAEDEADYYCSSYTSSSTLDVVFGGGTKLTVL | 174 |
| CLL-1 | 139116 (human) | EVQLVESGGGVVQPGGSLRLSCAASGFTFDDYAMHWVRQAPGKGLEWVSLIS GDGGSTYYADSVKGRFTISRDNSKNTLYLQMNSLRVEDTAVYYCARVFDSYY MDVWGKGTTVTVSSGGGGSGGGGSGSGGSEIVLTQSPLSLPVTPGQPASISC RSSQSLVYTDGNTYLNWFQQRPGQSPRRLIYKVSNRDSGVPDRFSGSGSDTD FTLKISRVEAEDVGIYYCMQGTHWSFTFGQGTRLEIK | 175 |
| CLL-1 | 139118 (human) | QVQLQESGPGLVKPSETLSLTCTVSGGSISSSSYYWGWIRQPPGKGLEWIGS IYYSGSTYYNPSLKSRVSISVDTSKNQFSLKLKYVTAADTAVYYCATPGTYY DFLSGYYPFYWGQGTLVTVSSGGGGSGGGGSGGGGSDIVMTQSPSSLSASVG DRVTITCRASQGISSYLAWYQQKPGKAPKLLIYAASTLQSGVPSRFSGSGSG TDFTLTISSLQPEDFATYYCQQLNSYPYTFGQGTKLEIK | 176 |
| CLL-1 | 139122 (human) | QVQLVESGGGLVQPGGSLRLSCAASGFTFSSYWMSWVRQAPGKGLEWVANIN EDGSAKFYVDSVKGRFTISRDNAKNSLYLQMNSLRAEDTAVYFCARDLRSGR YWGQGTLVTVSSGGGGSGGGGSGGGGSEIVLTQSPGTLSLSPGGRATLSCRA SQSISGSFLAWYQQKPGQAPRLLIYGASSRATGIPDRFSGSGSGTDFTLTIS RLEPEDFAVYYCQQYGSSPPTFGLGTKLEIK | 177 |
| CLL-1 | 139117 (human) | EVQLQQSGPGLVRPSETLSLTCTVSGGPVRSGSHYWNWIRQPPGRGLEWIGY IYYSGSTNYNPSLENRVTISIDTSNNHFSLKLSSVTAADTALYFCARGTATF DWNFPFDSWGQGTLVTVSSGGGGSGGGGSGSGGSDIQMTQSPSSLSASIGDR VTITCRASQSISSYLNWYQQKPGKAPKLLIYAASSLQSGVPSRFSGSGSGTD FTLTISSLQPEDFATYYCQQSYSTPWTFGQGTKLEIK | 178 |

TABLE 7-continued

Exemplary Antigen Binding Domains

| Target Antigen | Name | Amino Acid Sequence | SEQ ID NO: |
|---|---|---|---|
| CLL-1 | 139119 (human) | QVQLQESGAGLLKPSETLSLTCAVYGGSFSGYYWSWIRQPPGKGLEWVGEIN HSGSTNYNPSLKSRVTISVDTSKNQFSLKLSSVTAADTAVYYCARGSGLVVY AIRVGSGWFDYWGQGTLVTVSSGGGGSGGGDSGGGGSDIQMTQSPSSLSASV GDRVTITCRASQSISSYLNWYQQKPGKAPKLLMYAASSLQSGVPSRFSGSGS GTDFTLTISSLQPEDFATYYCQQSYSTPPWTFGQGTKVDIK | 179 |
| CLL-1 | 139120 (human) | EVQLVESGGGLVKPGGSLRLSCAASGFTFSSYSMNWVRQAPGKGLEWVSSIS SSSSYIYYADSVKGRFTISRDNAKNSLYLQMNSLRAEDTAVYYCARDPSSSG SYYMEDSYYYGMDVWGQGTTVTVSSGGGGSGGGGSGGGGSNFMLTQPHSVSE SPGKTVTISCTGSSGSIASNYVQWYQQRPGSAPTTVIYEDNQRPSGVPDRFS GSIDSSSNSASLTISGLKTEDEADYYCQSYDSSNQVVFGGGTKLTVL | 180 |
| CLL-1 | 139121 (human) | QVNLRESGGGLVQPGGSLRLSCAASGFTFSSYEMNWVRQAPGKGLEWVSYIS SSGSTIYYADSVKGRFTISRDNAKNSLYLQMNSLRAEDTAVYYCAREALGSS WEWGQGTTVTVSSGGGGSGGGGSGGGGSDIQMTQSPSSLSASVGDRVTITCQ ASQDISNYLNWYQQKPGKAPKLLIYDASNLETGVPSRFSGSGSGTDFTFTIS SLQPEDIATYYCQQYDNLPLTFGGGTKLEIK | 181 |
| CLL-1 | 146259 (human) | QVQLVQSGAEVKKPGASVKVSCKAPANTFSDHVMHWVRQAPGQRFEWMGYIH AANGGTHYSQKFQDRVTITRDTSANTVYMDLSSLRSEDTAVYYCARGGYNSD AFDIWGQGTMVTVSSGGGGSGGGGSGGGGSGGGGSDIVMTQSPSSVSASVGD RVTITCRASQDISSWLAWYQQKPGKAPKLLIYAASSLQSGVPSRFNGSGSGT DFTLTISSLQPEDFATYYCQQSYSTPLTFGGGTKVEIK | 182 |
| CLL-1 | 146261 (human) | QVQLVQSGGGLVQPGGSLRLSCAASGFTFSSYSMNWVRQAPGKGLEWVSYIS SSSSTIYYADSVKGRFTISRDNAKNSLYLQMNSLRAEDTAVYYCARDLSVRA IDAFDIWGQGTMVTVSSGGGGSGGGGSGGGGSGGGGSDIVLTQSPSSLSASV GDRVTITCQASQDISNYLNWYQQKPGKAPKLLIYDASNLETGVPSRFSGSGS GTDFTFTISSLQPEDFATYYCQQAYSTPFTFGPGTKVEIK | 183 |
| CLL-1 | 146262 (human) | EVQLVQSGGGVVRSGRSLRLSCAASGFTFNSYGLHWVRQAPGKGLEWVALIE YDGSNKYYGDSVKGRFTISRDKSKSTLYLQMDNLRAEDTAVYYCAREGNEDL AFDIWGQGTLVTVSSGGGGSGGGGSGGGGSGGGGSEIVLTQSPSSLSASVGD RVTITCQASQFIKKNLNWYQHKPGKAPKLLIYDASSLQTGVPSRFSGNRSGT TFSFTISSLQPEDVATYYCQQHDNLPLTFGGGTKVEIK | 184 |
| CLL-1 | 146263 (human) | QVQLVESGGGLVQPGGSLRLSCAASGFNVSSNYMTWVRQAPGKGLEWVSVIY SGGATYYGDSVKGRFTVSRDNSKNTVYLQMNRLTAEDTAVYYCARDRLYCGN NCYLYYYYGMDVWGQGTLVTVSSGGGGSGGGGSGGGGSGGGGSDIQVTQSPS SLSASVGDRVTITCRASQSISSYLNWYQQKPGKAPKLLIYAASSLQSGVPSR FSGSGSGTDFTLTISSLQPEDFATYYCQQSYSTPPLTFGQGTKVEIK | 185 |
| CLL-1 | 146264 (human) | QVQLVQSGAEVKKSGASVKVSCKASGYPFTGYYIQWVRQAPGQGLEWMGWID PNSGNTGYAQKFQGRVTMTRNTSISTAYMELSSLRSEDTAVYYCASDSYGYY YGMDVWGQGTLVTVSSGGGGSGGGGSGGGGSGGGGSDIQMTQSPSSLSASVG DRVTFTCRASQGISSALAWYQQKPGKPPKLLIYDASSLESGVPSRFSGSGSG TDFTLTISSLQPEDFATYYCQQFNNYPLTFGGGTKVEIK | 186 |
| CLL-1 | 181268 (human) | EVQLVESGGGLVQPGGSLRLSCAASGFTFSSYEMNWVRQAPGKGLEWVSYIS SSGSTIYYADSVKGRFTISRDNAKNSLYLQMNSLRAEDTAVYYCARDPYSSS WHDAFDIWGQGTMVTVSSGGGGSGGGGSGGGGSEIVLTQSPGTLSLSPGERA TLSCRASQSVSSSYLAWYQQKPGQAPRLLIYGASSRATGIPDRFSGSGSGTD FTLTISRLEPEDFAVYYCQQYGSSPLTFGGGTKVDIK | 187 |
| BCMA | 139103 (human) | QVQLVESGGGLVQPGRSLRLSCAASGFTFSNYAMSWVRQAPGKGLGWVSGIS RSGENTYYADSVKGRFTISRDNSKNTLYLQMNSLRDEDTAVYYCARSPAHYY GGMDVWGQGTTVTVSSASGGGGSGGRASGGGGSDIVLTQSPGTLSLSPGERA TLSCRASQSISSSFLAWYQQKPGQAPRLLIYGASRRATGIPDRFSGSGSGTD FTLTISRLEPEDSAVYYCQQYHSSPSWTFGQGTKLEIK | 188 |
| BCMA | 139105 (human) | QVQLVESGGGLVQPGRSLRLSCAASGFTFDDYAMHWVRQAPGKGLEWVSGIS WNSGSIGYADSVKGRFTISRDNAKNSLYLQMNSLRAEDTALYYCSVHSFLAY WGQGTLVTVSSASGGGGSGGRASGGGGSDIVMTQTPLSLPVTPGEPASISCR SSQSLLHSNGYNYLDWYLQKPGQSPQLLIYLGSNRASGVPDRFSGSGSGTDF TLKISRVEAEDVGVYYCMQALQTPYTFGQGTKVEIK | 189 |
| BCMA | 139111 (human) | EVQLLESGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSDIVMTQTPLSVTPGQPASISCK SSQSLLRNDGKTPLYWYLQKAGQPPQLLIYEVSNRFSGVPDRFSGSGSGTDF TLKISRVEAEDVGAYYCMQNIQFPSFGGGTKLEIK | 190 |

TABLE 7-continued

Exemplary Antigen Binding Domains

| Target Antigen | Name | Amino Acid Sequence | SEQ ID NO: |
|---|---|---|---|
| BCMA | 139100 (human) | QVQLVQSGAEVRKTGASVKVSCKASGYIFDNFGINWVRQAPGQGLEWMGWIN PKNNNTNYAQKFQGRVTITADESTNTAYMEVSSLRSEDTAVYYCARGPYYYQ SYMDVWGQGTMVTVSSASGGGGSGGRASGGGGSDIVMTQTPLSLPVTPGEPA SISCRSSQSLLHSNGYNYLNWYLQKPGQSPQLLIYLGSKRASGVPDRFSGSG SGTDFTLHITRVGAEDVGVYYCMQALQTPYTFGQGTKLEIK | 191 |
| BCMA | 139101 (human) | QVQLQESGGGLVQPGGSLRLSCAASGFTFSSDAMTWVRQAPGKGLEWVSVIS GSGGTTYYADSVKGRFTISRDNSKNTLYLQMNSLRAEDTAVYYCAKLDSSGY YYARGPRYWGQGTLVTVSSASGGGGSGGRASGGGGSDIQLTQSPSSLSASVG DRVTITCRASQSISSYLNWYQQKPGKAPKLLIYGASTLASGVPARFSGSGSG THFTLTINSLQSEDSATYYCQQSYKRASFGQGTKVEIK | 192 |
| BCMA | 139102 (human) | QVQLVQSGAEVKKPGASVKVSCKASGYTFSNYGITWVRQAPGQGLEWMGWIS AYNGNTNYAQKFQGRVTMTRNTSISTAYMELSSLRSEDTAVYYCARGPYYYY MDVWGKGTMVTVSSASGGGGSGGRASGGGGSEIVMTQSPLSLPVTPGEPASI SCRSSQSLLYSNGYNYVDWYLQKPGQSPQLLIYLGSNRASGVPDRFSGSGSG TDFKLQISRVEAEDVGIYYCMQGRQFPYSFGQGTKVEIK | 193 |
| BCMA | 139104 (human) | EVQLLETGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSEIVLTQSPATLSVSPGESATLSCR ASQSVSSNLAWYQQKPGQAPRLLIYGASTRASGIPDRFSGSGSTDFTLTIS SLQAEDVAVYYCQQYGSSLTFGGGTKVEIK | 194 |
| BCMA | 139106 (human) | EVQLVETGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSEIVMTQSPATLSVSPGERATLSCR ASQSVSSKLAWYQQKPGQAPRLLMYGASIRATGIPDRFSGSGSTEFTLTIS SLEPEDFAVYYCQQYGSSSWTFGQGTKVEIK | 195 |
| BCMA | 139107 (human) | EVQLVETGGGVVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSEIVLTQSPGTLSLSPGERATLSCR ASQSVGSTNLAWYQQKPGQAPRLLIYDASNRATGIPDRFSGGGSGTDFTLTI SRLEPEDFAVYYCQQYGSSPPWTFGQGTKVEIK | 196 |
| BCMA | 139108 (human) | QVQLVESGGGLVKPGGSLRLSCAASGFTFSDYYMSWIRQAPGKGLEWVSYIS SSGSTIYYADSVKGRFTISRDNAKNSLYLQMNSLRAEDTAVYYCARESGDGM DVWGQGTTVTVSSASGGGGSGGRASGGGGSDIQMTQSPSSLSASVGDRVTIT CRASQSISSYLNWYQQKPGKAPKLLIYAASSLQSGVPSRFSGSGSTDFTLT ISSLQPEDFATYYCQQSYTLAFGQGTKVDIK | 197 |
| BCMA | 139109 (human) | EVQLVESGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSDIQLTQSPSSLSASVGDRVTITCR ASQSISSYLNWYQQKPGKAPKLLIYAASSLQSGVPSRFSGSGSTDFTLTIS SLQPEDFATYYCQQSYSTPYTFGQGTKVEIK | 198 |
| BCMA | 139110 (human) | QVQLVQSGGGLVKPGGSLRLSCAASGFTFSDYYMSWIRQAPGKGLEWVSYIS SSGNTIYYADSVKGRFTISRDNAKNSLYLQMNSLRAEDTAVYYCARSTMVRE DYWGQGTLVTVSSASGGGGSGGRASGGGGSDIVLTQSPLSLPVTLGQPASIS CKSSESLVHNSGKTYLNWFHQRPGQSPRRLIYEVSNRDSGVPDRFTGSGSGT DFTLKISRVEAEDVGVYYCMQGTHWPGTFGQGTKLEIK | 199 |
| BCMA | 139112 (human) | QVQLVESGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSDIRLTQSPSPLSASVGDRVTITCQ ASEDINKFLNWYHQTPGKAPKLLIYDASTLQTGVPSRFSGSGSTDFTLTIN SLQPEDIGTYYCQQYESLPLTFGGGTKVEIK | 200 |
| BCMA | 139113 (human) | EVQLVETGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSETTLTQSPATLSVSPGERATLSCR ASQSVGSNLAWYQQKPGQGPRLLIYGASTRATGIPARFSGSGSTEFTLTIS SLQPEDFAVYYCQQYNDWLPVTFGQGTKVEIK | 201 |
| BCMA | 139114 (human) | EVQLVESGGGLVQPGGSLRLSCAVSGFALSNHGMSWVRRAPGKGLEWVSGIV YSGSTYYAASVKGRFTISRDNSRNTLYLQMNSLRPEDTAIYYCSAHGGESDV WGQGTTVTVSSASGGGGSGGRASGGGGSEIVLTQSPGTLSLSPGERATLSCR ASQSIGSSSLAWYQQKPGQAPRLLMYGASSRASGIPDRFSGSGSTDFTLTI SRLEPEDFAVYYCQQYAGSPPFTFGQGTKVEIK | 202 |

TABLE 7-continued

Exemplary Antigen Binding Domains

| Target Antigen | Name | Amino Acid Sequence | SEQ ID NO: |
|---|---|---|---|
| BCMA | 149362 (human) | QVQLQESGPGLVKPSETLSLTCTVSGGSISSSYYYWGWIRQPPGKGLEWIGSIYYSGSAYYNPSLKSRVTISVDTSKNQFSLRLSSVTAADTAVYYCARHWQEWPDAFDIWGQGTMVTVSSGGGGSGGGGSGGGGSETTLTQSPAFMSATPGDKVIISCKASQDIDDAMNWYQQKPGEAPLFIIQSATSPVPGIPPRFSGSGFGTDFSLTINNIESEDAAYYFCLQHDNFPLTFGQGTKLEIK | 203 |
| BCMA | 149363 (human) | VNLRESGPALVKPTQTLTLTCTFSGFSLRTSGMCVSWIRQPPGKALEWLARIDWDEDKFYSTSLKTRLTISKDTSDNQVVLRMTNMDPADTATYYCARSGAGGTSATAFDIWGPGTMVTVSSGGGGSGGGGSGGGGSDIQMTQSPSSLSASVGDRVTITCRASQDIYNNLAWFQLKPGSAPRSLMYAANKSQSGVPSRFSGSASGTDFTLTISSLQPEDFATYYCQHYYRFPYSFGQGTKLEIK | 204 |
| BCMA | 149364 (human) | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCAKTIAAVYAFDIWGQGTTVTVSSGGGGSGGGGSGGGGSEIVLTQSPLSLPVTPEEPASISCRSSQSLLHSNGYNYLDWYLQKPGQSPQLLIYLGSNRASGVPDRFSGSGSGTDFTLKISRVEAEDVGVYYCMQALQTPYTFGQGTKLEIK | 205 |
| BCMA | 149365 (human) | EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDLRGAFDIWGQGTMVTVSSGGGGSGGGGSGGGGSSYVLTQSPSVSAAPGYTATISCGGNNIGTKSVHWYQQKPGQAPLLVIRDDSVRPSKIPGRFSGSNSGNMATLTISGVQAGDEADFYCQVWDSDSEHVVFGGGTKLTVL | 206 |
| BCMA | 149366 (human) | QVQLVQSGAEVKKPGASVKVSCKPSGYTVTSHYIHWVRRAPGQGLEWMGMINPSGGVTAYSQTLQGRVTMTSDTSSSTVYMELSSLRSEDTAMYYCAREGSGSGWYFDFWGRGTLVTVSSGGGGSGGGGSGGGGSSYVLTQPPSVSVSPGQTASITCSGDGLSKKYVSWYQQKAGQSPVVLISRDKERPSGIPDRFSGSNSADTATLTISGTQAMDEADYYCQAWDDTTVVFGGGTKLTVL | 207 |
| BCMA | 149367 (human) | QVQLQESGPGLVKPSQTLSLTCTVSGGSISSGGYYWSWIRQHPGKGLEWIGYIYYSGSTYYNPSLKSRVTISVDTSKNQFSLKLSSVTAADTAVYYCARAGIAARLRGAFDIWGQGTMVTVSSGGGGSGGGGSGGGGSDIVMTQSPSSVSASVGDRVIITCRASQGIRNWLAWYQQKPGKAPNLLIYAASNLQSGVPSRFSGSGSGADFTLTISSLQPEDVATYYCQKYNSAPFTFGPGTKVDIK | 208 |
| BCMA | 149368 (human) | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARRGGYQLLRWDVGLLRSAFDIWGQGTMVTVSSGGGGSGGGGSGGGGSSYVLTQPPSVSVAPGQTARITCGGNNIGSKSVHWYQQKPGQAPVLVLYGKNNRPSGVPDRFSGSRSGTTASLTITGAQAEDEADYYCSSRDSSGDHLRVFGTGTKVTVL | 209 |
| BCMA | 149369 (human) | EVQLQQSGPGLVKPSQTLSLTCAISGDSVSSNSAAWNWIRQSPSRGLEWLGRTYYRSKWYSFYAISLKSRIIINPDTSKNQFSLQLKSVTPEDTAVYYCARSSPEGLFLYWFDPWGQGTLVTVSSGGDGSGGGGSGGGGSSSELTQDPAVSVALGQTIRITCQGDSLGNYYATWYQQKPGQAPVLVIYGTNNRPSGIPDRFSASSSGNTASLTITGAQAEDEADYYCNSRDSSGHHLLFGTGTKVTVL | 210 |
| BCMA | EBB-C1978-A4 (human) | EVQLVESGGGLVQPGGSLRLSCAASGFTFSSYAMSWVRQAPGKGLEWVSAISGSGGSTYYADSVKGRFTISRDNSKNTLYLQMNSLRAEDTAVYYCAKVEGSGSLDYWGQGTLVTVSSGGGGSGGGGSGGGGSEIVMTQSPGTLSLSPGERATLSCRASQSVSSAYLAWYQQKPGQPPRLLISGASTRATGIPDRFGGSGSGTDFLTISRLEPEDFAVYYCQHYGSSFNGSSLFTFGQGTRLEIK | 211 |
| BCMA | EBB-C1978-G1 (human) | EVQLVETGGGLVQPGGSLRLSCAASGITFSRYPMSWVRQAPGKGLEWVSGISDSGVSTYYADSAKGRFTISRDNSKNTLFLQMSSLRDEDTAVYYCVTRAGSEASDIWGQGTMVTVSSGGGGSGGGGSGGGGSEIVLTQSPATLSLSPGERATLSCRASQSVSNSLAWYQQKPGQAPRLLIYDASSRATGIPDRFSGSGSGTDFTLTISRLEPEDFAIYYCQQFGTSSGLTFGGGTKLEIK | 212 |
| BCMA | EBB-C1979-C1 (human) | QVQLVESGGGLVQPGGSLRLSCAASGFTFSSYAMSWVRQAPGKGLEWVSAISGSGGSTYYADSVKGRFTISRDNAKNSLYLQMNSLRAEDTAIYYCARATYKRELRYYYGMDVWGQGTMVTVSSGGGGSGGGGSGGGGSEIVMTQSPGTVSLSPGERATLSCRASQSVSSSFLAWYQQKPGQAPRLLIYGASSRATGIPDRFSGSGSGTDFTLTISRLEPEDSAVYYCQQYHSSPSWTFGQGTRLEIK | 213 |
| BCMA | EBB-1978-C7 (human) | EVQLVETGGGLVQPGGSLRLSCAASGFTFSSYAMSWVRQAPGKGLEWVSAISGSGGSTYYADSVKGRFTISRDNSKNTLYLQMNTLKAEDTAVYYCARATYKRELRYYYGMDVWGQGTLVTVSSGGGGSGGGGSGGGGSEIVLTQSPSTLSLSPGESATLSCRASQSVSTTFLAWYQQKPGQAPRLLIYGSSNRATGIPDRFSGSGSGTDFTLTIRRLEPEDFAVYYCQQYHSSPSWTFGQGTKVEIK | 214 |

TABLE 7-continued

Exemplary Antigen Binding Domains

| Target Antigen | Name | Amino Acid Sequence | SEQ ID NO: |
|---|---|---|---|
| BCMA | EBB-1978-D10 | EVQLVETGGGLVQPGRSLRLSCAAS<u>GFTFDDYAMH</u>WVRQAPGKGLEWVS<u>GIS WNSGSIGYADSVKG</u>RFTISRDNAKNSLYLQMNSLRDEDTAVYYCAR<u>VGKAVP DV</u>WGQGTTVTVSSGGGGSGGGGSGGGGSDIVMTQTPSSLSASVGDRVTITC<u>R ASQSISSYLN</u>WYQQKPGKAPKLLIY<u>AASSLQS</u>GVPSRFSGSGSGTDFTLTIS SLQPEDFATYYC<u>QQSYSTPYSF</u>GQGTRLEIK | 215 |
| BCMA | EBB-1979-C12 (human) | EVQLVESGGGLVQPGRSLRLSCTAS<u>GFTFDDYAMH</u>WVRQRPGKGLEWVA<u>SIN WKGNSLAYGDSVKG</u>RFAISRDNAKNTVFLQMNSLRTEDTAVYYCAS<u>HQGVAY YNYAMDV</u>WGRGTLVTVSSGGGGSGGGGSGGGGSEIVLTQSPGTLSLSPGERA TLSC<u>RATQSIGSSFLA</u>WYQQRPGQAPRLLIY<u>GASQRAT</u>GIPDRFSGRGSGTD FTLTISRVEPEDSAVYYC<u>QHYESSPSWTF</u>GQGTKVEIK | 216 |
| BCMA | EBB-1980-G4 (human) | EVQLVESGGGLVQPGGSLRLSCAAS<u>GFTFSSYAMS</u>WVRQAPGKGLE WVS<u>AISGSGGSTYYADSVKG</u>RFTISRDNSKNTLYLQMNSLRAEDTAV YYCAK<u>VVRDGMDV</u>WGQGTTVTVSSGGGGSGGGGSGGGGSEIVLTQ SPATLSLSPGERATLSC<u>RASQSVSSSYLA</u>WYQQKPGQAPRLLIY<u>GASS RAT</u>GIPDRFSGNGSGTDFTLTISRLEPEDFAVYYC<u>QQYGSPPRFTF</u>GPG TKVDIK | 217 |
| BCMA | EBB-1980-D2 (human) | EVQLLESGGGLVQPGGSLRLSCAAS<u>GFTFSSYAMS</u>WVRQAPGKGLEWVS<u>AIS GSGGSTYYADSVKG</u>RFTISRDNSKNTLYLQMNSLRAEDTAVYYCAK<u>IPQTGT FDY</u>WGQGTLVTVSSGGGGSGGGGSGGGGSEIVLTQSPGTLSLSPGERATLSC <u>RASQSVSSSYLA</u>WYQQRPGQAPRLLIY<u>GASSRAT</u>GIPDRFSGSGSGTDFTLT ISRLEPEDFAVYYC<u>QHYGSSPSWTF</u>GQGTRLEIK | 218 |
| BCMA | EBB-1978-A10 (human) | EVQLVETGGGLVQPGGSLRLSCAAS<u>GFTFSSYAMS</u>WVRQAPGKGLEWVS<u>AIS GSGGSTYYADSVKG</u>RFTMSRENDKNSVFLQMNSLRVEDTGVVYYCAR<u>ANYKR ELRYYYGMD</u>VWGQGTMVTVSSGGGGSGGGGSGGGGSEIVMTQSPGTLSLSPG ESATLSC<u>RASQRVASNYLA</u>WYQHKPGQAPSLLISGASSRATGVPDRFSGSGS GTDFTLAISRLEPEDSAVYYC<u>QHYDSSPSWTF</u>GQGTKVEIK | 219 |
| BCMA | EBB-1978-D4 | EVQLLETGGGLVQPGGSLRLSCAAS<u>GFSFSSYAMS</u>WVRQAPGKGLEWVS<u>AIS GSGGSTYYADSVKG</u>RFTISRDNSKNTLYLQMNSLRAEDTAVYYCAK<u>ALVGAT GAFDI</u>WGQGTLVTVSSGGGGSGGGGSGGGGSEIVLTQSPGTLSLSPGERATL SC<u>RASQSLSSNFLA</u>WYQQKPGQAPGLLIY<u>GASNWAT</u>GTPDRFSGSGSGTDFT LTITRLEPEDFAVYYC<u>QYYGTSPMYTF</u>GQGTKVEIK | 220 |
| BCMA | EBB-1980-A2 (human) | EVQLLESGGGLVQPGGSLRLSCAAS<u>GFTFSSYAMS</u>WVRQAPGKGLEWVS<u>AIS GSGGSTYYADSVKG</u>RFTISRDNSKNTLYLQMNSLRAEDTAVYYCVL<u>WFGEGF DP</u>WGQGTLVTVSSGGGGSGGGGSGGGGSDIVMTQSPLSLPVTPGEPASISC<u>R SSQSLLHSNGYNYLD</u>WYLQKPGQSPQLLIY<u>LGSNRAS</u>GVPDRFSGSGSGTDF TLKISRVEAEDVGVYYC<u>MQALQTPLTF</u>GGGTKVDIK | 221 |
| BCMA | EBB-1981-C3 | QVQLVESGGGLVQPGGSLRLSCAAS<u>GFTFSSYAMS</u>WVRQAPGKGLEWVS<u>AIS GSGGSTYYADSVKG</u>RFTISRDNSKNTLYLQMNSLRAEDTAVYYCAK<u>VGYDSS GYYRDYYGMDV</u>WGQGTTVTVSSGGGGSGGGGSGGGGSEIVLTQSPGTLSLSP GERATLSC<u>RASQSVSSSYLA</u>WYQQKPGQAPRLLIY<u>GTSSRAT</u>GISDRFSGSG SGTDFTLTISRLEPEDFAVYYC<u>QHYGNSPPKFTF</u>GPGTKLEIK | 222 |
| BCMA | EBB-1978-G4 (human) | EVQLVESGGGLVQPGGSLRLSCAAS<u>GFTFSSYAMS</u>WVRQAPGKGLEWVS<u>AIS GSGGSTYYADSVKG</u>RFTISRDNSKNTLYLQMNSLRAEDTAVYYCAK<u>MGWSSG YLGAFDI</u>WGQGTTVTVSSGGGGSGGGGSGGGGSEIVLTQSPGTLSLSPGERA TLSC<u>RASQSVASSFLA</u>WYQQKPGQAPRLLIY<u>GASGRAT</u>GIPDRFSGSGSGTD FTLTISRLEPEDFAVYYC<u>QHYGGSPRLTF</u>GGGTKVDIK | 223 |
| BCMA | humanized | Q V Q L V Q S G A E V K K P G S S V K V S C K A S G G T F S N Y W M H W V R Q A P G Q G L E W M G A T Y R G H S D T Y Y N Q K F K G R V T I T A D K S T S T A Y M E L S S L R S E D T A V Y Y C A R G A I Y N G Y D V L D N W G Q G T L V T V S S G G G G S G G G G S G G G G S G G S D I Q M T Q S P S S L S A S V G D R V T I T C S A S Q D I S N Y L N W Y Q Q K P G K A P K L L I Y Y T S N L H S G V P S R F S G S G S G T D F T L T I S S L Q P E D F A T Y Y C Q Q Y R K L P W T F G Q G T K L E I K R | 224 |
| BCMA | humanized | DIQMTQSPSS LSASVGDRVT ITCSASQDIS NYLNWYQQKP GKAPKLLIYY TSNLHSGVPS RFSGSGSGTD FTLTISSLQP EDFATYYCQQ YRKLPWTFGQ GTKLEIKRGG GGSGGGGSGG GGSGGGGSQV QLVQSGAEVK KPGSSVKVSC KASGGTFSNY WMHWVRQAPG QGLEWMGATY RGHSDTYYNQ KFKGRVTITA DKSTSTAYME LSSLRSEDTA VYYCARGAIY NGYDVLDNWG QGTLVTVSS | 225 |

TABLE 7-continued

Exemplary Antigen Binding Domains

| Target Antigen | Name | Amino Acid Sequence | SEQ ID NO: |
|---|---|---|---|
| CD33 | 141643 (human) | QVQLVQSGAEVKKPGESLKISCKGS<u>GYSFTSYWIG</u>WVRQMPGKGLEWMG<u>IIY PGDSDTRYSPSFQG</u>QVTISADKSISTAYLQWSSLKASDTAMYYCAR<u>LGGSLP DYGMDV</u>WGQGTMVTVSSASGGGGSGGGGSGGGGSEIVLTQSPLSLPVTGEP ASISC<u>RSSQSLLHSNGYNYLD</u>WYLQKPGQSPQLLIY<u>LGSNRAS</u>GVPDRFSGS GSGTDFTLKISRVEAEDVGVYYC<u>MQALQTLIT</u>FGQGTKVDIK | 226 |
| CD33 | 141644 (human) | QVQLVQSGAEVKKPGASVRVSCKAS<u>GYIFTNYYVH</u>WVRQAPGQGLEWMG<u>IIS PSGGSPTYAQRLQG</u>RVTMTRDLSTSTVYMELSSLTSEDTAVYFCAR<u>ESRLRG NRLGLQSSIFDH</u>WGQGTLVTVSSASGGGGSGGGGSGGGGSDIRMTQSPPSLS ASVGDRVTIPC<u>QASQDINNHLN</u>WYQQKPGKAPQLLIY<u>DTSNLEI</u>GVPSRFSG SGSGTDFTLTISSLQPEDIATYYC<u>QQYENLPLT</u>FGGGTKVEIK | 227 |
| CD33 | 141645 (human) | QVQLVQSGGGLVQPGGSLRLSCAAS<u>GFTFSSYAMS</u>WVRQAPGKGLEWVS<u>AIS GSGGSTYYADSVKG</u>RFTISRDNSKNTLYLQMNSLRAEDTAVYYCAKE<u>DTIRG PNYYYYGMDV</u>WGQGTTVTVSSASGGGGSGGGGSGGGGSETTLTQSPSSVSAS VGDRVSITC<u>RASQDIDTWLA</u>WYQLKPGKAPKLLMY<u>AASNLQG</u>GVPSRFSGSG SGTDFILTISSLQPEDFATYYC<u>QQASIFPPT</u>FGGGTKVDIK | 228 |
| CD33 | 141646 (human) | QVQLVQSGAEVKKPGESLKISCKGS<u>GYSFTSYWIG</u>WVRQMPGKGLEWMG<u>IIY PGDSDTRYSPSFQG</u>QVTISADKSITTAYLQWSSLRASDSAMYYCAR<u>GGYSDY DYYFDF</u>WGQGTLVTVSSASGGGGSGGGGSGGGGSEIVMTQSPLSLPVTPGEP ASISC<u>RSSQSLLHSNGYNYLD</u>WYLQKPGQSPQLLIY<u>LGSNRAS</u>GVPDRFSGS GSGTDFTLKISRVEAEDVGVYYC<u>MQALQTPFT</u>FGGGTKVEIK | 229 |
| CD33 | 141647 (human) | QVQLVQSGGDLAQPGRSLRLSCAAS<u>GFTFDDYAMH</u>WVRQAPGKGLEWVA<u>VIW PDGGQKYYGDSVKG</u>RFTVSRDNPKNTLYLQMNSLRAEDTAIYYCVR<u>HFNAWD YW</u>GQGTLVTVSSASGGGGSGGGGSGGGGSDIQLTQSPSSLSAYVGGRVTITC<u>QASQGISQFLN</u>WFQQKPGKAPKLLIS<u>DASNLEP</u>GVPSRFSGSGSGTDFTFTI TNLQPEDIATYYC<u>QQYDDLPLT</u>FGGGTKVEIK | 230 |
| CD33 | 141648 (human) | QVQLVQSGGGVVQPGKSLRLSCAAS<u>GFTFSIFAMH</u>WVRQAPGKGLEWVA<u>TIS YDGSNAFYADSVEG</u>RFTISRDNSKDSLYLQMDSLRPEDTAVYYCVK<u>AGDGGY DVFDS</u>WGQGTLVTVSSASGGGGSGGGGSGGGGSEIVMTQSPLSLPVTPGEPA SISC<u>RSSQSLLHSNGYNYLD</u>WYLQKPGQSPQLLIY<u>LGSNRAS</u>GVPDRFSGSG SGTDFTLKISRVEAEDVGVYYC<u>MQALQTPT</u>FGPGTKVDIK | 231 |
| CD33 | 141649 (human) | EVQLVESGGGLVQPGGSLRLSCAAS<u>GFTFSSYAMS</u>WVRQAPGKGLEWVS<u>AIS GSGGSTYYADSVKG</u>RFTISRDNSKNTLYLQMNSLRAEDTAVYYCAKE<u>TDYYG SGTFDY</u>WGQGTLVTVSSASGGGGSGGGGSGGGGSDIQMTQSPSSLSASVGDR VTISC<u>RASQGIGIYLAW</u>YQQRSGKPPQLLIH<u>GASTLQS</u>GVPSRFSGSGSGTD FTLTISSLQPEDFASYWC<u>QQSNNFPPT</u>FGQGTKVEIK | 232 |
| CD33 | 141650 (human) | QVQLVQSGAEVKKPGASVRVSCKAS<u>GYMFTDFFIH</u>WVRQAPGQGLEWMG<u>WIN PNSGVTKYAQKFQG</u>RVTMTRNTSISTAYMELSSLRSEDTAVYYCAT<u>WYSSGW YGIANI</u>WGQGTMVTVSSASGGGGSGGGGSGGGGSDIQLTQSPSSLSASVGDR VTITC<u>QASHDISNYLH</u>WYQQKPGKAPKLLIY<u>DASNLET</u>GVPSRFTGSGSGTD FTLTIRSLQPEDVAAYYC<u>QQSDDLPHT</u>FGQGTKVDIK | 233 |
| CD33 | 141651 (human) | QVQLVQSGAEVKKPGESLKISCKGS<u>GYSFTNYWIG</u>WVRQMPGKGLEWMG<u>IIY PGDSDTRYSPSFQG</u>QVTISADKSISTAYLQWSSLKASDTAMYYCAR<u>HGPSSW GEFDY</u>WGQGTLVTVSSASGGGGSGGGGSGGGGSDIRLTQSPSSLSASVGDRV TITC<u>RASQSISSYLN</u>WYQQKPGKAPKLLIY<u>AASSLQS</u>GVPSRFSGSGSGTDF TLTISSLQPEDFATYYC<u>QQSYSTPLT</u>FGGGTKVDIK | 234 |
| CD33 | 2213 (humanized) | NIMLTQSPSSLAVSAGEKVTMSCKSS<u>QSVFFSSSQKNYLA</u>WYQQIPGQSPKL LIY<u>WASTRES</u>GVPDRFTGSGSGTDFTLTISSVQSEDLAIYYC<u>HQYLSSRT</u>FG GGTKLEIKRGGGGSGGGGSSGGGSQVQLQQPGAEVVKPGASVKMSCKASGYT FTSYYIHWIKQTPGQGLEWVGVIYPGNDDISYNQKFKGKATLTADKSSTTAY MQLSSLTSEDSAVYYCAREVRLRYFDWGAGTTVTVSS | 235 |
| CD33 | My96 (humanized) | EIVLTQSPGSLAVSPGERVTMSCKSS<u>QSVFFSSSQKNYLA</u>WYQQIPGQSPRL LIY<u>WASTRES</u>GVPDRFTGSGSGTDFTLTISSVQPEDLAIYYC<u>HQYLSSRT</u>FG QGTKLEIKRGGGGSGGGGSSGGGSQVQLQQPGAEVVKPGASVKMSCKASGYT FTSYYIHWIKQTPGQGLEWVGVIYPGNDDISYNQKFQGKATLTADKSSTTAY MQLSSLTSEDSAVYYCAREVRLRYFDWGQGTTVTVSS | 236 |
| Claudin6 | muMAB64A | EVQLQQSGPELVKPGASMKISCKAS<u>GYSFTGYTMN</u>WVKQSHGKNLE WIG<u>LINPYNGGTIYNQKFKG</u>KATLTVDKSSSTAYMELLSLTSEDSA VYYCAR<u>DYGFVLDY</u>WGQGTTLTVSSGGGGSGGGGSGGGGSGGGGSQ IVLTQSPSIMSVSPGEKVTITC<u>SASSSVSYMH</u>WFQQKPGTSPKLCI Y<u>STSNLAS</u>GVPARFSGRGSGTSYSLTISRVAAEDAATYYC<u>QQRSNY PPWT</u>FGGGTKLEIK | 237 |

TABLE 7-continued

Exemplary Antigen Binding Domains

| Target Antigen | Name | Amino Acid Sequence | SEQ ID NO: |
|---|---|---|---|
| Claudin6 | mAb206-LCC | EVQLQQSGPELVKPGASMKISCKAS<u>GYSFTGYTMN</u>WVKQSHGKNLE WIGL<u>INPYNGGTIYNQKFKG</u>KATLTVDKSSSTAYMELLSLTSEDSA VYYCAR<u>DYGFVLDY</u>WGQGTTLTVSSGGGGSGGGGSGGGGSGGGGSQ IVLTQSPAIMSASPGEKVTITC<u>SASSSVSYLH</u>WFQQKPGTSPKLWV Y<u>STSNLPS</u>GVPARFGGSGSGTSYSLTISRMEAEDAATYYC<u>QQRSIY PPWT</u>FGGGTKLEIK | 238 |
| Claudin6 | mAb206-SUBG | EVQLQQSGPELVKPGASMKISCKAS<u>GYSFTGYTMN</u>WVKQSHGKNLE WIGL<u>INPYNGGTIYNQKFKG</u>KATLTVDKSSSTAYMELLSLTSEDSA VYYCAR<u>DYGFVLDY</u>WGQGTTLTVSSGGGGSGGGGSGGGGSGGGGSQ IVLTQSPSIMSVSPGEKVTITC<u>SASSSVSYMH</u>WFQQKPGTSPKLGI Y<u>STSNLAS</u>GVPARFGRGSGTSYSLTISRVAAEDAATYYC<u>QQRSNY PPWT</u>FGGGTKLEIK | 239 |
| WT1 | ESK-1 | QAVVTQPPSA SGTPGQRVTI SCSGSSSNIG SNTVNWYQQV PGTAPKLLIY SNNQRPSGVP DRFSGSKSGT SASLAISGLQ SEDEADYYCA AWDDSLNGWV FGGGTKLTVL GSRGGGGSGG GGSGGGGSLE MAQMQLVQSG AEVKEPGESL RISCKGSGYS FTNFWISWVR QMPGKGLEWM GRVDPGYSYS TYSPSFQGHV TISADKSTST AYLQWNSLKA SDTAMYYCAR VQYSGYYDWF DPWGQGTLVT VSS | 240 |
| WT1 | WT1-2 | QTVVTQPPSA SGTPGQRVTI SCSGSSSNIG SNYVYWYQQL PGTAPKLLIY RSNQRPSGVP DRFSGSKSGT SASLAISGPR SVDEADYYCA AWDDSLNGVV FGGGTKLTVL GSRGGGGSGG GGSGGGGSLEM AQVQLVQSGA EVKPGSSVK VSCKASGGTF SSYAISWVRQ APGQGLEWMG GIIPIFGTAN YAQKFQGRVT ITADESTSTA YMELSSLRSE DTAVYYCARR IPPYYGMDVW GQGTTVTVSS | 241 |
| WT1 | WT1-3 | DIQMTQSPSS LSASVGDRVT ITCRASQSIS SYLNWYQQKP GKAPKLLIYA ASSLQSGVPS RFSGSGSGTD FTLTISSLQP EDFATYYCQQ SYSTPLTFGG GTKVDIKRSR GGGGSGGGGS GGGGSLEMAQ VQLQQSGPGL VKPSQTLSLT CAISGDSVSS NSAAWNWIRQ SPSRGLEWLG RTYYGSKWYN DYAVSVKSRI TINPDTSKNQ FSLQLNSVTP EDTAVYYCAR GRLGDAFDIW GQGTMVTVSS | 242 |
| WT1 | WT1-4 | DIQMTQSPST LSASVGDRVT ITCRASQNIN KWLAWYQQRP GKAPQLLIYK ASSLESGVPS RFSGSGSGTE YTLTISSLQP DDFATYYCQQ YNSYATFGQG TKVEIKRSRG GGGSGGGGSG GGGSLEMAQV QLVQSGAEVK KPGESLKISC KGSGYNFSNK WIGWVRQLPG RGLEWIAIIY PGYSDITYSP SFQGRVTISA DTSINTAYLH WHSLKASDTA MYYCVRHTAL AGFDYWGLGT LVTVSS | 243 |
| WT1 | WT1-5 | QSVVTQPPSV SVAPGKTARI TCGRNNIGSK SVHWYQQKPG QAPVLVVYDD SDRPSGIPER FSGSNSGNTA TLTISRVEAG DEADYYCQVW DSSSDHVVFG GGTKLTVLGS RGGGGSGGGG SGGGSLEMAEV QLVQSGGGVV RPGGSLRLSC AASGFTFDDY GMSWVRQAPG KGLEWVSGIN WNGGSTGYAD SVRGRFTISR DNAKNSLYLQ MNSLRAEDTA LYYCARERGY GYHDPHDYWG QGTLVTVSS | 244 |
| WT1 | WT1-6 | QSVLTQPPSV SGAPGQRVTI SCTGSSSNIG AGYDVHWYQQ LPGTAPKLLI YGNSNRPSGV PDRFSGSKSG TSASLAISGL QSEDEADYYC AAWDDSLNGY VFGTGTKLTV LGSRGGGGSG GGSGGGGSL EMAEVQLVET GGGLLQPGGS LRLSCAASGF SVSGTYMGWV RQAPGKGLEW VALLYSGGGT YHPASLQGRF IVSRDSSKNM VYLQMNSLKA EDTAVYYCAK GGAGGGHFDS WGQGTLVTVS S | 245 |

TABLE 7-continued

Exemplary Antigen Binding Domains

| Target Antigen | Name | Amino Acid Sequence | SEQ ID NO: |
|---|---|---|---|
| WT1 | WT1-7 | EVQLLESGGG LVQPGGSLRL SCAASGFTFS SYAMSWVRQA PGKGLEWVSQ IDPWGQETLY ADSVKGRFTI SRDNSKNTLY LQMNSLRAED TAVYYCAKLT GRFDYWGQGT LVTVSSGGGG SGGGGSGGGG STDIQMTQSP SSLSASVGDR VTITCRASQS ISSYLNWYQQ KPGKAPKLLI YSASQLQSGV PSRFSGSGSG TDFTLTISSL QPEDFATYYC QQGPGTPNTF GQGTKVEIKR A | 246 |

In an embodiment, the antigen binding domain comprises an anti-CD19 antibody, or fragment thereof, e.g., an scFv. For example, the antigen binding domain comprises a variable heavy chain and a variable light chain listed in Table 12. The linker sequence joining the variable heavy and variable light chains can be any of the linker sequences described herein, or alternatively, can be GSTSGSGKPGSGEGSTKG (SEQ ID NO: 247).

In some embodiments, the antigen binding domain comprises a HC CDR1, a HC CDR2, and a HC CDR3 of any heavy chain binding domain amino acid sequences listed in Table 7. In embodiments, the antigen binding domain further comprises a LC CDR1, a LC CDR2, and a LC CDR3. In embodiments, the antigen binding domain comprises a LC CDR1, a LC CDR2, and a LC CDR3 of any light chain binding domain amino acid sequences listed in Table 7.

In some embodiments, the antigen binding domain comprises one, two or all of LC CDR1, LC CDR2, and LC CDR3 of any light chain binding domain amino acid sequences listed in Table 7, and one, two or all of HC CDR1, HC CDR2, and HC CDR3 of any heavy chain binding domain amino acid sequences listed in Table 7.

In some embodiments, the CDRs are defined according to the Kabat numbering scheme, the Chothia numbering scheme, or a combination thereof.

In embodiments, the order in which the VL and VH domains appear in the scFv is varied (i.e., VL-VH, or VH-VL orientation), and where either three or four copies of the "G4S" (SEQ ID NO:35) subunit, in which each subunit comprises the sequence GGGGS (SEQ ID NO:35) (e.g., (G4S)3 (SEQ ID NO:37) or (G4S)4 (SEQ ID NO:36)), connect the variable domains to create the entirety of the scFv domain. Alternatively, the CAR construct can include, for example, a linker including the sequence GSTSGSGKPGSGEGSTKG (SEQ ID NO: 247).

Exemplary sequences of various scFv fragments and other CAR components are provided herein. It is noted that these CAR components (e.g., of SEQ ID Nos. 11 and 260) without a leader sequence (e.g., without the amino acid sequence of SEQ ID NO: 277 or the nucleotide sequence of SEQ ID NO:278), are also provided herein.

Leader sequences are provided as:

leader (amino acid sequence):

(SEQ ID NO: 273)
MALPVTALLLPLALLLHAARP leader (nucleic acid sequence):

(SEQ ID NO: 274)
ATGGCCCTGCCTGTGACAGCCCTGCTGCTGCCTCTGGCTCTGCTGCTGC

ATGCCGCTAGACCC

In embodiments, the CAR sequences described herein contain a Q/K residue change in the signal domain of the co-stimulatory domain derived from CD3zeta chain.

TABLE 12

Anti-CD 19 antibody binding domains

| Antibody | VH Sequence | VL Sequence |
|---|---|---|
| SJ25-C1 | QVQLLESGAELVRPGSSVKISCKASGYAF SSYWMNWVKQRPGQGLEWIGQIYPGDGDT NYNGKFKGQATLTADKSSSTAYMQLSGLT SEDSAVYSCARKTISSVVDFYFDYWGQGT TVT (SEQ ID NO: 248) | ELVLTQSPKFMSTSVGDRVSVTCKASQNVGT NVAWYQQKPGQSPKPLIYSATYRNSGVPDRF TGSGSGTDFTLTITNVQSKDLADYFYFCQYN RYPYTSGGGTKLEIKRRS (SEQ ID NO: 249) |

Any known CD19 CAR, e.g., the CD19 antigen binding domain of any known CD19 CAR, in the art can be used in accordance with the instant invention. For example, LG-740; CD19 CAR described in the U.S. Pat. Nos. 8,399, 645; 7,446,190; Xu et al., Leuk Lymphoma. 2013 54(2): 255-260 (2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39 (2013); and 16th Annu Meet Am Soc Gen Cell Ther (ASGCT) (May 15-18, Salt Lake City) 2013, Abst 10.

In one embodiment, the portion of the CAR comprising the antigen binding domain comprises an antigen binding domain that targets CD19. In one aspect, the antigen binding domain targets human CD19. In one aspect, the antigen binding domain of the CAR has the same or a similar binding specificity as the FMC63 scFv fragment described in Nicholson et al. Mol. Immun. 34 (16-17): 1157-1165 (1997). In one embodiment, the antigen binding domain of the CAR includes the scFv fragment described in Nicholson et al. Mol. Immun. 34 (16-17): 1157-1165 (1997). A CD19 antibody molecule can be, e.g., an antibody molecule (e.g., a humanized anti-CD19 antibody molecule) described in WO2014/153270, which is incorporated herein by reference in its entirety. WO2014/153270 also describes methods of assaying the binding and efficacy of various CART constructs.

In one aspect, the parental murine scFv sequence is the CAR19 construct provided in PCT publication WO2012/079000 (incorporated herein by reference) and provided herein as SEQ ID NO:129. In one embodiment, the anti-CD19 binding domain is a scFv described in WO2012/079000 and provided in SEQ ID NO:129.

In one aspect, the CAR comprises the polypeptide sequence provided as SEQ ID NO: 12 in PCT publication WO2012/079000, and provided herein as SEQ ID NO: 260, wherein the scFv domain is substituted by one or more sequences selected from SEQ ID NOS: 117-128. In one aspect, the scFv domains of SEQ ID NOS: 117-128 are humanized variants of the scFv domain of SEQ ID NO:129, which is an scFv fragment of murine origin that specifically binds to human CD19. Humanization of this mouse scFv may be desired for the clinical setting, where the mouse-specific residues may induce a human-anti-mouse antigen (HAMA) response in patients who receive CART19 treatment, e.g., treatment with T cells transduced with the CAR19 construct.

The CD19 CAR provided as SEQ ID NO: 12 in PCT publication WO2012/079000 is:

```
                                          (SEQ ID NO: 260)
MALPVTALLLPLALLLHAARPdiqmtqttsslsaslgdrvtiscrasqdi skylnwyqqkpdgtvklliyhtsrlhsgvpsrfsgsgsgtdysltisnle qediatyfcqqgntlpytfgggtkleitgggsggggsggggsevklqes gpglvapsqslsvtctvsgvslpdygvswirqpprkglewlgviwgsett yynsalksrltiikdnsksqvflkmnslqtddtaiyycakhyyyggsyam dywgqgtsvtvsstttpaprpptpaptiasqplslrpeacrpaaggavht rgldfacdiyiwaplagtcgvlllslvitlyckrgrkkllyifkqpfmrp vqttqeedgcscrfpeeeeggcelrvkfsrsadapaykqgqnqlynelnl grreeydvldkrrgrdpemggkprrknpqeglynelqkdkmaeayseigm kgerrrgkghdglyqglstatkdtydalhmqalppr
```

Cancer Associated Antigens

The present invention provides immune effector cells (e.g., T cells, NK cells) that are engineered to contain one or more CARs that direct the immune effector cells to cancer cells. This can be achieved through a binding domain on CARs that are specific for cancer associated antigens. There are two classes of cancer associated antigens (tumor markers or antigens) can be targeted by the CARs of the instant invention: (1) cancer associated antigens that are expressed on the surface of cancer cells; and (2) cancer associated antigens that itself is intracellular, however, a fragment of such antigen (peptide) is presented on the surface of the cancer cells by MHC (major histocompatability complex).

Accordingly, the present invention provides CARX's, e.g., CARTs, that target, e.g., the following cancer associated antigens (tumor markers): CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor beta, TEM1/CD248, TEM7R, CLDN6, TSHR, GPRCSD, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6,E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In some embodiments, the tumor antigen is a tumor antigen described in International Application PCT/US2015/020606, which is herein incorporated by reference in its entirety. In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, tumor antigen bound by the encoded CAR molecule is chosen from one or more of: TSHR, CD171, CS-1, CLL-1, GD3, Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene), NA17, PAX3, Androgen receptor, Cyclin B1, MYCN, RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In certain embodiments, the tumor antigen bound by the encoded CAR molecule is chosen from one or more of: TSHR, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, and OR51E2.

A CAR as described herein includes a CAR comprising an antigen binding domain (e.g., antibody or antibody fragment) that binds to a MHC presented-peptide. Normally, peptides derived from endogenous proteins fill the pockets of Major histocompatability complex (MHC) class I molecules, and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Bood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library. Accordingly, the present invention provides a CAR, e.g., a RCAR described herein, that comprises an antigen binding domain that binds to a MHC presented peptide of a molecule selected from any tumor antigen described above that is expressed intracellularly, e.g., p53, BCR-Abl, Ras, K-ras, and c-met.

Non-Antibody Scaffolds

In embodiments, the antigen binding domain comprises a non antibody scaffold, e.g., a fibronectin, ankyrin, domain antibody, lipocalin, small modular immuno-pharmaceutical, maxybody, Protein A, or affilin. The non antibody scaffold has the ability to bind to target antigen on a cell. In embodiments, the antigen binding domain is a polypeptide or fragment thereof of a naturally occurring protein expressed on a cell. In some embodiments, the antigen binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

Fibronectin scaffolds can be based on fibronectin type III domain (e.g., the tenth module of the fibronectin type III ($^{10}$Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). Because of this structure, this non-antibody scaffold mimics antigen binding properties that are similar in nature and affinity to those of antibodies. These scaffolds can be used in a loop randomization and shuffling strategy in vitro that is similar to the process of affinity maturation of antibodies in vivo.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as HER3. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies; they have a molecular weight of 6 kDa, compared to the molecular weight of antibodies, which is 150 kDa. In spite of its small size, the binding site of affibody molecules is similar to that of an antibody.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

An antigen binding domain can comprise a single domain antibody, e.g., which relies only on a heavy chain variable region for binding, e.g., a nanobody. Nanobodies suitable for use herein can be made by the methods described in US2010/0028341, WO2009/030285, and WO2010/007376.

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005, 079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH (VH1) upstream of its VL (VL1) and the downstream antibody or antibody fragment (e.g., scFv) is arranged with its VL (VL2) upstream of its VH (VH2), such that the overall bispecific antibody molecule has the arrangement VH1-VL1-VL2-VH2. In other embodiments, the upstream antibody or antibody fragment (e.g., scFv) is arranged with its VL (VL1) upstream of its VH (VH1) and the downstream antibody or antibody fragment (e.g., scFv) is arranged with its VH (VH2) upstream of its VL (VL2), such that the overall bispecific antibody molecule has the arrangement VL1-VH1-VH2-VL2. Optionally, a linker is disposed between the two antibodies or antibody fragments (e.g., scFvs), e.g., between VL1 and VL2 if the construct is arranged as VH1-VL1-VL2-VH2, or between VH1 and VH2 if the construct is arranged as VL1-VH1-VH2-VL2. The linker may be a linker as described herein, e.g., a $(Gly_4\text{-}Ser)_n$ linker, wherein n is 1, 2, 3, 4, 5, or 6, preferably 4 (SEQ ID NO: 36). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for a first cancer-associated antigen, e.g., comprises a scFv as described herein, e.g., as described in Table 7, or comprises the light chain CDRs and/or heavy chain CDRs from a scFv described herein, and a second immunoglobulin variable domain sequence that has binding specificity for a second epitope on a different antigen. In some aspects the second immunoglobulin variable domain sequence has binding specificity for an antigen expressed on AML cells. For example, the second immunoglobulin variable domain sequence has binding specificity for CD123. As another example, the second immunoglobulin variable domain sequence has binding specificity for CD33. As another example, the second immunoglobulin variable domain sequence has binding specificity for CLL-1. As another example, the second immunoglobulin variable domain sequence has binding specificity for CD34. As another example, the second immunoglobulin variable domain sequence has binding specificity for FLT3. For example, the second immunoglobulin variable domain sequence has binding specificity for folate receptor beta. In some aspects, the second immunoglobulin variable domain sequence has binding specificity for an antigen expressed on B-cells, for example, CD19, CD20, CD22 or ROR1.

Chimeric TCR

In one aspect, the antibodies and antibody fragments disclosed herein (for example, those disclosed in Table 7) can be grafted to one or more constant domain of a T cell receptor ("TCR") chain, for example, a TCR alpha or TCR beta chain, to create an chimeric TCR that binds specifically to a cancer associated antigen. Without being bound by theory, it is believed that chimeric TCRs will signal through the TCR complex upon antigen binding. For example, an scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, an antibody fragment, for example a VL domain as described herein, can be grafted to the constant domain of a TCR alpha chain, and an antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of an antibody or antibody fragment, e.g., the CDRs of an antibody or antibody fragment as described in Table 3 may be grafted into a TCR alpha and/or beta chain to create a chimeric TCR that binds specifically to a cancer associated antigen. For example, the LC CDRs disclosed herein may be grafted into the variable domain of a TCR alpha chain and the HC CDRs disclosed herein may be grafted to the variable domain of a TCR beta chain, or vice versa. Such chimeric TCRs may be produced by any appropriate method (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Mismatched Antigen Binding Domains

It has been discovered, that cells having a plurality of CARs each comprising an antigen binding domain that interactions between the antigen binding domain of the CARs can be undesirable, e.g., because it inhibits the ability of one or more of the antigen binding domains to bind its cognate antigen. Accordingly, disclosed herein are a first and a second CAR, comprising antigen binding domains that minimize such interactions when expressed in the same cell. In an embodiment, the antigen binding domain of one or both CARs was added by sortase mediated addition. In an embodiment, one or both CARs comprises a sortase transfer signature.

In some embodiments, the first CAR and/or the second CAR bind the same or different targets. In some embodiments, the target or targets are chosen from CD19, CD123, CD22, CD30, CD34, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRCSD, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6,E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

In one embodiment, when the CARX cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence or a non-antibody scaffold. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of said first CAR said second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CMER.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

Natural Killer Cell Receptor (NKR) Cars

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CARX cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CARX cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CARX cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CARX cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins $\alpha v\beta 3$, $\alpha 4$, $\alpha I3/4\beta 3$, $\alpha 4\beta 7$, $\alpha 5\beta 1$, $\alpha v\beta 3$, $\alpha v$), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD1 1, CD1 1a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CARX cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8)853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8) 1277-1287). Other methods for depleting CAR-expressing cells described herein include administration of CAMPATH®, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g., ADCC or ADC activities, thereby reducing the number of CAR-expressing cells. In other embodiments, the CAR ligand, e.g., the anti-idiotypic antibody can be coupled to an agent that induces cell killing, e.g., a toxin, thereby reducing the number of CAR-expressing cells. In other embodiments, CAR-expressing cells can be selectively targeted using a CAR ligand, e.g., an anti-idiotypic antibody. In some embodiments, the anti-idiotypic antibody can cause effector cell activity, e.g, ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In an aspect, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. In one embodiment, the CARs of the present invention utilizes a dimerization switch as those described in, e.g., WO2014127261, which is incorporated by reference herein. Additional description and exemplary configurations of such regulatable CARs are provided herein and in International Publication No. WO 2015/090229, hereby incorporated by reference in its entirety.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets CD19, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed). In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 4-1BB, CD28, CD27, ICOS, and OX40, and in embodiments, no primary intracellular signaling domain. In an embodiment, the antigen binding member comprises the following costimulatory signaling domains, from the extracellular to intracellular direction: 4-1BB-CD27; 4-1BB-CD27; CD27-4-1BB; 4-1BB-CD28; CD28-4-1BB; OX40-CD28; CD28-OX40; CD28-4-1BB; or 4-1BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 4-1BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) Identification of an 11-kDa FKBP12-rapamycin-binding domain within the 289-kDa FKBP12-rapamycin-associated protein and characterization of a critical serine residue. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

```
FKBP
                                        (SEQ ID NO: 5)
D V P D Y A S L G G P S S P K K K R K V S R G V Q

V E T I S P G D G R T F P K R G Q T C V V H Y T G

M L E D G K K F D S S R D R N K P F K F M L G K Q

E V I R G W E E G V A Q M S V G Q R A K L T I S P

D Y A Y G A T G H P G I I P P H A T L V F D V E L

L K L E T S Y
```

In embodiments, an FKBP switch domain can comprise a FRB binding fragment of FKBP, e.g., the underlined portion of SEQ ID NO: 5, which is:

```
                                        SEQ ID NO: 6
V Q V E T I S P G D G R T F P K R G Q T C V V H Y

T G M L E D G K K F D S S R D R N K P F K F M L G

K Q E V I R G W E E G V A Q M S V G Q R A K L T I

S P D Y A Y G A T G H P G I I P P H A T L V F D V

E L L K L E T S.
```

The sequence of FRB is as follows:

```
                                        (SEQ ID NO: 7)
ILWHEMWHEG LEEASRLYFG ERNVKGMFEV LEPLHAMMER

GPQTLKETSF NQAYGRDLME AQEWCRKYMK SGNVKDLTQA

WDLYYHVFRR ISK
```

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 5 or 6; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 7. In an embodiment, a RCAR described herein comprises one switch domain comprises amino acid residues disclosed in SEQ ID NO: 5 (or SEQ ID NO: 6), and one switch domain comprises amino acid residues disclosed in SEQ ID NO: 7.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), e.g., SEQ ID NO: 252, or leucine (E2032L), e.g., SEQ ID NO: 253. In an embodiment, a mutant FRB comprises a mutation at T2098, where T2098 is mutated to phenylalanine (T2098F) or leucine (T2098L), e.g., SEQ ID NO: 254. In an embodiment, a mutant FRB comprises a mutation at E2032 and at T2098, where E2032 is mutated to any amino acid, and where T2098 is mutated to any amino acid, e.g., SEQ ID NO: 255. In an embodiment, a mutant FRB comprises an E2032I and a T2098L mutation, e.g., SEQ ID NO: 256. In an embodiment, a mutant FRB comprises an E2032L and a T2098L mutation, e.g., SEQ ID NO: 257.

TABLE 14

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETS FNQAYGRDLMEAQEWCRKYMKSGNVKDLTQAWDLYYHVFRRISKTS | 252 |
| E2032L mutant | ILWHEMWHEGLLEASRLYFGERNVKGMFEVLEPLHAMMERGPQTLKETS FNQAYGRDLMEAQEWCRKYMKSGNVKDLTQAWDLYYHVFRRISKTS | 253 |
| T2098L mutant | ILWHEMWHEGLEEASRLYFGERNVKGMFEVLEPLHAMMERGPQTLKETS FNQAYGRDLMEAQEWCRKYMKSGNVKDLLQAWDLYYHVFRRISKTS | 254 |
| E2032, T2098 mutant | ILWHEMWHEGLXEASRLYFGERNVKGMFEVLEPLHAMMERGPQTLKETS FNQAYGRDLMEAQEWCRKYMKSGNVKDLXQAWDLYYHVFRRISKTS | 255 |
| E2032I, T2098L mutant | ILWHEMWHEGLIEASRLYFGERNVKGMFEVLEPLHAMMERGPQTLKETS FNQAYGRDLMEAQEWCRKYMKSGNVKDLLQAWDLYYHVFRRISKTS | 256 |

TABLE 14-continued

Exemplary mutant FRB having increased affinity for a dimerization molecule.

| FRB mutant | Amino Acid Sequence | SEQ ID NO: |
|---|---|---|
| E2032L, T2098L mutant | ILWHEMWHEGLLEASRLYFGERNVKGMFEVLEPLHAMMERGPQTLKETS FNQAYGRDLMEAQEWCRKYMKSGNVKDLLQAWDLYYHVFRRISKTS | 257 |

In an embodiment, a mutant FRB comprises a sequence of SEQ ID NO: 8 as follows:

FRB (T2098L)
(SEQ ID NO: 8)
M A S R I L W H E M W H E G L E E A S R L Y F G E
R N V K G M F E V L E P L H A M M E R G P Q T L K
E T S F N Q A Y G R D L M E A Q E W C R K Y M K S
G N V K D L L Q A W D L Y Y H V F R R I S K T S

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

In an embodiment, a Halotag/SNAP-tag dimerization comprises a first switch domain comprising a Halo-Tag moiety, e.g., SEQ ID NO: 9, or a functional derivative or fragment thereof, and a second switch domain comprising a SNAP-Tag, e.g., SEQ ID NO: 10, or a functional derivative or fragment thereof. In embodiments the dimerization molecule comprises functional groups for linking a Halo-Tag with a SNAP-Tag along with a cell penetrating core.

A Halo-tag Domain
(SEQ ID NO: 9)
Gseigtgfpfdphyvevlgermhyvdvgprdgtpvlflhgnptssyvwrn iiphvapthrciapdligmgksdkpdlgyffddhvrfmdafiealgleev vlvihdwgsalgfhwakrnpervkgiafmefirpiptwdewpefaretfq afrttdvgrkliidqnvfiegtlpmgvvrpltevemdhyrepflnpvdre plwrfpnelpiagepanivalveeymdwlhqspvpkllfwgtpgvlippa eaarlakslpnckavdigpglnllqednpdligseiarwlstleisg A SNAP-tag domain
(SEQ ID NO: 10)
Mdkdcemkrttldsplgklelsgceqglhriiflgkgtsaadavevpapa avlggpeplmqatawlnayfhqpeaieefpvpalhhpvfqqesftrqvlw kllkvvkfgevisyshlaalagnpaataavktalsgnpvpilipchrvvq gdldvggyegglavkewllaheghrlgkpglg Dimerization Molecule Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "mTOR inhibitors".

Split CAR

In some embodiments, the CARX cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 4-1BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CARX cell is only fully activated in the presence of both antigens. In embodiments, the first antigen binding domain recognizes a cancer associated antigen described herein (e.g., CD19, CD123, CD22, CD30, CD34, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor beta, TEM1/CD248, TEM7R, CLDN6, TSHR, GPRCSD, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6,E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1).

RNA Transfection

Disclosed herein are methods for producing an in vitro transcribed RNA encoding a polypeptide described herein, e.g., a RNA encoding a sortase acceptor member, or RNA encoding an antigen binding domain and a sortase recognition motif. The present invention also includes a RNA construct, e.g., encoding a CAR, that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the CAR.

In one aspect the anti-CARs of the present invention is encoded by a messenger RNA (mRNA). In one aspect the mRNA encoding the anti-CARs of the present invention is introduced into an immune effector cell, e.g., a T cell or NK cell, for production of a CARX cell, e.g., a CART cell or a CAR NK.

In one embodiment, the in vitro transcribed RNA can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription can be, e.g., a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail, e.g., having a length of 50-5000 nucleotides, or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines nucleotides.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotide results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a polypeptide described herein, e.g., a CAR, a sortase acceptor member, or an antigen binding domain comprising a sortase recognition motif, into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1 (2011):R14-20; Singh et al. Cancer Res. 15 (2008):2961-2971; Huang et al. Mol. Ther. 16(2008):580-589; Grabundzija et al. Mol. Ther. 18 (2010):1200-1209; Kebriaei et al. Blood. 122.21 (2013): 166; Williams. Molecular Therapy 16.9 (2008):1515-16; Bell et al. Nat. Protoc. 2.12 (2007):3153-65; and Ding et al. Cell. 122.3 (2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3 (2013): 1829-47; and Singh et al. Cancer Res. 68.8 (2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a polypeptide described herein, e.g., a CAR. Provided herein are methods of generating a cell, e.g., T cell or NK cell, that stably expresses a polypeptide described herein, e.g., a CAR, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Intracellular Signaling Domains

Both RCARs and uCARs comprise intracellular signaling domains.

In embodiments, an intracellular signaling domain produces an intracellular signal when an extracellular domain, e.g., an antigen binding domain, to which it is fused, or coupled by a dimerization switch, binds a counter ligand. Intracellular signaling domains can include primary intracellular signaling domains and costimulatory signaling domains. In an embodiment, a CAR molecule can be constructed for expression in an immune cell, e.g., a T cell, such that the CAR molecule comprises a domain, e.g., a primary intracellular signaling domains, costimulatory signaling domain, inhibitory domains, etc., that is derived from a polypeptide that is typically associated with the immune cell. For example, a CAR for expression in a T cell can comprise a 4-1BB domain and a CD3 zeta domain. In this instance, both the 4-1BB and CD3 zeta domains are derived from polypeptides associated with the T cell. In another embodiment, a CAR molecule can be constructed for expression in an immune cell e.g., a T cell, such that the CAR molecule comprises a domain that is derived from a polypeptide that is not typically associated with the immune cell. For example, a CAR for expression in a T cell can comprise a KIR domain derived from a NK cell. Alternatively, a CAR for expression in a NK cell can comprise a 4-1BB domain and a CD3 zeta domain derived from a T cell (See e.g. WO2013/033626, incorporated herein by reference).

Primary Intracellular Signaling Domain

In an embodiment a primary intracellular signaling domain produces an intracellular signal when an extracellular domain, e.g., an antigen binding domain, to which it is fused, or coupled by a dimerization switch, binds cognate antigen. It is derived from a primary stimulatory molecule, e.g., it comprises intracellular sequence of a primary stimulatory molecule. It comprises sufficient primary stimulatory molecule sequence to produce an intracellular signal, e.g., when an antigen binding domain to which it is fused, or coupled by a dimerization switch, binds cognate antigen.

A primary stimulatory molecule, is a molecule, that upon binding cognate ligand, mediates an immune effector response, e.g., in the cell in which it is expressed. Typically, it generates an intracellular signal that is dependent on binding to a cognate ligand that comprises antigen. The TCR/CD3 complex is an exemplary primary stimulatory molecule; it generates an intracellular signal upon binding to cognate ligand, e.g., an MHC molecule loaded with a peptide. Typically, e.g., in the case of the TCR/CD3 primary stimulatory molecule, the generation of an intracellular signal by a primary intracellular signaling domain is dependent on binding of the primary stimulatory molecule to antigen.

Primary stimulation can mediate altered expression of certain molecules, such as downregulation of TGF-$\beta$, and/or reorganization of cytoskeletal structures, and the like. Stimulation, can, e.g., in the presence of costimulation, result in an optimization, e.g., an increase, in an immune effector function of the CARX cell, e.g., CART cell. Stimulation, e.g., in the context of a CART cell, can mediate a T cell response, e.g., proliferation, activation, differentiation, and the like.

In an embodiment, the primary intracellular signaling domain comprises a signaling motif, e.g., an immunoreceptor tyrosine-based activation motif or ITAMs. A primary intracellular signaling domain can comprise ITAM containing cytoplasmic signaling sequences from TCR zeta (CD3 zeta), FcR gamma, FcR beta, CD3 gamma, CD3 delta, CD3 epsilon, CD5, CD22, CD79a, CD79b, CD278 (also known as "ICOS") and CD66d.

Exemplary primary intracellular signaling domains are provided in Table 8.

TABLE 8

Primary Intracellular Signaling Domains In embodiments the domain comprises an ITAM TCR zeta
FcR gamma
FcR beta
CD3 gamma
CD3 delta
CD3 epsilon
CD3 zeta
CD5
CD22
CD79a
CD79b
CD66d
DAP10
DAP12
CD32

A primary intracellular signaling domain comprises a functional fragment, or analog, of a primary stimulatory molecule (e.g., CD3 zeta—GenBank acc no. BAG36664.1). It can comprise the entire intracellular region or a fragment of the intracellular region which is sufficient for generation of an intracellular signal when an antigen binding domain to which it is fused, or coupled by a dimerization switch, binds cognate antigen. In embodiments the primary intracellular signaling domain has at least 70, 75. 80. 85, 90, 95, 98, or 99% sequence identity with a naturally occurring primary stimulatory molecule, e.g., a human (GenBank Acc. No. BAG36664.1), or other mammalian, e.g., a nonhuman species, e.g., rodent, monkey, ape or murine intracellular primary stimulatory molecule. In embodiments the primary intracellular signaling domain has at least 70, 75. 80. 85, 90, 95, 98, or 99% sequence identity with SEQ ID NO: 3.

In embodiments the primary intracellular signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human primary stimulatory molecule, e.g., a naturally occurring human primary stimulatory molecule disclosed herein.

Costimulatory Signaling Domain

Embodiments of RCARs and uCARs comprise costimulatory signaling domains.

In an embodiment, a costimulatory signaling domain produces an intracellular signal when an extracellular domain, e.g., an antigen binding domain to which it is fused, or coupled by a dimerization switch, binds cognate ligand. It is derived from a costimulatory molecule. It comprises sufficient primary costimulatory molecule sequence to produce an intracellular signal, e.g., when an extracellular domain, e.g., an antigen binding domain, to which it is fused, or coupled by a dimerization switch, binds cognate ligand.

Costimulatory molecules are cell surface molecules, other than antigen receptors or their counter ligands that promote an immune effector response. In some cases they are required for an efficient or enhanced immune response. Typically, a costimulatory molecule generates an intracellular signal that is dependent on binding to a cognate ligand that is, in embodiments, other than an antigen, e.g., the antigen recognized by an antigen binding domain of a CARX cell, e.g., CART cell. Typically, signaling from a primary stimulatory molecule and a costimulatory molecule contribute to an immune effector response, and in some cases both are required for efficient or enhanced generation of an immune effector response.

A costimulatory domain comprises a functional fragment, or analog, of a costimulatory molecule (e.g., 4-1BB). It can comprise the entire intracellular region or a fragment of the intracellular region which is sufficient for generation of an intracellular signal, e.g., when an antigen binding domain to which it is fused, or coupled by a dimerization switch, binds cognate antigen. In embodiments the costimulatory domain has at least 70, 75, 80. 85, 90, 95, 98, or 99% sequence identity with a naturally occurring costimulatory molecule, e.g., a human, or other mammalian, e.g., a nonhuman species, e.g., rodent, monkey, ape or murine intracellular costimulatory molecule. In embodiments the costimulatory domain has at least 70, 75. 80. 85, 90, 95, 98, or 99% sequence identity with SEQ ID NO: 2.

Exemplary costimulatory signaling domains (intracellular signaling domains) are provided in Table 9.

TABLE 9

Costimulatory Signaling Domains for RCARX (identified by the Costimulatory Molecules from which they are derived)

CD27
CD28
4-1BB (CD137)
OX40
CD30
CD40
ICOS (CD278)
ICAM-1
LFA-1 (CD11a/CD18)
CD2
CD7
LIGHT
NKG2C
B7-H3
a ligand that specifically binds with CD83
CDS
GITR
BAFFR
HVEM (LIGHTR)
SLAMf7
NKP80 (KLRF1)
NKp44, NKp30, NKp46
CD160 (BY55)
CD19
CD4
CD8 alpha
CD8 beta
IL2R beta
IL2R gamma
IL7R alpha
ITGA4
VLA1
CD49a
ITGA4
IA4
CD49D
ITGA6
VLA-6
C49f
ITGAD
CD11d
ITGAE
CD103
ITGAL
CD11a
LFA-1
ITGAM
CD11b
ITGAX
CD11c
ITGB1
CD29
ITGB2
CD18
ITGB7
TNFR2
TRANCE/RANKL
DNAM1 (CD226)
SLAMF4 (C244, 2B4)
CD84
CD96 (Tactile)
CEACAM1
CRTAM
Ly9 (CD229)
PSGL1
C100 (SEMA4D)
CD69
SLAMF6 (NTB-A, Ly108)
SLAM (SLAMF1, CD150, IPO-3)
BLAME (SLAMF8)
SELPLG (CD162)
LTBR
LAT
GADS
SLP-76

TABLE 9-continued

Costimulatory Signaling Domains for RCARX (identified by
the Costimulatory Molecules from which they are derived)

PAG/Cbp
NKG2D
NKG2C

In embodiments the costimulatory signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human primary stimulatory molecule, e.g., a naturally occurring human costimulatory molecule disclosed herein.

Auxiliary Antigen Binding Member

A sortase based method can be used to attach an antigen binding domain to other elements of an auxiliary antigen binding member. In an embodiment, an auxiliary antigen binding member comprises a sortase transfer signature, e.g., disposed between an antigen binding domain and a transmembrane domain.

An auxiliary antigen binding member can be included in a CAR. In embodiments, its inclusion can increase the safety and efficacy of the CARX cell, e.g., by increasing specificity by the binding to an additional, e.g., second target cell antigen. In embodiments, binding of both the antigen binding member, and the auxiliary antigen binding member can give greater specificity than seen with either alone. In embodiments the CAR will include two, three, four, five, six, seven, eight, nine, or ten, auxiliary antigen binding members, all of which bind different antigens.

In an embodiment the auxiliary antigen binding domain does not comprise a switch domain that can form a dimerization switch with a switch domain on the antigen binding member or the intracellular signaling member. In embodiments the auxiliary antigen binding domain does not comprise an intracellular signaling domain. In an embodiment, the antigen binding domain is directed against a mesothelin receptor and the auxiliary antigen binding domain is directed against a folate receptor. In an embodiment, the antigen binding domain is directed against a folate receptor and the auxiliary antigen binding domain is directed against a mesothelin receptor.

Inhibitory Molecules: Inhibition

Inhibitory molecules, e.g., PD1, can, in some embodiments, decrease the ability of a CARX cell to mount an immune effector response. Inhibition of an inhibitory molecule, e.g., by inhibition at the DNA, RNA or protein level, can optimize CARX cell performance. In embodiments an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CARX cell. In an embodiment the inhibitor is an shRNA. In an embodiment, the inhibitory molecule is inhibited within a CARX cell. In these embodiments, a dsRNA molecule that inhibits expression of the inhibitory molecule is linked to the nucleic acid that encodes a component, e.g., all of the components, of the CAR.

Exemplary inhibitory molecules, useful e.g., as shRNA targets, are provided in Table 10.

TABLE 10

Inhibitory molecules

CD160
2B4
PD1
PD-L2
TIM3
CEACAM (e.g., CEACAM-1, CEACAM-3 and/or CEACAM-5)
LAG3
TIGIT
CTLA-4
BTLA
LAIR1
PD-L1
VISTA
CD80
CD86
B7-H3 (CD276)
B7-H4 (VTCN1)
HVEM (TNFRSF14 or CD270)
KIR
A2aR
MHC class I
MHC class II
GAL9

Agents that Enhance the Activity of a CARX Cell

In another aspect, the CARX cell described herein can further express another agent, e.g., an agent which enhances the activity of a CARX cell. For example, in one embodiment, the agent can be an agent which inhibits an inhibitory molecule. Inhibitory molecules, e.g., PD1, can, in some embodiments, decrease the ability of a CARX cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signalling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signalling domain described herein (e.g., comprising a costimulatory domain (e.g., 4-1BB, CD27, ICOS, or CD28, e.g., as described herein) and/or a primary signalling domain (e.g., a CD3 zeta signalling domain described herein). In one embodiment, the agent comprises a first polypeptide of PD1 or a fragment thereof (e.g., at least a portion of an extracellular domain of PD1), and a second polypeptide of an intracellular signalling domain described herein (e.g., a CD28 signalling domain described herein and/or a CD3 zeta signalling domain described herein). In embodiments, the CARX cell described herein comprises a switch costimulatory receptor, e.g., as described in WO 2013/019615, which is incorporated herein by reference in its entirety. PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

Redirected Switchable Inhibitory Receptors: Inhibitory Extracellular Domains

Extracellular domains of inhibitory receptors can be coupled, e.g., directly in the case of a uCAR, or by dimerization switches in the case of an RCAR, to intracellular signaling domains that promote an immune effector response. Thus, engagement with a counterligand of the coinhibitory molecule is redirected into an optimization of immune effector response. Sortase based transfer can be used to couple the extracellular domain of an inhibitory receptor to other elements of a CAR member. In an embodiment a CAR member comprises a sortase transfer signature and extracellular domain of an inhibitory receptor. In an embodiment a CAR member comprises a sortase transfer signature disposed between an extracellular domain of an inhibitory receptor and a transmembrane domain.

In one embodiment, the extracellular domain (ECD) of an inhibitory molecule, e.g., an inhibitory molecule described herein such as, e.g., Programmed Death 1 (PD1), can be fused to a transmembrane domain and intracellular signaling domain described herein, e.g., an intracellular signaling domain comprising a costimulatory signaling domain such as, e.g., 4-1BB OX40, CD28, CD27, and/or a primary signaling domain, e.g., of CD3 zeta. In one embodiment, the inhibitory molecule RCAR, e.g., PD1 RCAR, can be used alone. In one embodiment, the inhibitory molecule CAR, e.g., inhibitory molecule RCAR, e.g., PD1 RCAR, can be used in combination with another CAR, e.g., CD19CAR (e.g., a CD19RCAR). In one embodiment, the PD1 RCAR (or PD1 CAR) improves the persistence of the immune effector cell, e.g. T cell. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, e.g., as described herein. In one embodiment, the inhibitory molecule CAR comprises a first polypeptide, e.g., of an inhibitory molecule such as PD1, LAG3, CTLA4, CD160, BTLA, LAIR1, TIM3, CEACAM (e.g., CEACAM-1, CEACAM-3 and/or CEACAM-5), 2B4 and TIGIT, or a fragment of any of these (e.g., at least a portion of an extracellular domain of any of these), and a second polypeptide which is an intracellular signaling domain described herein (e.g., comprising a costimulatory domain (e.g., 4-1BB, ICOS, CD27 or CD28, e.g., as described herein) and/or a primary signaling domain (e.g., a CD3 zeta signaling domain described herein).

In one embodiment, the inhibitory molecule CAR comprises the extracellular domain (ECD) of PD1 fused to a transmembrane domain and intracellular signaling domains such as 4-1BB and CD3 zeta (also referred to herein as a PD1 CAR). In one embodiment, the PD1 CAR improves the persistence of the CARX cell. In one embodiment, the PD1 CAR comprises the extracellular domain of PD1 indicated as underlined in SEQ ID NO: 11. In one embodiment, the PD1 CAR comprises, the amino acid sequence of SEQ ID NO:11.

```
                                         (SEQ ID NO: 11)
Malpvtalllplalllhaarppqwfldspdrpwnpptfspallvvtegdn atftcsfsntsesfvlnwyrmspsnqtdklaafpedrsqpgqdcrfrvtq lpnqrdfhmsvvrarrndsqtylcgaislapkaqikeslraelrvterra evptahpspsprpagqfqtlvtttpaprpptpaptiasqplslrpeacrp aaggavhtrgldfacdiyiwaplagtcgvlllslvitlyckrgrkkllyi fkqpfmrpvqttqeedgcscrfpeeeeggcelrvkfsrsadapaykqgqn qlynelnlgrreeydvldkrrgrdpemggkprrknpqeglynelqkdkma eayseigmkgerrrgkghdglyqglstatkdtydalhmqalppr.
```

In one embodiment, the PD1 CAR comprises the amino acid sequence provided below.

```
                                         (SEQ ID NO: 12)
pqwfldspdrpwnpptfspallvvtegdnatftcsfsntsesfvlnwyrm spsnqtdklaafpedrsqpgqdcrfrvtqlpnqrdfhmsvvrarrndsqt ylcgaislapkaqikeslraelrvterraevptahpspsprpagqfqtlv tttpaprpptpaptiasqplslrpeacrpaaggavhtrgldfacdiyiwa plagtcgvlllslvitlyckrgrkkllyifkqpfmrpvqttqeedgcscr fpeeeeggcelrvkfsrsadapaykqgqnqlynelnlgrreeydvldkrr grdpemggkprrknpqeglynelqkdkmaeayseigmkgerrrgkghdgl yqglstatkdtydalhmqalppr
```

In one embodiment, the PD1 CAR, e.g., the PD1 CAR described herein, is encoded by a nucleic acid sequence shown below, or at least the comprises the nucleic acid sequence encoding the extracellular domain of PDA (shown in underline below).

```
                                         (SEQ ID NO: 13)
atggccctccctgtcactgccctgcttctcccctcgcactcctgctcca cgccgctagaccacccggatggtttctggactctccggatcgcccgtgga atccccaaccttctcaccggcactcttggttgtgactgagggcgataat gcgaccttcacgtgctcgttctccaacacctccgaatcattcgtgctgaa ctggtaccgcatgagcccgtcaaaccagaccgacaagctcgccgcgtttc cggaagatcggtcgcaaccgggacaggattgtcggttccgcgtgactcaa ctgccgaatggcagagacttccacatgagcgtggtccgcgctaggcgaaa cgactccgggacctacctgtgcggagccatctcgctggcgcctaaggccc aaatcaaagagagcttgagggccgaactgagagtgaccgagcgcagagct gaggtgccaactgcacatccatcccatcgcctcggcctgcgggcagtt tcagacctggtcacgaccactccggcgccgcgcccaccgactccggccc caactatcgcgagccagcccctgtcgctgaggccggaagcatgccgccct gccgccggaggtgctgtgcataccggggattggacttcgcatgcgacat ctacatttgggctcctctcgccggaacttgtggcgtgctccttctgtccc
```

```
tggtcatcaccctgtactgcaagcggggtcggaaaaagcttctgtacatt ttcaagcagcccttcatgaggcccgtgcaaaccacccaggaggaggacgg ttgctcctgccggttccccgaagaggaagaaggaggttgcgagctgcgcg tgaagttctcccggagcgccgacgcccccgcctataagcagggccagaac cagctgtacaacgaactgaacctgggacggcgggaagagtacgatgtgct ggacaagcggcgcggccgggaccccgaaatgggcgggaagcctagaagaa agaaccctcaggaaggcctgtataacgagctgcagaaggacaagatggcc gaggcctactccgaaatTgggatgaagggagagcggcggaggggaaaggg gcacgacggcctgtaccaaggactgtccaccgccaccaaggacacatacg atgccctgcacatgcaggcccttcccCctcgc
```

Exemplary inhibitory extracellular domains are provided in Table 11.

TABLE 11

Extracellular counter ligand binding domains from coinhibitory molecules (identified by the Coinibitory Molecules from which they are derived)

B7-H1
B7-1
CD160
P1H
2B4
PD1
TIM3
LAG3
TIGIT
CTLA-4
BTLA
LAIR1

In embodiments the inhibitory extracellular domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human inhibitory molecule, e.g., a naturally occurring human primary stimulatory molecule disclosed herein.

Costimulatory Molecule Ligand Binding Domains

Extracellular ligand binding domains of costimulatory molecules, referred to as a Costimulatory ECD domain, can be coupled, e.g., directly in the case of a uCAR, or by dimerization switches in the case of an RCAR, to intracellular signaling domains that promote an immune effector response. Thus, engagement with a counter ligand of the costimulatory molecule results in optimization of immune effector response. Sortase based transfer can be used to couple the costimulatory ECD domain to other elements of a CAR member. In an embodiment a CAR member comprises a sortase transfer signature and a costimulatory ECD domain. In an embodiment a CAR member comprises a sortase transfer signature disposed between a costimulatory ECD domain and a transmembrane domain.

Exemplary Costimulatory ECD domains are provided in the Table 12.

TABLE 12

Costimulatory ECD domains from costimulatory molecules (identified by the Costimulatory Molecules from which they are derived)

ICOS
CD28

TABLE 12-continued

Costimulatory ECD domains from costimulatory molecules (identified by the Costimulatory Molecules from which they are derived)

CD27
HVEM
LIGHT
CD40L
4-1BB
OX40
DR3
GITR
CD30
TIM1
SLAM
CD2
CD226

In embodiments the Costimulatory ECD domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human inhibitory molecule, e.g., a naturally occurring human costimulatory molecule disclosed herein.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR e.g., in one embodiment, the transmembrane domain may be from the same protein that the signaling domain, costimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CARX cell. In a different aspect the amino acid sequence of the transmembrane domain may be modified or substituted so as to minimize interactions with the binding domains of the native binding partner present in the same CARX cell.

In embodiments, a CAR comprises a transmembrane domain that is coupled to an extracellular sequence, e.g., an extracellular recognition element, which can comprise an antigen binding domain, an inhibitory counter ligand binding domain, or costimulatory ECD domain. Sortase based method can be used to couple these elements.

In an embodiment, the transmembrane domain is one that naturally is associated with one of the domains in the CAR. In an embodiment, the transmembrane domain is one that is not naturally associated with one of the domains in the CAR.

In embodiments, the transmembrane domain is one which minimizes interactions with other elements, e.g., other transmembrane domains. In some instances, the transmembrane domain minimizes binding of such domains to the transmembrane domains of the same or different surface membrane proteins, e.g., to minimize interactions with other members of the receptor complex. Suitable examples can be derived by selection or modification of amino acid substitution of a known transmembrane domain. In an embodiment, the transmembrane domain is capable of promoting homodimerization with another CAR on the cell surface.

The transmembrane domain may comprise a naturally occurring, or a non-naturally occurring synthetic sequence. Where naturally occurring, the transmembrane domain may be derived from any membrane-bound or transmembrane protein. In an embodiment, the transmembrane region is capable of signaling, via a dimerization switch, to the intracellular domain(s) whenever the CAR has bound to a target.

Transmembrane regions suitable for use in molecules described herein may be derived from any one or more of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C. In an embodiment the transmembrane domain is derived from CD8. In an embodiment the transmembrane domain is derived from CD28. In one aspect, the transmembrane domain is a transmembrane domain from the sequence provided as SEQ ID NO: 14, below:

(SEQ ID NO: 14)
IYIWAPLAGTCGVLLLSLVITLYC

In an embodiment, a sequence, e.g., a hinge or spacer sequence, can be disposed between a transmembrane domain and another sequence or domain to which it is fused. In embodiments, a variety of human hinges (aka "spacers") can be employed as well, e.g., including but not limited to the human Ig (immunoglobulin) hinge. Optionally, a short oligo- or polypeptide linker, between 2 and 10 amino acids in length may form the linkage between the transmembrane domain and another domain, e.g., a switch or intracellular signaling domain, of a CAR. A glycine-serine doublet provides a particularly suitable linker. In one aspect, the hinge or spacer is the amino acid sequence provided as SEQ ID NO: 15 below:

(SEQ ID NO: 15)
TTTPAPRPPTPAPTIASQPLSLRPEACRPAAGGAVHTRGLDFACD

In one aspect, the hinge or spacer comprises a KIR2DS2 hinge.

In an embodiment, the transmembrane domain may be a non-naturally occurring sequence, in which case can comprise predominantly hydrophobic residues such as leucine and valine. In an embodiment, a triplet of phenylalanine, tryptophan and valine will be found at each end of a transmembrane domain.

iCARs

An inhibitory CAR (iCAR) is a CAR that recognizes an antigen on a non-target cell and produces a inhibitory signal, minimizing the activation of the cell. The extracellular domain of an iCAR can be added by sortase mediated transfer.

An iCAR member comprises: an antigen binding domain (or other extracellular domain) that recognizes an antigen on a non-target, e.g., a noncancer, cell; a transmembrane domain; and, an inhibitory intracellular signaling domain, e.g., from PD-1, CTLA4, or from a protein listed in Table 13. In an embodiment, the iCAR member comprises a second inhibitory intracellular signaling domain, e.g., from PD-1, CTLA4, or from a protein listed in Table 13.

Upon engagement of the antigen binding domain (or other extracellular domain) of the iCAR member with its target antigen (or counter-ligand), the iCAR contributes to inhibiting, e.g., reversibly inhibiting, or minimizing, activation of the cell comprising the iCAR. As such, inclusion of an iCAR member in a CAR, e.g., and CART, cell, can limit damage to non-target, e.g., bystander, cells. While not wishing to be bound by theory, it is believed that an iCAR member, upon engagement with its antigen (or counter-ligand), limits one or more of cytokine secretion, cytotoxicity, and proliferation. In embodiments the effect is temporary, and upon subsequent engagement with a target cell the CAR, e.g., CART, cell is activated and attacks the target cell.

A target antigen for an iCAR member can be an antigen that has an expression profile on target cells and non-target cells such that an acceptably high level of attack on target cells and an acceptably low level of attack on non-target cells is achieved. Not only choice of antigen, but iCAR affinity for its antigen (or counter-ligand), CAR affinity for its antigen, level of expression of the iCAR, or levels of expression of the CAR can be used to optimize the ratio of on-target/off-target response.

In an embodiment, the antigen is absent, or down-regulated on tumor cells. In an embodiment the antigen comprises an HLA molecule. In an embodiment the antigen comprises a cell surface tumor suppressor antigen. In an embodiment the antigen comprises PCML (or another antigen that is down-regulated in lymphomas, breast or prostate cancer), HYAL2, DCC, or SMAR1.

In an embodiment, the antigen comprises a protein, carbohydrate, lipid, or a post-translational modification of a cell surface moiety, e.g., a mucin-type O-glycan (a core 3 O-glycan).

In an embodiment, the antigen comprises a moiety that is down-regulated by tumor cells undergoing an epithelial to mesenchymal transition.

In an embodiment, the antigen comprises E-cadherin.

In an embodiment an inhibitory intracellular signaling domain, e.g., an intracellular signaling domain from PD-1 or CTLA4, produces an intracellular signal when an extracellular domain, e.g., an antigen binding domain, to which it is fused binds cognate antigen (or counter ligand). The inhibitory intracellular signaling domain is derived from an inhibitory molecule, e.g., it comprises intracellular sequence of an inhibitory molecule. It comprises sufficient inhibitory molecule sequence to produce an intracellular signal, e.g., when an antigen binding domain to which it is fused binds cognate antigen.

In an embodiment, the primary intracellular signaling domain comprises a signaling motif, e.g., an immunoreceptor tyrosine-based activation motif or ITIM.

An inhibitory intracellular signaling domain comprises a functional fragment, or analog, of an inhibitory molecule intracellular domain. It can comprise the entire intracellular region or a fragment of the intracellular region which is sufficient for generation of an intracellular signal when an antigen binding domain to which it is fused, binds cognate antigen. In embodiments the inhibitory intracellular signaling domain has at least 70, 75, 80, 85, 90, 95, 98, or 99% sequence identity with, or differs by no more than 30, 25, 20, 15, 10, 5, 4, 3, 2, or 1 amino acid residues from, the corresponding residues of a naturally occurring inhibitory molecule, e.g., a molecule from Table 13.

Exemplary inhibitory molecules which can provide intracellular signaling domains are provided in Table 13.

TABLE 13

| Inhibitory molecules |
| --- |
| B7-H1 |
| B7-1 |
| CD160 |
| P1H |
| 2B4 |
| PD1 |
| TIM3 |
| LAG3 |
| TIGIT |
| CTLA-4 |
| BTLA |
| LAIR1 |

Thus, in one, aspect, disclosed herein is, a CAR comprising an iCAR member. The iCAR member comprises:

an antigen binding domain (or other extracellular domain) that recognizes an antigen on a non-target, e.g., a noncancer cell;

a transmembrane domain; and an inhibitory intracellular signaling domain, e.g., from PD-1, CTLA4, or from a protein listed in Table 4.

In an embodiment, the iCAR member comprises a second inhibitory intracellular signaling domain, e.g., from PD-1, CTLA4, or from a protein listed in Table 13.

In another aspect, the invention features, a nucleic acid, e.g., an isolated nucleic acid, encoding a CAR that comprises an iCAR member.

In an embodiment sequence encoding the iCAR member and a second member of the CAR are present in a single nucleic acid molecule.

In an embodiment sequence encoding the iCAR member is operatively linked to a first control region and sequence encoding the second member of the CAR is operatively linked to a second control region.

In an embodiment sequence encoding the iCAR member is translated as a first RNA and sequence encoding second member of the CAR is translated as a second RNA.

In a another aspect, the invention features, a vector system, e.g., a vector system comprising one or more vectors, comprising nucleic acid encoding a CAR comprising an iCAR member.

In an embodiment, all of the elements of a CAR are encoded on a single vector.

In an embodiment, the iCAR member is encoded on a first vector and another member of the RCAR is encoded on a second vector, of the vector system.

In an embodiment, the vector system comprises a DNA, a RNA, a plasmid, a lentivirus vector, adenoviral vector, or a retrovirus vector.

In an embodiment, the vector system comprises a bi-cistronic or tri-cistronic lentivirus vector.

In an embodiment, the vector system comprises a bi-cistronic or tri-cistronic promoter.

In another aspect, the invention features, a cell, e.g., a T cell or NK cell, comprising a vector system described herein.

In another aspect, the invention features, a cell, e.g., a T cell or NK cell, an RCAR comprising an iCAR member.

iCAR member containing cells can be used in method described herein. Thus, in another aspect, the invention features, a method of treating a mammal, e.g., a method of providing an anti-tumor immunity in a mammal, comprising administering to the mammal an effective amount of a CARX cell comprising an iCAR member.

In an embodiment the CARX cell is an autologous T cell.

In an embodiment the CARX cell is an allogeneic T cell.

In an embodiment the CARX cell is an autologous NK cell.

In an embodiment the CARX cell is an allogeneic NK cell.

In an embodiment the mammal is a human.

In another aspect, the invention features, a method of evaluating a human who has been treated with a CARX cell comprising an iCAR for a side effect of said treatment.

Vectors

The present invention also provides vectors which comprise CAR encoding sequence, e.g., sortase acceptor member sequence. Vectors derived from viruses, e.g., lentivirus, are suitable tools to achieve long-term gene transfer since they allow long-term, stable integration of a transgene and its propagation in daughter cells. Lentiviral vectors have the added advantage over vectors derived from retroviruses e.g., murine leukemia viruses, in that they can transduce non-proliferating cells, such as hepatocytes. They also have the added advantage of low immunogenicity.

A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In an embodiment, the expression of nucleic acids encoding a CAR member, e.g., a sortase acceptor member, is achieved by a nucleic acid encoding the CAR polypeptide or portions or components thereof operably linked to a promoter, which is incorporated into an expression vector. The vectors can be suitable for replication and integration into eukaryotes. Typical vectors contain transcription and translation terminators, initiation sequences, and promoters useful for regulation of the expression of the desired nucleic acid sequence.

In an embodiment, the vector is a viral vector. Viral vector technology is known in the art and is described, for example, in Sambrook et al., 2012, Molecular Cloning: A Laboratory Manual, volumes 1-4, Cold Spring Harbor Press, NY), and in other virology and molecular biology manuals. In an embodiment, viruses, which are useful as vectors are retroviruses, adenoviruses, adeno-associated viruses, herpes viruses, and lentiviruses. In an embodiment the vector is a lentivirus vector. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In an embodiment, a vector which expresses two or more genes, each gene is expressed separately under the control of a different promoter region, e.g., by using bi or tri-cistronic promoters. Expression of two or more genes from the same vector can be achieved by using either a multiple promoter plasmid e.g., bi or tri-cistronic promoters. Examples of multiple promoter containing lentivirus vectors are known in the literature. For example the vector pLENTI-bi-cistronic drives the expression of two genes using the PKG promoter and the mini CMV promoter in opposite directions (Applied Biological Material Inc., Richmond, BC, Canada). Similar the tri-cistronic vector pLENTI-tri-cistronic drives expression of three genes. In this configuration one gene can be induced by the mini-CMV promoter while the second and third gene can be induced by the PGK promoter separating the two genes with a T2A peptide cleavage site.

In another embodiment, bi- or tri-cistronic vectors may also be constructed making use of internal ribosomal entry sites (IRES) such as for example the element from the encephalomyocarditis virus (EMCV) for translation of two or more open reading frames (ORFs). Such vectors are designed to drive transcription of the bi- or tri-cistronic message under control of a strong human promoter regulatory region e.g. CMV or EF1alpha. IRESs are relatively short DNA sequences that can initiate RNA translation in a 5' cap-independent fashion. Whereas the first cistron is translated in a cap-dependent manner driven by a strong mammalian promoter, the subsequent ones utilize intercistronic regions of viral origin such as the internal ribosomal entry site of poliovirus or the cap-independent translation enhancer of encephalomyocarditis virus for enhanced translation. (N Chinnasamy et al. (2009), Production of Multicistronic HIV-1 Based Lentiviral Vectors; Methods Mol Biol 515: 1-14).

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter (EF1α), the hemoglobin promoter, and the creatine kinase promoter. Further, embodiments are not limited to the use of constitutive promoters. Embodiments comprise inducible promoters. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In an embodiment, the promoter is a PGK promoter, e.g., a truncated PGK promoter as described herein.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below. WT PGK Promoter (SEQ ID NO: 266)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT

Exemplary Truncated PGK Promoters:

PGK100:
(SEQ ID NO: 267)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK200:
(SEQ ID NO: 268)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:

```
                                         (SEQ ID NO: 269)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK400:
                                         (SEQ ID NO: 270)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCGG

GTGTTCCCATCGCCGCTTCTAGGCCCACTGCGACGCTTGCCTGCACTTCT

TACACGCTCTGGGTCCCAGCCG
```

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

Sequence encoding various elements of a CAR can be disposed on the same nucleic acid molecule, e.g., the same plasmid or vector, e.g., viral vector, e.g., lentiviral vector. E.g., both (i) sequence encoding sortase acceptor member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products).

In an embodiment, (i) sequence encoding a sortase acceptor member and (ii) sequence encoding an intracellular signaling member, are present on a single nucleic acid molecule, are transcribed as a single transcription product, and are configured as follows:

a promoter, e.g., a promoter described herein, e.g., an EF1alpha promoter, is operably linked to (i), (ii), and to (iii) sequence encoding peptide, e.g., a cleavable peptide, e.g., a P2A or F2A sequence. Element (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment element (iii) comprises: a P2A or P3A sequence, or effective fragment thereof.

Examples of peptide cleavage sites include the following, wherein an N-terminal GSG may be present or added (e.g., may be added to SEQ ID NO: 19 or removed from SEQ ID NO: 16, 278, or 265):

```
P2A:
                                         (SEQ ID NO: 16)
Ggcagcggcgccaccaacttcagcctgctgaagcaggccggcgacgtgga ggaaaaccctggcccc (SEQ ID NO: 17)
GSGATNFSLLKQAGDVEENPGP F2A:
                                         (SEQ ID NO: 18)
Gtgaagcagaccctgaacttcgacctgctgaaactggccggcgacgtgga gagcaatcccggccct (SEQ ID NO: 19)
VKQTLNFDLLKLAGDVESNPGP T2A:
                                         (SEQ ID NO: 275)
(GSG) EGRGSLLTCGDVEENPGP E2A:
                                         (SEQ ID NO: 265)
(GSG) QCTNYALLKLAGDVESNPGP
```

In an embodiment, (i) sequence encoding an sortase acceptor member and (ii) sequence encoding an intracellular signaling member, are present on a single nucleic acid molecule, are transcribed as a single transcription product, and are configured as follows:

a promoter, e.g., a promoter described herein, e.g., an EF1alpha promoter, is operably linked to (i), (ii), and to (iii) sequence encoding an IRES, e.g., an EMCV or EV71 IRES. In an embodiment (iii) is disposed between (i) and (ii). In an embodiment, (i), (ii), and (iii) are transcribed as a single RNA. In an embodiment, the order, on the nucleic acid, is (i)-(iii)-(ii). In an embodiment, the order, on the nucleic acid, is (ii)-(iii)-(i).

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory domain, e.g., a 4-1BB domain.

In another embodiment, (i) sequence encoding sortase acceptor member and (ii) sequence encoding an intracellular signaling member, are transcribed as separate transcription products, are present on a single nucleic acid molecule, and are configured as follows:

a promoter, e.g., a promoter described herein, e.g., an EF1alpha promoter, is operably linked to (i), and a second promoter, e.g., a promoter described herein, can be operably linked to (ii). In an embodiment (i) and (ii) are transcribed as separate mRNAs. In an embodiment, the order, on the nucleic acid, is first promoter-(i)-second promoter-(ii). In an embodiment, the order, on the nucleic acid, is first promoter-(ii)-second promoter-(i). In an embodiment the first promoter is a promoter described herein, e.g., an EF1alpha promoter. In an embodiment, the second promoter is a promoter described herein, e.g., a CMV or EF1 promoter. In an embodiment the second promoter is a minimal promoter.

In an embodiment (i) and (ii) form an RCAR having an intracellular switch.

In an embodiment (i) and (ii) form an RCAR having an extracellular switch.

In an embodiment (ii) comprises sequence that encode a 4-1BB domain and a CD3zeta domain.

In an embodiment (i) comprises sequence that encode a costimulatory domain, e.g., a 4-1BB domain.

In an embodiment a promoter that is capable of expressing RAR transgene in a mammalian immune effector cell, e.g. T cell is the EF1alpha promoter (EF1α). The native EF1α promoter drives expression of the alpha subunit of the elongation factor-1 complex, which is responsible for the enzymatic delivery of aminoacyl tRNAs to the ribosome. The EF1α promoter has been used in mammalian expression plasmids and has been shown to be effective in driving CAR expression from transgenes cloned into a lentiviral vector. See, e.g., Milone et al., Mol. Ther. 17(8): 1453-1464 (2009). In an embodiment, the EF1α promoter comprises the sequence provided as SEQ ID NO: 20 below:

```
                                          (SEQ ID NO: 20)
CGTGAGGCTCCGGTGCCCGTCAGTGGGCAGAGCGCACATCGCCCACAGTC

CCCGAGAAGTTGGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC

GAATCTGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

TTGGGGGAGGGGTTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTCTTCCATTTCAGGTGTCGTGA
```

In embodiments, CAR scFv fragments are cloned into lentiviral vectors to create a full length CAR construct in a single coding frame, and using a promoter, e.g., EF1 alpha promoter, for expression (SEQ ID NO: 20).

In order to assess the expression of a CAR polypeptide or portions thereof, the vector to be introduced into a cell can also contain either a selectable marker gene or a reporter gene or both to facilitate identification and selection of expressing cells from the population of cells sought to be transfected or infected through viral vectors. In embodiments, the selectable marker may be carried on a separate piece of DNA and used in a co-transfection procedure. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes in a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, Molecular Cloning: A Laboratory Manual, volumes 1-4, Cold Spring Harbor Press, NY).

Biological methods for introducing a polynucleotide into a host cell include the use of DNA and RNA vectors as described above. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles.

In some embodiments, the mRNA can be introduced directly to the cell or patient in a non-viral delivery system and injected directly into the patient. In the case where a non-viral delivery system is utilized, an exemplary delivery vehicle is a liposome. The use of lipid formulations is contemplated for the introduction of the nucleic acids into a host cell (in vitro, ex vivo or in vivo). In an embodiment, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −200 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

CAR components can be encoded on one or more nucleic acid molecules. Exemplary nucleic acid molecules include viral vectors, e.g., lentiviral vectors, retroviral vectors, adenoviral vectors, and the like. In embodiments, the components can be provided on a single nucleic acid molecule, e.g., viral vector, e.g., lentiviral vector, retroviral vectors, adenoviral vectors, and the like, or can be disposed on more than one nucleic acid molecule, e.g., viral vector, e.g., lentiviral vector, retroviral vectors, adenoviral vectors, and the like.

Nucleic Acid Based Inhibitors

Double Stranded RNA (dsRNA)

CARX cells, e.g., CART cells, can include a nucleic acid based inhibitor useful for decreasing the expression of target gene. The inhibitory molecule can comprise dsRNA, such as shRNA. While not wishing to be bound by theory it is believed that the dsRNA acts by an RNAi mechanism. RNAi refers to the process of sequence-specific post-transcriptional gene silencing in animals mediated by short interfering RNAs (siRNAs). dsRNA, as used herein includes siRNA and shRNA.

The dsRNA can be chemically synthesized, expressed from a vector or enzymatically synthesized. dsRNAs can be unmodified or, e.g., in the case of dsRNAs administered as RNA, can be chemically modified. Enzymatically synthesized dsRNAs can be chemically to improve various properties of native dsRNA molecules, such as through increased resistance to nuclease degradation in vivo and/or through improved cellular uptake.

The dsRNAs targeting nucleic acid can be composed of two separate RNA molecules referred to herein as siRNA, or of one RNA molecule, which is folded to form a hairpin structure, referred to herein as shRNA. In embodiments, a suitable dsRNA for inhibiting expression of a target gene can be identified by screening an siRNA library, such as an adenoviral or lentiviral siRNA library. A dsRNA, e.g., a shRNA, can be provided to a cell as RNA, or in the form of a DNA that is transcribed to provide the dsRNA, e.g., shRNA. A dsRNA, e.g., a shRNA, gene can be expressed from a vector, e.g., viral vector, such as a lentiviral or adenoviral vector. A dsRNA, e.g., an shRNA, can be expressed by a polymerase III promoters, e.g. a U6 or H1 promoter or by a polymerase II promoter. shRNA can be expressed in the cell from a DNA construct encoding a sequence of single stranded RNA and its complement, separated by a stuffer, or linker, fragment, allowing the RNA molecule to fold back on itself, creating a dsRNA molecule with a hairpin loop. While not wishing to be bound by theory, it is believed that shRNA expressed from a DNA sequence encoding the shRNA is processed by Dicer to siRNA, which continues along the RNAi pathway via RISC to silence the target gene.

In an embodiment the inhibitor is a dsRNA. e.g., an shRNA, that comprises a duplexed region that is about 15 to about 30 base pairs in length (e.g., about 16, 17, 18, 19, 20, 21, 22, 23, 24, 25, 26, 27, 28, or 29 base pairs in length. In an embodiment the inhibitor is an shRNA, comprising a duplexed region that is about 15 to about 30 base pairs in length (e.g., about 16, 17, 18, 19, 20, 21, 22, 23, 24, 25, 26, 27, 28, or 29 base pairs in length).

In an embodiment, the dsRNA, includes overhanging ends of about 1 to about 3 (e.g., about 1, 2, or 3) nucleotides. By "overhang" is meant that 3'-end of one strand of the dsRNA extends beyond the 5'-end of the other strand, or vice versa. The dsRNA can have an overhang on one or both ends of the dsRNA molecule. In some embodiments, the single-stranded overhang is located at the 3'-terminal end of the antisense strand, or, alternatively, at the 3'-terminal end of the sense strand. In some embodiments, the overhang is a TT or UU dinucleotide overhang, e.g., a TT or UU dinucleotide overhang. For example, in an embodiment, the dsRNA includes a 21-nucleotide antisense strand, a 19 base pair duplex region, and a 3'-terminal dinucleotide. In yet another embodiment, a dsRNA includes a duplex nucleic acid where both ends are blunt, or alternatively, where one of the ends is blunt.

In an embodiment the shRNA, after intracellular processing (e.g., by Dicer), results in a 19-23 nucleotide duplex siRNA with 2 nucleotide 3' overhangs.

In an embodiment, the dsRNA, e.g., a shRNA, includes a first and a second sequence, each sequence is about 18 to about 28 nucleotides in length, e.g., about 19 to about 23 nucleotides in length, wherein the first sequence of the dsRNA includes a nucleotide sequence having sufficient complementarity to the target RNA for the dsRNA to direct cleavage of the target via RNA interference, and the second sequence of the dsRNA includes a nucleotide sequence that is complementary to the first strand.

In an embodiment, an dsRNA includes a first and a second sequence that form a duplexed region, wherein each sequence of the duplexed region is about 18 to about 28 nucleotides in length, e.g., about 19 to about 23 nucleotides in length. The first sequence of the dsRNA (e.g., shRNA)

includes a nucleotide sequence having sufficient complementarity to the target RNA for the dsRNA (e.g., shRNA) to direct cleavage of the target via RNA interference, and the second strand of the dsRNA (e.g., shRNA) includes a nucleotide sequence that is complementary to the first strand.

In an embodiment, the dsRNA (e.g., the sequences or strands of the duplexed region of an shRNA) includes an antisense sequence having a nucleotide sequence that is complementary to a nucleotide sequence of the target gene or a portion thereof, and a sense sequence having a nucleotide sequence substantially similar to the nucleotide sequence of the target gene or a portion thereof. In an embodiment, the antisense sequence and the sense sequence, independently, include about 15 to about 30 (e.g., about 15, 16, 17, 18, 19, 20, 21, 22, 23, 24, 25, 26, 27, 28, 29, or 30) nucleotides, where the antisense sequence includes about 15 to about 30 (e.g., about 15, 16, 17, 18, 19, 20, 21, 22, 23, 24, 25, 26, 27, 28, 29, or 30) nucleotides that are complementary to nucleotides of the sense sequence.

In an embodiment, a dsRNA is provided as an RNA (and not as a DNA which is transcribed to provide the dsRNA) and includes one or more chemical modifications. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. Such chemical modifications have been shown to preserve RNAi activity in cells while at the same time, dramatically increasing the serum stability of these compounds. Furthermore, one or more phosphorothioate substitutions are well-tolerated and have been shown to confer substantial increases in serum stability for modified dsRNA constructs. The dsRNA can include modified nucleotides as a percentage of the total number of nucleotides present in the molecule. As such, the dsRNA can generally include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides).

Antisense

Suitable nucleic acid based inhibitors include antisense nucleic acids. While not being bound by theory it is believed that antisense inhibition is typically based upon hydrogen bonding-based hybridization of oligonucleotide strands or segments such that at least one strand or segment is cleaved, degraded, or otherwise rendered inoperable.

An antisense agent can have a chemical modification described above as being suitable for dsRNA.

Antisense agents can include, for example, from about 8 to about 80 nucleobases (i.e., from about 8 to about 80 nucleotides), e.g., about 8 to about 50 nucleobases, or about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

While not being bound by theory it is believed that the functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Sequence Identity

Percent identity in the context of two or more nucleic acids or polypeptide sequences, refers to two or more sequences that are the same. Two sequences are "substantially identical" if two sequences have a specified percentage of amino acid residues or nucleotides that are the same (i.e., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence, e.g., of the shorter of the compared sequences), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In an embodiment, the present invention contemplates modifications of the antigen binding domain (e.g., scFv) amino acid sequence that generate functionally equivalent molecules. For example, the VH or VL of an scFv of RCAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL sequences of the scFv.

In certain embodiments the polypeptide sequences encoded by the nucleic acid sequences are modified by replacing one or more amino acid residues with another amino acid residue from the same side chain family, i.e., one or more conservative substitutions. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Sources of Cells

In embodiments, prior to expansion and genetic modification or other modification, a source of cells, e.g., T cells or natural killer (NK) cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. Immune effector cells, e.g., T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CARX, e.g., CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a checkpoint inhibitor, e.g., a checkpoint inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary checkpoint inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step, e.g., as described herein.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" Clinical & Translational Immunology (2015) 4, e31; doi:10.1038/cti.2014.31.

In an embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In an embodiment, a population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

T Cells

In an embodiment, the cells are T cells. T cell lines available in the art, may be used. In embodiments, T cells can be obtained from a unit of blood collected from a subject using any number of techniques known to the skilled artisan, such as Ficoll™ separation. In an embodiment, cells from the circulating blood of an individual are obtained by apheresis. The apheresis product typically contains lymphocytes, including T cells, monocytes, granulocytes, B cells, other nucleated white blood cells, red blood cells, and platelets. In an embodiment, the cells collected by apheresis may be washed to remove the plasma fraction and to place the cells in an appropriate buffer or media for subsequent processing steps. In an embodiment, the cells are washed with phosphate buffered saline (PBS). In an alternative embodiment, the wash solution lacks calcium and may lack magnesium or may lack many if not all divalent cations. Surprisingly, the initial activation steps in the absence of calcium lead to magnified signal activation. A washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In an embodiment, T cells are isolated from peripheral blood lymphocytes by lysing the red blood cells and depleting the monocytes, for example, by centrifugation through a PERCOLL gradient or by counterflow centrifugal elutriation. A specific subpopulation of T cells, such as CD3+, CD28+, CD4+, CD8+, CD45RA+, and CD45R0+ T cells, can be further isolated by positive or negative selection techniques. For example, in an embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In an embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In an embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. In an embodiment, a concentration of 10 billion cells/ml, 9 billion/ml, 8 billion/ml, 7 billion/ml, 6 billion/ml, 5 billion/ml, or 2 billion cells/ml is used. In an embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet an embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In an embodiment, the concentration of cells used is $5 \times 10^6$/ml. In other embodiments, the concentration used can be from about $1 \times 10^5$/ml to $1 \times 10^6$/ml, and any integer value in between. In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods described herein.

In an embodiment the collection of blood samples or apheresis product from a subject is made at a time period prior to when the expanded cells might be needed. As such, the source of the cells to be expanded can be collected at any time point necessary, and desired cells, such as T cells, isolated and frozen for later use in, e.g., T cell therapy for any number of diseases or conditions that would benefit from such T cell therapy. In an embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signalling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In an embodiment, the cells are isolated prior to and can be frozen for later use for treatment following B-cell ablative therapy such as agents that react with CD20, e.g., Rituxan.

In a further embodiment, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

NK Cells

In an embodiment, the cells are natural killer cells. These cells can be isolated from patients. In an embodiment, the cells are stable cell lines of natural killer cells, e.g., a stable allogeneic NK-92 cell line available, from Conkwest. These stable NK-92 cell lines were derived from NK-92 cells that were obtained, transfected and cultured using the methods described by Gong et al (April 1994), Leukemia Macmillan Press, Ltd, 8: 652-658, and disclosed in EP1007630, incorporated herein by reference. An NK cell line with properties similar to the NK-92 cell line can also be used. In an embodiment, NK cells from the circulating blood of an individual are obtained by apheresis. In an embodiment, NK cells are engineered to express RCAR, and these engineered RCARN cells can be used to treat a patient other than a patient from whom the NK cells were isolated, Hence, these RCARN cells are "universal" cells in that can be administered to multiple patients without adverse effects. That is to say that NK cells can be isolated from one patient and engineered to express RCAR, thereby producing RCARN cells, and these RCARN cells can then be administered to the same or different patient. NK cells, e.g., NK-92 cells, do not express killer inhibitory receptors, and therefore cannot be inactivated by evading cancer cells. Methods for isolation and use of NK cells (e.g., NK-92 cell lines or similar NK cell lines derived from peripheral blood mononuclear cells from a patient with non-Hodgkin lymphoma) have been described (See Zhang et al (2013) Retargeting NK-92 for anti-melanoma activity by a TCR-like single domain antibody; Immunol Cell Biol. 91: 615-624; Tonn et al. (2013) Treatment of patients with advanced cancer with the natural killer cell-line NK-92, Cytotherapy, 15: 1563-1570.

The NK-92 cell line was found to exhibit the $CD56^{bright}$, CD2, CD7, CD1 la, CD28, CD45, and CD54 surface markers It furthermore does not display the CD1, CD3. CD4, CD5, CD8, CD10, CD14, CD 16, CD19, CD20, CD23, and CD34 markers Growth of NK-92 cells in culture is dependent upon the presence of recombinant interleukin 2 (rIL-2), with a dose as low as 10 IU/mL being sufficient to maintain proliferation. NK cell lines with similar properties can also be used.

NK-92 cells are readily maintained in culture medium, such as enriched alpha minimum essential medium (MEM, Sigma Chemical Co, St Louis, Mo.) supplemented with fetal calf serum (for example, at 12.5%, Sigma Chemical Co., St Louis, Mo.), and horse serum (for example, at 12.5%, (Sigma Chemical Co., St Louis, Mo.) Initially, 10M hydrocortisone is required, but in subsequent passages it is found that hydrocortisone may be omitted. In addition, IL-2, such as recombinant human IL-2 (500 U/mL, Chiron, Emeryville, Calif.), is required for long-term growth. When suspension cultures are maintained in this fashion with semiweekly changes of medium, the cells exhibit a doubling time of about 24 h.

NK-92 cells in vitro demonstrate lytic activity against a broad range of malignant target cells. These include cell lines derived from circulating target cells such as acute and chronic lymphoblastic and myelogenous leukemia, lymphoma, myeloma, melanoma, as well as cells from solid tumors such as prostate cancer, neuroblastoma, and breast cancer cell lines.

Other Immune Effector Cells

In another embodiment, any number of immune effector cells may be isolated and engineered to express RCARs, e.g., B cell, mast cells. Myeloid derived phagocytes, NKT cells, or γδT cells. Exemplary immune effector cells are listed in FIG. 8.

Allogeneic CARX, e.g., CART

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some embodiments, downregulation of HLA may be accomplished by reducing or eliminating expression of beta-2 microglobulin (B2M).

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. a cell engineered by any method described herein. For example, the cell can be a cell that does not express or expresses at low levels an inhibitory molecule, e.g., that can decrease the ability of a CARX cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CARX cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No. 2012/0321667. Exemplary siRNA and shRNA that downregulate expression of HLA class I and/or HLA class II genes are described, e.g., in U.S. publication No. US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs is required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; and Guo et al. (2010) J. Mol. Biol. 400: 96; U.S. Patent Publication 2011/0158957; and U.S. Patent Publication 2012/0060230.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CARX cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells or NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

(SEQ ID NO: 258)
MPRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAFG

FALLDGARGGPPEAFTTSVRSYLPNTVTDALRGSGAWGLLLRRVGDDVLV

HLLARCALFVLVAPSCAYQVCGPPLYQLGAATQARPPPHASGPRRRLGCE

RAWNHSVREAGVPLGLPAPGARRRGGSASRSLPLPKRPRRGAAPEPERTP

VGQGSWAHPGRTRGPSDRGFCVVSPARPAEEATSLEGALSGTRHSHPSVG

RQHHAGPPSTSRPPRPWDTPCPPVYAETKHFLYSSGDKEQLRPSFLLSSL

RPSLTGARRLVETIFLGSRPWMPGTPRRLPRLPQRYWQMRPLFLELLGNH

AQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKH

AKLSLQELTWKMSVRGCAWLRRSPGVGCVPAAEHRLREEILAKFLHWLMS

VYVVELLRSFFYVTETTFQKNRLFFYRKSVWSKLQSIGIRQHLKRVQLRE

LSEAEVRQHREARPALLTSRLRFIPKPDGLRPIVNMDYVVGARTFRREKR

AERLTSRVKALFSVLNYERARRPGLLGASVLGLDDIHRAWRTFVLRVRAQ

DPPPELYFVKVDVTGAYDTIPQDRLTEVIASIIKPQNTYCVRRYAVVQKA

AHGHVRKAFKSHVSTLTDLQPYMRQFVAHLQETSPLRDAVVIEQSSSLNE

ASSGLFDVFLRFMCHHAVRIRGKSYVQCQGIPQGSILSTLLCSLCYGDME

NKLFAGIRRDGLLLRLVDDFLLVTPHLTHAKTFLRTLVRGVPEYGCVVNL

RKTVVNFPVEDEALGGTAFVQMPAHGLFPWCGLLLDTRTLEVQSDYSSYA

RTSIRASLTFNRGFKAGRNMRRKLFGVLRLKCHSLFLDLQVNSLQTVCTN

IYKILLLQAYRFHACVLQLPFHQQVWKNPTFFLRVISDTASLCYSILKAK

NAGMSLGAKGAAGPLPSEAVQWLCHQAFLLKLTRHRVTYVPLLGSLRTAQ

TQLSRKLPGTTLTALEAAANPALPSDFKTILD

In an embodiment, the hTERT has a sequence at least 80%, 85%, 90%, 95%, 96^, 97%, 98%, or 99% identical to the sequence of SEQ ID NO: 258. In an embodiment, the hTERT has a sequence of SEQ ID NO: 258. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

(SEQ ID NO: 259)

```
   1 caggcagcgt ggtcctgctg cgcacgtggg aagccctggc cccggccacc cccgcgatgc
  61 cgcgcgctcc ccgctgccga gccgtgcgct ccctgctgcg cagccactac cgcgaggtgc
 121 tgccgctggc cacgttcgtg cggcgcctgg ggccccaggg ctggcggctg gtgcagcgcg
 181 gggacccggc ggctttccgc gcgctggtgg cccagtgcct ggtgtgcgtg ccctgggacg
 241 cacggccgcc ccccgccgcc ccctccttcc gccaggtgtc ctgcctgaag gagctggtgg
 301 cccgagtgct gcagaggctg tgcgagcgcg gcgcgaagaa cgtgctggcc ttcggcttcg
 361 cgctgctgga cggggcccgc gggggccccc ccgaggcctt caccaccagc gtgcgcagct
 421 acctgcccaa cacggtgacc gacgcactgc ggggagcgg ggcgtggggg ctgctgttgc
 481 gccgcgtggg cgacgacgtg ctggttcacc tgctggcacg ctgcgcgctc tttgtgctgg
 541 tggctcccag ctgcgcctac caggtgtgcg ggccgccgct gtaccagctc ggcgctgcca
 601 ctcaggcccg ccccgcca cacgctagtg accccgaag gcgtctggga tgcgaacggg
 661 cctggaacca tagcgtcagg gaggccgggg tccccctggg cctgccagcc ccgggtgcga
 721 ggaggcgcgg gggcagtgcc agccgaagtc tgccgttgcc caagaggccc aggcgtggcg
 781 ctgcccctga gccggagcgg acgcccgttg gcaggggtc ctgggcccac ccgggcagga
 841 cgcgtggacc gagtgaccgt ggtttctgtg tggtgtcacc tgccagaccc gccgaagaag
 901 ccacctcttt ggagggtgcg ctctctggca cgcgccactc ccacccatcc gtgggccgcc
 961 agcaccacgc gggccccca tccacatcgc ggccaccacg tccctgggac acgccttgtc
1021 ccccggtgta cgccgagacc aagcacttcc tctactcctc aggcgacaag gagcagctgc
1081 ggccctcctt cctactcagc tctctgaggc ccagcctgac tggcgctcgg aggctcgtgg
1141 agaccatctt tctgggttcc aggccctgga tgccagggac tccccgcagg ttgccccgcc
1201 tgccccagcg ctactggcaa atgcggcccc tgtttctgga gctgcttggg aaccacgcgc
1261 agtgccccta cggggtgctc ctcaagacgc actgcccgct gcgagctgcg gtcaccccag
1321 cagccggtgt ctgtgcccgg gagaagcccc agggctctgt ggcggccccc gaggaggagg
1381 acacagaccc ccgtcgcctg gtgcagctgc tccgccagca cagcagcccc tggcaggtgt
1441 acggcttcgt gcgggcctgc ctgcgccggc tggtgccccc aggcctctgg ggctccaggc
1501 acaacgaacg ccgcttcctc aggaacacca agaagttcat ctccctgggg aagcatgcca
1561 agctctcgct gcaggagctg acgtggaaga tgagcgtgcg gggctgcgct tggctgcgca
1621 ggagcccagg ggttggctgt gttccggccg cagagcaccg tctgcgtgag gagatcctgg
1681 ccaagttcct gcactggctg atgagtgtgt acgtcgtcga gctgctcagg tctttctttt
1741 atgtcacgga gaccacgttt caaaagaaca ggctcttttt ctaccggaag agtgtctgga
1801 gcaagttgca aagcattgga atcagacagc acttgaagag ggtgcagctg cgggagctgt
1861 cggaagcaga ggtcaggcag catcgggaag ccaggcccgc cctgctgacg tccagactcc
1921 gcttcatccc caagcctgac gggctgcggc cgattgtgaa catggactac gtcgtgggag
1981 ccagaacgtt ccgcagagaa aagagggccg agcgtctcac ctcgagggtg aaggcactgt
2041 tcagcgtgct caactacgag cgggcgcggc gccccgcct cctgggcgcc tctgtgctgg
2101 gcctggacga tatccacagg gcctggcgca ccttcgtgct gcgtgtgcgg gcccaggacc
2161 cgccgcctga gctgtacttt gtcaaggtgg atgtgacggg cgcgtacgac accatccccc
2221 aggacaggct cacggaggtc atcgccagca tcatcaaacc ccagaacacg tactgcgtgc
2281 gtcggtatgc cgtggtccag aaggccgccc atgggcacgt ccgcaaggcc ttcaagagcc
2341 acgtctctac cttgacagac ctccagccgt acatgcgaca gttcgtggct cacctgcagg
```

```
-continued
2401 agaccagccc gctgagggat gccgtcgtca tcgagcagag ctcctccctg aatgaggcca 2461 gcagtggcct cttcgacgtc ttcctacgct tcatgtgcca ccacgccgtg cgcatcaggg 2521 gcaagtccta cgtccagtgc cagggatcc cgcagggctc catcctctcc acgctgctct 2581 gcagcctgtg ctacgcgac atggagaaca agctgtttgc ggggattcgg cgggacgggc 2641 tgctcctgcg tttggtggat gatttcttgt tggtgacacc tcacctcacc cacgcgaaaa 2701 ccttcctcag gaccctggtc cgaggtgtcc ctgagtatgg ctgcgtggtg aacttgcgga 2761 agacagtggt gaacttccct gtagaagacg aggccctggg tggcacggct tttgttcaga 2821 tgccggccca cggcctattc ccctggtgcg gcctgctgct ggatacccgg accctggagg 2881 tgcagagcga ctactccagc tatgcccgga cctccatcag agccagtctc accttcaacc 2941 gcggcttcaa ggctgggagg aacatgcgtc gcaaactctt tggggtcttg cggctgaagt 3001 gtcacagcct gtttctggat ttgcaggtga acagcctcca gacggtgtgc accaacatct 3061 acaagatcct cctgctgcag gcgtacaggt ttcacgcatg tgtgctgcag ctcccatttc 3121 atcagcaagt ttggaagaac cccacatttt tcctgcgcgt catctctgac acggcctccc 3181 tctgctactc catcctgaaa gccaagaacg cagggatgtc gctggggcc aagggcgccg 3241 ccggccctct gccctccgag gccgtgcagt ggctgtgcca ccaagcattc ctgctcaagc 3301 tgactcgaca ccgtgtcacc tacgtgccac tcctggggtc actcaggaca gcccagacgc 3361 agctgagtcg gaagctcccg gggacgacgc tgactgccct ggaggccgca gccaacccgg 3421 cactgccctc agacttcaag accatcctgg actgatggcc acccgccac agccaggccg 3481 agagcagaca ccagcagccc tgtcacgccg ggctctacgt cccagggagg gaggggcggc 3541 ccacacccag gcccgcaccg ctgggagtct gaggcctgag tgagtgtttg gccgaggcct 3601 gcatgtccgc ctgaaggctg agtgtccggc tgaggcctga gcgagtgtcc agccaagggc 3661 tgagtgtcca gcacacctgc cgtcttcact tccccacagg ctggcgctcg gctccacccc 3721 agggccagct tttcctcacc aggagcccgg cttccactcc ccacatagga atagtccatc 3781 cccagattcg ccattgttca ccccctcgcc tgccctcctt tgccttccac ccccaccatc 3841 caggtggaga ccctgagaag gaccctggga gctctgggaa tttggagtga ccaaaggtgt 3901 gccctgtaca caggcgagga ccctgcacct ggatgggggt ccctgtgggt caaattgggg 3961 ggaggtgctg tgggagtaaa atactgaata tatgagtttt tcagttttga aaaaaaaaa 4021 aaaaaaa
```

In an embodiment, the hTERT is encoded by a nucleic acid having a sequence at least 80%, 85%, 90%, 95%, 96, 97%, 98%, or 99% identical to the sequence of SEQ ID NO: 259. In an embodiment, the hTERT is encoded by a nucleic acid of SEQ ID NO: 259.

Activation and Expansion of Immune Effector Cells, e.g., T Cells

In an embodiment, the immune effector cell is a T cell. Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

The procedure for ex vivo expansion of hematopoietic stem and progenitor cells described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells can comprise: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3 L, IL-1, IL-3 and c-kit ligand, can be used for culturing and expansion of the cells.

In an embodiment, the T cells are expanded by contact with a surface having attached thereto an agent that stimulates a CD3/TCR complex associated signal and a ligand that stimulates a costimulatory molecule on the surface of the T cells. In a T cell a costimulatory molecule is a binding partner on a T cell that binds to a costimulatory ligand, mediating a costimulatory response in the T cell, i.e., an MHC class I molecule, e.g., CD28. In particular, T cell populations may be stimulated as described herein, e.g., by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For stimulation of an accessory molecule (e.g., CD3) on the surface of the T cells, a ligand that binds the accessory molecule is used. A population of T cells can be expanded with an anti-CD3 antibody and an anti-CD28 antibody under conditions appropriate for stimulating proliferation of the T cells. To stimulate proliferation of either CD4+ T cells or CD8+ T cells, an anti-CD3 antibody and an anti-CD28 antibody would be used. Examples of an anti-CD28 antibody include 9.3, B-T3, XR-CD28 (Diaclone, Besançon, France; (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary activation signal and the costimulatory signal for the immune effector cell, e.g. T cell, may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In an embodiment, the agent providing the costimulatory signal is bound to a cell surface and the agent providing the primary activation signal is in solution or coupled to a surface. In certain embodiments, both agents can be in solution. In an embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells.

In an embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In an embodiment, a 1:1 ratio of each antibody bound to the beads for CD4+ immune effector cell, e.g. T cell, expansion and immune effector cell, e.g. T cell, growth is used. In certain embodiments, a ratio of anti CD3:CD28 antibodies bound to the beads is used such that an increase in immune effector cell, e.g. T cell, expansion is observed as compared to the expansion observed using a ratio of 1:1. In an embodiment an increase of from about 1 to about 3 fold is observed as compared to the expansion observed using a ratio of 1:1.

In an embodiment, the ratio of CD3:CD28 antibody bound to the beads ranges from 100:1 to 1:100 and all integer values there between. In an embodiment, more anti-CD28 antibody is bound to the particles than anti-CD3 antibody, i.e., the ratio of CD3:CD28 is less than one. In certain embodiments, the ratio of anti CD28 antibody to anti CD3 antibody bound to the beads is greater than 2:1. In an embodiment, a 1:100 CD3:CD28 ratio of antibody bound to beads is used. In an embodiment, a 1:75 CD3:CD28 ratio of antibody bound to beads is used. In a further embodiment, a 1:50 CD3:CD28 ratio of antibody bound to beads is used. In an embodiment, a 1:30 CD3:CD28 ratio of antibody bound to beads is used. In an embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells or other target cells. The ratio of anti-CD3- and anti-CD28-coupled particles to immune effector cells, e.g. T cells, that result in cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per immune effector cell, e.g. T cell. In an embodiment, a ratio of particles to cells of 1:1 or less is used. In one particular embodiment, a preferred particle: cell ratio is 1:5. In further embodiments, the ratio of particles to cells can be varied depending on the day of stimulation. For example, in an embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In an embodiment, particles are added on a daily or every other day basis to a final ratio of 1:1 on the first day, and 1:5 on the third and fifth days of stimulation. In an embodiment, the ratio of particles to cells is 2:1 on the first day of stimulation and adjusted to 1:10 on the third and fifth days of stimulation. In an embodiment, particles are added on a daily or every other day basis to a final ratio of 1:1 on the first day, and 1:10 on the third and fifth days of stimulation. One of skill in the art will appreciate that a variety of other ratios may be suitable for use. In particular, ratios will vary depending on particle size and on cell size and type. In an embodiment, the most typical ratios for use are in the neighborhood of 1:1, 2:1 and 3:1 on the first day.

In further embodiments, the cells, e.g., T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the immune effector cell, e.g. T cells. In an embodiment the cells (e.g., $10^4$ to $10^9$ T cells) and beads (e.g., DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. In certain embodiments, it may be desirable to significantly decrease the volume in which particles and cells are mixed together (i.e., increase the concentration of cells), to ensure maximum contact of cells and particles. For example, in an embodiment, a concentration of about 10 billion cells/ml, 9 billion/ml, 8 billion/ml, 7 billion/ml, 6 billion/ml, 5 billion/ml, or 2 billion cells/ml is used. In an embodiment, greater than 100 million cells/ml is used. In a further embodiment, a concentration of cells of 10, 15, 20, 25, 30, 35, 40, 45, or 50 million cells/ml is used. In yet an embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a CD19 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In an embodiment, the mixture may be cultured for several hours (about 3 hours) to about 14 days or any hourly integer value in between. In an embodiment, the mixture may be cultured for 21 days. In an embodiment the beads and the immune effector cells, e.g., T cells, are cultured together for about eight days. In an embodiment, the beads and immune effector cells, e.g., T cells, are cultured together for 2-3 days.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CARX cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CARX cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CARX cell, e.g., ex vivo. In embodiments, a CARX cell described herein is contacted with a composition comprising a IL-15 polypeptide during the manufacturing of the CARX cell, e.g., ex vivo. In embodiments, a CARX cell described herein is contacted with a composition comprising a combination of both a IL-15 polypeptide and a IL-15 Ra polypeptide during the manufacturing of the CARX cell, e.g., ex vivo. In embodiments, a CARX cell described herein is contacted with a composition comprising hetIL-15 during the manufacturing of the CARX cell, e.g., ex vivo.

In one embodiment the CARX cell described herein is contacted with a composition comprising hetIL-15 during ex vivo expansion. In an embodiment, the CARX cell described herein is contacted with a composition comprising an IL-15 polypeptide during ex vivo expansion. In an embodiment, the CARX cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

In an embodiment, the method of making disclosed herein further comprises contacting the population of immune effector cells with a nucleic acid encoding a telomerase subunit, e.g., hTERT. The nucleic acid encoding the telomerase subunit can be DNA.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Various assays can be used to evaluate the activity of the CAR molecule, such as but not limited to, the ability to expand T cells following antigen stimulation, sustain T cell expansion in the absence of re-stimulation, and anti-cancer activities in appropriate animal models. Assays to evaluate the effects of the CAR, e.g., an EGFRvIII RCAR, are described in further detail below Western blot analysis of CAR expression in primary T cells can be used to detect their presence using published methods for CARs. See, e.g., Milone et al., Molecular Therapy 17(8): 1453-1464 (2009). Very briefly, T cells (1:1 mixture of CD4$^+$ and CD8$^+$ T cells) expressing the RCARs are expanded in vitro for more than 10 days followed by lysis and SDS-PAGE under reducing conditions. RCARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CAR$^+$ T cells (i.e., CART cells) following antigen stimulation can be measured by flow cytometry. For example, a mixture of CD4$^+$ and CD8$^+$ T cells are stimulated with αCD3/αCD28 beads followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4$^+$ and/or CD8$^+$ T cell subsets by flow cytometry. See, e.g., Milone et al., Molecular Therapy 17(8): 1453-1464 (2009). Alternatively, a mixture of CD4$^+$ and CD8$^+$ T cells are stimulated with αCD3/αCD28 coated magnetic beads on day 0, and transduced with RCAR on day 1 using a bicistronic lentiviral vector expressing RCAR along with eGFP using a 2A ribosomal skipping sequence. Cultures are re-stimulated with RCAR constructs in the presence of antiCD3 and anti-CD28 antibody (K562-BBL-3/28) following washing. Exogenous IL-2 is added to the cultures every other day at 100 IU/ml. GFP T cells are enumerated by flow cytometry using bead-based counting. See, e.g., Milone et al., Molecular Therapy 17(8): 1453-1464 (2009).

Sustained CAR$^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated RCAR on day 1.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with target cells, such as U87MG, BHK or CHO cells expressing EGFRvIII or EGFR wildtype (wt) or CD32 and CD137 (KT32-BBL) for a final T-cell:target cell ratio of 1:1. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8$^+$ T cell expansion ex vivo. T cells are enumerated in cultures using CountBright™ fluorescent beads (Invitrogen, Carlsbad, Calif.) and flow cytometry as described by the manufacturer. CAR$^+$ T cells are identified by GFP expression using T cells that are engineered with eGFP-2A linked RCAR-expressing lentiviral vectors. For RCAR+ T cells not expressing GFP, the CAR+ T cells are detected with biotinylated recombinant protein, e.g., EGFRvIII and a secondary avidin-PE conjugate. CD4+ and CD8$^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by a standard $^{51}$Cr-release assay. See, e.g., Milone et al., Molecular Therapy 17(8): 1453-1464 (2009). Briefly, target cells (e.g., U87MG, BHK or CHO cells expressing RCAR, e.g., EGFRvIII or EGFR wildtype (wt) are loaded with $^{51}$Cr (as NaCrO$_4$, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}$Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average $^{51}$Cr released for each experimental condition. Alternative cytotoxicity assays may also be used, such as flow based cytotoxicity assays. Other assays, including those described in the Example section herein as well as those that are known in the art can also be used to evaluate the CAR constructs.

Alternatively, or in combination to the methods disclosed herein, methods and compositions for one or more of detection and/or quantification of CARX cells (e.g., in vitro or in vivo (e.g., clinical monitoring)), immune cell expansion and/or activation, and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CARX cells is disclosed. For example, the CAR ligand can be used to detect and/or quantify CARX cells in vitro or in vivo (e.g., clinical monitoring of CARX cells in a patient, or dosing a patient). The method includes:

providing the CAR ligand (optionally, a labelled CAR ligand, e.g., a CAR ligand that includes a tag, a bead, a radioactive or fluorescent label);

acquiring the CARX cell (e.g., acquiring a sample containing CARX cells, such as a manufacturing sample or a clinical sample);

contacting the CARX cell with the CAR ligand under conditions where binding occurs, thereby detecting the level (e.g., amount) of the CARX cells present. Binding of the CARX cell with the CAR ligand can be detected using standard techniques such as FACS, ELISA and the like.

In other embodiments, a method of expanding and/or activating cells (e.g., immune effector cells) is disclosed. The method includes:

providing a CAR-expressing cell (e.g., a first CAR-expressing cell or a transiently expressing CAR cell);

contacting said CAR-expressing cell with a CAR ligand, e.g., a CAR ligand as described herein), under conditions where immune cell expansion and/or proliferation occurs, thereby producing the activated and/or expanded cell population.

In another aspect, the CAR ligand is present on (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In one embodiment, the CAR ligand is attached (e.g., covalently attached) to a bead. In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In other embodiments, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting (e.g., reducing and/or killing) a CAR expressing cell is provided. The method includes contacting the CAR expressing cell with a CAR ligand as described herein; and targeting the cell on the basis of binding of the CAR ligand thereby reducing the number, and/or killing, the CAR-expressing cell. In one embodiment, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference. In one embodiment, the anti-idiotypic antibody molecule recognizes an anti-CD19 antibody molecule, e.g., an anti-CD19 scFv. For instance, the anti-idiotypic antibody molecule can compete for binding with the CD19-specific CAR mAb clone no. 136.20.1 described in Jena et al., PLOS March 2013 8:3 e57838; may have the same CDRs (e.g., one or more of, e.g., all of, VH CDR1, VH CDR2, CH CDR3, VL CDR1, VL CDR2, and VL CDR3, using the Kabat definition, the Chothia definition, or a combination of the Kabat and Chothia definitions) as the CD19-specific CAR mAb clone no. 136.20.1; may have one or more (e.g., 2) variable regions as the CD19-specific CAR mAb clone no. 136.20.1, or may comprise the CD19-specific CAR mAb clone no. 136.20.1. In some embodiments, the anti-idiotypic antibody was made according to a method described in Jena et al. In another embodiment, the anti-idiotypic antibody molecule is an anti-idiotypic antibody molecule described in WO 2014/190273. In some embodiments, the anti-idiotypic antibody molecule has the same CDRs (e.g., one or more of, e.g., all of, VH CDR1, VH CDR2, CH CDR3, VL CDR1, VL CDR2, and VL CDR3) as an antibody molecule of WO 2014/190273 such as 136.20.1; may have one or more (e.g., 2) variable regions of an antibody molecule of WO 2014/190273, or may comprise an antibody molecule of WO 2014/190273 such as 136.20.1. In other embodiments, the anti-CAR antibody binds to a constant region of the extracellular binding domain of the CAR molecule, e.g., as described in WO 2014/190273. In some embodiments, the anti-CAR antibody binds to a constant region of the extracellular binding domain of the CAR molecule, e.g., a heavy chain constant region (e.g., a CH2-CH3 hinge region) or light chain constant region. For instance, in some embodiments the anti-CAR antibody competes for binding with the 2D3 monoclonal antibody described in WO 2014/190273, has the same CDRs (e.g., one or more of, e.g., all of, VH CDR1, VH CDR2, CH CDR3, VL CDR1, VL CDR2, and VL CDR3) as 2D3, or has one or more (e.g., 2) variable regions of 2D3, or comprises 2D3 as described in WO 2014/190273.

In some aspects and embodiments, the compositions and methods herein are optimized for a specific subset of T cells, e.g., as described in U.S. Ser. No. 62/031,699 filed Jul. 31, 2014, the contents of which are incorporated herein by reference in their entirety. In some embodiments, the optimized subsets of T cells display an enhanced persistence compared to a control T cell, e.g., a T cell of a different type (e.g., CD8+ or CD4+) expressing the same construct.

In some embodiments, a CD4+ T cell comprises a CAR described herein, which CAR comprises an intracellular signalling domain suitable for (e.g., optimized for, e.g., leading to enhanced persistence in) a CD4+ T cell, e.g., an ICOS domain. In some embodiments, a CD8+ T cell comprises a CAR described herein, which CAR comprises an intracellular signalling domain suitable for (e.g., optimized for, e.g., leading to enhanced persistence of) a CD8+ T cell, e.g., a 4-1BB domain, a CD28 domain, or another costimulatory domain other than an ICOS domain. In some embodiments, the CAR described herein comprises an antigen binding domain described herein Therapeutic Application of Target Expressing Diseases and Disorders Methods for inhibiting the proliferation or reducing a cancer in a cancer antigen-expressing cell population, e.g., an EGFRvIII-expressing cell population, are provided herein. In certain embodiments, the immune effector cell engineered to express a CAR (i.e., CARX cells, e.g., CART cells, CARN cells, etc) reduces the quantity, number, amount or percentage of cells and/or cancer cells by at least 25%, at least 30%, at least 40%, at least 50%, at least 65%, at least 75%, at least 85%, at least 95%, or at least 99% in a subject with a cancer associated with antigen-expressing cells relative to a negative control. In an embodiment, the subject is a human.

Methods disclosed herein includes a type of cellular therapy where immune effector cell, e.g. T cells, are genetically modified to express CAR and the resulting CARX cells is infused into a recipient in need thereof. The infused RCARX cell is able to kill or inhibit tumor cells in the recipient.

Without wishing to be bound by any particular theory, the anti-cancer immunity response elicited by the CARX cells, e.g., CART cells, may be an active or a passive immune response, or alternatively may be due to a direct vs. indirect immune response. In an embodiment, the CARX cells, e.g., CART cells, exhibit specific proinflammatory cytokine secretion and potent cytolytic activity in response to human cancer cells expressing the target antigen, resist soluble CAR inhibition, mediate bystander killing and mediate regression of an established human tumor.

A procedure for ex vivo expansion of hematopoietic stem and progenitor cells is described in U.S. Pat. No. 5,199,942, incorporated herein by reference, can be applied to the cells described herein. Other suitable methods are known in the art therefore the methods disclosed herein are not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

Generally, the cells activated and expanded as described herein may be utilized in the treatment and prevention of diseases that arise in individuals who are immunocompromised. In particular, the CARX, cells e.g., CART cells, are used in the treatment of diseases, disorders and conditions associated with expression of a tumor antigen. In certain embodiments, the CARX, cells e.g., CART cells, are used in the treatment of patients at risk for developing diseases, disorders and conditions associated with expression of tumor antigen. Thus, the present disclosure provides methods for the treatment or prevention of diseases, disorders and conditions associated with expression of tumor antigen comprising administering to a subject in need thereof, a therapeutically effective amount of CARX modified cells, e.g., CART cells.

The CARX cells, e.g., CART cells, may be administered either alone, or as a pharmaceutical composition in combination with diluents and/or with other components such as IL-2 or other cytokines or cell populations.

The present invention provides methods for inhibiting the proliferation or reducing a cell population expressing a cancer associated antigen as described herein, the methods comprising contacting a population of cells comprising a cancer associated antigen as described herein with a CARX cell (e.g., T cell) of the invention that binds to the cancer associated antigen as described herein. In a specific aspect, the present invention provides methods for inhibiting the proliferation or reducing the population of cancer cells expressing a cancer associated antigen as described herein, the methods comprising contacting a cancer cell population expressing a cancer associated antigen as described herein with a CARX cell of the present invention that binds to the cell expressing the cancer associated antigen. In an embodiment, the immune effector cell (e.g., T cell) can be from a subject treated with a low, immune enhancing, dose of an mTOR inhibitor, e.g., an allosteric inhibitor, e.g., RAD001, or a catalytic inhibitor. In an embodiment, the immune effector cells (e.g., T cells) have been contacted with an amount of an mTOR inhibitor, e.g., an allosteric inhibitor, e.g., RAD001, or a catalytic inhibitor sufficient to decrease the number of PD1 positive immune effector cells, increase the number of PD1 negative immune effector cells, e.g., T cells, increase the ratio of PD1 negative immune effector cells, e.g., T cells/PD1 positive immune effector cells, e.g., T cells, increase the number of naïve T cells, increase the number of memory T cell precursors, or increase the expression level of memory T cell precursor markers, as described herein. In certain aspects, a CAR of the present invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for a cancer associated with a cancer associated antigen as described herein (e.g., a hematological cancer) relative to a negative control. In one aspect, the subject is a human.

The present invention also provides methods for preventing, treating and/or managing a disease associated with a cancer associated antigen as described herein-expressing cells (e.g., a cancer associated with a cancer associated antigen as described herein, e.g., a hematological cancer), the methods comprising administering to a subject in need a CARX cell (e.g., T cell) of the invention that binds to a cell expressing a cancer associated antigen as described herein.

The present invention provides methods for preventing relapse of cancer associated with a cancer associated antigen as described herein, the methods comprising administering to a subject in need thereof a CARX cell, e.g., a T cell, of the invention that binds to a cancer associated antigen as described herein.

Indications for Treatment with a Redirected Switchable Inhibitor Receptor

In one aspect, the present invention relates to treatment of a subject in vivo using a PD1 CAR such that growth of cancerous tumors is inhibited. A PD1 CAR may be used alone to inhibit the growth of cancerous tumors. Alternatively, PD1 CAR may be used in conjunction with other CARs, immunogenic agents, standard cancer treatments, or other antibodies. In an embodiment, the PD1 CAR comprises a sortase transfer signature, e.g., disposed between an extracellular domain and a transmembrane domain.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) *Int. Immunol.* 17:133-144) can be effected using the antibody molecules described herein.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein.

Pharmaceutical Compositions and Treatments

Pharmaceutical compositions may comprise a CARX cells e.g., CART cells or CARN cells, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In an embodiment, the pharmaceutical compositions are formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-cancer effective amount," "a cancer-inhibiting effective amount," or "therapeutic amount" is indicated, the precise amount of the compositions to be administered can be determined by a physician with consideration of individual differences in age, weight, disease state, e.g., tumor size, extent of infection or metastasis, and condition of the patient (subject). In embodiments, a pharmaceutical composition comprising the CARX cells, e.g., CART cells, described herein may be administered at a dosage of $10^4$ to $10^9$ cells/kg body weight, in some instances $10^5$ to $10^6$ cells/kg body weight, including all integer values within those ranges. Immune effector cell, e.g. T cell, compositions may also be administered multiple times at these dosages.

In certain embodiments CARX cells, e.g., CART are activated and expanded to therapeutic levels, and are administered to a patient by using infusion techniques that are commonly known in immunotherapy (see, e.g., Rosenberg et al., New Eng. J. of Med. 319:1676, 1988). The optimal dosage and treatment regime for a particular patient can be determined by one skilled in the art of medicine by monitoring the patient for signs of disease and adjusting the treatment accordingly.

In embodiments, the RCARX cells with RCARs comprising one or more switch domains, generate an intracellular signal that promotes an immune effector response in the presence of a dimerization molecule, e.g., a small molecule heterodimerization molecule, e.g., RAD001 or AP21967.

The administration of the dimerization molecule may be carried out in any convenient manner, including by aerosol inhalation, injection, ingestion, transfusion, or implantation. In an embodiment the dimerization molecule is administered orally. The dimerization molecule may be administered to a patient transarterially, subcutaneously, intradermally, intratumorally, intranodally, intramedullary, intramuscularly, by intravenous (i.v.) injection, or intraperitoneally. In an embodiment, the dimerization molecule is administered orally, e.g., in tablet form. In an embodiment, the dimerization molecule is administered by intradermal or subcutaneous injection. In an embodiment, an embodiment the dimerization molecule is administered by i.v. injection.

In an embodiment, the dimerization molecule is administered after the RCARX cells, e.g., RCART cells, have been infused into the patient. In one embodiment, the dimerization molecule is administered one day after the RCARX cells, e.g., RCART cells, have been infused into the patient. In one embodiment, the dimerization molecule is administered 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after the RCARX cells, e.g., RCART cells, have been infused into the patient. In an embodiment the dimerization molecule is administered after administration of the RCARX cells, e.g., on or after 1, 2, 3, 4, 5, 6, 7, 8, 9, 10, 11, 12, 16, 17, 18, 19, 20, 21, 22, or 23 hours, or on or after 1, 2, 3, 4, 5, 6, 7 or 8 days, after administration of the RCARX cells. In one embodiment, the dimerization molecule is administered more than once to the after the RCARX cells, e.g., RCART cells, have been infused into the patient, e.g., based on a dosing schedule tailored for the patient, e.g., administration of the dimerization molecule on a bi-weekly, weekly, monthly, 6-monthly, yearly basis. In an embodiment, dosing of the dimerization molecule will be daily, every other day, twice a week, or weekly, but in embodiments will not exceed 5 mg, 10 mg, 15 mg, 20 mg, 30 mg, 40 mg, or 50 mg, weekly. In an embodiment, the dimerization molecule is dosed continuously, e.g. by use of a pump, e.g., a wearable pump. In an embodiment continuous administration lasts for at least 4 hours, 12 hours, 24 hours, 2 days, 3 days, 4 days or 5 days. In an embodiment, a FKBP-FRB heterodimerization molecule, e.g., rapamycin, or a rapalog, e.g., AP21967 or RAD001, is administered at a dose of no greater than about 0.5 mg in a 24 hr period.

In an embodiment a dimerization molecule is administered at the same time, e.g., on the same day, as the administration of the RCARX cells.

In an embodiment, the patient is monitored after the dimerization molecule has been administered for a decrease in cancer. If the cancer reappears, the dimerization molecule can be readministered at that time. In an embodiment, a subject will undergo additional or subsequent, e.g., second, third or fourth, RCART cell infusions, e.g., at weekly or monthly intervals, or as determined to be needed. In an embodiment, a subsequent administration is accompanied with, or followed by, administration of the dimerization molecule. In an embodiment subsequent administration of RCARX, or dimerization molecule continues, e.g., until tumor burden is cleared, no additional benefit is perceived, or a preselected criterion is met. In an embodiment, a method disclosed herein comprises administration of cellular therapy wherein immune effector cells, e.g. T cells, are genetically modified to express a chimeric antigen receptor (CAR). The CARX, e.g., CART cell is infused to a recipient in need thereof. The infused cell is able to kill tumor cells in the recipient but only in the presence of the dimerization molecule. In addition, in the presence of the dimerization molecule, RCARX, e.g., RCART cells will expand and replicate in vivo upon engagement of their target antigen which will lead to sustained tumor control. Cytokine release during tumor cell killing may also be measured in the serum. This expansion and cytokine production can be measured in the patient by routine blood draws and subsequent analysis of CAR expression and serum cytokine levels. This method will also inform one skilled in the art to modify dosing strategy of the dimerization molecule to maintain the functional RCARX, e.g., RCART cell population. It is envisioned that dosing of the dimerization molecule will continue as long as tumor burden is being reduced.

Dosages of dimerization molecules depend on the type of dimerization molecule being used and the PK properties of the individual dimerization molecules.

Also provided herein are compositions comprising a FKBP-FRB heterodimerization molecule, e.g., rapamycin, or a rapalog, e.g., AP21967 or RAD001 at a concentration of about 0.005-1.5 mg, about 0.005-1.5 mg, about 0.01-1 mg, about 0.01-0.7 mg, about 0.01-0.5 mg, or about 0.1-0.5 mg. In a further aspect the present invention provides compositions comprising a FKBP-FRB heterodimerization molecule, e.g., rapamycin, or a rapalog, e.g., AP21967 or RAD001 at a concentration of 0.005-1.5 mg, 0.005-1.5 mg, 0.01-1 mg, 0.01-0.7 mg, 0.01-0.5 mg, or 0.1-0.5 mg. More particularly, in one aspect, the invention provides compositions comprising a FKBP-FRB heterodimerization molecule, e.g., rapamycin, or a rapalog, e.g., AP21967 or RAD001 at a dose of about 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, the FKBP-FRB heterodimerization molecule, e.g., rapamycin, or a rapalog, e.g., AP21967 or RAD001 is at a dose of 0.5 mg or less. In a still further aspect, a FKBP-FRB heterodimerization molecule, e.g., rapamycin, or a rapalog, e.g., AP21967 or RAD001 is at a dose of about 0.5 mg. In a further aspect, the invention provides compositions comprising a FKBP-FRB heterodimerization molecule, e.g., rapamycin, or a rapalog, e.g., AP21967 or RAD001 at a dose of 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, or 1.0 mg. In one aspect, a FKBP-FRB heterodimerization molecule, e.g., rapamycin, or a rapalog, e.g., AP21967 or RAD001 is at a dose of 0.5 mg or less. In a still further aspect, a FKBP-FRB heterodimerization molecule, e.g., rapamycin, or a rapalog, e.g., AP21967 or RAD001 is at a dose of 0.5 mg. In a further aspect, the invention relates to compositions comprising an rapamycin, or a rapamycin analog, that is not RAD001, in an amount that is bioequivalent to the specific amounts or doses specified for RAD001. In a further aspect, the invention relates to compositions comprising a FKBP-FRB heterodimerization molecule, e.g., rapamycin, or a rapalog, e.g., AP21967 or RAD001 in an amount sufficient to promote RCART activation following target engagement, as measured by NFAT activation, tumor cell killing or cytokine production. In an embodiment the dose of the a FKBP-FRB heterodimerization molecule, e.g., rapamycin, or a rapalog, e.g., AP21967 or RAD001 is not immunsuppressive. In an embodiment a dose provided here is designed to produce only partial or minimal inhibition of mTOR activity.

Also within the invention are unit dosage forms of a heterodimerization molecule, e.g., rapamycin, or a rapalog, e.g., AP21967 or RAD001, that contain 25%, 50%, 100%, 150% or 200% of any daily dosage referred to herein.

A FKBP-FRB heterodimerization molecule, e.g., rapamycin, or a rapalog, e.g., AP21967 or RAD001, can be administered at a dose that results in a therapeutic effect.

In an embodiment, rapamycin, or a rapalog, e.g., AP21967 or RAD001, is administered at a dose of about 0.005-1.5 mg daily, about 0.01-1 mg daily, about 0.01-0.7 mg daily, about 0.01-0.5 mg daily, or about 0.1-0.5 mg daily.

In an embodiment, rapamycin, or a rapalog, e.g., AP21967 or RAD001, is administered at a dose of 0.005-1.5 mg daily, 0.005-1.5 mg daily, 0.01-1 mg daily, 0.01-0.7 mg daily, 0.01-0.5 mg daily, or 0.1-0.5 mg daily.

In an embodiment, rapamycin, or a rapalog, e.g., AP21967 or RAD001, is administered at a dose of about: 0.005 mg daily, 0.006 mg daily, 0.007 mg daily, 0.008 mg daily, 0.009 mg daily, 0.01 mg daily, 0.02 mg daily, 0.03 mg daily, 0.04 mg daily, 0.05 mg daily, 0.06 mg daily, 0.07 mg daily, 0.08 mg daily, 0.09 mg daily, 0.1 mg daily, 0.2 mg daily, 0.3 mg daily, 0.4 mg daily, 0.5 mg daily, 0.6 mg daily, 0.7 mg daily, 0.8 mg daily, 0.9 mg daily, or 1.0 mg daily.

In an embodiment, rapamycin, or a rapalog, e.g., AP21967 or RAD001, is administered at a dose of 0.5 mg daily, or less than 0.5 mg daily.

In an embodiment, rapamycin, or a rapalog, e.g., AP21967 or RAD001, is administered at a dose of about 0.1-20 mg weekly, about 0.5-15 mg weekly, about 1-10 mg weekly, or about 3-7 mg weekly.

In an embodiment, rapamycin, or a rapalog, e.g., AP21967 or RAD001, is administered at a dose of 0.1-20 mg weekly, 0.5-15 mg weekly, 1-10 mg weekly, or 3-7 mg weekly.

In an embodiment, rapamycin, or a rapalog, e.g., AP21967 or RAD001, is administered at a dose of no greater than about: 0.7 mg in a 24 hour period; 0.5 mg in a 24 hour period. In some embodiments, rapamycin, or a rapalog, e.g., AP21967 or RAD001, can be administered at a dose of or 0.5 mg, or less daily. In some embodiments, rapamycin, or a rapalog, e.g., AP21967 or RAD001 can be administered at a dose of 0.5 mg daily.

In an embodiment, rapamycin, or a rapalog, e.g., AP21967 or RAD001, is administered at a dose of about: 0.1 mg weekly, 0.2 mg weekly, 0.3 mg weekly, 0.4 mg weekly, 0.5 mg weekly, 0.6 mg weekly, 0.7 mg weekly, 0.8 mg weekly, 0.9 mg weekly, 1 mg weekly, 2 mg weekly, 3 mg weekly, 4 mg weekly, 5 mg weekly, 6 mg weekly, 7 mg weekly, 8 mg weekly, 9 mg weekly, 10 mg weekly, 11 mg weekly, 12 mg weekly, 13 mg weekly, 14 mg weekly, 15 mg weekly, 16 mg weekly, 17 mg weekly, 18 mg weekly, 19 mg weekly, or 20 mg weekly.

In an embodiment, the invention can utilize an FKBP-FRB heterodimerization molecule other than RAD001 in an amount that is bioequivalent, in terms of its ability to activate a RCAR, to the specific amounts or doses specified for RAD001.

In an embodiment, rapamycin, or a rapalog, e.g., AP21967 or RAD001, is administered at a dosage of about: 30 pM to 4 nM; 50 pM to 2 nM; 100 pM to 1.5 nM; 200 pM to 1 nM; 300 pM to 500 pM; 50 pM to 2 nM; 100 pM to 1.5 nM; 200 pM to 1 nM; or 300 pM to 500 pM.

In an embodiment, rapamycin, or a rapalog, e.g., AP21967 or RAD001, is administered at a dosage of about: 30 pM, 40 pM, 50 pM, 60 pM, 70 pM, 80 pM, 90 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 1.5 nM, 2 nM, 2.5 nM, 3 nM, 3.5 nM, or 4 nM.

In an embodiment, rapamycin, or a rapalog, e.g., AP21967 or RAD001, is administered to a subject at a dosage that provides a target trough level. As used herein, the term "trough level" refers to the concentration of a drug in plasma just before the next dose, or the minimum drug concentration between two doses. In an embodiment, the trough level is significantly lower than trough levels associated with dosing regimens used in organ transplant and cancer patients. In an embodiment rapamycin, or a rapalog, e.g., AP21967 or RAD001, is administered to result in a trough level that is less than ½, ¼, ¹⁄₁₀, or ¹⁄₂₀ of the trough level that results in immunosuppression or an anticancer effect. In an embodiment rapamycin, or a rapalog, e.g., AP21967 or RAD001, is administered to result in a trough level that is less than ½, ¼, ¹⁄₁₀, or ¹⁄₂₀ of the trough level provided on the FDA approved packaging insert for use in immunosuppression or an anticancer indications.

In an embodiment, a heterodimerization molecule, e.g., rapamycin, or a rapalog, e.g., AP21967 or RAD001, is administered in sufficient amounts to provide a trough level in a selected range. In an embodiment the range is selected from between: 0.1 and 4.9 ng/ml; 2.4 and 4.9 ng/ml; about 0.1 and 2.4 ng/ml; about 0.1 and 1.5 ng/ml.

In an embodiment, a heterodimerization molecule, e.g., rapamycin, or a rapalog, e.g., AP21967 or RAD001, is administered in sufficient amounts to provide a trough level of about: 0.1 ng/ml; 0.2 ng/ml; 0.3 ng/ml; 0.4 ng/ml; 0.5 ng/ml; 0.6 ng/ml; 0.7 ng/ml; 0.8 ng/ml; 0.9 ng/ml; 1.0 ng/ml; 1.1 ng/ml; 1.2 ng/ml; 1.3 ng/ml; 1.4 ng/ml; and 1.5 ng/ml.

In an embodiment, a heterodimerization molecule, e.g., rapamycin, or a rapalog, e.g., AP21967 or RAD001, is administered in sufficient amounts to provide a trough level of less than: 5 ng/ml; 2.5 ng/ml; 2 ng/ml; 1.9 ng/ml; 1.8 ng/ml; 1.7 ng/ml; 1.6 ng/ml; 1.5 ng/ml; 1.4 ng/ml; 1.3 ng/ml; 1.2 ng/ml; 1.1 ng/ml; 1.0 ng/ml; 0.9 ng/ml; 0.8 ng/ml; 0.7 ng/ml; 0.6 ng/ml; 0.5 ng/ml; 0.4 ng/ml; 0.3 ng/ml; 0.2 ng/ml; or 0.1 ng/ml.

Also within the invention are unit dosage forms of a heterodimerization molecule, e.g., rapamycin, or a rapalog, e.g., AP21967 or RAD001, that contain any daily dosage referred to herein.

The use of low, immune enhancing, doses of mTOR inhibitors, e.g., for optimizing the ratio of PD1 negative immune effector cells/PD1 positive immune effector cells, is described herein (see the section entitled "Combination With A Low, Immune Enhancing, Dose of An mTOR Inhibitor". In an embodiment, an allosteric mTOR inhibitor, e.g., RAD001, dosing regimen, or formulation, from that section can be used as a dimerization molecule with FKBP/FRB dimerization switches.

In an embodiment, an RCAR, e.g., an RCART, cell is treated with dimerization molecule after removal from the body but before introduction into the subject.

In an embodiment, an RCAR, e.g., an RCART, cell is treated with dimerization molecule after ex vivo generation of the RCAR and prior to introduction into the subject.

In an embodiment the RCAR comprises a GyrB-GyrB based switch, e.g., an GyrB-GyrB based switch described herein, e.g., an GyrB-GyrB based switch as described herein, e.g., in the Dimerization Switch Module.

In an embodiment the RCAR comprises a GAI-GID1 based switch, e.g., an GAI-GID1 based switch described herein, e.g., an GAI-GID1 based switch as described herein, e.g., in the Dimerization Switch Module.

In an embodiment the RCAR comprises a Halotag/SNAP-tag based switch, e.g., a Halotag/SNAP-tag based switch described herein, e.g., a Halotag/SNAP-tag based switch as described herein, e.g., in the Dimerization Switch Module.

In an embodiment, the RCARX, e.g., RCART, cell is contacted with dimerization molecule at a concentration selected from the following:

2,000-0.01 nM; 2,000-100 nM; 1000-0.01 nM; 500-0.01 nM; 100-0.01 nM; 100-0.05 nM; 100-0.5 nM; 100-1 nM 100-10 nM; 25-0.01 nM; 20 to 0.01 nM; 10-0.01 nM; 10-0.1 nM; or 10-1.0 nM.

In an embodiment, the RCAR comprises a FKBP-FRAP based switch, e.g., an FKBP-FRAP based switch described herein, e.g., an FKBP-FRAP based switch as described herein, e.g., in the Dimerization Switch Module.

In an embodiment, the RCARX, e.g., RCART, comprises an FKBP-FRAP dimerization switch and the dimerization molecule is rapamycin or a rapamycin analog, e.g., a rapamycin analog disclosed herein, e.g., RAD001 or AP21967, and is the RCARX cell is contacted with dimerization molecule at a concentration selected from the following:

2,000-0.01 nM; 2,000-100 nM; 1000-0.01 nM; 500-0.01 nM; 100-0.01 nM; 100-0.05 nM; 100-0.5 nM; 100-1 nM 100-10 nM; 25-0.01 nM; 20 to 0.01 nM; 10-0.01 nM; 10-0.1 nM; or 10-1.0 nM.

In further embodiments, the CARX cells, e.g., CART cells may be used in a treatment regimen in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. Drugs that inhibit either the calcium dependent phosphatase calcineurin (cyclosporine and FK506) or inhibit the p70S6 kinase that is important for growth factor induced signalling (rapamycin). (Liu et al., Cell 66:807-815, 1991; Henderson et al., Immun. 73:316-321, 1991; Bierer et al., Curr. Opin. Immun. 5:763-773, 1993) can also be used.

In a further embodiment, the cell compositions are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In an embodiment, the cell compositions are administered following B-cell ablative therapy such as agents that react with CD20, e.g., Rituxan. For example, in an embodiment, subjects may undergo standard treatment with high dose chemotherapy followed by peripheral blood stem cell transplantation. In certain embodiments, following the transplant, subjects receive an infusion of the expanded immune cells described herein. In an embodiment where CARX cells, e.g., CART cells, are administered post-transplant, the immune effector cells, e.g., T cells, used to make the CARX cells, e.g., RCART cells, are obtained from the subject after transplant. In an embodiment, the immune effector cells, e.g., T cells, used to make the CARX, e.g., CART cell, are of donor origin, e.g., they are derived from donor cells implanted in the subject.

In an additional embodiment, expanded cells are administered before or following surgery. In an embodiment, CARX, e.g., CART cells, are administered to the subject after surgery that debulks the tumor.

In a particular exemplary embodiment, subjects may undergo leukapheresis, wherein leukocytes are collected, enriched, or depleted ex vivo to select and/or isolate the cells of interest, e.g., immune effector cells, e.g., T cells. These immune effector cell, e.g. T cell, isolates may be expanded by methods known in the art and treated such that one or more CAR constructs of the disclosed herein may be introduced, thereby creating a CARX, e.g., CART cell. Subjects in need thereof may subsequently undergo standard treatment with high dose chemotherapy followed by peripheral blood stem cell transplantation. In certain embodiments, following or concurrent with the transplant, subjects receive an infusion of the expanded CARX, e.g., CART cells disclosed herein. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. In an embodiment, the dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

Combination with a Low, Immune Enhancing, Dose of an mTOR Inhibitor.

Methods described herein use low, immune enhancing, doses of mTOR inhibitors, e.g., allosteric mTOR inhibitors, including rapalogs such as RAD001. Administration of a low, immune enhancing, dose of an mTOR inhibitor (e.g., a dose that is insufficient to completely suppress the immune system, but sufficient to improve immune function) can optimize the performance of immune effector cells, e.g., T cells or CARX cells, in the subject. Methods for measuring mTOR inhibition, dosages, treatment regimens, and suitable pharmaceutical compositions are described in U.S. Patent Application No. 2015/01240036, hereby incorporated by reference.

In an embodiment, administration of a low, immune enhancing, dose of an mTOR inhibitor can result in one or more of the following:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$ $CD27^+$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$ increased $CD27^+$, decreased KLRG1, and increased BCL2;

and wherein any of the foregoing, e.g., i), ii), iii), iv), v), vi), or vii), occurs e.g., at least transiently, e.g., as compared to a non-treated subject.

In another embodiment, administration of a low, immune enhancing, dose of an mTOR inhibitor results in increased or prolonged proliferation or persistence of CARX cells, e.g., in culture or in a subject, e.g., as compared to non-treated CARX cells or a non-treated subject. In embodiments, increased proliferation or persistence is associated with in an increase in the number of CARX cells. Methods for measuring increased or prolonged proliferation are described in Examples 9 and 10. In another embodiment, administration of a low, immune enhancing, dose of an mTOR inhibitor results in increased killing of cancer cells by CARX cells, e.g., in culture or in a subject, e.g., as compared to non-treated CARX cells or a non-treated subject. In embodiments, increased killing of cancer cells is associated with in a decrease in tumor volume. Methods for measuring increased killing of cancer cells are described, e.g., in International Application WO2014/153270, which is herein incorporated be reference in its entirety.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001, or a bioequivalent dose thereof. In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001, or a bioequivalent dose thereof.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, at least 70 but no more than 90%, at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, at least 60 but no more than 80%, at least 5 but no more than 70%, at least 10 but no more than 70%, at least 15, but no more than 70%, at least 20 but no more than 70%, at least 30 but no more than 70%, at least 40 but no more than 70%, at least 50 but no more than 70%, at least 5 but no more than 60%, at least 10 but no more than 60%, at least 15, but no more than 60%, at least 20 but no more than 60%, at least 30 but no more than 60%, at least 40 but no more than 60%, at least 5 but no more than 50%, at least 10 but no more than 50%, at least 15, but no more than 50%, at least 20 but no more than 50%, at least 30 but no more than 50%, at least 40 but no more than 50%, at least 5 but no more than 40%, at least 10 but no more than 40%, at least 15, but no more than 40%, at least 20 but no more than 40%, at least 30 but no more than 40%, at least 35 but no more than 40%, at least 5 but no more than 30%, at least 10 but no more than 30%, at least 15, but no more than 30%, at least 20 but no more than 30%, or at least 25 but no more than 30%.

The extent of mTOR inhibition can be conveyed as, or corresponds to, the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by various methods, such as measuring P70 S6 kinase activity by the Boulay assay, as described in U.S. Patent Application No. 2015/01240036, hereby incorporated by reference, or as described in U.S. Pat. No. 7,727,950, hereby incorporated by reference; measuring the level of phosphorylated S6 by western blot; or evaluating a change in the ratio of PD1 negative immune effector cells to PD1 positive immune effector cells.

As used herein, the term "mTOR inhibitor" refers to a compound or ligand, or a pharmaceutically acceptable salt thereof, which inhibits the mTOR kinase in a cell. In an embodiment, an mTOR inhibitor is an allosteric inhibitor. Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity. In an embodiment, an mTOR inhibitor is a catalytic inhibitor.

Rapamycin is a known macrolide antibiotic produced by *Streptomyces hygroscopicus* having the structure shown in Formula A.

(A)

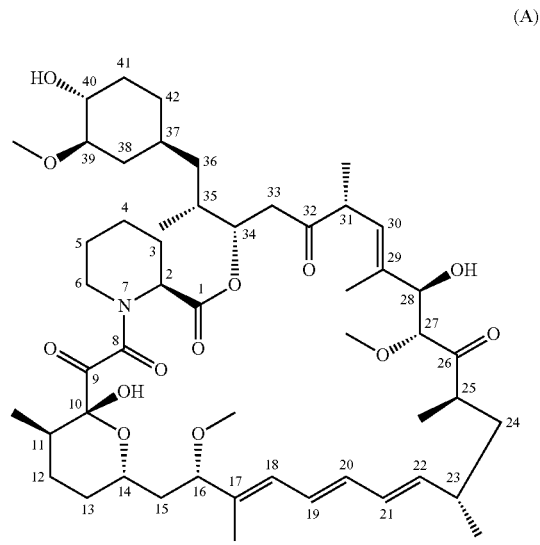 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as everolimus, as described in U.S. Pat. No. 5,665,772 and WO94/09010, the contents of each are incorporated by reference.

Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'- yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)kapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807, the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R, 23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9] hexatriaconta-16,24,26,28-tetraene-2,3,10,14,20-pentaone, as described in U.S. Pat. No. 5,665,772 and WO94/09010, the contents of each are incorporated by reference.

Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibtors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form (the synthesis of BEZ235 is described in WO2006/122806); CCG168 (otherwise known as AZD-8055, Chresta, C. M., et al., Cancer Res, 2010, 70(1), 288-298) which has the chemical name {5-[2,4-bis-((S)-3-methylmorpholin-4-yl)-pyrido[2,3d]pyrimidin-7-yl]-2-methoxyphenyl}-methanol; 3-[2,4-bis[(3S)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); and (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTOR inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Biopolymer Delivery Methods

In some embodiments, one or more CARX cells as disclosed herein, can be administered or delivered to the subject via a biopolymer scaffold, e.g., a biopolymer implant. Biopolymer scaffolds can support or enhance the delivery, expansion, and/or dispersion of the CARX cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4, 6-pentaacetyl α-D-galactose), cellulose, chitin, chitosan, collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly (lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CARX cells described herein are seeded onto the biopolymer scaffold prior to delivery to the subject. In embodiments, the biopolymer scaffold further comprises one or more additional therapeutic agents described herein (e.g., another CARX cell, an antibody, or a small molecule) or agents that enhance the activity of a CARX cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., Nature Biotechnology, 2015, 33:97-101; and WO2014/110591.

Combination Therapies

Methods described herein that comprise administering a CARX cell described herein may be used in combination with other known agents and therapies.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CARX cell described herein and the at least one additional therapeutic agent can be administered simultaneously, in the same or in separate compositions, or sequentially. The agents can be administered in any order. For example, in sequential administration the CARX cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before another treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, administration of a CARX cell described herein may be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, administration of a CARX cell described herein can be used in combination with an mTOR pathway inhibitor, e.g., an agent that reduces mTOR pathway activation by acting on a target, other than mTOR, which target is in a biological pathway with mTOR. Without wishing to be bound by theory, in some embodiments, by combining an mTOR inhibitor with an mTOR pathway inhibitor, more pronounced mTOR inhibition can be achieved. In some embodiments, the mTOR pathway inhibitor is an activator of adenosine monophosphate activated protein kinase (AMPK), such as metformin or an analog, pharmaceutically acceptable form, or prodrug thereof. According to the non-limiting theory herein, stimulation of AMPK (e.g., by metformin) can lead to inhibition of the mTOR ribosomal S6 kinase pathway. In some embodiments, the mTOR pathway inhibitor is selected from the group consisting of: vitamin E, vitamin A, an antibacterial antibiotic, an antioxidant, L-carnitine, lipoic acid, metformin, resveratrol, leptine, a non-steroid anti-inflammatory drug, or a COX inhibitor, or an analog, pharmaceutically acceptable form, or prodrug thereof. In some embodiments, the mTOR pathway inhibitor is an agent described in International Application WO2010/056754 or WO2008/110491, or Liu et al, Anticancer Res., 32: 1627-1638 (2012), each of which is incorporated herein by reference in its entirety.

In one embodiment, administration of a CARX cell described herein can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents for use in combination with a CAR cell therapy include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents for use in combination with a CAR cell therapy include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary immunomodulators for use in combination with a CAR cell therapy include, e.g., afutuzumab (available from Roche®); pegfilgrastim (Neulasta®); lenalidomide (CC-5013, Revlimid®); thalidomide (Thalomid®), pomalidomide, actimid (CC4047); and IRX-2 (mixture of human cytokines including interleukin 1, interleukin 2, and interferon γ, CAS 951209-71-5, available from IRX Therapeutics).

Exemplary anthracyclines for use in combination with a CAR cell therapy include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids for use in combination with a CAR cell therapy include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors for use in combination with a CAR cell therapy include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Exemplary GITR agonists for use in combination a CAR cell therapy include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726.

In an embodiment, cells expressing a CAR described herein, are administered to a subject in combination with a molecule that decreases the Treg cell population. Methods that decrease the number of (e.g., deplete) Treg cells are known in the art and include, e.g., CD25 depletion, cyclophosphamide administration, and modulating GITR function. Without wishing to be bound by theory, it is believed that reducing the number of Treg cells in a subject prior to apheresis or prior to administration of a CARX cell described herein reduces the number of unwanted immune cells (e.g., $T_{regs}$) in the tumor microenvironment and reduces the subject's risk of relapse. In one embodiment, a low, immune enhancing, dose, of an mTOR inhibitor, e.g., an allosteric inhibitor, e.g., RAD001, or a catalytic inhibitor and a CAR expressing cell described herein are administered to a subject in combination with a molecule targeting GITR and/or modulating GITR functions, such as a GITR agonist and/or a GITR antibody that depletes regulatory T cells ($T_{regs}$). In one embodiment, a low, immune enhancing, dose, of an mTOR inhibitor, e.g., an allosteric inhibitor, e.g., RAD001, or a catalytic inhibitor and a CAR expressing cell described herein are administered to a subject in combination with cyclophosphamide. In one embodiment, the GITR binding molecule and/or molecule modulating GITR function (e.g., GITR agonist and/or Treg depleting GITR antibodies) is administered prior to the CARX cell. For example, in one embodiment, the GITR agonist can be administered prior to apheresis of the cells. In embodiments, cyclophosphamide is administered to the subject prior to administration (e.g., infusion or re-infusion) of the CARX cell or prior to aphersis of the cells. In embodiments, cyclophosphamide and an anti-GITR antibody are administered to the subject prior to administration (e.g., infusion or re-infusion) of the CARX cell or prior to apheresis of the cells. In one embodiment, the subject has cancer (e.g., a solid cancer or a hematological cancer such as ALL or CLL). In one embodiment, the subject has CLL. In embodiments, the subject has a solid cancer, e.g., a solid cancer described herein.

Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726.

In one embodiment, a CARX cell described herein can be used in combination with a kinase inhibitor.

In one embodiment, the kinase inhibitor is an MNK inhibitor, e.g., a MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the kinase inhibitor is 4-amino-5-(4-fluoroanilino)-pyrazolo [3,4-d] pyrimidine.

In one embodiment, the kinase inhibitor is a CDK4 inhibitor selected from 7-cyclopentyl-N,N-dimethyl-2-((5-(piperazin-1-yl)pyridine-2-yl)amino)-7H-pyrrolo[2,3-d]pyrimidine-6-carboxamide (also referred to as LEE011); aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., a CDK4 inhibitor described herein, e.g., a CDK4/6 inhibitor, such as, e.g., 7-cyclopentyl-N,N-dimethyl-24(5-(piperazin-1-yl)pyridine-2-yl)amino)-7H-pyrrolo[2,3-d]pyrimidine-6-carboxamide (also referred to as LEE011) or 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment, the kinase inhibitor is a BTK inhibitor, e.g., selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

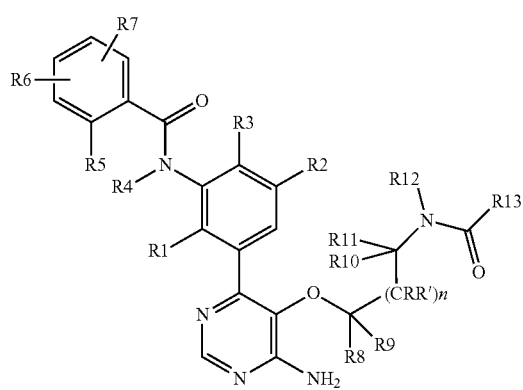

(I)

wherein,
R1 is hydrogen, C1-C6 alkyl optionally substituted by hydroxy;
R2 is hydrogen or halogen;
R3 is hydrogen or halogen;
R4 is hydrogen;
R5 is hydrogen or halogen;
or R4 and R5 are attached to each other and stand for a bond, —CH2-, —CH2-CH2-, —CH═CH—, —CH═CH—CH2-; —CH2-CH═CH—; or —CH2-CH2-CH2-;
R6 and R7 stand independently from each other for H, C1-C6 alkyl optionally substituted by hydroxyl, C3-C6 cycloalkyl optionally substituted by halogen or hydroxy, or halogen;
R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;
R12 is hydrogen or C1-C6 alkyl optionally substituted by halogen or C1-C6 alkoxy;
or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;
n is 0 or 1; and
R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-

4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

In one embodiment, the kinase inhibitor is an mTOR inhibitor. MTOR inhibitors can be selected from the section elsewhere herein entitled mTOR Inhibitors. The dose referred to here is not the low, immune enhancing, dose of an mTOR inhibitor, but rather a dose sufficient to give an anti-cancer effect, and is higher than the low, immune enhancing, dose, described herein, e.g., a dose. Thus, in an embodiment, two different administrations of an mTOR inhibitor are given, a low, immune enhancing dose, e.g., to optimize immune effector cell function, and a higher dose given for an anticancer effect.

In one embodiment, the kinase inhibitor is an mTOR inhibitor, e.g., rapamycin, and the rapamycin is administered at a dose sufficient to give an anti-cancer effect, and higher than the low, immune enhancing, dose, described herein, e.g., a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered.

In one embodiment, the kinase inhibitor is an mTOR inhibitor, e.g., everolimus and the everolimus is administered at a dose sufficient to give an anti-cancer effect, and higher than the low, immune enhancing, dose, described herein, e.g., a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

Drugs that inhibit either the calcium dependent phosphatase calcineurin (cyclosporine and FK506) or inhibit the p70S6 kinase that is important for growth factor induced signalling (rapamycin). (Liu et al., Cell 66:807-815, 1991; Henderson et al., Immun. 73:316-321, 1991; Bierer et al., Curr. Opin. Immun. 5:763-773, 1993) can also be used.

In some embodiments, a CARX cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1 (2010):135-43.

In some embodiments, a CARX cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3 (2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Catala d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, the subject can be administered an agent which reduces or ameliorates a side effect associated with the administration of a CARX cell. Side effects associated with the administration of a CARX cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symsptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures. Accordingly, the methods described herein can comprise administering a CARX cell described herein to a subject and further administering one or more agents to manage elevated levels of a soluble factor resulting from treatment with a CARX cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antibody fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule or an anti-IL-6 receptor antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 receptor antibody molecule is tocilizumab. An example of an IL-1R based inhibitor is anakinra.

In one embodiment, the subject can be administered an agent which enhances the activity of a CARX cell. For example, in one embodiment, the agent can be an agent which inhibits an inhibitory molecule, e.g., the agent is a checkpoint inhibitor. Inhibitory molecules, e.g., Programmed Death 1 (PD-1), can, in some embodiments, decrease the ability of a CARX cell to mount an immune effector response. Examples of inhibitory molecules include PD-1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CARX cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CARX cell. In an embodiment the inhibitor is an shRNA. In an embodiment, the inhibitory molecule is inhibited within a CARX cell. In these embodiments, a dsRNA molecule that inhibits expression of the inhibitory molecule is linked to the nucleic acid that encodes a component, e.g., all of the components, of the CAR.

In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CARX cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CARX cell. In an embodiment, the nucleic acid molecule that encodes a dsRNA molecule that inhibits expression of the molecule that modulates or regulates, e.g., inhibits, T-cell function is stably integrated into the genome of a CARX cell. In an embodiment, the molecule that modulates or regulates, e.g., inhibits, T-cell function is PD-1.

In one embodiment, the inhibitor of an inhibitory signal can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206). In an embodiment, the agent is an antibody or antibody fragment that binds to TIM3. In an embodiment, the agent is an antibody or antibody fragment that binds to LAG3. In embodiments, the agent that enhances the activity of a CARX cell, e.g., inhibitor of an inhibitory molecule, is administered in combination with an allogeneic CAR, e.g., an allogeneic CAR described herein (e.g., described in the Allogeneic CAR section herein). In an embodiment PD1 inhibitors are administered after the administration of a low, immune enhancing, dose, of an mTOR inhibitor, e.g., an allosteric inhibitor, e.g., RAD001, or a catalytic inhibitor, or after such administration results in an increase in PD1 negative immune effector cells, e.g., T cells, or after an increase in the ratio of PD1 negative immune effector cells, e.g., T cells/PD1 positive immune effector cells, e.g., T cells.

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are known and may be used combination with a CAR of the present invention described herein. For example, nivolumab (also referred to as BMS- 936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No. 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM3 (T cell immunoglobulin-3) also negatively regulates T cell function, particularly in IFN-g-secreting CD4+T helper 1 and CD8+T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent which enhances the activity of a CARX cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10.1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, BMS-986016 (Bristol-Myers Squib) is a monoclonal antibody that targets LAG3. IMP701 (Immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CARX cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express an anti-CAR of the present invention.

In one embodiment, the agent which enhances activity of a CARX cell described herein is miR-17-92.

In one embodiment, the agent which enhances activity of a CAR-described herein is a cytokine. Cytokines have important functions related to T cell expansion, differentiation, survival, and homeostasis. Cytokines that can be administered to the subject receiving a CARX cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CARX cells. The cytokine can be administered simultaneously or concurrently with the CARX cells, e.g., administered on the same day. The cytokine may be prepared in the same pharmaceutical composition as the CARX cells, or may be prepared in a separate pharmaceutical composition. Alternatively, the cytokine can be administered shortly after administration of the CARX cells, e.g., 1 day, 2 days, 3 days, 4 days, 5 days, 6 days, or 7 days after administration of the CARX cells. In embodiments where the cytokine is administered in a dosing regimen that occurs over more than one day, the first day of the cytokine dosing regimen can be on the same day as administration with the CARX cells, or the first day of the cytokine dosing regimen can be 1 day, 2 days, 3 days, 4 days, 5 days, 6 days, or 7 days after administration of the CARX cells. In one embodiment, on the first day, the CARX cells are administered to the subject, and on the second day, a cytokine is administered once a day for the next 7 days. In a preferred embodiment, the cytokine to be administered in combination with the CARX cells is IL-7, IL-15, or IL-21, or a combination thereof.

In other embodiments, the cytokine is administered a sufficient period of time after administration of the CARX cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CARX cells. In one embodiment, the cytokine is administered after assessment of the subject's response to the CARX cells. For example, the subject is administered CARX cells according to the dosage and regimens described herein. The response of the subject to CARX, e.g., CART, therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CARX cells, using any of the methods described herein, including inhibition of tumor growth, reduction of circulating tumor cells, or tumor regression. Subjects that do not exhibit a sufficient response to CARX, e.g., CART, therapy can be administered a cytokine. Administration of the cytokine to the subject that has sub-optimal response to the CARX therapy improves CARX efficacy or anti-tumor activity. In a preferred embodiment, the cytokine administered after administration of CARX cells is IL-7.

In some embodiments, an mTOR inhibitor, e.g., an mTOR inhibitor described herein, is administered at low, immune enhancing, dose together with an immune effector cell, e.g., a T cell or a NK cell, having a CAR, to a subject who has cancer, e.g., a cancer described herein. The subject may receive treatment with an additional therapeutic agent, such as an approved drug for that type of cancer, in combination with the mTOR inhibitor. For example, Table 15 below provides a list of various cancers and their approved treatments.

TABLE 15

| Cancers and Approved Treatment(s) | |
|---|---|
| Cancer | Treatment(s) |
| Acute Lymphoblastic Leukemia | Abitrexate (Methotrexate); Adriamycin PFS (Doxorubicin Hydrochloride); Adriamycin RDF (Doxorubicin Hydrochloride); Arranon (Nelarabine); Asparaginase *Erwinia chrysanthemi*; Cerubidine (Daunorubicin Hydrochloride); Clafen (Cyclophosphamide); Clofarabine; Clofarex (Clofarabine); Clolar (Clofarabine); Cyclophosphamide; Cytarabine; Cytosar-U (Cytarabine); Cytoxan (Cyclophosphamide); Dasatinib; Daunorubicin Hydrochloride; Doxorubicin Hydrochloride; Erwinaze (Asparaginase *Erwinia Chrysanthemi*); Folex (Methotrexate); Folex PFS (Methotrexate); Gleevec (Imatinib Mesylate); Iclusig (Ponatinib Hydrochloride); Imatinib Mesylate; Marqibo (Vincristine Sulfate Liposome); Mercaptopurine; Methotrexate; Methotrexate LPF (Methorexate); Mexate (Methotrexate); Mexate-AQ (Methotrexate); Nelarabine; Neosar (Cyclophosphamide); Oncaspar (Pegaspargase); Pegaspargase; Purinethol (Mercaptopurine); Purixan (Mercaptopurine); Rubidomycin (Daunorubicin Hydrochloride); Sprycel (Dasatinib); Tarabine PFS (Cytarabine); Vincasar PFS (Vincristine Sulfate); Vincristine Sulfate; or Vincristine Sulfate Liposome. DRUG COMBINATIONS hyper-CVAD: Cyclophosphamide; Vincristine Sulfate; Doxorubicin Hydrochloride (Adriamycin); Dexamethasone. |
| Acute Myeloid Leukemia | Adriamycin PFS (Doxorubicin Hydrochloride); Adriamycin RDF (Doxorubicin Hydrochloride); Arsenic Trioxide; Cerubidine (Daunorubicin Hydrochloride); Clafen (Cyclophosphamide); Cyclophosphamide; Cytarabine; Cytosar-U (Cytarabine); Cytoxan (Cyclophosphamide); Daunorubicin Hydrochloride; Doxorubicin Hydrochloride; Neosar (Cyclophosphamide); Rubidomycin (Daunorubicin Hydrochloride); Tarabine PFS (Cytarabine); Trisenox (Arsenic Trioxide); Vincasar PFS (Vincristine Sulfate); or Vincristine Sulfate. |

TABLE 15-continued

Cancers and Approved Treatment(s)

| Cancer | Treatment(s) |
|---|---|
| | DRUG COMBINATIONS<br>ADE: Cytarabine; Daunorubicin Hydrochloride; and Etoposide. |
| AIDS-Related Kaposi Sarcoma | Dox-SL (Doxorubicin Hydrochloride Liposome); Doxil (Doxorubicin Hydrochloride Liposome); Doxorubicin Hydrochloride Liposome; Evacet (Doxorubicin Hydrochloride Liposome); Intron A (Recombinant Interferon Alfa-2b); LipoDox (Doxorubicin Hydrochloride Liposome); Paclitaxel; Recombinant Interferon Alfa-2b; Taxol (Paclitaxel); Velban (Vinblastine Sulfate); Velsar (Vinblastine Sulfate); or Vinblastine Sulfate. |
| Basal Cell Carcinoma | Adrucil (Fluorouracil); Aldara (Imiquimod); Efudex (Fluorouracil); Erivedge (Vismodegib); Fluoroplex (Fluorouracil); Fluorouracil; Imiquimod; or Vismodegib. |
| Bladder Cancer | Adriamycin PFS (Doxorubicin Hydrochloride); Adriamycin RDF (Doxorubicin Hydrochloride); Cisplatin; Doxorubicin Hydrochloride; Platinol (Cisplatin); or Platinol-AQ (Cisplatin). |
| Bone Cancer | Abitrexate (Methotrexate); Adriamycin PFS (Doxorubicin Hydrochloride); Adriamycin RDF (Doxorubicin Hydrochloride); Doxorubicin Hydrochloride; Folex (Methotrexate); Folex PFS (Methotrexate); Methotrexate; Methotrexate LPF (Methotrexate); Mexate (Methotrexate); or Mexate-AQ (Methotrexate). |
| Brain Tumor | Afinitor (Everolimus); Afinitor Disperz (Everolimus); Avastin (Bevacizumab); Bevacizumab; CeeNu (Lomustine); Everolimus; Lomustine; Methazolastone (Temozolomide); Temodar (Temozolomide); or Temozolomide. |
| Breast Cancer | Abitrexate (Methotrexate); Abraxane (Paclitaxel Albumin-stabilized Nanoparticle Formulation); Ado-Trastuzumab Emtansine; Adriamycin PFS (Doxorubicin Hydrochloride); Adriamycin RDF (Doxorubicin Hydrochloride); Adrucil (Fluorouracil); Afinitor (Everolimus); Anastrozole; Aredia (Pamidronate Disodium); Arimidex (Anastrozole); Aromasin (Exemestane); Capecitabine; Clafen (Cyclophosphamide); Cyclophosphamide; Cytoxan (Cyclophosphamide); Docetaxel; Doxorubicin Hydrochloride; Efudex (Fluorouracil); Ellence (Epirubicin Hydrochloride); Epirubicin Hydrochloride; Everolimus; Exemestane; Fareston (Toremifene); Faslodex (Fulvestrant); Femara (Letrozole); Fluoroplex (Fluorouracil); Fluorouracil; Folex (Methotrexate); Folex PFS (Methotrexate); Fulvestrant; Gemcitabine Hydrochloride; Gemzar (Gemcitabine Hydrochloride); Goserelin Acetate; Herceptin (Trastuzumab); Ixabepilone; Ixempra (Ixabepilone); Kadcyla (Ado-Trastuzumab Emtansine); Lapatinib Ditosylate; Letrozole; Megace (Megestrol Acetate); Megestrol Acetate; Methotrexate; Methotrexate LPF (Methotrexate); Mexate (Methotrexate); Mexate-AQ (Methotrexate); Neosar (Cyclophosphamide); Nolvadex (Tamoxifen Citrate); Novaldex (Tamoxifen Citrate); Paclitaxel; Paclitaxel Albumin-stabilized Nanoparticle Formulation; Pamidronate Disodium; Perjeta (Pertuzumab); Pertuzumab; Tamoxifen Citrate; Taxol (Paclitaxel); Taxotere (Docetaxel); Trastuzumab; Toremifene; Tykerb (Lapatinib Ditosylate); Xeloda (Capecitabine); or Zoladex (Goserelin Acetate).<br>DRUG COMBINATIONS<br>AC: Doxorubicin Hydrochloride (Adriamycin) and Cyclophosphamide.<br>AC-T: Doxorubicin Hydrochloride (Adriamycin); Cyclophosphamide; and Paclitaxel (Taxol).<br>CAF: Cyclophosphamide; Doxorubicin Hydrochloride (Adriamycin); and Fluorouracil.<br>CMF: Cyclophosphamide; Methotrexate; and Fluorouracil.<br>FEC: Fluorouracil; Epirubicin Hydrochloride; and Cyclophosphamide.<br>TAC: Docetaxel (Taxotere); Doxorubicin Hydrochloride (Adriamycin); and Cyclophosphamide. |
| Cervical Cancer | Blenoxane (Bleomycin); Bleomycin; Cisplatin; Hycamtin (Topotecan Hydrochloride); Platinol (Cisplatin); Platinol-AQ (Cisplatin); or Topotecan Hydrochloride.<br>DRUG COMBINATIONS<br>Gemcitabine-Cisplatin: Gemcitabine Hydrochloride and Cisplatin. |

TABLE 15-continued

Cancers and Approved Treatment(s)

| Cancer | Treatment(s) |
|---|---|
| Chronic Lymphocytic Leukemia | Alemtuzumab; Ambochlorin (Chlorambucil); Amboclorin (Chlorambucil); Arzerra (Ofatumumab); Bendamustine Hydrochloride; Campath (Alemtuzumab); Chlorambucil; Clafen (Cyclophosphamide); Cyclophosphamide; Cytoxan (Cyclophosphamide); Fludara (Fludarabine Phosphate); Fludarabine Phosphate; Gazyva (Obinutuzumab); Ibrutinib; Imbruvica (Ibrutinib); Leukeran (Chlorambucil); Linfolizin (Chlorambucil); Neosar (Cyclophosphamide); Obinutuzumab; Ofatumumab; or Treanda (Bendamustine Hydrochloride). DRUG COMBINATIONS CHLORAMBUCIL-PREDNISONE: Chlorambucil and Prednisone. CVP: Cyclophosphamide; Vincristine Sulfate; and Prednisone. |
| Chronic Myelogenous Leukemia | Bosulif (Bosutinib); Bosutinib; Busulfan; Busulfex (Busulfan); Clafen; Cyclophosphamide; Cyclophosphamide; Cytarabine; Cytosar-U (Cytarabine); Cytoxan (Cyclophosphamide); Dasatinib; Gleevec (Imatinib Mesylate); Iclusig (Ponatinib Hydrochloride); Imatinib Mesylate; Myleran (Busulfan); Neosar (Cyclophosphamide); Nilotinib; Omacetaxine Mepesuccinate; Ponatinib Hydrochloride; Sprycel (Dasatinib); Synribo (Omacetaxine Mepesuccinate); Tarabine PFS (Cytarabine); or Tasigna (Nilotinib). |
| Colon Cancer | Adrucil (Fluorouracil); Avastin (Bevacizumab); Bevacizumab; Camptosar (Irinotecan Hydrochloride); Capecitabine; Cetuximab; Efudex (Fluorouracil); Eloxatin (Oxaliplatin); Erbitux (Cetuximab); Fluoroplex (Fluorouracil); Fluorouracil; Irinotecan Hydrochloride; Leucovorin Calcium; Oxaliplatin; Panitumumab; Regorafenib; Stivarga (Regorafenib); Vectibix (Panitumumab); Wellcovorin (Leucovorin Calcium); Xeloda (Capecitabine); Zaltrap (Ziv-Aflibercept); or Ziv-Aflibercept. DRUG COMBINATIONS CAPOX: Capecitabine and Oxaliplatin. FOLFIRI: Leucovorin Calcium (Folinic Acid); Fluorouracil; and Irinotecan Hydrochloride. FOLFIRI-BEVACIZUMAB: Leucovorin Calcium (Folinic Acid); Fluorouracil; Irinotecan Hydrochloride; and Bevacizumab. FOLFIRI-CETUXIMAB: Leucovorin Calcium (Folinic Acid); Fluorouracil; Irinotecan Hydrochloride; and Cetuximab. FOLFOX: Leucovorin Calcium (Folinic Acid); Fluorouracil; and Oxaliplatin. XELOX: Capecitabine (Xeloda) and Oxaliplatin. |
| Endometrial Cancer | Megace (Megestrol Acetate) or Megestrol Acetate. |
| Gastric (Stomach) Cancer | Adriamycin PFS (Doxorubicin Hydrochloride); Adriamycin RDF (Doxorubicin Hydrochloride); Adrucil (Fluorouracil); Cyramza (Ramucirumab); Docetaxel; Doxorubicin Hydrochloride; Efudex (Fluorouracil); Fluoroplex (Fluorouracil); Fluorouracil; Herceptin (Trastuzumab); Mitomycin C; Mitozytrex (Mitomycin C); Mutamycin (Mitomycin C); Ramucirumab; Taxotere (Docetaxel); or Trastuzumab. |
| Gastrointestinal stromal tumors | Gleevec (Imatinib Mesylate); Imatinib Mesylate; Regorafenib; Stivarga (Regorafenib); Sunitinib Malate; Sutent (Sunitinib Malate) |
| Head and neck cancer | Abitrexate (Methotrexate); Adrucil (Fluorouracil); Blenoxane (Bleomycin); Bleomycin; Cetuximab; Cisplatin; Docetaxel; Efudex (Fluorouracil); Erbitux (Cetuximab); Fluoroplex (Fluorouracil); Fluorouracil; Folex (Methotrexate); Folex PFS (Methotrexate); Methotrexate; Methotrexate LPF (Methotrexate); Mexate (Methotrexate); Mexate-AQ (Methotrexate); Platinol (Cisplatin); Platinol-AQ (Cisplatin); or Taxotere (Docetaxel). |
| Hodkin Lymphoma | Adcetris (Brentuximab Vedotin); Adriamycin PFS (Doxorubicin Hydrochloride); Adriamycin RDF (Doxorubicin Hydrochloride); Ambochlorin (Chlorambucil); Amboclorin (Chlorambucil); Blenoxane (Bleomycin); Bleomycin; Brentuximab Vedotin; Chlorambucil; Clafen (Cyclophosphamide); Cyclophosphamide; Cytoxan (Cyclophosphamide); Dacarbazine; Doxorubicin Hydrochloride; DTIC-Dome (Dacarbazine); Leukeran (Chlorambucil); Linfolizin (Chlorambucil); Lomustine; Matulane (Procarbazine Hydrochloride); Neosar (Cyclophosphamide); Procarbazine Hydrochloride; Velban (Vinblastine Sulfate); Velsar (Vinblastine Sulfate); Vinblastine |

TABLE 15-continued

Cancers and Approved Treatment(s)

| Cancer | Treatment(s) |
|---|---|
| | Sulfate; Vincasar PFS (Vincristine Sulfate); or Vincristine Sulfate.<br>DRUG COMBINATIONS:<br>ABVD: Doxorubicin Hydrochloride (Adriamycin); Bleomycin; Vinblastine Sulfate; and Dacarbazine.<br>ABVE: Doxorubicin Hydrochloride (Adriamycin); Bleomycin; Vinblastine Sulfate; and Etoposide.<br>ABVE-PC: Doxorubicin Hydrochloride (Adriamycin); Bleomycin; Vinblastine Sulfate; Etoposide; Prednisone; and Cyclophosphamide.<br>BEACOPP: Bleomycin; Etoposide; Doxorubicin Hydrochloride (Adriamycin); Cyclophosphamide; Vincristine Sulfate (Oncovin); Procarbazine Hydrochloride; and Prednisone.<br>COPP: Cyclophosphamide; Vincristine Sulfate (Oncovin); Procarbazine Hydrochloride; and Prednisone.<br>COPP-ABV: Cyclophosphamide; Vincristine Sulfate (Oncovin); Procarbazine Hydrochloride; Prednisone; Doxorubicin Hydrochloride (Adriamycin); Bleomycin; and Vinblastine Sulfate.<br>ICE: Ifosfamide; Carboplatin; and Etoposide.<br>MOPP: Mechlorethamine Hydrochloride; Vincristine Sulfate (Oncovin); Procarbazine Hydrochloride; and Prednisone.<br>OEPA: Vincristine Sulfate (Oncovin); Etoposide; Prednisone; and Doxorubicin Hydrochloride (Adriamycin).<br>OPPA: Vincristine Sulfate (Oncovin); Procarbazine Hydrochloride; Prednisone; and Doxorubicin Hydrochloride (Adriamycin).<br>STANFORD V: Mechlorethamine Hydrochloride; Doxorubicin Hydrochloride; Vinblastine Sulfate; Vincristine Sulfate; Bleomycin; Etoposide; and Prednisone.<br>VAMP: Vincristine Sulfate; Doxorubicin Hydrochloride (Adriamycin); and Methotrexate; and Prednisone. |
| Kidney (Renal Cell) Cancer | Afinitor (Everolimus); Aldesleukin; Avastin (Bevacizumab); Axitinib; Bevacizumab; Everolimus; Inlyta (Axitinib); Nexavar (Sorafenib Tosylate); Pazopanib Hydrochloride; Proleukin (Aldesleukin); Sorafenib Tosylate; Sunitinib Malate; Sutent (Sunitinib Malate); Temsirolimus; Torisel (Temsirolimus); or Votrient (Pazopanib Hydrochloride). |
| Liver Cancer | Nexavar (Sorafenib Tosylate) or Sorafenib Tosylate. |
| Melanoma | Aldesleukin; Dabrafenib; Dacarbazine; DTIC-Dome (Dacarbazine); Intron A (Recombinant Interferon Alfa-2b); Ipilimumab; Mekinist (Trametinib); Peginterferon Alfa-2b; PEG-Intron (Peginterferon Alfa-2b); Proleukin (Aldesleukin); Recombinant Interferon Alfa-2b; Sylatron (Peginterferon Alfa-2b); Tafinlar (Dabrafenib); Trametinib; Vemurafenib; Yervoy (Ipilimumab); or Zelboraf (Vemurafenib). |
| Malignant Mesothelioma | Alimta (Pemetrexed Disodium); Cisplatin; Pemetrexed Disodium; Platinol (Cisplatin); or Platinol-AQ (Cisplatin). |
| Multiple myeloma | Aredia (Pamidronate Disodium); Bortezomib; Carfilzomib; Clafen (Cyclophosphamide); Cyclophosphamide; Cytoxan (Cyclophosphamide); Doxil (Doxorubicin Hydrochloride Liposome); Doxorubicin Hydrochloride Liposome; Dox-SL (Doxorubicin Hydrochloride Liposome); Evacet (Doxorubicin Hydrochloride Liposome); Kyprolis (Carfilzomib); Lenalidomide; LipoDox (Doxorubicin Hydrochloride Liposome); Mozobil (Plerixafor); Neosar (Cyclophosphamide); Pamidronate Disodium; Plerixafor; Pomalidomide (Pomalyst); Pomalyst; Revlimid (Lenalidomide); Synovir (Thalidomide); Thalidomide; Thalomid (Thalidomide); Velcade (Bortezomib); Zoledronic Acid; Zometa (Zoledronic Acid) |
| Myeloproliferative Disorders | Adriamycin PFS (Doxorubicin Hydrochloride); Adriamycin RDF (Doxorubicin Hydrochloride); Arsenic Trioxide; Azacitidine; Cerubidine (Daunorubicin Hydrochloride); Clafen (Cyclophosphamide); Cyclophosphamide; Cytarabine; Cytosar-U (Cytarabine); Cytarabine; Cytoxan (Cyclophosphamide); Dacogen (Decitabine); Dasatinib; Daunorubicin Hydrochloride; Decitabine; Doxorubicin Hydrochloride; Gleevec (Imatinib Mesylate); Imatinib Mesylate; Jakafi (Ruxolitinib Phosphate); Lenalidomide; Mylosar (Azacitidine); Neosar (Cyclophosphamide); Nilotinib; Revlimid (Lenalidomide); Rubidomycin (Daunorubicin Hydrochloride); Ruxolitinib Phosphate; Sprycel (Dasatinib); Tarabine PFS (Cytarabine); Tasigna (Nilotinib); Trisenox (Arsenic Trioxide); Vidaza (Azacitidine); Vincasar PFS |

TABLE 15-continued

Cancers and Approved Treatment(s)

| Cancer | Treatment(s) |
|---|---|
| | (Vincristine Sulfate); or Vincristine Sulfate.<br>DRUG COMBINATIONS<br>ADE: Cytarabine; Daunorubicin Hydrochloride; and Etoposide. |
| Neuroblastoma | Adriamycin PFS (Doxorubicin Hydrochloride); Adriamycin RDF (Doxorubicin Hydrochloride); Clafen (Cyclophosphamide); Cyclophosphamide; Cytoxan (Cyclophosphamide); Doxorubicin Hydrochloride; Neosar (Cyclophosphamide); Vincasar PFS (Vincristine Sulfate); or Vincristine Sulfate. |
| Non-Hodkin Lymphoma | Abitrexate (Methotrexate); Adcetris (Brentuximab Vedotin); Adriamycin PFS (Doxorubicin Hydrochloride); Adriamycin RDF (Doxorubicin Hydrochloride); Ambochlorin (Chlorambucil); Amboclorin (Chlorambucil); Arranon (Nelarabine); Bendamustine Hydrochloride; Bexxar (Tositumomab and Iodine I 131 Tositumomab); Blenoxane (Bleomycin); Bleomycin; Bortezomib; Brentuximab Vedotin; Chlorambucil; Clafen (Cyclophosphamide); Cyclophosphamide; Cytoxan (Cyclophosphamide); Denileukin Diftitox; DepoCyt (Liposomal Cytarabine); Doxorubicin Hydrochloride; DTIC-Dome (Dacarbazine); Folex (Methotrexate); Folex PFS (Methotrexate); Folotyn (Pralatrexate); Ibritumomab Tiuxetan; Ibrutinib; Imbruvica (Ibrutinib); Intron A (Recombinant Interferon Alfa-2b); Istodax (Romidepsin); Lenalidomide; Leukeran (Chlorambucil); Linfolizin (Chlorambucil); Liposomal Cytarabine; Matulane (Procarbazine Hydrochloride); Methotrexate; Methotrexate LPF (Methotrexate); Mexate (Methotrexate); Mexate-AQ (Methotrexate); Mozobil (Plerixafor); Nelarabine; Neosar (Cyclophosphamide); Ontak (Denileukin Diftitox); Plerixafor; Pralatrexate; Recombinant Interferon Alfa-2b; Revlimid (Lenalidomide); Rituxan (Rituximab); Rituximab; Romidepsin; Tositumomab and Iodine I 131 Tositumomab; Treanda (Bendamustine Hydrochloride); Velban (Vinblastine Sulfate); Velcade (Bortezomib); Velsar (Vinblastine Sulfate); Vinblastine Sulfate; Vincasar PFS (Vincristine Sulfate); Vincristine Sulfate; Vorinostat; Zevalin (Ibritumomab Tiuxetan); or Zolinza (Vorinostat).<br>DRUG COMBINATIONS<br>CHOP: Cyclophosphamide; Doxorubicin Hydrochloride (Hydroxydaunomycin); Vincristine Sulfate (Oncovin); and Prednisone.<br>COPP: Cyclophosphamide; Vincristine Sulfate (Oncovin); Procarbazine Hydrochloride; and Prednisone.<br>CVP: Cyclophosphamide; Vincristine Sulfate; and Prednisone.<br>EPOCH: Etoposide; Prednisone; Vincristine Sulfate (Oncovin); Cyclophosphamide; and Doxorubicin Hydrochloride (Hydroxydaunomycin).<br>Hyper-CVAD: Cyclophosphamide; Vincristine Sulfate; Doxorubicin Hydrochloride (Adriamycin); and Dexamethasone.<br>ICE: Ifosfamide; Carboplatin; and Etoposide.<br>R-CHOP: Rituximab; Cyclophosphamide; Doxorubicin Hydrochloride (Hydroxydaunomycin); Vincristine Sulfate (Oncovin); and Prednisone. |
| Non-Small Cell Lung Cancer | Abitrexate (Methotrexate); Abraxane (Paclitaxel Albumin-stabilized Nanoparticle Formulation); Afatinib Dimaleate; Alimta (Pemetrexed Disodium); Avastin (Bevacizumab); Bevacizumab; Carboplatin; Ceritinib; Cisplatin; Crizotinib; Docetaxel; Erlotinib Hydrochloride; Folex (Methotrexate); Folex PFS (Methotrexate); Gefitinib; Gilotrif (Afatinib Dimaleate); Gemcitabine Hydrochloride; Gemzar (Gemcitabine Hydrochloride); Iressa (Gefitinib); Methotrexate; Methotrexate LPF (Methotrexate); Mexate (Methotrexate); Mexate-AQ (Methotrexate); Paclitaxel; Paclitaxel Albumin-stabilized Nanoparticle Formulation; Paraplat (Carboplatin); Paraplatin (Carboplatin); Pemetrexed Disodium; Platinol (Cisplatin); Platinol-AQ (Cisplatin); Tarceva (Erlotinib Hydrochloride); Taxol (Paclitaxel); Taxotere (Docetaxel); Xalkori (Crizotinib); or Zykadia (Ceritinib).<br>DRUG COMBINATIONS<br>CARBOPLATIN-TAXOL; Carboplatin and Paclitaxel (Taxol). |

TABLE 15-continued

Cancers and Approved Treatment(s)

| Cancer | Treatment(s) |
|---|---|
| | Gemcitabine-Cisplatin: Gemcitabine Hydrochloride and Cisplatin. |
| Ovarian Cancer | Adriamycin PFS (Doxorubicin Hydrochloride); Adriamycin RDF (Doxorubicin Hydrochloride); Carboplatin; Clafen (Cyclophosphamide); Cisplatin; Cyclophosphamide; Cytoxan (Cyclophosphamide); Doxorubicin Hydrochloride; Dox-SL (Doxorubicin Hydrochloride Liposome); DOXIL (Doxorubicin Hydrochloride Liposome); Doxorubicin Hydrochloride Liposome; Evacet (Doxorubicin Hydrochloride Liposome); Gemcitabine Hydrochloride; Gemzar (Gemcitabine Hydrochloride); Hycamtin (Topotecan Hydrochloride); LipoDox (Doxorubicin Hydrochloride Liposome); Neosar (Cyclophosphamide); Paclitaxel; Paraplat (Carboplatin); Paraplatin (Carboplatin); Platinol (Cisplatin); Platinol-AQ (Cisplatin); Taxol (Paclitaxel); or Topotecan Hydrochloride.<br>DRUG COMBINATIONS<br>BEP: Bleomycin; Etoposide; and Cisplatin (Platinol).<br>CARBOPLATIN-TAXOL: Carboplatin and Paclitaxel (Taxol).<br>Gemcitabine-Cisplatin: Gemcitabine Hydrochloride and Cisplatin. |
| Pancreatic cancer | Adrucil (Fluorouracil); Afinitor (Everolimus); Efudex (Fluorouracil); Erlotinib Hydrochloride; Everolimus; Fluoroplex (Fluorouracil); Fluorouracil; Gemcitabine Hydrochloride; Gemzar (Gemcitabine Hydrochloride); Mitomycin C; Mitozytrex (Mitomycin C); Mutamycin (Mitomycin C); Sunitinib Malate; Sutent (Sunitinib Malate); or Tarceva (Erlotinib Hydrochloride).<br>DRUG COMBINATIONS<br>GEMCITABINE-OXALIPLATIN: Gemcitabine Hydrochloride and Oxaliplatin. |
| Penile cancer | Blenoxane (Bleomycin); Bleomycin |
| Rectal Cancer | Adrucil (Fluorouracil); Avastin (Bevacizumab); Bevacizumab; Camptosar (Irinotecan Hydrochloride); Cetuximab; Efudex (Fluorouracil); Erbitux (Cetuximab); Fluoroplex (Fluorouracil); Fluorouracil; Irinotecan Hydrochloride; Panitumumab; Regorafenib; Stivarga (Regorafenib); Vectibix (Panitumumab); Zaltrap (Ziv-Aflibercept); or Ziv-Aflibercept.<br>DRUG COMBINATIONS<br>CAPOX: Capecitabine and Oxaliplatin.<br>FOLFIRI: Leucovorin Calcium (Folinic Acid); FluorouracilL; Irinotecan Hydrochloride.<br>FOLFIRI-BEVACIZUMAB: Leucovorin Calcium (Folinic Acid); Fluorouracil; Irinotecan Hydrochloride; and Bevacizumab.<br>FOLFIRI-CETUXIMAB: Leucovorin Calcium (Folinic Acid); Fluorouracil; Irinotecan Hydrochloride; and Cetuximab.<br>FOLFOX: Leucovorin Calcium (Folinic Acid); Fluorouracil; and Oxaliplatin.<br>XELOX: Capecitabine (Xeloda) and Oxaliplatin. |
| Renal Cell Carcinoma | Afinitor (Everolimus); Aldesleukin; Avastin (Bevacizumab); Axitinib; Bevacizumab; Everolimus; Inlyta (Axitinib); Nexavar (Sorafenib Tosylate); Pazopanib hydrochloride; Proleukin (Aldesleukin); Sorafenib Tosylate; Temsirolimus; Torisel (Temsirolimus); Votrient (Pazopanib Hydrochloride) |
| Retinoblastoma | Clafen (Cyclophosphamide); Cyclophosphamide; Cytoxan (Cyclophosphamide); or Neosar (Cyclophosphamide). |
| Rhabdomyosarcoma | Cosmegen (Dactinomycin); Dactinomycin; Vincasar PFS (Vincristine Sulfate); or Vincristine Sulfate. |
| Skin cancer (basal cell carcinoma) | Adrucil (Fluorouracil); Aldara (Imiquimod); Efudex (Fluorouracil); Erivedge (Vismodegib); Fluoroplex (Fluorouracil); Fluorouracil; Imiquimod; or Vismodegib. |
| Skin cancer (melanoma) | Aldesleukin; Dacarbazine; DTIC-Dome (Dacarbazine); Ipilimumab; Proleukin (Aldesleukin); Vemurafenib; Yervoy (Ipilimumab); or Zelboraf (Vemurafenib). |
| Small cell lung cancer | Abitrexate (Methotrexate); Etopophos (Etoposide Phosphate); Etoposide; Etoposide Phosphate; Folex (Methotrexate); Folex PFS (Methotrexate); Hycamtin (Topotecan Hydrochloride); Methotrexate; Methotrexate LPF (Methotrexate); Mexate (Methotrexate); Mexate-AQ (Methotrexate); Toposar (Etoposide); Topotecan Hydrochloride; or VePesid (Etoposide). |

TABLE 15-continued

Cancers and Approved Treatment(s)

| Cancer | Treatment(s) |
|---|---|
| Soft tissue sarcoma | Adriamycin PFS (Doxorubicin Hydrochloride); Adriamycin RDF (Doxorubicin Hydrochloride); Cosmegen (Dactinomycin); Dactinomycin; or Doxorubicin Hydrochloride. |
| Testicular cancer | Blenoxane (Bleomycin); Bleomycin; Cisplatin; Cosmegen (Dactinomycin); Cyfos (Ifosfamide); Dactinomycin; Etopophos (Etoposide Phosphate); Etoposide; Etoposide Phosphate; Ifex (Ifosfamide); Ifosfamide; Ifosfamidum (Ifosfamide); Platinol (Cisplatin); Platinol-AQ (Cisplatin); Toposar (Etoposide;; Velban (Vinblastine Sulfate); Velsar (Vinblastine Sulfate); or VePesid (Etoposide); Vinblastine Sulfate. |
| Thyroid cancer | Adriamycin PFS (Doxorubicin Hydrochloride); Adriamycin RDF (Doxorubicin Hydrochloride); Cabozantinib-S-Malate; Caprelsa (Vandetanib); Cometriq (Cabozantinib-S-Malate); Doxorubicin Hydrochloride; Nexavar (Sorafenib Tosylate); or Sorafenib Tosylate; Vandetanib. |
| Vaginal cancer | Gardasil (Recombinant HPV Quadrivalent Vaccine); or Recombinant Human Papillomavirus (HPV) Quadrivalent Vaccine. |
| Vulvar cancer | Blenoxane (Bleomycin); Bleomycin; Gardasil (Recombinant HPV Quadrivalent Vaccine); or Recombinant Human Papillomavirus (HPV) Quadrivalent Vaccine. |
| Wilms Tumor or other childhood kidney cancers | Adriamycin PFS (Doxorubicin Hydrochloride); Adriamycin RDF (Doxorubicin Hydrochloride); Cosmegen (Dactinomycin); Dactinomycin; Doxorubicin Hydrochloride; Vincasar PFS (Vincristine Sulfate); or Vincristine Sulfate. |

In one embodiment, CARX cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor, e.g., an SHP-2 inhibitor described herein.

In embodiments, a lymphodepleting chemotherapy is administered to the subject prior to, concurrently with, or after administration (e.g., infusion) of CAR cells, e.g., CARX cells described herein. In an example, the lymphodepleting chemotherapy is administered to the subject prior to administration of CAR cells. For example, the lymphodepleting chemotherapy ends 1-4 days (e.g., 1, 2, 3, or 4 days) prior to CAR cell infusion. In embodiments, multiple doses of CAR cells are administered, e.g., as described herein. For example, a single dose comprises about 5×108 CAR cells. In embodiments, a lymphodepleting chemotherapy is administered to the subject prior to, concurrently with, or after administration (e.g., infusion) of a CARX cell described herein. In embodiments, the lymphodepletion comprises administering one or more of melphalan, cytoxan, cyclophosphamide, and fludarabine.

In some embodiments, a CARX cell described herein, is administered to a subject in combination with a CD19 CARX cell, e.g., CTL019, e.g., as described in WO2012/079000, incorporated herein by reference, for treatment of a disease associated with the expression of cancer antigen, e.g., a cancer described herein. Without being bound by theory, it is believed that administering a CD19 CARX cell in combination with another CARX cell improves the efficacy of a CARX cell described herein by targeting early lineage cancer cells, e.g., cancer stem cells, modulating the immune response, depleting regulatory B cells, and/or improving the tumor microenvironment. For example, a CD19 CARX cell binds specifically to cancer cells that express early lineage markers, e.g., cancer stem cells and CD19-expressing cells, while the other CARX cell described herein binds specifically to cancer cells that express later lineage markers, e.g., CD33. This preconditioning approach can improve the efficacy of the CARX cell described herein. In such embodiments, the CD19 CARX cell is administered prior to, concurrently with, or after administration (e.g., infusion) of the second CARX cell.

In embodiments, a CARX cell which expresses a CAR targeting a cancer antigen other than CD19 also expresses a CAR targeting CD19, e.g., a CD19 CAR. In an embodiment, the cell expressing a non-CD19 CAR and a CD19 CAR is administered to a subject for treatment of a cancer described herein, e.g., AML. In an embodiment, the configurations of one or both of the CAR molecules comprise a primary intracellular signaling domain and a costimulatory signaling domain. In another embodiment, the configurations of one or both of the CAR molecules comprise a primary intracellular signaling domain and two or more, e.g., 2, 3, 4, or 5 or more, costimulatory signaling domains. In such embodiments, the non-CD19 CAR molecule and the CD19 CAR may have the same or a different primary intracellular signaling domain, the same or different costimulatory signaling domains, or the same number or a different number of costimulatory signaling domains. Alternatively, the non-CD19 CAR and the CD19 CAR are configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

Methods and Biomarkers for Evaluating CAR-Effectiveness or Sample Suitability

In another aspect, the invention features a method of evaluating or monitoring the effectiveness of a CARX cell therapy, in a subject (e.g., a subject having a cancer), or the suitability of a sample (e.g., an apheresis sample) for a CAR therapy. The method includes acquiring a value of effectiveness to the CAR therapy, or sample suitability, wherein said value is indicative of the effectiveness or suitability of the CARX cell therapy.

In embodiments, the value of effectiveness to the CAR therapy, or sample suitability, comprises a measure of one, two, three, four, five, six or more (all) of the following:

(i) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in a sample (e.g., an apheresis sample or a manufactured CAR-expressing cell product sample);

(ii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in a sample (e.g., an apheresis sample or a manufactured CAR-expressing cell product sample);

(iii) the level or activity of an immune cell exhaustion marker, e.g., one, two or more immune checkpoint inhibitors (e.g., PD-1, PD-L1, TIM-3 and/or LAG-3) in a sample (e.g., an apheresis sample or a manufactured CAR-expressing cell product sample). In one embodiment, an immune cell has an exhausted phenotype, e.g., co-expresses at least two exhaustion markers, e.g., co-expresses PD-1 and TIM-3. In other embodiments, an immune cell has an exhausted phenotype, e.g., co-expresses at least two exhaustion markers, e.g., co-expresses PD-1 and LAG-3;

(iv) the level or activity of CD27 and/or CD45RO− (e.g., CD27+CD45RO−) immune effector cells, e.g., in a CD4+ or a CD8+ T cell population, in a sample (e.g., an apheresis sample or a manufactured CAR-expressing cell product sample);

(v) the level or activity of one, two, three, four, five, ten, twenty or more of the biomarkers chosen from CCL20, IL-17a and/or IL-6, PD-1, PD-L1, LAG-3, TIM-3, CD57, CD27, CD122, CD62L, KLRG1;

(vi) a cytokine level or activity (e.g., quality of cytokine reportoire) in a CAR-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (e.g., a population) of CAR-expressing immune effector cells, e.g., a plurality (e.g., a population) of T cells or NK cells, or a combination thereof.

In some embodiments of any of the methods disclosed herein, the measure of one or more of (i)-(vii) is obtained from an apheresis sample acquired from the subject. The apheresis sample can be evaluated prior to infusion or re-infusion.

In some embodiments of any of the methods disclosed herein, the measure of one or more of (i)-(vii) is obtained from a manufactured CAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of (i)-(vii) evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of (i)-(vii).

In some embodiments of any of the methods disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment, a relapser is a patient having, or who is identified as having, an increased level of expression of one or more of (e.g., 2, 3, 4, or all of) the following genes, compared to non relapsers: MIR199A1, MIR1203, uc021ovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDMSD, USP9Y, PRKY, RPS4Y2, RPS4Y1, NCRNA00185, SULT1E1, and EIF1AY.

In some embodiments of any of the methods disclosed herein, a complete responder has, or is identified as having, a greater, e.g., a statistically significant greater, percentage of CD8+ T cells compared to a reference value, e.g., a non-responder percentage of CD8+ T cells.

In some embodiments of any of the methods disclosed herein, a complete responder has, or is identified as having, a greater percentage of CD27+CD45RO− immune effector cells, e.g., in the CD8+ population, compared to a reference value, e.g., a non-responder number of CD27+CD45RO− immune effector cells.

In some embodiments of any of the methods disclosed herein, a complete responder or a partial responder has, or is identified as having, a greater, e.g., a statistically significant greater, percentage of CD4+ T cells compared to a reference value, e.g., a non-responder percentage of CD4+ T cells.

In some embodiments of any of the methods disclosed herein, a complete responder has, or is identified as having, a greater percentage of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, compared to a reference value, e.g., a non-responder number of resting $T_{EFF}$ cells, resting $T_{REG}$ cells, younger T cells (e.g., younger CD4 or CD8 cells), or early memory T cells.

In some embodiments of any of the methods disclosed herein, a non-responder has, or is identified as having, a greater percentage of one, two, three, or more (e.g., all) of activated $T_{EFF}$ cells, activated $T_{REG}$ cells, older T cells (e.g., older CD4 or CD8 cells), or late memory T cells, or a combination thereof, compared to a reference value, e.g., a responder number of activated $T_{EFF}$ cells, activated $T_{REG}$ cells, older T cells (e.g., older CD4 or CD8 cells), or late memory T cells.

In some embodiments of any of the methods disclosed herein, a non-responder has, or is identified as having, a greater percentage of an immune cell exhaustion marker, e.g., one, two or more immune checkpoint inhibitors (e.g., PD-1, PD-L1, TIM-3 and/or LAG-3). In one embodiment, a non-responder has, or is identified as having, a greater percentage of PD-1, PD-L1, or LAG-3 expressing immune effector cells (e.g., CD4+ T cells and/or CD8+ T cells) (e.g., CAR-expressing CD4+ cells and/or CD8+ T cells) compared to the percentage of PD-1 or LAG-3 expressing immune effector cells from a responder.

In one embodiment, a non-responder has, or is identified as having, a greater percentage of immune cells having an exhausted phenotype, e.g., immune cells that co-express at least two exhaustion markers, e.g., co-expresses PD-1, PD-L1 and/or TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population compared to a responder (e.g., a complete responder) to the CAR-expressing cell therapy.

In some embodiments of any of the methods disclosed herein, a partial responder has, or is identified as having, a higher percentages of PD-1/PD-L1+/LAG-3+ cells, than a responder, in the CAR-expressing cell population.

In some embodiments of any of the methods disclosed herein, a non-responder has, or is identified as having, an exhausted phenotype of PD1/PD-L1+ CAR+ and co-expression of LAG3 in the CAR-expressing cell population.

In some embodiments of any of the methods disclosed herein, a non-responder has, or is identified as having, a greater percentage of PD-1/PD-L1+/TIM-3+ cells in the CAR-expressing cell population compared to the responder (e.g., a complete responder).

In some embodiments of any of the methods disclosed herein, a partial responders has, or is identified as having, a higher percentage of PD-1/PD-L1+/TIM-3+ cells, than responders, in the CAR-expressing cell population.

In some embodiments of any of the methods disclosed herein, the presence of CD8+CD27+CD45RO− T cells in an apheresis sample is a positive predictor of the subject response to a CAR-expressing cell therapy.

In some embodiments of any of the methods disclosed herein, a high percentage of PD1+ CAR+ and LAG3+ or TIM3+ T cells in an apheresis sample is a poor prognostic predictor of the subject response to a CAR-expressing cell therapy.

In some embodiments of any of the methods disclosed herein, the responder (e.g., the complete or partial responder) has one, two, three or more (or all) of the following profile:

(i) has a greater number of CD27+ immune effector cells compared to a reference value, e.g., a non-responder number of CD27+ immune effector cells;

(ii) (i) has a greater number of CD8+ T cells compared to a reference value, e.g., a non-responder number of CD8+ T cells;

(iii) has a lower number of immune cells expressing one or more checkpoint inhibitors, e.g., a checkpoint inhibitor chosen from PD-1, PD-L1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting $T_{EFF}$ cells, resting $T_{REG}$ cells, naïve CD4 cells, unstimulated memory cells or early memory T cells, or a combination thereof, compared to a reference value, e.g., a non-responder number of resting $T_{EFF}$ cells, resting $T_{REG}$ cells, naïve CD4 cells, unstimulated memory cells or early memory T cells.

In some embodiments of any of the methods disclosed herein, the cytokine level or activity of (vi) is chosen from one, two, three, four, five, six, seven, eight, or more (or all) of cytokine CCL20/MIP3a, IL17A, IL6, GM-CSF, IFNγ, IL10, IL13, IL2, IL21, IL4, IL5, IL9 or TNFα, or a combination thereof. The cytokine can be chosen from one, two, three, four or more (all) of IL-17a, CCL20, IL2, IL6, or TNFα. In one embodiment, an increased level or activity of a cytokine is chosen from one or both of IL-17a and CCL20, is indicative of increased responsiveness or decreased relapse.

In some embodiments of any of the methods disclosed herein, a transduction efficiency of 15% or higher in (vii) is indicative of increased responsiveness or decreased relapse.

In some embodiments of any of the methods disclosed herein, a transduction efficiency of less than 15% in (vii) is indicative of decreased responsiveness or increased relapse.

In embodiments, the responder, a non-responder, a relapser or a non-relapser identified by the methods herein can be further evaluated according to clinical criteria. For example, a complete responder has, or is identified as, a subject having a disease, e.g., a cancer, who exhibits a complete response, e.g., a complete remission, to a treatment. A complete response may be identified, e.g., using the NCCN Guidelines® (which are incorporated by reference herein in their entireties), as described herein. A partial responder has, or is identified as, a subject having a disease, e.g., a cancer, who exhibits a partial response, e.g., a partial remission, to a treatment. A partial response may be identified, e.g., using the NCCN Guidelines®, as described herein. A non-responder has, or is identified as, a subject having a disease, e.g., a cancer, who does not exhibit a response to a treatment, e.g., the patient has stable disease or progressive disease. A non-responder may be identified, e.g., using the NCCN Guidelines®, as described herein.

Alternatively, or in combination with the methods disclosed herein, responsive to said value, performing one, two, three, four or more of:

administering e.g., to a responder or a non-relapser, a CAR-expressing cell therapy;

administered an altered dosing of a CAR-expressing cell therapy;

altering the schedule or time course of a CAR-expressing cell therapy;

administering, e.g., to a non-responder or a partial responder, an additional agent in combination with a CAR-expressing cell therapy, e.g., a checkpoint inhibitor, e.g., a checkpoint inhibitor described herein;

administering to a non-responder or partial responder a therapy that increases the number of younger T cells in the subject prior to treatment with a CAR-expressing cell therapy;

modifying a manufacturing process of a CAR-expressing cell therapy, e.g., enriching for younger T cells prior to introducing a nucleic acid encoding a CAR, or increasing the transduction efficiency, e.g., for a subject identified as a non-responder or a partial responder;

administering an alternative therapy, e.g., for a non-responder or partial responder or relapser; or if the subject is, or is identified as, a non-responder or a relapser, decreasing the $T_{REG}$ cell population and/or $T_{REG}$ gene signature, e.g., by one or more of CD25 depletion, administration of cyclophosphamide, anti-GITR antibody, or a combination thereof.

In certain embodiments, the subject is pre-treated with an anti-GITR antibody. In certain embodiment, the subject is treated with an anti-GITR antibody prior to infusion or re-infusion.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

In Vitro Characterization of the *S. aureus* Sortase A Mutant

The [P94R/E105K/E108Q/D160N/D165A/K190E/K196T] sortaseA mutant was expressed in *E. coli* and purified by affinity chromatography exploring the polyhistidine tag comprised at its C-terminus, following established protocols (Guimaraes et al., 2013). The introduced mutations did not seem to interfere with expression or protein folding as high yields of soluble, monodispersed protein were obtained.

Characterization of the enzyme was initially done in vitro using purified proteins. As the reaction substrate, a scFV directed to CD19 (scFV19) comprising a sortase A recognition motif (LPETGG, SEQ ID NO: 21) and a His8 (SEQ ID NO: 111) purification handle at the C-terminus (also referred to herein as scFv19.LPETGG.His8 ("LPETGG" and "His8" disclosed as SEQ ID NOS 21 and 111, respectively)) was cloned, expressed, and purified. This is the same scFV19 that was used in subsequent examples to test site-specific attachment to live cells using sortase:

```
                                          (SEQ ID NO: 22)
METDTLLLWVLLLWVPGSTGEIVMTQSPATLSLSPGERATLSCRASQD

ISKYLNWYQQKPGQAPRLLIYHTSRLHSGIPARFSGSGSGTDYTLTIS

SLQPEDFAVYFCQQGNTLPYTFGQGTKLEIKGGGGSGGGGSGGGGSQV

QLQESGPGLVKPSETLSLTCTVSGVSLPDYGVSWIRQPPGKGLEWIGV

IWGSETTYYSSSLKSRVTISKDNSKNQVSLKLSSVTAADTAVYY

CAKHYYYGGSYAMDYWGQGTLVTVSS[LPETGG]LDVLFEGPHHHHHHHH (The lgK signal peptide which is cleaved off cotranslationally is underlined).
```

As a nucleophile for these test reactions fluorescently labeled peptide: GGGK(TAMRA) (KRUEGANA-001-EXP022) (SEQ ID NO:23) was synthesized and purified. The fluorophore moiety allowed for convenient monitoring of the reaction by SDS-PAGE followed by fluorescent scanning.

Example 2

The Mutant Sortase is Ca2+ Independent and Displays Fast Kinetics

The activities of mutant and wild-type (SrtA aureus_His6SrtA26-206 ("His6" disclosed as SEQ ID NO: 110)) sortases were compared side-by-side in the absence or presence of 10 mM calcium in 50 mM Tris-Cl, pH 7.4, 150 mM NaCl buffer, using final concentrations of 40 µM sortase, 20 µM scFV.LPETG.His$_8$ ("LPETG" and "His8" disclosed as SEQ ID NOS 112 and 111, respectively), and 1 mM GGGK(TAMRA) (SEQ ID NO:23). The reactions were incubated at 37° for different periods of time (as indicated in FIG. 2), and analyzed by reducing SDS-PAGE followed by fluorescent scanning (using a ChemiDoc gel imaging system from BioRad) and coomassie staining.

Figure 2:
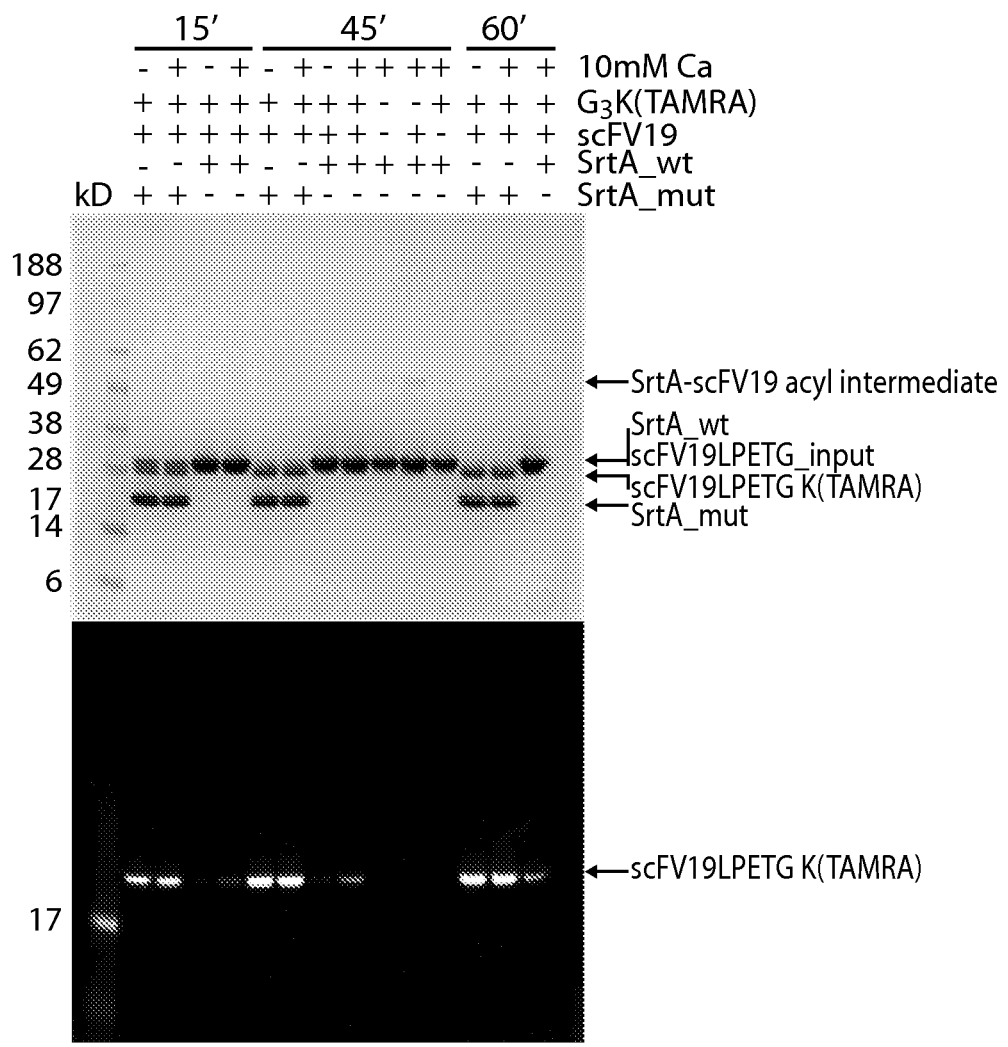
FIG. 2 is an image demonstrating labeling of a scFV directed to the CD19 protein harboring a LPXTG (SEQ ID NO: 109) sortase-recognition motif followed by a His8 (SEQ ID NO: 111) at its C-terminus (scFV19, 20 µM) with either WT (40 µM) or mutant [P94R/E105K/E108Q/D160N/D165A/K190E/K196T] sortase A (40 µM), in the presence or absence of 10 mM calcium chloride, and $G_3K(TAMRA)$ peptide (1 mM) (SEQ ID NO: 23), at 37° C., for the times indicated. The reactions were analyzed by reducing SDS-PAGE followed by fluorescent scanning (bottom panel) and coomassie-blue staining (upper panel). The molecular weight markers are shown on the left. The predicted identity of the various protein bands observed in the gel is indicated by the arrows. The Figure discloses "LPETG" and "LPETG$_3$K" as SEQ ID NOS 112 and 250, respectively.

Only when sortase, scFV19, and the fluorescent peptide are incubated together, was fluorescent protein band detected, compatible with the size of the scFV19 conjugated to the TAMRA peptide (FIG. 2). This was true for the mutant sortase, regardless of whether calcium was present in the reaction mixture. Calcium was however essential for the activity of the wild-type sortase, as the labeled product was detected only if calcium was included in the buffer (FIG. 2). The mutant sortase was also faster. In both cases an increase in fluorescence was observed over time, but there was a clear distinction between the fluorescent intensities observed for the wild type and mutant enzymes. The mutant sortase demonstrated fluorescence as early as 15 minutes of incubation, while no fluorescence was detected at the same timepoint for the wild-type sortase reaction. Increased fluorescence was also detected for the reactions containing mutant sortase when compared to reactions containing wild-type sortase at all three timepoints. Under the reaction conditions described, labeling of the scFV19 with the TAMRA-decorated peptide and mutant sortase was complete after 45' incubation at 37° C.

Example 3

The Mutant Sortase A is Active in Cell Culture Media

Figure 3:
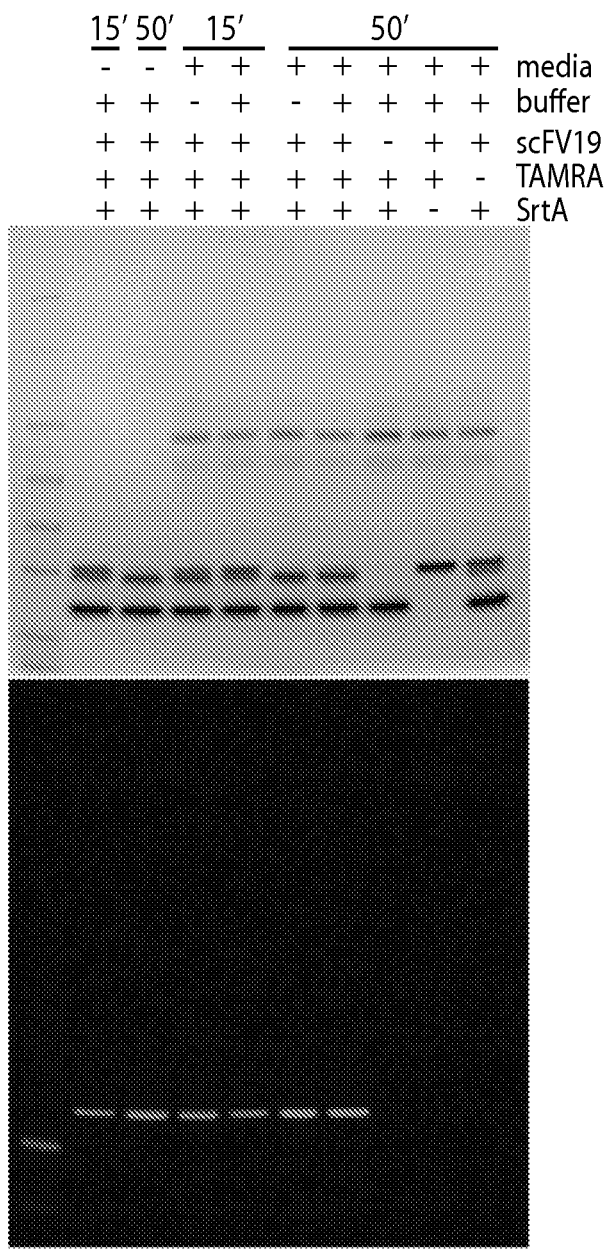
FIG. 3 is an image demonstrating labeling of a scFV directed to the CD19 protein harboring a LPXTG (SEQ ID NO: 109) sortase-recognition motif followed by a His8 (SEQ ID NO: 111) at its C-terminus (scFV19, 20 µM) with the mutant [P94R/E105K/E108Q/D160N/D165A/K190E/K196T] sortase A (40 µM), $G_3K(TAMRA)$ peptide (1 mM) (SEQ ID NO: 23) in RPMI+1% FBS media supplemented or not with 50 mM Tris-Cl, pH 7.4, 150 mM NaCl buffer, at 37° C., for the times indicated. The reactions were monitored by reducing SDS-PAGE, followed by fluorescent scanning (bottom panel) and coomassie-blue staining (upper panel).

The activity of mutant sortase A was active in culture media (RMPI supplemented with 1% FBS) was determined using the same reaction conditions as in Example 2. The presence of the fluorescent bands indicates the successful coupling of scFv19 to the TAMRA-labeled peptide in the presence of cell culture media. No major labeling differences were detected between the reaction kinetics or the intensity of the fluorescence between reactions in buffer or in culture media. Thus, the results presented herein suggest the enzyme is also active in this culture media. As in Example 2, the reaction was complete upon 45' incubation at 37° C. (FIG. 3). The results presented herein demonstrate the specificity of the reaction, as no proteins from the serum (detected upon coomassie staining) were labeled with a fluorophore.

Example 4

The Mutant Sortase A is Active in a Wide Range of Temperatures

Figure 4:
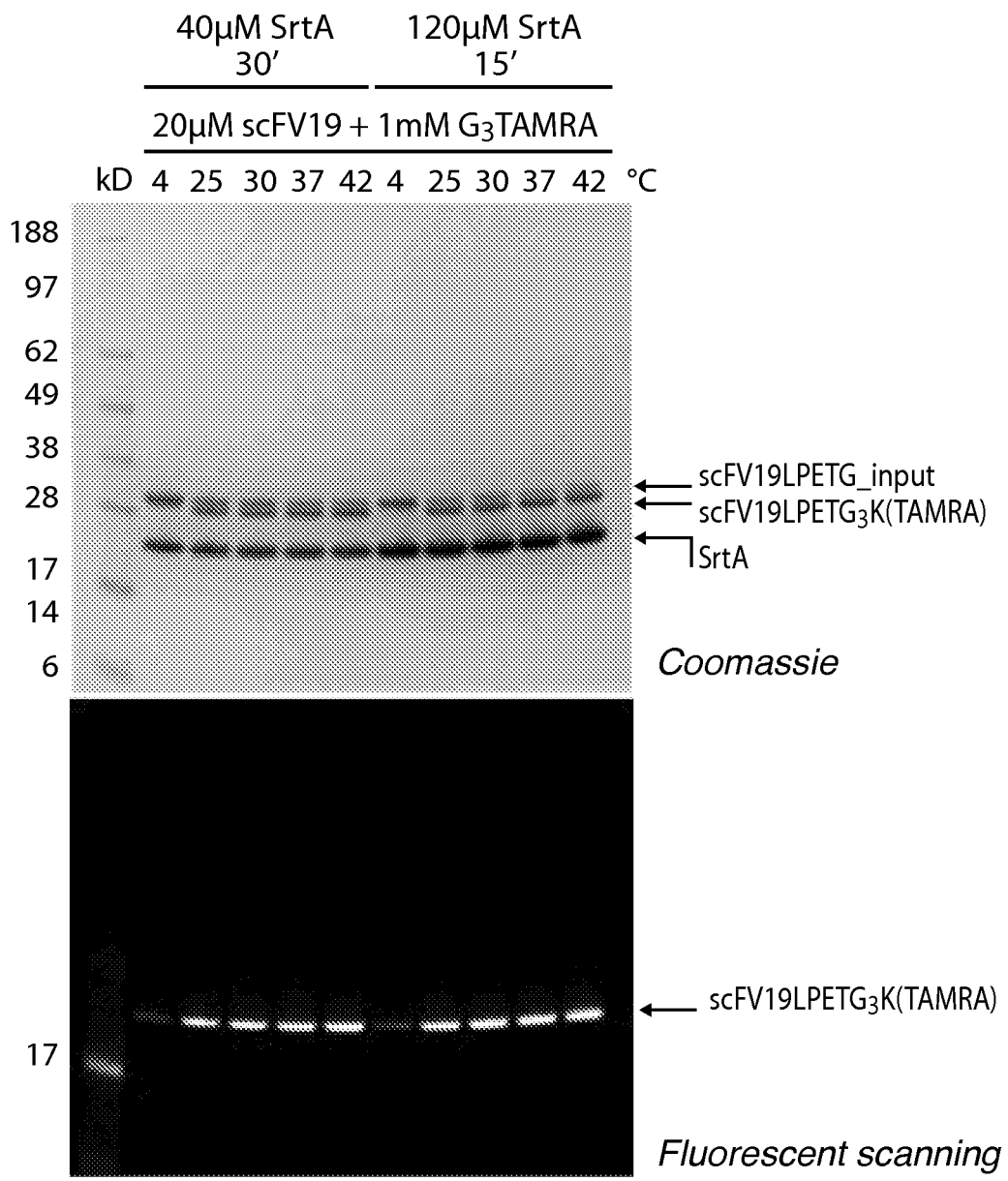
FIG. 4 is an image demonstrating labeling of a scFV directed to the CD19 protein harboring a LPXTG (SEQ ID NO: 109) sortase-recognition motif followed by a His8 (SEQ ID NO: 111) at its C-terminus (scFV19, 20 µM) with the mutant [P94R/E105K/E108Q/D160N/D165A/K190E/K196T] sortase A (40 µM or 120 µM), $G_3K(TAMRA)$ peptide (SEQ ID NO: 23) (1 mM) in 50 mM Tris-Cl, pH 7.4, 150 mM NaCl buffer, at the temperatures and times indicated. The reactions were monitored by reducing SDS-PAGE, followed by fluorescent scanning and coomassie-blue staining. The molecular weight markers are shown on the left. The predicted identity of the various protein bands observed in the gel is indicated by the arrows. The Figure discloses "LPETG" and "LPETG$_3$K" as SEQ ID NOS 112 and 250, respectively.

Because reaction temperature can influence enzyme activity, whether kinetics could be improved using temperatures above or below 37° C. was determined. The results presented herein demonstrate that the fluorescence was equivalent at each temperature point between 25 and 42° C., indicating that the mutant sortase A performed equally well at temperatures ranging from 25° C. to 42° C. (FIG. 4).

In this same experiment, whether the sortase concentration influences the reaction rate was also determined. The same labeling proportion in half of the time was observed, when using a three-fold higher concentration of enzyme (FIG. 4).

Example 5

In Vitro Characterization of the scFV19 to be Attached to pseudoCARTs

Figure 5:
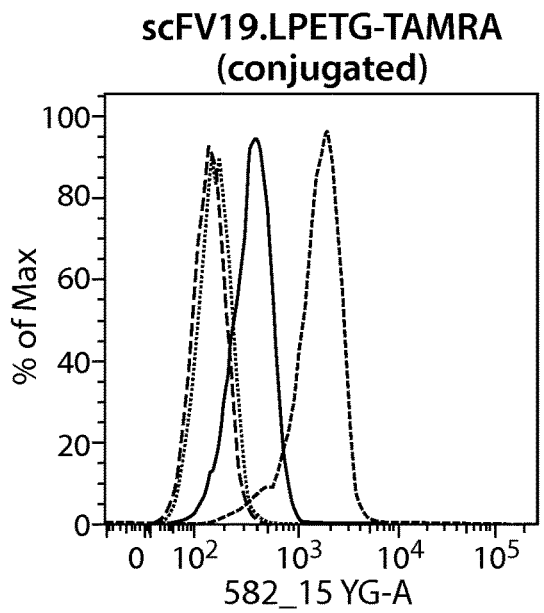
FIG. 5 shows a graph of untransduced K562 cells or K562 cells expressing CD19 at their surface incubated for 30 min at 4° C. with various concentrations of a scFV directed to CD19 which had been conjugated to TAMRA (scFV19.LPETG-TAMRA_conjugated (SEQ ID NO: 112)) through a sortase-mediated reaction. As a control, scFV19 subjected to the same reaction conditions to label the scFV with TAMRA, but omitting sortase (scFV19.LPETG+TAMRA_not conjugated (SEQ ID NO: 112)) was used. Flow cytometry analysis comparing cell labeling is shown.
Figure 5:
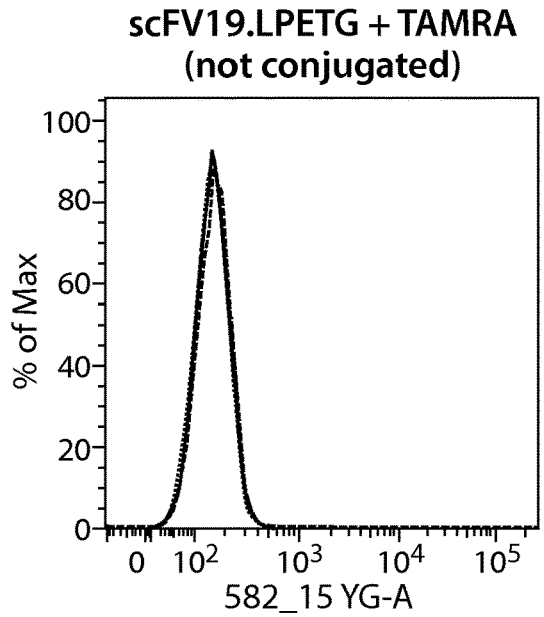
Figure 5:
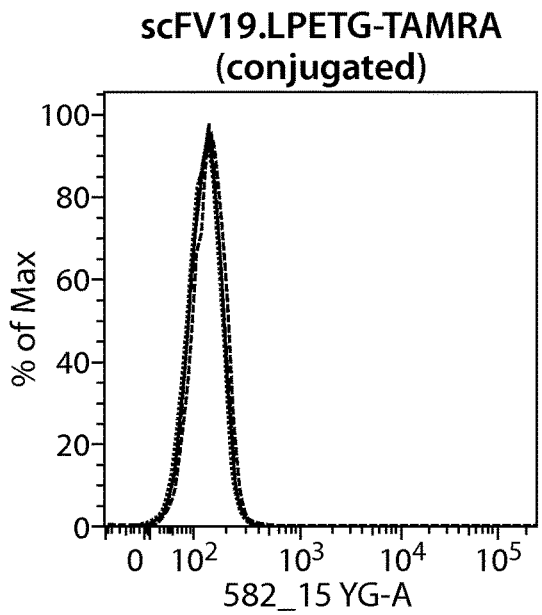
Figure 5:
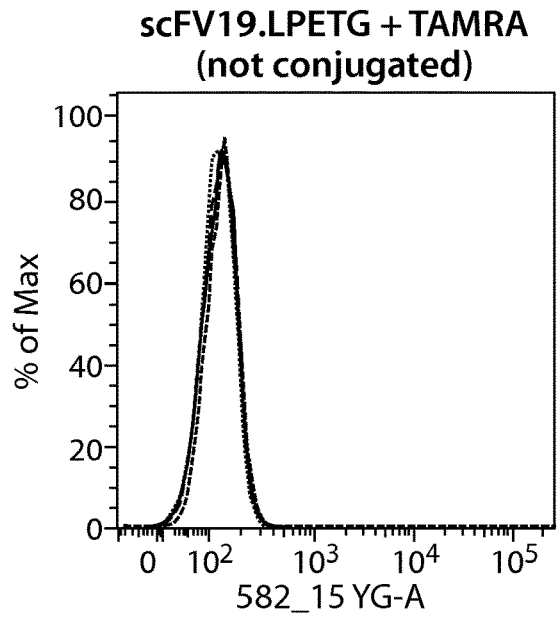

To determine whether the presence of the sortase-recognition motif interferes with the ability of the scFV19 to recognize CD19, the scFV19.LPETGG.His$_8$ ("LPETGG" and "His$_8$" disclosed as SEQ ID NOS 21 and 111, respectively) was labeled with the G$_3$K(TAMRA) peptide (SEQ ID NO:23) using the mutant sortase A as described in Example 1. A control reaction which did not include sortase was performed in parallel. Upon reaction, each of the preparations were filtered through a desalting column to remove unreacted G$_3$K(TAMRA) peptide (SEQ ID NO: 23). Different concentrations of the scFV19.LPETG$_3$K(TAMRA) conjugate ("LPETG$_3$K" disclosed as SEQ ID NO: 250) and unconjugated control were then used to label untransduced K562 cells or K562 overexpressing CD19. It was shown by flow cytometry that cell labeling was observed only with the conjugate and only on K562 cells expressing CD19 (FIG. 5). These results demonstrated that the conjugation of the scFv19 molecule to the fluorescent TAMRA peptide by sortase did not interfere or impair scFv19 function, e.g., specific binding to CD19 expressed on the cell surface of K562 cells. Thus, the results presented herein confirm that the scFV19.LPETGG.His$_8$ substrate ("LPETGG" and "His$_8$" disclosed as SEQ ID NOS 21 and 111, respectively) for sortase is functional and that the sortase labeling strategy can be used to create new tools for FACS staining.

Example 6

Rationale Underlying Engineering pseudoCARTs to be Used in Sortase-Mediated Reactions After ensuring that the engineered mutant *S. aureus* sortase A displayed the desired properties and that the minimally modified scFV19 was functional (as described in Examples 1-5), constructs were made for rendering the T cells passive to functionalization by sortase. *S. aureus* sortase A recognizes the LPETG motif (SEQ ID NO: 112) at the C-terminus of scFV19 and requires a stretch of glycines to resolve the intermediate (FIG. 1). Thus, the scFV19 of CART19 was replaced with either three glycines or with three glycines preceding a Myc epitope tag (EQKLISEEDL) (SEQ ID NO: 24). The purpose of the tag was to increase T cell transduction. The Myc tag provides a handle for cell sorting by flow-cytometry, if needed.

Because the size of the CD8 hinge is important for a proper immunological synapse to occur, the same CD8 hinge length was maintained across the various constructs. The CD8 hinge was truncated at different residues to accommodate the sortase-recognition motif and glycines. The corresponding controls were also genetically engineered (FIG. 6).

Example 7

Characterization of pseudoCARTs

Figure 6:
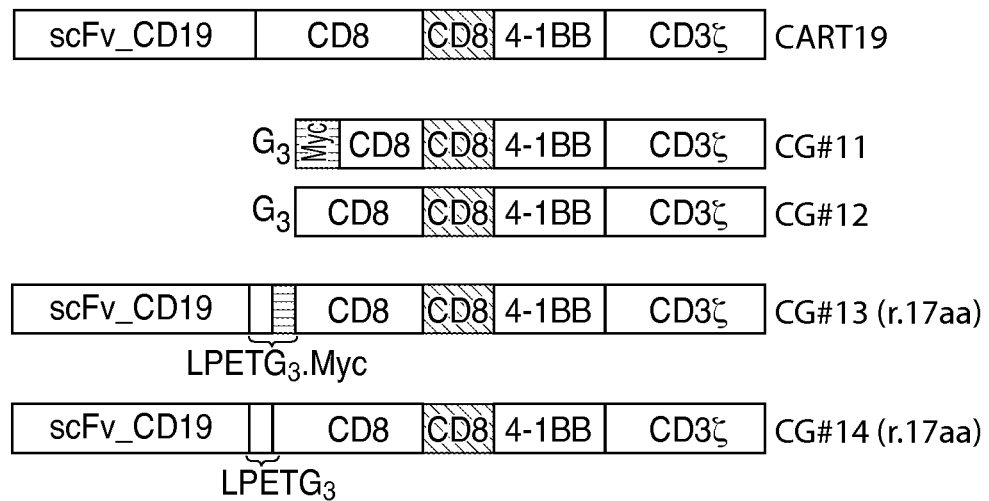
FIG. 6 is a schematic representation of the constructs generated to transduce cells for sortase-mediated functionalization of their surface using sortase A. The scFV directed to CD19 (scFv_CD19) is at the N-terminus of the construct and oriented to the extracellular space. This domain is followed by the CD8 hinge, the CD8 transmembrane region (shaded box) and the intracellular signaling domains 4-1BB and CD3ζ. The length of the hinge in the various constructs is the same; CG #13 and CG #14 have 17 or 7 amino acids of the CD8 hinge replaced with the LPETG$_3$Myc or LPETG sequences, respectively (SEQ ID NOS 26 and 112, respectively).
Figure 7A:
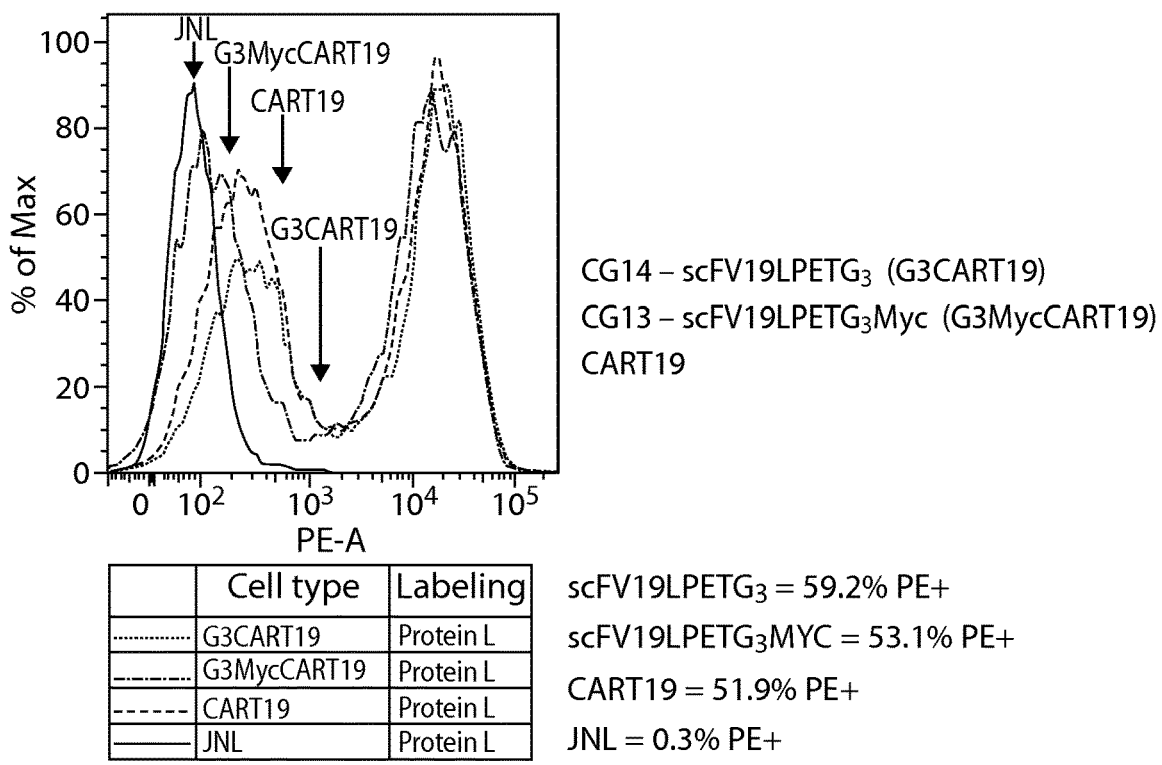
FIGS. 7A and 7B are a series of graphical representations of Jurkat cells transduced with the various constructs indicated in FIG. 6 stained either with biotinylated protein L (FIG. 7A, 1 µg/ml) or mouse α-Myc antibody (FIG. 7B, 1:1000) and revealed with streptavidin or anti-mouse secondary antibody both conjugated to PE, respectively. Flow cytometry analysis comparing cell labeling is shown as well as the percentage of cells that stained positively for PE. The Figure discloses "LPETG$_3$" and "LPETG$_3$Myc" as SEQ ID NOS 25 and 26, respectively.
Figure 7B:
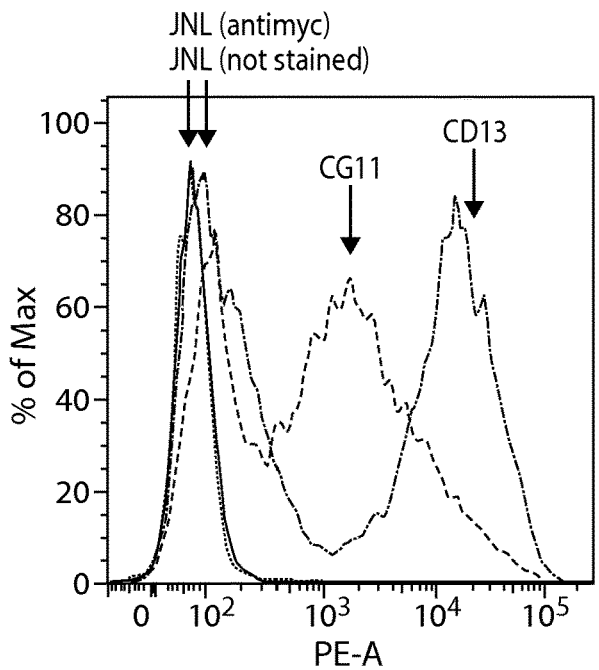

The constructs described in Example 6 and shown in FIG. 6 were built in the pELPs vector. Viruses were made, and transduced Jurkat cells using standard protocols. FACS staining using protein L (for scFV detection) or an anti-Myc antibody (Cell Signalling Technology 9B11 clone) revealed that the efficiency of transduction was close to 50%, with exception of the construct comprising Myc, glycines, and no scFV (FIG. 7, construct CG11 in FIG. 6). In this case we detected low and heterogeneous expression of the Myc tag was detected (FIG. 7). Due to the lack of a specific marker, the transduction rate could not be assessed when using the construct that contains glycines and no Myc tag (construct CG12 in FIG. 6).

Figure 8:
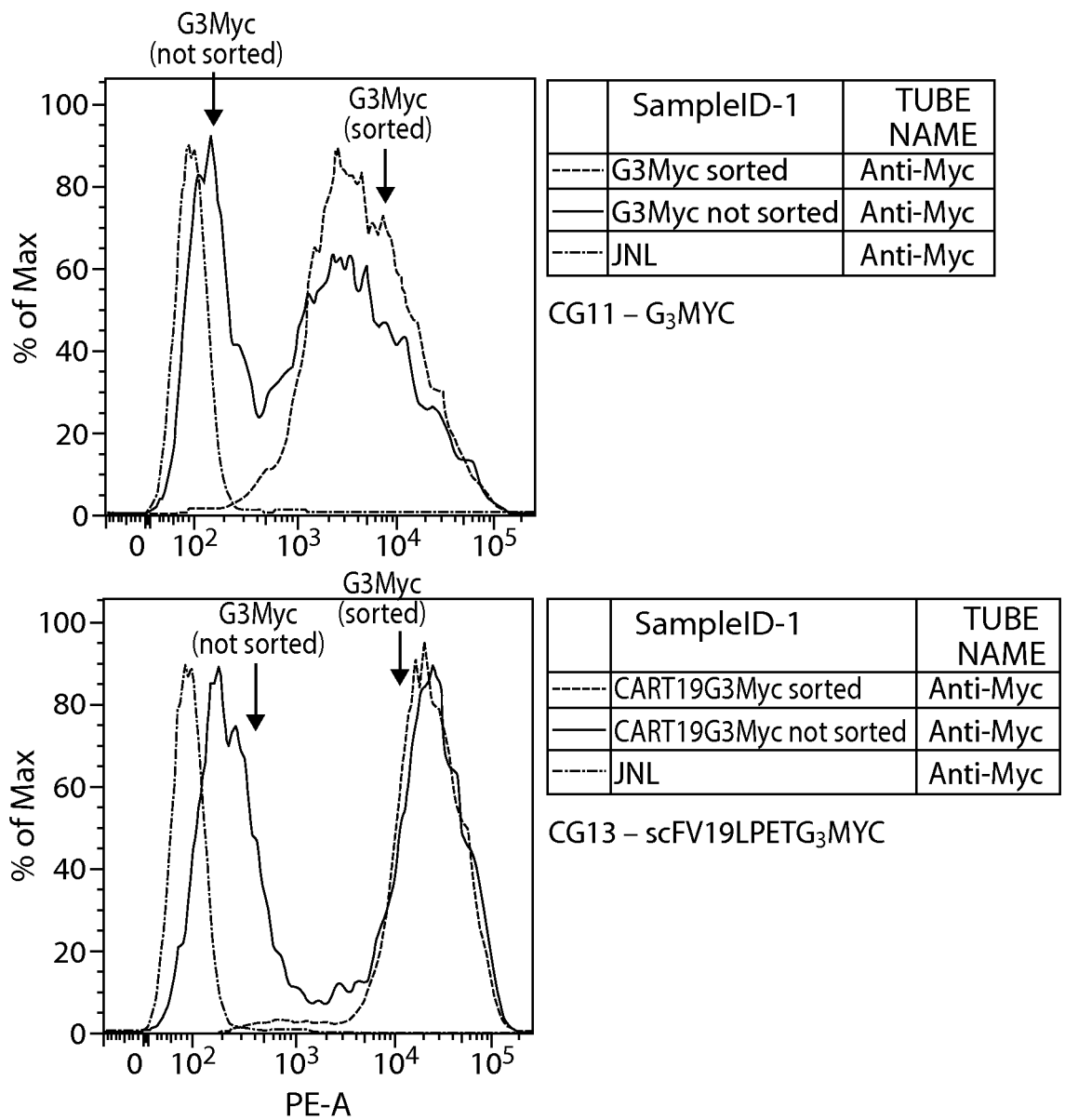
FIG. 8 shows a graphical representation of Jurkat cells transduced with constructs CG11 or CG13 (FIG. 6) FACS sorted based on the expression of the Myc tag. Figure discloses SEQ ID NO: 26.

In principle, the more glycines fused to the CAR signalling domains the cells display at the surface, the higher the functionalization efficiency will be, as more glycines will be available for reaction. This also helps to increase reaction specificity. Because *S. aureus* sortase A-mediated reactions rely on glycines to resolve the acyl-intermediate (FIG. 1) and because in most cases a single glycine suffices, controlling the specificity of the reaction can be difficult. The extent of the background will depend on how many proteins are expressed with their N-terminus exposed to the extracellular space and how many of these exposed proteins display an N-terminal glycine in their mature form. Some heterogeneity was observed for cells expressing Myc and glycines (construct CG11 in FIG. 6). The cells were FACS sorted for higher expressors. Although eliminate untransduced cells were eliminated, FACS staining performed 10 days after FACS sorting showed again diversity with regard to level of expression of the constructs among the engineered cells (FIG. 8). One possibility is that truncation of the hinge destabilizes the protein folding, or interferes with membrane docking and/or targeting along the secretory pathway.

Figure 9A:
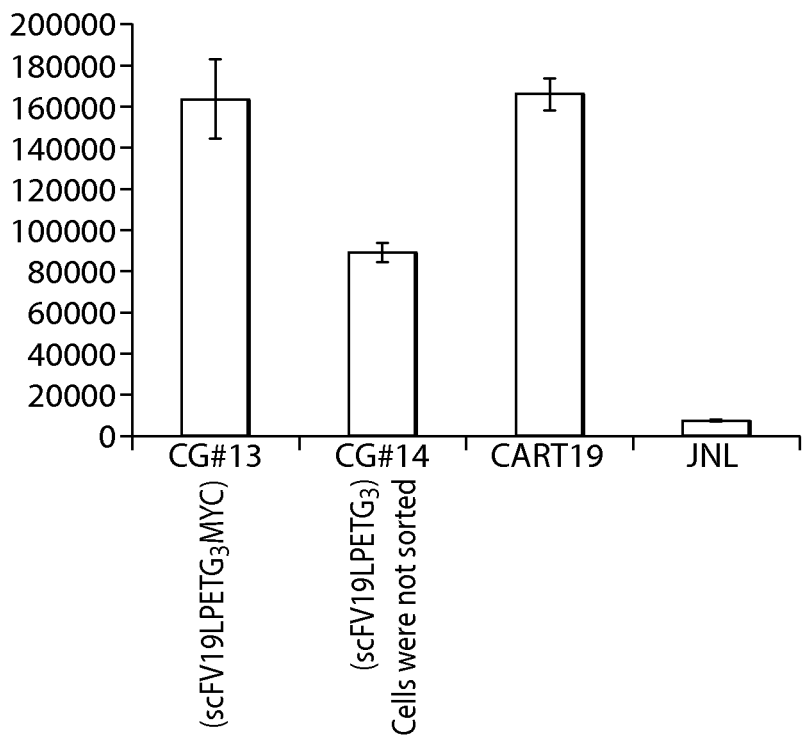
FIGS. 9A and 9B are a series of graphical representations showing a luciferase reporter assay to determine whether the LPETG3 and LPETG$_3$Myc sequences (SEQ ID NOS 25 and 26, respectively) interfere with activation of the engineered CARTs (FIG. 9A). The Jurkat cells transduced with the indicated constructs in FIG. 6 also comprised a NFAT-luciferase reporter system. $50 \times 10^3$ transduced cells were plated in 50 µl of RPMI supplemented with 1% FBS in a 96 well plate black with clear bottom. $15 \times 10^3$ K562-expressing CD19 were then added in 50 µl of the same media. Cells were incubated at 37° C., $CO_2$ for 20 hrs. 100 µl of the Bright-Glo Luciferase Assay mixture (Promega) was added to each of the wells. The cells were incubated at room temperature for 10 minutes before measuring the luminescence. Transduced cells containing just the NFAT-luciferase reporter but not any CART (referred to as JNL) were used as control. The values indicated in the Y-axis correspond to the levels of luminescence detected by the machine. Errors bars show standard deviations of three independent measurements. All the cells used were FACS-sorted, except the ones transduced with the CG14 construct for lack of a handle for FACS.
Figure 9B:
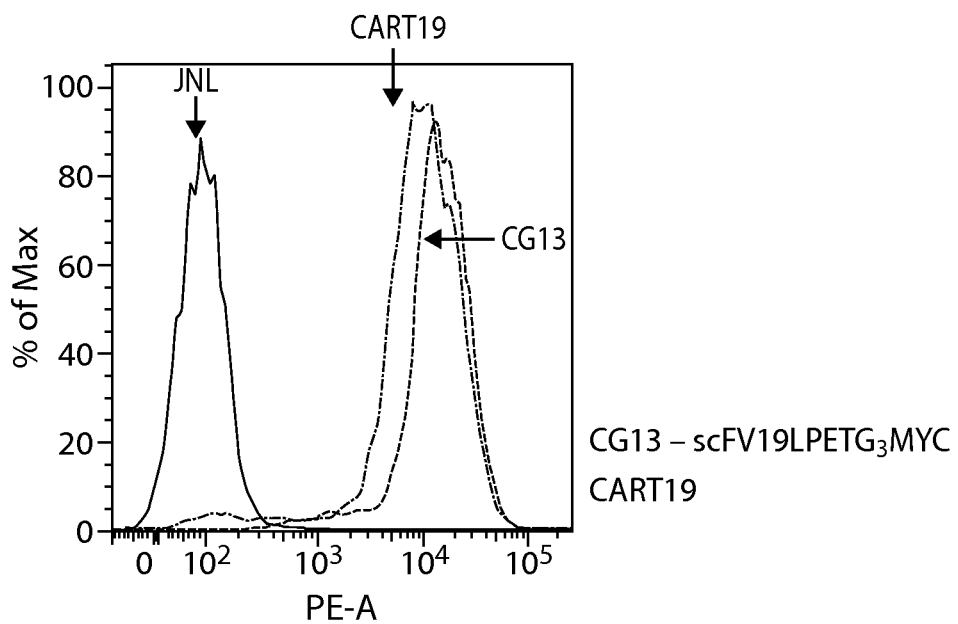

To further characterize the pseudoCARTs, it was verified that the presence of the LPETG motif (SEQ ID NO: 112) and glycines does not interfere with CART activation. The functionality of the genetically engineered counterparts (constructs CG13 and CG14, FIG. 6) was tested using a luciferase-based assay that reports on the ability of CARTs to be activated (here, by CD19). The Jurkat cells transduced with the constructs shown in FIG. 6 also contain a cassette encoding the luciferase gene under the control of the interleukin-2 (IL-2) promoter. In T cells, engagement of the antigen-specific T-cell receptor activates the NFAT (nuclear factor of activated T cells) pathway, leading to activation of the IL-2 promoter with subsequent increase in luciferase production that can be measured enzymatically. Thus, activation of these cells can be determined by increased expression of IL-2, and subsequent luciferase production can be quantified. In the case of CART19, luciferase production should be increased when these cells are co-cultured with K562 cells expressing CD19. The data presented herein showed that the LPETG$_3$ (SEQ ID NO: 25) sequence and the LPETG$_3$Myc (SEQ ID NO: 26) sequence were compatible with activation (FIG. 9a). Given that expression of the scFV19 in CART19 control and scFV19.LPETG$_3$Myc (SEQ ID NO: 26) is approximately the same, as assessed by FACS (FIG. 9b) it is not surprising that similar results were observed with both CARTs. The activity observed with the LPETG$_3$ (SEQ ID NO: 25) construct was, however, significantly lower than that observed for the cell lines containing CART19 and scFV19.LPETG3Myc (SEQ ID NO: 26), yet higher than in cells that do not express any CAR (JNLs, FIG. 9a).

Example 8

Functionalizing pseudoCARTs with a (TAMRA)KLPETGG Peptide (SEQ ID NO: 27) Using Sortase Labeling cells at their surface is much more complicated than labeling proteins in solution using sortase. Not only do cells represent a more complex mixture of proteins, lipids, sugars, etc, but labeling is also affected by the health status of the cells. In addition, cells are not static entities and hence the recycling rate of the plasma membrane that is being labeled influences the end result. Thus, the concentration of sortase and of the functional group to be attached, as well as the number and concentration of cells must be determined empirically and the conditions may widely differ from what was established in vitro.

Figure 10A:
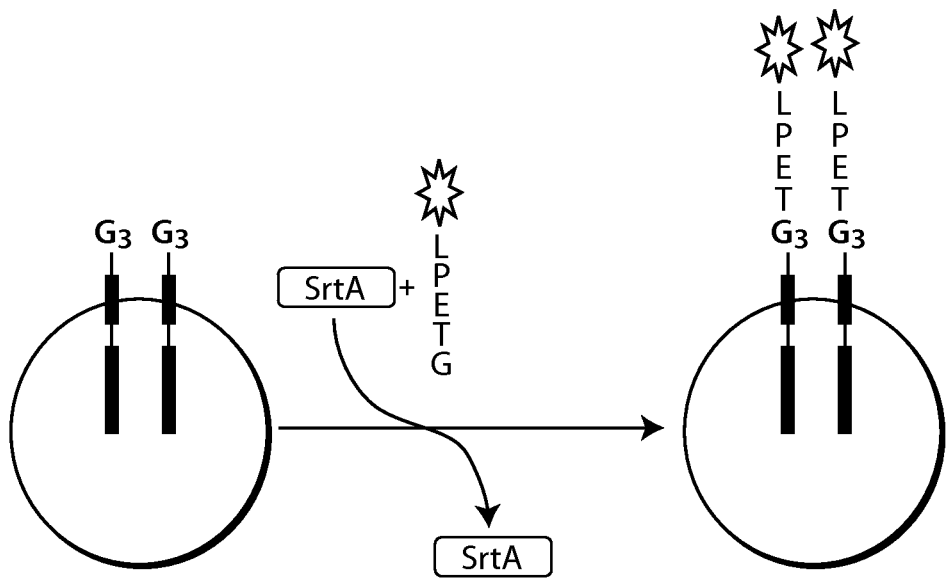
FIGS. 10A and 10B.

A (TAMRA)-labelled KLPETGG peptide (FLYERAL1-008-EXP074-001) (SEQ ID NO: 27) was used to determine the best conditions for in vitro sortase labeling so that the reaction could easily be followed by FACS analysis (FIG. 10a). The peptide also enabled positive selection of the transduced cells with the construct containing glycines (CG12, FIG. 6) by flow cytometry, upon sortase-mediated reaction.

The experimental set up for the initial experiment was as follows: $0.2 \times 10^6$ of either FACS sorted $G_3$Myc-pseudo-CART (CG11 construct, FIG. 6) or nontransduced cells was plated per well in a 96 well plate, in RPMI+1% FBS media. 40 μM mutant sortase A and various concentrations of the (TAMRA)-KLPETGG peptide (SEQ ID NO: 27) was then added, and the cells were incubated at 37° C., 5% $CO_2$, for 30 min. The cells were washed twice with RPMI+1% FBS and prepared for FACS analysis.

Figure 10B:
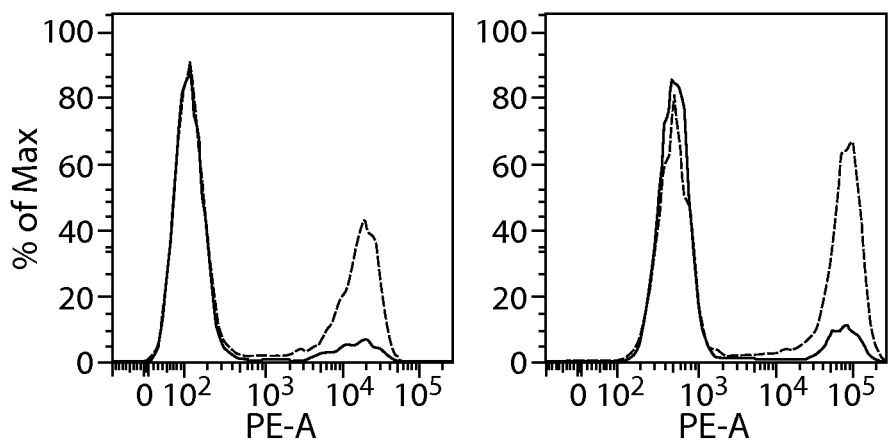

The data presented herein show that a subpopulation of cells was being labeled with TAMRA regardless of whether they were expressing $G_3$.Myc (FIG. 10b). However, the labeled population is greater when $G_3$.Myc is expressed (20.5% versus 55.2% TAMRA-positive cells, when 1 μM fluorophore is used). Reaction conditions can be adjusted to minimize background and a more stable glycine containing construct is being engineered to improve reaction yield.

Figure 11:
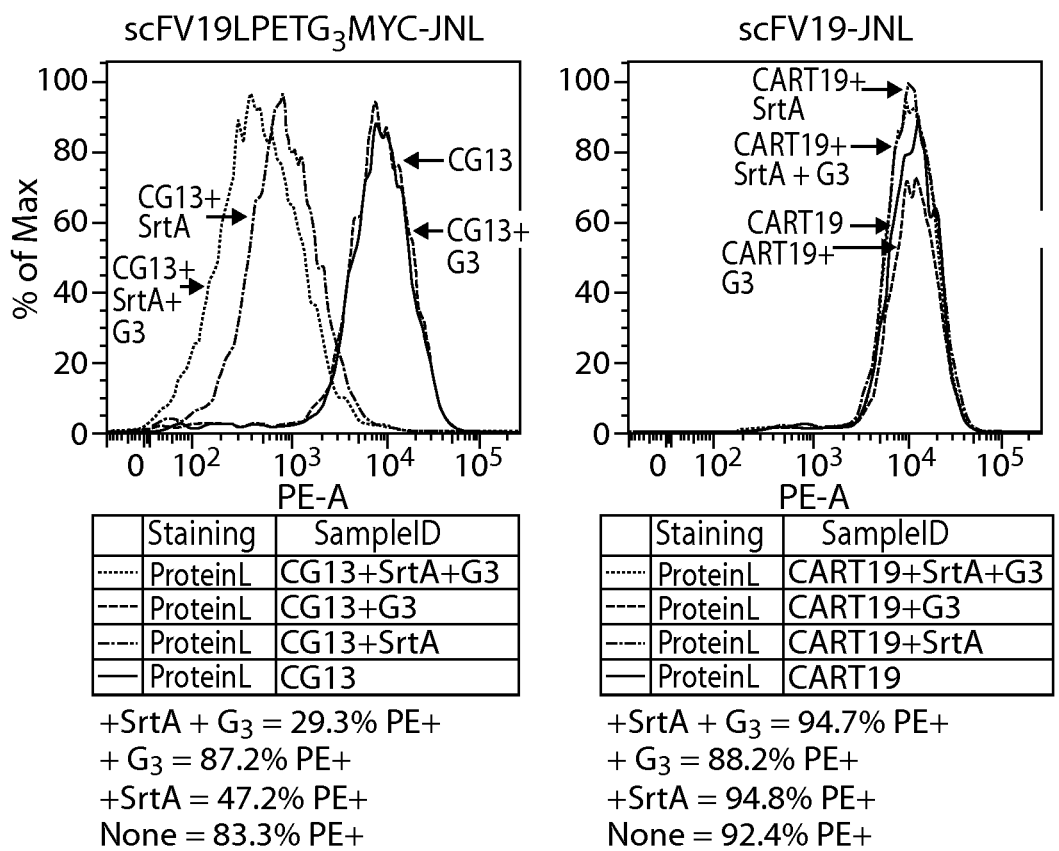
FIG. 11 shows a graph of cleavage of the LPETG motif (SEQ ID NO: 112) in transduced Jurkat cells with construct CG13 (scFV19LPETG$_3$MYC-JNL ("LPETG$_3$" disclosed as SEQ ID NO: 26), FIG. 6). Cells expressing the same scFV but not comprising the LPETG motif (SEQ ID NO: 112) (scFV19-JNL; CART19 in FIG. 6) were taken as control. Cells were incubated with 120 μM mutant sortaseA and 1 mM triglycine at 37° C. for 30 min (+SrtA+G3). Control reactions included: sortase only (+SrtA), triglycine only (+G3), and nothing added (None). Cells were processed for FACS analysis using biotinylated protein L that was detected with streptavidin conjugated to PE. The number of PE positive cells (PE+) is indicated.

If concentration, accessibility, and orientation of the $G_3$.Myc matters to achieve a successful reaction, then this should also apply to the reverse reaction and sortase A should efficiently cleave a LPETG-containing construct ("LPETG" disclosed as SEQ ID NO: 112) displayed at the cell surface. To test this, scFV19.LPETG$_3$Myc-CART19 ("LPETG$_3$" disclosed as SEQ ID NO: 26) (CG13, FIG. 6) expressing cells and the control CART19 cells (which do not have the required LPETG motif (SEQ ID NO: 112) for sortase-mediated reactions) were used. $2 \times 10^5$ cells/well were plated in a 96 well-plate and added 120 μM sortase A. One reaction containing 120 μM sortase A plus 0.5 mM tryglicine nucleophile was also included. Upon incubation at 37° C., 5% $CO_2$, for 30 min., the cells were washed, stained with protein L and the samples were processed for FACS analysis. A decrease in fluorescence was observed only in the presence of sortase and only when the construct containing the sortase-recognition motif was used (scFV19.LPETG$_3$Myc, CG13) ("LPETG$_3$" disclosed as SEQ ID NO: 26) (FIG. 11). The results presented herein suggest that this is a result of sortase A acting upon the LPETG motif (SEQ ID NO: 112) and releasing the anchored scFvs. The decrease in fluorescence was more pronounced when triglycine was added, likely because it helps releasing the acyl intermediate, liberating the enzyme for more cleavage cycles. Because it is known that the sortase-recognition motif needs to be engineered in a flexible and exposed region for the reaction to occur, the results presented herein suggest that a moiety as large as a scFV conferring stability to the CD8 hinge can serve as a cap and be removed before functionalizing the cells with a scFV of interest.

Example 9: Low Dose RAD001 Stimulates CART Proliferation in a Cell Culture Model The effect of low doses of RAD001 on CAR T cell proliferation in vitro was evaluated by co-culturing CART-expressing cells with target cells in the presence of different concentrations of RAD001.

Materials and Methods
Generation of CAR-Transduced T Cells

A humanized, anti-human CD19 CAR (huCART19) lentiviral transfer vector was used to produce the genomic material packaged into VSVg pseudotyped lentiviral particles. The amino acid and nucleotide sequence of the humanized anti-human CD19 CAR (huCART19) is CAR 1, ID 104875, described in PCT publication, WO2014/153270, filed Mar. 15, 2014, and is designated SEQ ID NOs. 85 and 31 therein.

Lentiviral transfer vector DNA is mixed with the three packaging components VSVg env, gag/pol and rev in combination with lipofectamine reagent to transfect Lenti-X 293T cells. Medium is changed after 24 h and 30 h thereafter, the virus-containing media is collected, filtered and stored at −80° C. CARTs are generated by transduction of fresh or frozen naïve T cells obtained by negative magnetic selection of healthy donor blood or leukopak. T cells are activated by incubation with anti-CD3/anti-CD28 beads for 24 h, after which viral supernatant or concentrated virus (MOI=2 or 10, respectively) is added to the cultures. The modified T cells are allowed to expand for about 10 days. The percentage of cells transduced (expressing the CARs on the cell surface) and the level of CAR expression (relative fluorescence intensity, Geo Mean) are determined by flow cytometric analysis between days 7 and 9. The combination of slowing growth rate and T cell size approaching ~350 fL determines the state for T cells to be cryopreserved for later analysis.

Evaluating Proliferation of CARTs

To evaluate the functionality of CARTs, the T cells are thawed and counted, and viability is assessed by Cellometer. The number of CAR-positive cells in each culture is normalized using non-transduced T cells (UTD). The impact of RAD001 on CARTs was tested in titrations with RAD001, starting at 50 nM. The target cell line used in all co-culture experiments is Nalm-6, a human pre-B cell acute lymphoblastic leukemia (ALL) cell line expressing CD19 and transduced to express luciferase.

For measuring the proliferation of CARTs, T cells are cultured with target cells at a ratio of 1:1. The assay is run for 4 days, when cells are stained for CD3, CD4, CD8 and CAR expression. The number of T cells is assessed by flow cytometry using counting beads as reference.

Results

Figure 12:
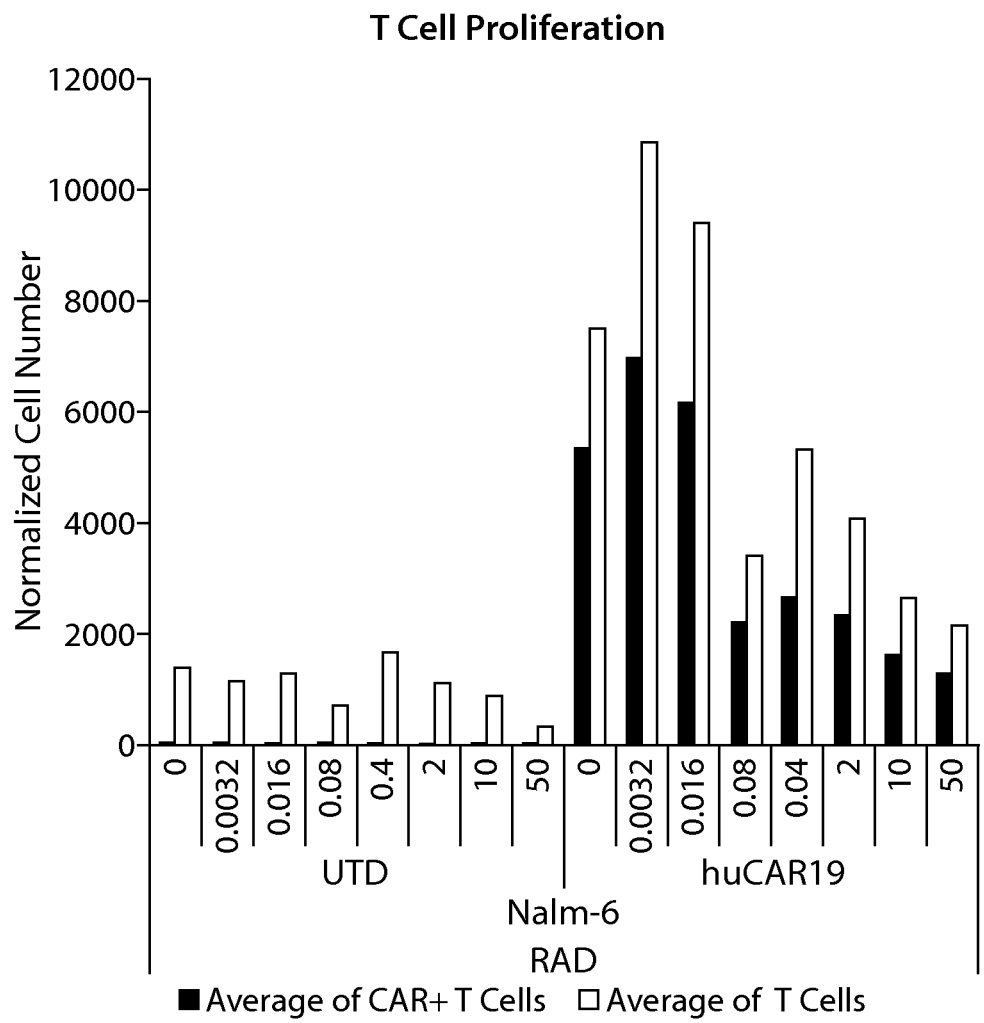
FIG. 12 shows that the proliferation of CAR-expressing, transduced T cells is enhanced by low doses of RAD001 in a cell culture system. CARTs were co-cultured with Nalm-6 cells in the presence of different concentrations of RAD001. The number of CAR-positive CD3-positive T cells (black) and total T cells (gray) was assessed after 4 days of co-culture.

The proliferative capacity of CART cells was tested in a 4 day co-culture assay. The number of CAR-positive CD3-positive T cells (dark bars) and total CD3-positive T cells (light bars) was assessed after culturing the CAR-transduced and non-transduced T cells with Nalm-6 (FIG. 12). huCART19 cells expanded when cultured in the presence of less than 0.016 nM of RAD001, and to a lesser extent at higher concentrations of the compound. Importantly, both at 0.0032 and 0.016 nM RAD001 the proliferation was higher than observed without the addition of RAD001. The non-transduced T cells (UTD) did not show detectable expansion.

Example 10: Low Dose RAD001 Stimulates CART Expansion In Vivo

This example evaluates the ability of huCAR19 cells to proliferate in vivo with different concentrations of RAD001.

Materials and Methods:

NALM6-luc cells: The NALM6 human acute lymphoblastic leukemia (ALL) cell line was developed from the peripheral blood of a patient with relapsed ALL. The cells were then tagged with firefly luciferase. These suspension cells grow in RPMI supplemented with 10% heat inactivated fetal bovine serum.

Mice: 6 week old NSG (NOD.Cg-PrkdcscidIl2rgtm1Wjl/SzJ) mice were received from the Jackson Laboratory (stock number 005557).

Tumor implantation: NALM6-luc cells were grown and expanded in vitro in RPMI supplemented with 10% heat inactivated fetal bovine serum. The cells were then transferred to a 15 ml conical tube and washed twice with cold sterile PBS. NALM6-luc cells were then counted and resuspended at a concentration of 10×106 cells per milliliter of PBS. The cells were placed on ice and immediately (within one hour) implanted in the mice. NALM6-luc cells were injected intravenously via the tail vein in a 100 µl volume, for a total of 1×106 cells per mouse.

CAR T cell dosing: Mice were administered 5×106 CAR T cells 7 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of 50×106 CAR T cells per ml of cold PBS and kept on ice until the mice were dosed. The mice were injected intravenously via the tail vein with 100 µl of the CAR T cells for a dose of 5×106 CAR T cells per mouse. Eight mice per group were treated either with 100 µl of PBS alone (PBS), or humanized CD19 CAR T cells.

RAD001 dosing: A concentrated micro-emulsion of 50 mg equal to 1 mg RAD001 was formulated and then resuspended in D5W (dextrose 5% in water) at the time of dosing. Mice were orally dosed daily (via oral gavage) with 200 µl of the desired doses of RAD001.

PK analysis: Mice were dosed daily with RAD001 starting 7 days post tumor implantation. Dosing groups were as follows: 0.3 mg/kg, 1 mg/kg, 3 mg/kg, and 10 mg/kg. Mice were bled on days 0 and 14 following the first and last dose of RAD001, at the following time points for PK analysis: 15 minutes, 30 minutes, 1 hour, 2 hours, 4 hours, 8 hours, 12 hours, and 24 hours.

Figure 13:
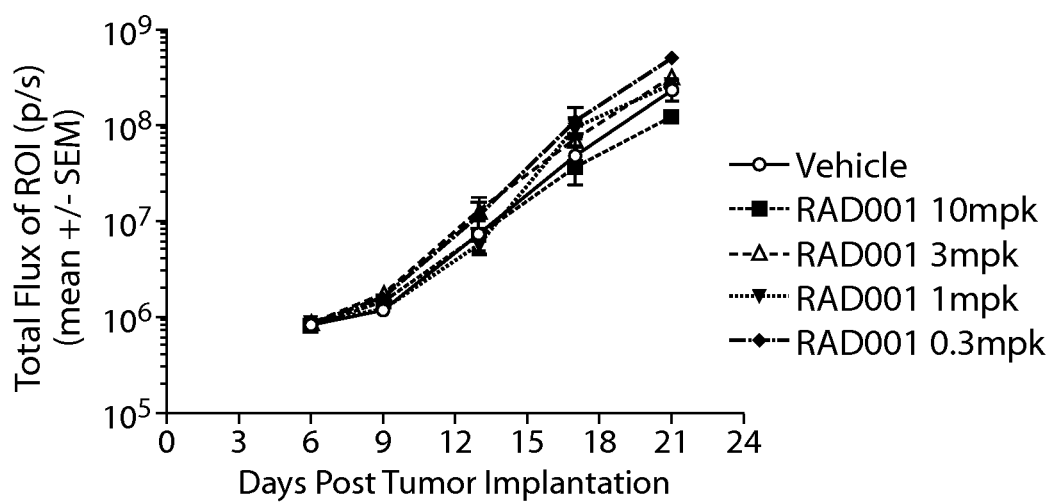
FIG. 13 depicts tumor growth measurements of NALM6-luc cells with daily RAD001 dosing at 0.3, 1, 3, and 10 mg/kg (mpk) or vehicle dosing. Circles denote the vehicle; squares denote the 10 mg/kg dose of RAD001; triangles denote the 3 mg/kg dose of RAD001, inverted triangles denote the 1 mg/kg dose of RAD001; and diamonds denote the 0.3 mg/kg dose of RAD001.
Figure 14A:
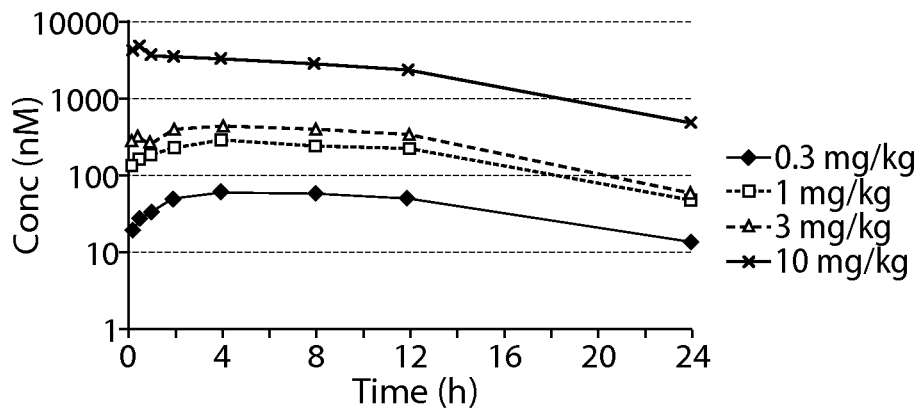
FIGS. 14A and 14B show pharmacokinetic curves showing the amount of RAD001 in the blood of NSG mice with NALM6 tumors.
Figure 14B:
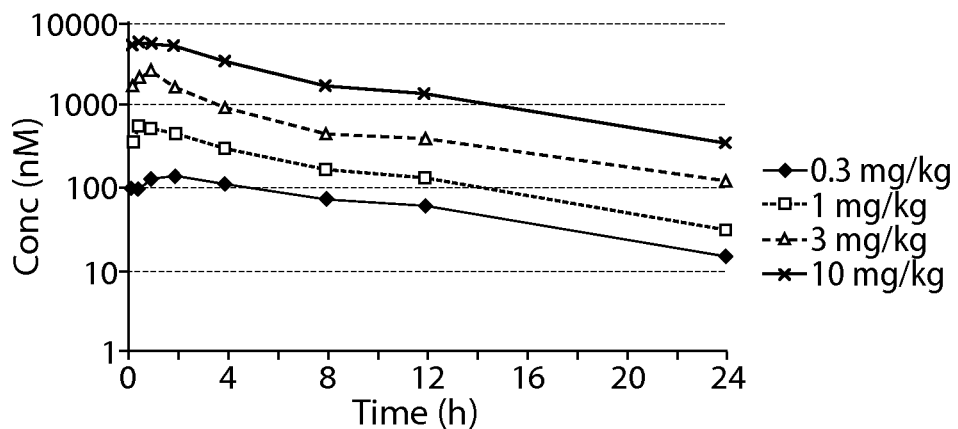

Results:

The expansion and pharmacokinetics of RAD001 was tested in NSG mice with NALM6-luc tumors. Daily oral dosing of RAD001 alone did not have an impact on the growth of NALM6-luc tumors (FIG. 13). The pharmacokinetic analysis of RAD001 shows that it is fairly stable in the blood of tumor bearing mice (FIGS. 14A and 14B). Both the day 0 and day 14 PK analyses show that the RAD001 concentrations in the blood is above 10 nm even 24 hours after dosing at the lowest dose tested (0.3 mg/kg).

Based on these doses, huCAR19 CAR T cells were dosed with and without RAD001 to determine the proliferative ability of these cells. The highest dose used was 3 mg/kg based on the levels of RAD001 in the blood 24 hours after dosing. As the concentration of RAD001 was above 10 nM 24 hours after the final dose of RAD001, several lower doses of RAD001 were used in the in vivo study with CAR T cells. The CAR T cells were dosed IV one day prior to the start of the daily oral RAD001 dosing. Mice were monitored via FACS for T cell expansion.

Figure 15A:
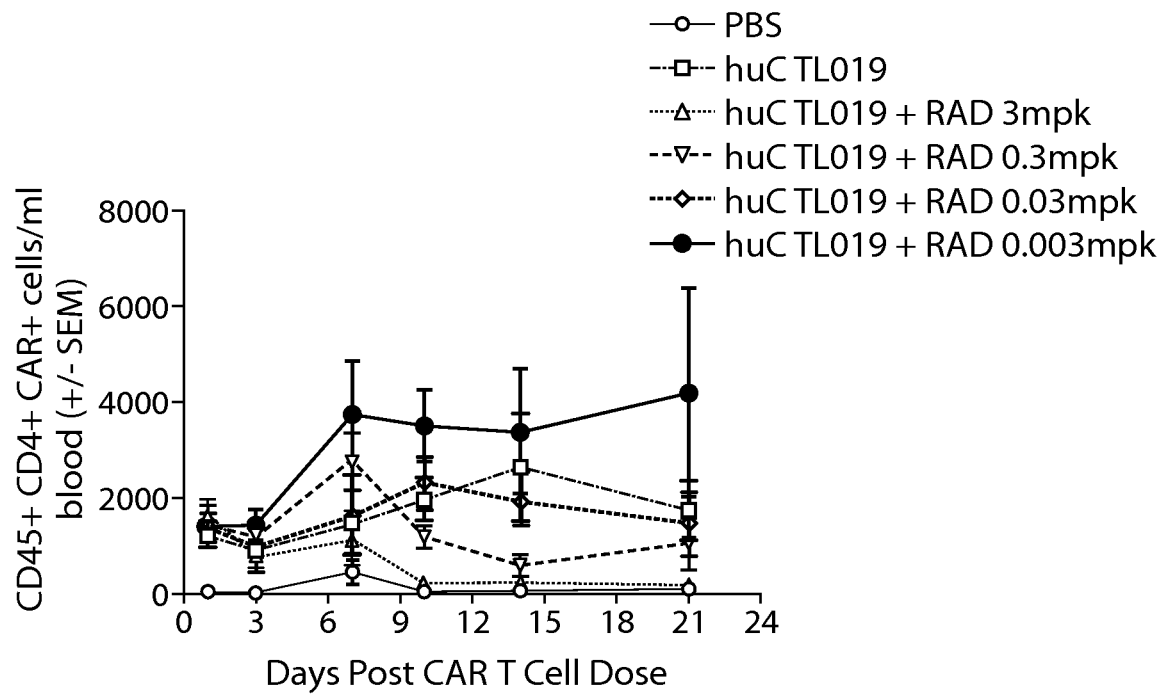
FIGS. 15A and 15B show in vivo proliferation of humanized CD19 CART cells with and without RAD001 dosing. Low doses of RAD001 (0.003 mg/kg) daily lead to an enhancement in CAR T cell proliferation, above the normal level of huCAR19 proliferation.
Figure 15B:
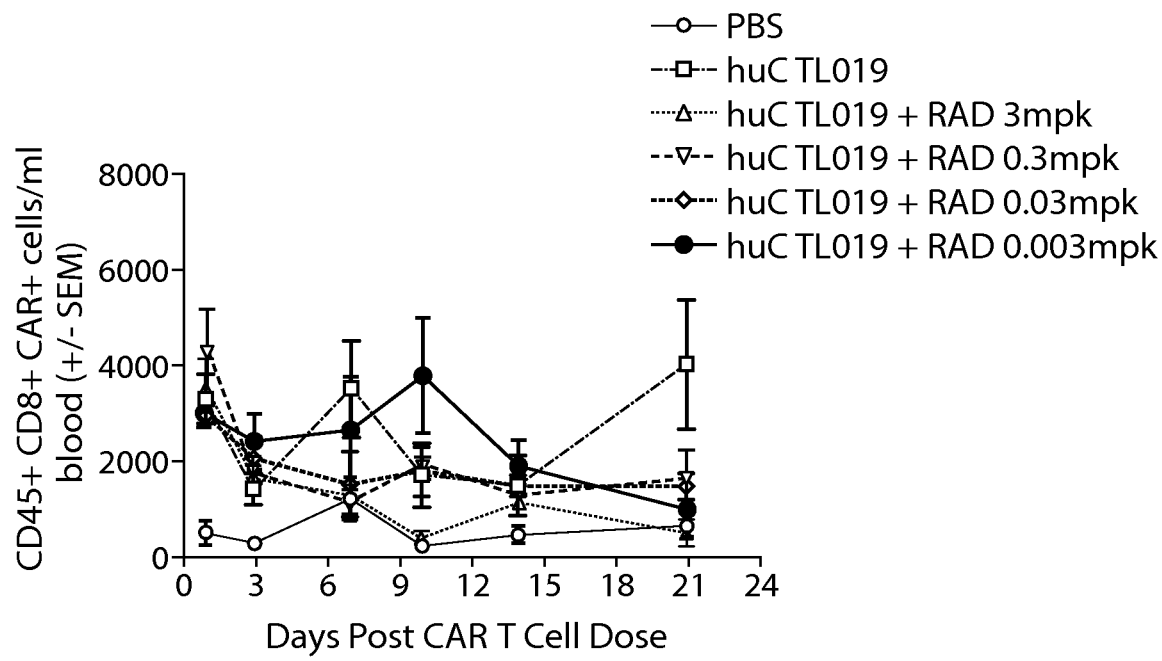

The lowest doses of RAD001 show an enhanced proliferation of the CAR T cells (FIGS. 15A and 15B). This enhanced proliferation is more evident and prolonged with the CD4+ CAR T cells than the CD8+ CAR T cells. However, with the CD8+ CAR T cells, enhanced proliferation can be seen at early time points following the CAR T cell dose.

What is claimed is:

1. A chimeric antigen receptor (CAR) comprising, in order of N terminal to C terminal:
   (i) an extracellular antigen binding domain, an extracellular domain (ECD) of an inhibitory molecule, or a costimulatory ECD domain;
   (ii) a sortase transfer signature;
   (iii) a Gly-Gly-Gly sequence;
   (iv) a hinge domain;
   (v) a transmembrane domain; and
   (vi) an intracellular signaling domain,
   wherein the CAR is capable of stimulating an immune effector function of an immune effector cell comprising the CAR.

2. The CAR of claim 1, wherein the sortase transfer signature comprises a sortase recognition motif comprising the sequence of any one of SEQ ID NOs: 39-108.

3. The CAR of claim 1, wherein the sortase transfer signature comprises the sequence LPXT (SEQ ID NO: 30), wherein X is any amino acid.

4. A method for preparing a cell comprising the CAR of claim 1, comprising:
   a) providing the cell with a membrane protein comprising, in order of N terminal to C terminal:
      the Gly-Gly-Gly sequence;
      the hinge domain;
      the transmembrane domain; and
      the intracellular signaling domain; and
   b) contacting the membrane protein with the extracellular antigen binding domain, the extracellular domain (ECD) of the inhibitory molecule, or the costimulatory ECD domain in the presence of a sortase,
   wherein the extracellular antigen binding domain, the extracellular domain (ECD) of the inhibitory molecule, and the costimulatory ECD domain each comprises the sortase transfer signature at its N terminus,
   thereby coupling the extracellular antigen binding domain, the extracellular domain (ECD) of the inhibitory molecule, and the costimulatory ECD domain each comprising the sortase transfer signature at its N terminus to the membrane protein.

5. The method of claim 4, wherein the sortase is a calcium independent sortase, a sortase A, or a *Staphylococcus aureus* sortase.

6. A cell comprising the CAR of claim 1.

7. The CAR of claim 1, wherein the extracellular antigen binding domain comprises the amino acid sequence of any one of SEQ ID NOs: 117-246.

8. The CAR of claim 1, wherein the inhibitory molecule is chosen from PD1, PD-L1, PD-L2, CTLA4, TIM3, CEACAM, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

9. The CAR of claim 1, wherein the costimulatory ECD domain is an ECD domain from ICOS, CD28, CD27, HVEM, LIGHT, CD40L, 4-1BB, OX40, DR3, GITR, CD30, TIM1, SLAM, CD2, or CD226.

10. The CAR of claim 1, wherein the intracellular signaling domain comprises a primary intracellular signaling domain of TCR zeta, FcR gamma, FcR beta, CD3 gamma, CD3 delta, CD3 epsilon, CD3 zeta, CD5, CD22, CD79a, CD79b, CD66d, DAP10, DAP12, or CD32.

11. The CAR of claim 1, wherein the intracellular signaling domain comprises a costimulatory signaling domain of CD27, CD28, 4-1BB (CD137), OX40, CD30, CD40, ICOS (CD278), ICAM-1, LFA-1 (CD11a/CD18), CD2, CD7, LIGHT, NKG2C, B7-H3, a ligand that specifically binds with CD83, GITR, BAFFR, HVEM (LIGHTR), SLAMf7, NKP80 (KLRF1), NKp44, NKp30, NKp46, CD160 (BY55), CD19, CD4, CD8 alpha, CD8 beta, IL2R beta, IL2R gamma, IL7R alpha, ITGA4, VLA1, CD49a, ITGA4, IA4, CD49D, ITGA6, VLA-6, C49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (C244, 2B4), CD84, CD96 (Tactile), CEACAM1, CRTAM, Ly9 (CD229), PSGL1, C100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKG2D, or NKG2C.

12. The CAR of claim 1, further comprising a second intracellular signaling domain.

13. The cell of claim 6, wherein the cell is a T cell or an NK cell.

14. The CAR of claim 1, which comprises the extracellular antigen binding domain.

* * * * *

SEQUENCE LISTING

```
<160> NUMBER OF SEQ ID NOS: 275

<210> SEQ ID NO 1
<211> LENGTH: 206
<212> TYPE: PRT
<213> ORGANISM: Staphylococcus aureus

<400> SEQUENCE: 1

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125
```

```
Gln Phe Thr Asn Leu Lys Ala Ala Lys Lys Gly Ser Met Val Tyr Phe
            130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
            195                 200                 205

<210> SEQ ID NO 2
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 3
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 4
<211> LENGTH: 156
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 4

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Arg Glu Gln Leu Asn Arg Gly Val Ser Phe Ala Lys Glu
        35                  40                  45

Asn Gln Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
    130                 135                 140

Thr Glu Val Lys Leu Glu His His His His His
145                 150                 155

<210> SEQ ID NO 5
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130

<210> SEQ ID NO 6
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 6

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105

<210> SEQ ID NO 7
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90

<210> SEQ ID NO 8
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Leu Gln Ala Trp Asp Leu Tyr Tyr His Val Phe Arg Arg Ile Ser
            85                  90                  95

Lys Thr Ser

<210> SEQ ID NO 9
<211> LENGTH: 297
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gly Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295

<210> SEQ ID NO 10

-continued

```
<211> LENGTH: 182
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Ser His Leu Ala Ala Leu Ala Gly Asn Pro Ala Ala Thr Ala
        115                 120                 125

Ala Val Lys Thr Ala Leu Ser Gly Asn Pro Val Pro Ile Leu Ile Pro
    130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 11
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110
```

```
Arg Ala Arg Arg Asn Asp Ser Gly Thr Tyr Leu Cys Gly Ala Ile Ser
            115                 120                 125

Leu Ala Pro Lys Ala Gln Ile Lys Glu Ser Leu Arg Ala Glu Leu Arg
130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
                260                 265                 270

Pro Glu Glu Glu Glu Gly Gly Cys Glu Leu Arg Val Lys Phe Ser Arg
            275                 280                 285

Ser Ala Asp Ala Pro Ala Tyr Lys Gln Gly Gln Asn Gln Leu Tyr Asn
        290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
370                 375                 380

Ala Leu His Met Gln Ala Leu Pro Pro Arg
385                 390

<210> SEQ ID NO 12
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
```

```
            65                  70                  75                  80
    Pro Asn Gly Arg Asp Phe His Met Ser Val Val Arg Ala Arg Arg Asn
                        85                  90                  95

Asp Ser Gly Thr Tyr Leu Cys Gly Ala Ile Ser Leu Ala Pro Lys Ala
                    100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
            130                 135                 140

Gln Phe Gln Thr Leu Val Thr Thr Thr Pro Ala Pro Arg Pro Pro Thr
    145                 150                 155                 160

Pro Ala Pro Thr Ile Ala Ser Gln Pro Leu Ser Leu Arg Pro Glu Ala
                        165                 170                 175

Cys Arg Pro Ala Ala Gly Gly Ala Val His Thr Arg Gly Leu Asp Phe
                    180                 185                 190

Ala Cys Asp Ile Tyr Ile Trp Ala Pro Leu Ala Gly Thr Cys Gly Val
                195                 200                 205

Leu Leu Leu Ser Leu Val Ile Thr Leu Tyr Cys Lys Arg Gly Arg Lys
            210                 215                 220

Lys Leu Leu Tyr Ile Phe Lys Gln Pro Phe Met Arg Pro Val Gln Thr
    225                 230                 235                 240

Thr Gln Glu Glu Asp Gly Cys Ser Cys Arg Phe Pro Glu Glu Glu Glu
                        245                 250                 255

Gly Gly Cys Glu Leu Arg Val Lys Phe Ser Arg Ser Ala Asp Ala Pro
                    260                 265                 270

Ala Tyr Lys Gln Gly Gln Asn Gln Leu Tyr Asn Glu Leu Asn Leu Gly
                275                 280                 285

Arg Arg Glu Glu Tyr Asp Val Leu Asp Lys Arg Gly Arg Asp Pro
            290                 295                 300

Glu Met Gly Gly Lys Pro Arg Arg Lys Asn Pro Gln Glu Gly Leu Tyr
    305                 310                 315                 320

Asn Glu Leu Gln Lys Asp Lys Met Ala Glu Ala Tyr Ser Glu Ile Gly
                        325                 330                 335

Met Lys Gly Glu Arg Arg Arg Gly Lys Gly His Asp Gly Leu Tyr Gln
                    340                 345                 350

Gly Leu Ser Thr Ala Thr Lys Asp Thr Tyr Asp Ala Leu His Met Gln
                355                 360                 365

Ala Leu Pro Pro Arg
            370

<210> SEQ ID NO 13
<211> LENGTH: 1182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
atggccctcc ctgtcactgc cctgcttctc cccctcgcac tcctgctcca cgccgctaga      60
ccacccggat ggtttctgga ctctccggat cgccgtggaa tcccccaac cttctcaccg      120 gcactcttgg ttgtgactga gggcgataat gcgaccttca cgtgctcgtt ctccaacacc     180
tccgaatcat tcgtgctgaa ctggtaccgc atgagcccgt caaaccagac cgacaagctc     240
```

```
gccgcgtttc cggaagatcg gtcgcaaccg ggacaggatt gtcggttccg cgtgactcaa    300
ctgccgaatg gcagagactt ccacatgagc gtggtccgcg ctaggcgaaa cgactccggg    360
acctacctgt gcggagccat ctcgctggcg cctaaggccc aaatcaaaga gagcttgagg    420
gccgaactga gagtgaccga gcgcagagct gaggtgccaa ctgcacatcc atccccatcg    480
cctcggcctg cggggcagtt tcagaccctg gtcacgacca ctccggcgcc gcgcccaccg    540
actccggccc caactatcgc gagccagccc tgtcgctga ggccggaagc atgccgccct     600
gccgccggag gtgctgtgca tacccgggga ttggacttcg catgcgacat ctacatttgg    660
gctcctctcg ccggaacttg tggcgtgctc cttctgtccc tggtcatcac cctgtactgc    720
aagcggggtc ggaaaaagct tctgtacatt ttcaagcagc ccttcatgag gcccgtgcaa    780
accacccagg aggaggacgg ttgctcctgc cggttccccg aagaggaaga aggaggttgc    840
gagctgcgcg tgaagttctc ccggagcgcc gacgcccccg cctataagca gggccagaac    900
cagctgtaca cgaactgaa cctgggacgg cgggaagagt acgatgtgct ggacaagcgg    960
cgcggccggg accccgaaat gggcgggaag cctagaagaa agaaccctca ggaaggcctg   1020
tataacgagc tgcagaagga caagatggcc gaggcctact ccgaaattgg gatgaaggga   1080
gagcggcgga ggggaaaggg gcacgacggc ctgtaccaag gactgtccac cgccaccaag   1140
gacacatacg atgccctgca catgcaggcc cttccccctc gc                     1182
```

<210> SEQ ID NO 14
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 14

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 15
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 16
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 16

```
ggcagcggcg ccaccaactt cagcctgctg aagcaggccg gcgacgtgga ggaaaaccct     60
ggcccc                                                                66
```

<210> SEQ ID NO 17
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 18
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18

```
gtgaagcaga ccctgaactt cgacctgctg aaactggccg gcgacgtgga gagcaatccc     60
ggccct                                                                66
```

<210> SEQ ID NO 19
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 20
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20

```
cgtgaggctc cggtgcccgt cagtgggcag agcgcacatc gcccacagtc cccgagaagt     60
tggggggagg ggtcggcaat tgaaccggtg cctagagaag gtggcgcggg gtaaactggg    120
aaagtgatgt cgtgtactgg ctccgccttt ttcccgaggg tggggagaa ccgtatataa    180 gtgcagtagt cgccgtgaac gttctttttc gcaacgggtt tgccgccaga acacaggtaa    240
```

```
gtgccgtgtg tggttcccgc gggcctggcc tctttacggg ttatggccct tgcgtgcctt      300
gaattacttc cacctggctg cagtacgtga ttcttgatcc cgagcttcgg gttggaagtg      360
ggtgggagag ttcgaggcct tgcgcttaag gagccccttc gcctcgtgct tgagttgagg      420
cctggcctgg gcgctgggc cgccgcgtgc gaatctggtg gcaccttcgc gcctgtctcg       480
ctgctttcga taagtctcta gccatttaaa attttgatg acctgctgcg acgctttttt       540
tctgcaaga tagtcttgta aatgcgggcc aagatctgca cactggtatt tcggttttg       600
gggccgcggg cggcgacggg gcccgtgcgt cccagcgcac atgttcggcg aggcggggcc      660
tgcgagcgcg gccaccgaga tcggacgggg gtagtctca agctggccgg cctgctctgg      720
tgcctggcct cgcgccgccg tgtatcgccc cgccctgggc ggcaaggctg gcccggtcgg      780
caccagttgc gtgagcggaa agatggccgc ttcccggccc tgctgcaggg agctcaaaat      840
ggaggacgcg gcgctcggga gagcgggcgg gtgagtcacc cacacaaagg aaaagggcct      900
ttccgtcctc agccgtcgct tcatgtgact ccacggagta ccgggcgccg tccaggcacc      960
tcgattagtt ctcgagcttt tggagtacgt cgtctttagg ttgggggag gggttttatg      1020
cgatggagtt tccccacact gagtgggtgg agactgaagt taggccagct tggcacttga     1080
tgtaattctc cttggaattt gcccttttg agtttggatc ttggttcatt ctcaagcctc      1140
agacagtggt tcaaagtttt tttcttccat ttcaggtgtc gtga                      1184
```

```
<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Leu Pro Glu Thr Gly Gly
1               5

<210> SEQ ID NO 22
<211> LENGTH: 284
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Met Glu Thr Asp Thr Leu Leu Leu Trp Val Leu Leu Trp Val Pro
1               5                   10                  15

Gly Ser Thr Gly Glu Ile Val Met Thr Gln Ser Pro Ala Thr Leu Ser
                20                  25                  30

Leu Ser Pro Gly Glu Arg Ala Thr Leu Ser Cys Arg Ala Ser Gln Asp
            35                  40                  45

Ile Ser Lys Tyr Leu Asn Trp Tyr Gln Gln Lys Pro Gly Gln Ala Pro
        50                  55                  60

Arg Leu Leu Ile Tyr His Thr Ser Arg Leu His Ser Gly Ile Pro Ala
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Val Tyr Phe Cys Gln Gln Gly Asn
```

```
               100                 105                 110
Thr Leu Pro Tyr Thr Phe Gly Gln Gly Thr Lys Leu Glu Ile Lys Gly
        115                 120                 125
Gly Gly Gly Ser Gly Gly Gly Ser Gly Gly Gly Ser Gln Val
    130                 135                 140
Gln Leu Gln Glu Ser Gly Pro Gly Leu Val Lys Pro Ser Glu Thr Leu
145                 150                 155                 160
Ser Leu Thr Cys Thr Val Ser Gly Val Ser Leu Pro Asp Tyr Gly Val
                165                 170                 175
Ser Trp Ile Arg Gln Pro Pro Gly Lys Gly Leu Glu Trp Ile Gly Val
                180                 185                 190
Ile Trp Gly Ser Glu Thr Thr Tyr Tyr Ser Ser Leu Lys Ser Arg
        195                 200                 205
Val Thr Ile Ser Lys Asp Asn Ser Lys Asn Gln Val Ser Leu Lys Leu
        210                 215                 220
Ser Ser Val Thr Ala Ala Asp Thr Ala Val Tyr Tyr Cys Ala Lys His
225                 230                 235                 240
Tyr Tyr Tyr Gly Gly Ser Tyr Ala Met Asp Tyr Trp Gly Gln Gly Thr
                245                 250                 255
Leu Val Thr Val Ser Ser Leu Pro Glu Thr Gly Gly Leu Asp Val Leu
                260                 265                 270
Phe Glu Gly Pro His His His His His His His
        275                 280
```

<210> SEQ ID NO 23
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

```
Gly Gly Gly Lys
1
```

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Glu Gln Lys Leu Ile Ser Glu Glu Asp Leu
1               5                   10
```

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

```
Leu Pro Glu Thr Gly Gly Gly
1               5
```

-continued

```
<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Leu Pro Glu Thr Gly Gly Gly
1               5

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Lys Leu Pro Glu Thr Gly Gly
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 28

Leu Pro Xaa Thr Gly Gly Gly
1               5

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 29

Leu Pro Xaa Thr Ala Ala Ala
1               5

<210> SEQ ID NO 30
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: MOD_RES
<222> LOCATION: (3)..(3)
<223> OTHER INFORMATION: Any amino acid

<400> SEQUENCE: 30

Leu Pro Xaa Thr
1

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Gly Gly Gly
1

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Gly Gly Gly Gly
1               5

<210> SEQ ID NO 33
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Ala Ala Ala
1

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Ala Ala Ala Ala
1               5

<210> SEQ ID NO 35
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
```

```
<221> NAME/KEY: misc_feature
<222> LOCATION: (1)..(40)
<223> OTHER INFORMATION: /note="This sequence may encompass 1-10 'Gly
      Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 35

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 36
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Gly Gly Gly Ser Gly Gly Gly Gly Ser Gly Gly Gly Gly Ser Gly
1               5                   10                  15

Gly Gly Gly Ser
            20

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Gly Gly Gly Ser Gly Gly Gly Gly Ser Gly Gly Gly Gly Ser
1               5                   10                  15

<210> SEQ ID NO 38
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Gly Gly Ser
1

<210> SEQ ID NO 39
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: MOD_RES
<222> LOCATION: (3)..(3)
<223> OTHER INFORMATION: Any amino acid
<220> FEATURE:
<221> NAME/KEY: VARIANT
<222> LOCATION: (4)..(4)
<223> OTHER INFORMATION: /replace="Ala"
<220> FEATURE:
<221> NAME/KEY: MOD_RES
<222> LOCATION: (5)..(5)
<223> OTHER INFORMATION: Any amino acid
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 39

Leu Pro Xaa Thr Xaa
1               5

<210> SEQ ID NO 40
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 40

Leu Pro Xaa Thr
1

<210> SEQ ID NO 41
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (3)..(3)
<223> OTHER INFORMATION: /replace="Ala" or "Asn" or "Glu" or "Gln"
<220> FEATURE:
<221> NAME/KEY: VARIANT
<222> LOCATION: (4)..(4)
<223> OTHER INFORMATION: /replace="Ala"
<220> FEATURE:
<221> NAME/KEY: VARIANT
<222> LOCATION: (5)..(5)
<223> OTHER INFORMATION: /replace="Gly"
```

```
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 41

Leu Pro Lys Thr Ala
1               5

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ala" or "Asn" or "Glu" or "Gln"
<220> FEATURE:
<221> NAME/KEY: MOD_RES
<222> LOCATION: (5)..(5)
<223> OTHER INFORMATION: Any amino acid
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 42

Leu Pro Lys Thr Xaa
1               5

<210> SEQ ID NO 43
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ala" or "Asn" or "Glu" or "Gln"
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 43

Leu Pro Lys Thr Gly
1               5

<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Leu Pro Lys Thr Gly
```

```
1               5

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Leu Pro Ala Thr Gly
1               5

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Leu Pro Asn Thr Gly
1               5

<210> SEQ ID NO 47
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Leu Pro Glu Thr Gly
1               5

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 48

Leu Pro Xaa Ala Gly
1               5

<210> SEQ ID NO 49
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Leu Pro Asn Ala Gly
```

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (3)..(3)
<223> OTHER INFORMATION: Any amino acid

<400> SEQUENCE: 50

Leu Pro Xaa Thr Ala
1               5

<210> SEQ ID NO 51
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 51

Leu Pro Asn Thr Ala
1               5

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (3)..(3)
<223> OTHER INFORMATION: Any amino acid

<400> SEQUENCE: 52

Leu Gly Xaa Thr Gly
1               5

<210> SEQ ID NO 53
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 53

Leu Gly Ala Thr Gly
1               5

<210> SEQ ID NO 54
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<220> FEATURE:
<221> NAME/KEY: MOD_RES
<222> LOCATION: (3)..(3)
<223> OTHER INFORMATION: Any amino acid

<400> SEQUENCE: 54

Ile Pro Xaa Thr Gly
1               5

<210> SEQ ID NO 55
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ile Pro Asn Thr Gly
1               5

<210> SEQ ID NO 56
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ile Pro Glu Thr Gly
1               5

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ala" or "Ser"
<220> FEATURE:
<221> NAME/KEY: MOD_RES
<222> LOCATION: (3)..(3)
<223> OTHER INFORMATION: Any amino acid
<220> FEATURE:
<221> NAME/KEY: VARIANT
<222> LOCATION: (4)..(4)
<223> OTHER INFORMATION: /replace="Ser"
<220> FEATURE:
<221> NAME/KEY: MOD_RES
<222> LOCATION: (5)..(5)
<223> OTHER INFORMATION: Any amino acid
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 57

Asn Pro Xaa Thr Xaa
1               5

<210> SEQ ID NO 58
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ser" or "Ala"
<220> FEATURE:
<221> NAME/KEY: VARIANT
<222> LOCATION: (3)..(3)
<223> OTHER INFORMATION: /replace="Lys"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="His" or "Asn" or "Gly" or "Ser"
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 58

Asn Pro Gln Thr Ala
1               5

<210> SEQ ID NO 59
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 59

Asn Pro Xaa Thr Xaa
1               5

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Lys"
<220> FEATURE:
<221> NAME/KEY: VARIANT
<222> LOCATION: (5)..(5)
<223> OTHER INFORMATION: /replace="Asn" or "Gly" or "Ser"
<220> FEATURE:
<221> NAME/KEY: misc_feature
<222> LOCATION: (1)..(5)
<223> OTHER INFORMATION: /note="Variant residues given in the sequence
``` have no preference with respect to those in the annotations
for variant positions"

<400> SEQUENCE: 60

Asn Pro Gln Thr His
1               5

<210> SEQ ID NO 61
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Asn Pro Gln Thr Asn
1               5

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Asn Pro Lys Thr Gly
1               5

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Asn Ser Lys Thr Ala
1               5

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asn Pro Gln Thr Gly
1               5

<210> SEQ ID NO 65
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

```
Asn Ala Lys Thr Asn
1               5

<210> SEQ ID NO 66
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Asn Pro Gln Ser Ser
1               5

<210> SEQ ID NO 67
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 67

Leu Pro Xaa Thr Xaa
1               5

<210> SEQ ID NO 68
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ser" or "Glu" or "Leu" or "Ala" or
      "Asn"
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"

<400> SEQUENCE: 68

Leu Pro Lys Thr Gly
1               5

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

```
<222> LOCATION: (1)..(1)
<223> OTHER INFORMATION: /replace="Asn"
<220> FEATURE:
<221> NAME/KEY: VARIANT
<222> LOCATION: (2)..(2)
<223> OTHER INFORMATION: /replace="Ala"
<220> FEATURE:
<221> NAME/KEY: MOD_RES
<222> LOCATION: (3)..(3)
<223> OTHER INFORMATION: Any amino acid
<220> FEATURE:
<221> NAME/KEY: VARIANT
<222> LOCATION: (5)..(5)
<223> OTHER INFORMATION: /replace="Ala"

<400> SEQUENCE: 69

Leu Pro Xaa Thr Gly
1               5

<210> SEQ ID NO 70
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ala" or "Ser" or "His"

<400> SEQUENCE: 70

Asn Ala Glu Thr Gly
1               5

<210> SEQ ID NO 71
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 71

Leu Pro Xaa Thr Ala
1               5

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Leu Pro Asn Thr Ala
1               5

<210> SEQ ID NO 73
<211> LENGTH: 5
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 73

Leu Ala Xaa Thr Gly
1               5

<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 74

Leu Pro Xaa Thr Xaa
1               5

<210> SEQ ID NO 75
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Leu Pro Lys Thr Gly
1               5

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Leu Pro Ile Thr Gly
1               5

<210> SEQ ID NO 77
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Leu Pro Asp Thr Ala

```
<210> SEQ ID NO 78
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Leu Pro Leu Thr Gly
1               5

<210> SEQ ID NO 79
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Leu Pro Glu Thr Gly
1               5

<210> SEQ ID NO 80
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Leu Pro Met Thr Gly
1               5

<210> SEQ ID NO 81
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Leu Pro Gln Thr Ser
1               5

<210> SEQ ID NO 82
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
```

<400> SEQUENCE: 82

Leu Ala Xaa Thr Xaa
1               5

<210> SEQ ID NO 83
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Leu Ala Glu Thr Gly
1               5

<210> SEQ ID NO 84
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Leu Ala Ala Thr Gly
1               5

<210> SEQ ID NO 85
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Leu Ala His Thr Gly
1               5

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Leu Ala Ser Thr Gly
1               5

<210> SEQ ID NO 87
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Leu Ala Phe Thr Gly 1               5

<210> SEQ ID NO 88
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 88

Leu Pro Xaa Ala Xaa
1               5

<210> SEQ ID NO 89
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 89

Leu Ala Xaa Thr Xaa
1               5

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 90

Leu Gly Xaa Thr Xaa
1               5

<210> SEQ ID NO 91
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

```
            Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 91

Ile Pro Xaa Thr Xaa
1               5

<210> SEQ ID NO 92
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ile Pro Gln Thr Gly
1               5

<210> SEQ ID NO 93
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 93

Asn Pro Xaa Thr Xaa
1               5

<210> SEQ ID NO 94
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 94

Leu Pro Ser Thr Xaa
1               5

<210> SEQ ID NO 95
<211> LENGTH: 5
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 95

Leu Pro Ile Thr Xaa
1               5

<210> SEQ ID NO 96
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 96

Leu Ala Glu Thr Xaa
1               5

<210> SEQ ID NO 97
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 97

Asn Pro Gln Ser Xaa
1               5

<210> SEQ ID NO 98
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 98

Asn Ser Lys Thr Xaa
1               5

<210> SEQ ID NO 99
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: MOD_RES
<222> LOCATION: (5)..(5)
<223> OTHER INFORMATION: Any amino acid

<400> SEQUENCE: 99

Asn Pro Gln Thr Xaa
1               5

<210> SEQ ID NO 100
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 100

Asn Ala Lys Thr Xaa
1               5

<210> SEQ ID NO 101
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 101

Asn Pro Gln Ser Xaa
1               5

<210> SEQ ID NO 102
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Leu Ser Arg Thr Gly
1               5

<210> SEQ ID NO 103
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ser Pro Lys Thr Gly
1               5

<210> SEQ ID NO 104
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Leu Ser Arg Thr Gly
1               5

<210> SEQ ID NO 105
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Val Pro Asp Thr Gly
1               5

<210> SEQ ID NO 106
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Tyr Pro Arg Arg Gly
1               5

<210> SEQ ID NO 107
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gln Val Pro Thr Gly
1               5

<210> SEQ ID NO 108
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Asn" or "Ile" or "Tyr" or "Gln" or
      "Val" or "Ser"
<220> FEATURE:
<221> NAME/KEY: VARIANT
<222> LOCATION: (2)..(2)
<223> OTHER INFORMATION: /replace="Gly" or "Ala" or "Ser" or "Val"
<220> FEATURE:
<221> NAME/KEY: MOD_RES
<222> LOCATION: (3)..(3)
```

<223> OTHER INFORMATION: Any amino acid
<220> FEATURE:
<221> NAME/KEY: VARIANT
<222> LOCATION: (4)..(4)
<223> OTHER INFORMATION: /replace="Ala" or "Ser" or "Arg"
<220> FEATURE:
<221> NAME/KEY: MOD_RES
<222> LOCATION: (5)..(5)
<223> OTHER INFORMATION: Any amino acid
<220> FEATURE:
<221> NAME/KEY: misc_feature
<222> LOCATION: (1)..(5)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 108

Leu Pro Xaa Thr Xaa
1               5

<210> SEQ ID NO 109
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 109

Leu Pro Xaa Thr Gly
1               5

<210> SEQ ID NO 110
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 110

His His His His His His
1               5

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 111

His His His His His His His His
1               5

<210> SEQ ID NO 112
<211> LENGTH: 5
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 112

Leu Pro Glu Thr Gly
1               5

<210> SEQ ID NO 113
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(6)
<223> OTHER INFORMATION: /replace=" "
<220> FEATURE:
<221> NAME/KEY: misc_feature
<222> LOCATION: (1)..(6)
<223> OTHER INFORMATION: /note="Variant residues given in the sequence
      have no preference with respect to those in the annotations
      for variant positions"

<400> SEQUENCE: 113

Gly Gly Gly Gly Gly Gly
1               5

<210> SEQ ID NO 114
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(6)
<223> OTHER INFORMATION: /replace=" "
<220> FEATURE:
<221> NAME/KEY: misc_feature
<222> LOCATION: (1)..(6)
<223> OTHER INFORMATION: /note="Variant residues given in the sequence
      have no preference with respect to those in the annotations
      for variant positions"

<400> SEQUENCE: 114

Ala Ala Ala Ala Ala Ala
1               5

<210> SEQ ID NO 115
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid

<400> SEQUENCE: 115

Leu Pro Xaa Thr Gly Gly
1               5
```

```
<210> SEQ ID NO 116
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 116

Leu Pro Xaa Thr Xaa
1               5

<210> SEQ ID NO 117
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240
```

Ser Ser

<210> SEQ ID NO 118
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 119
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Lys Pro Gly
            165                 170                 175

Gln Ala Pro Arg Leu Leu Ile Tyr His Thr Ser Arg Leu His Ser Gly
        180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
        210                 215                 220

Gln Gly Asn Thr Leu Pro Tyr Thr Phe Gly Gln Gly Thr Lys Leu Glu
225                 230                 235                 240

Ile Lys

<210> SEQ ID NO 120
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala

```
              130                 135                 140
Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 121
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
            115                 120                 125

Val Gln Leu Gln Glu Ser Gly Pro Gly Leu Val Lys Pro Ser Glu Thr
        130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240
```

```
Thr Leu Val Thr Val Ser Ser
                245

<210> SEQ ID NO 122
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Glu Ile Val Met Thr Gln Ser Pro Ala Thr Leu Ser Leu Ser Pro Gly
1               5                  10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 123
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Gln Val Gln Leu Gln Glu Ser Gly Pro Gly Leu Val Lys Pro Ser Glu
1               5                  10                  15

Thr Leu Ser Leu Thr Cys Thr Val Ser Gly Val Ser Leu Pro Asp Tyr
```

```
                    20                  25                  30
Gly Val Ser Trp Ile Arg Gln Pro Gly Lys Gly Leu Glu Trp Ile
            35                  40                  45

Gly Val Ile Trp Gly Ser Glu Thr Thr Tyr Tyr Ser Ser Leu Lys
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Gly Ser Gly Gly Gly Gly Ser Glu Ile Val Met
        130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
            195                 200                 205

Thr Asp Tyr Thr Leu Thr Ile Ser Ser Leu Gln Pro Glu Asp Phe Ala
        210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 124
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Gly Lys Gly Leu Glu Trp Ile
            35                  40                  45

Gly Val Ile Trp Gly Ser Glu Thr Thr Tyr Tyr Gln Ser Ser Leu Lys
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
            115                 120                 125
```

Gly Ser Gly Gly Gly Ser Gly Gly Gly Ser Glu Ile Val Met
            130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 125
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 126
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 127
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Glu Ile Val Met Thr Gln Ser Pro Ala Thr Leu Ser Leu Ser Pro Gly

```
                 1               5                  10                  15
        Glu Arg Ala Thr Leu Ser Cys Arg Ala Ser Gln Asp Ile Ser Lys Tyr
                        20                  25                  30

Leu Asn Trp Tyr Gln Gln Lys Pro Gly Gln Ala Pro Arg Leu Leu Ile
                        35                  40                  45

Tyr His Thr Ser Arg Leu His Ser Gly Ile Pro Ala Arg Phe Ser Gly
         50                      55                  60

Ser Gly Ser Gly Thr Asp Tyr Thr Leu Thr Ile Ser Ser Leu Gln Pro
         65                  70                  75                  80

Glu Asp Phe Ala Val Tyr Phe Cys Gln Gln Gly Asn Thr Leu Pro Tyr
                            85                  90                  95

Thr Phe Gly Gln Gly Thr Lys Leu Glu Ile Lys Gly Gly Gly Gly Ser
                        100                 105                 110

Gly Gly Gly Gly Ser Gly Gly Gly Ser Gln Val Gln Leu Gln Glu
                    115                 120                 125

Ser Gly Pro Gly Leu Val Lys Pro Ser Glu Thr Leu Ser Leu Thr Cys
        130                     135                 140

Thr Val Ser Gly Val Ser Leu Pro Asp Tyr Gly Val Ser Trp Ile Arg
        145                 150                 155                 160

Gln Pro Pro Gly Lys Gly Leu Glu Trp Ile Gly Val Ile Trp Gly Ser
                        165                 170                 175

Glu Thr Thr Tyr Tyr Asn Ser Ser Leu Lys Ser Arg Val Thr Ile Ser
                    180                 185                 190

Lys Asp Asn Ser Lys Asn Gln Val Ser Leu Lys Leu Ser Ser Val Thr
                    195                 200                 205

Ala Ala Asp Thr Ala Val Tyr Tyr Cys Ala Lys His Tyr Tyr Gly
                210                 215                 220

Gly Ser Tyr Ala Met Asp Tyr Trp Gly Gln Gly Thr Leu Val Thr Val
        225                 230                 235                 240

Ser Ser

<210> SEQ ID NO 128
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gln Val Gln Leu Gln Glu Ser Gly Pro Gly Leu Val Lys Pro Ser Glu
        1               5                   10                  15

Thr Leu Ser Leu Thr Cys Thr Val Ser Gly Val Ser Leu Pro Asp Tyr
                        20                  25                  30

Gly Val Ser Trp Ile Arg Gln Pro Pro Gly Lys Gly Leu Glu Trp Ile
                        35                  40                  45

Gly Val Ile Trp Gly Ser Glu Thr Thr Tyr Tyr Asn Ser Ser Leu Lys
                    50                  55                  60

Ser Arg Val Thr Ile Ser Lys Asp Asn Ser Lys Asn Gln Val Ser Leu
        65                  70                  75                  80

Lys Leu Ser Ser Val Thr Ala Ala Asp Thr Ala Val Tyr Tyr Cys Ala
                            85                  90                  95

Lys His Tyr Tyr Gly Gly Ser Tyr Ala Met Asp Tyr Trp Gly Gln
                        100                 105                 110
```

```
Gly Thr Leu Val Thr Val Ser Gly Gly Gly Ser Gly Gly
            115                 120                 125

Gly Ser Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
            195                 200                 205

Thr Ile Ser Ser Leu Gln Pro Glu Asp Phe Ala Val Tyr Phe Cys Gln
210                 215                 220

Gln Gly Asn Thr Leu Pro Tyr Thr Phe Gly Gln Gly Thr Lys Leu Glu
225                 230                 235                 240

Ile Lys

<210> SEQ ID NO 129
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
        130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220
```

```
Gly Ser Tyr Ala Met Asp Tyr Trp Gly Gln Gly Thr Ser Val Thr Val
225                 230                 235                 240

Ser Ser

<210> SEQ ID NO 130
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys Gly
            100                 105                 110

Gly Gly Gly Ser Gly Gly Gly Ser Ser Gly Gly Gly Ser Gln Ile
        115                 120                 125

Gln Leu Val Gln Ser Gly Pro Glu Leu Lys Lys Pro Gly Glu Thr Val
    130                 135                 140

Lys Ile Ser Cys Lys Ala Ser Gly Tyr Ile Phe Thr Asn Tyr Gly Met
145                 150                 155                 160

Asn Trp Val Lys Gln Ala Pro Gly Lys Ser Phe Lys Trp Met Gly Trp
                165                 170                 175

Ile Asn Thr Tyr Thr Gly Glu Ser Thr Tyr Ser Ala Asp Phe Lys Gly
            180                 185                 190

Arg Phe Ala Phe Ser Leu Glu Thr Ser Ala Ser Thr Ala Tyr Leu His
        195                 200                 205

Ile Asn Asp Leu Lys Asn Glu Asp Thr Ala Thr Tyr Phe Cys Ala Arg
    210                 215                 220

Ser Gly Gly Tyr Asp Pro Met Asp Tyr Trp Gly Gln Gly Thr Ser Val
225                 230                 235                 240

Thr Val Ser Ser

<210> SEQ ID NO 131
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Asp Val Gln Ile Thr Gln Ser Pro Ser Tyr Leu Ala Ala Ser Pro Gly
1               5                   10                  15
```

Glu Thr Ile Thr Ile Asn Cys Arg Ala Ser Lys Ser Ile Ser Lys Asp
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Ser Gly Gly Ser Gln Val Gln Leu Gln Gln
            115                 120                 125

Pro Gly Ala Glu Leu Val Arg Pro Gly Ala Ser Val Lys Leu Ser Cys
130                 135                 140

Lys Ala Ser Gly Tyr Thr Phe Thr Ser Tyr Trp Met Asn Trp Val Lys
145                 150                 155                 160

Gln Arg Pro Asp Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Ser Thr Ala Tyr Met Gln Leu Ser Ser Leu
            195                 200                 205

Thr Ser Glu Asp Ser Ala Val Tyr Tyr Cys Ala Arg Gly Asn Trp Asp
        210                 215                 220

Asp Tyr Trp Gly Gln Gly Thr Thr Leu Thr Val Ser Ser
225                 230                 235

<210> SEQ ID NO 132
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Asn Thr Phe Met His Trp Tyr Gln Gln Lys Pro Gly Gln Pro Pro
            35                  40                  45

Lys Leu Leu Ile Tyr Arg Ala Ser Asn Leu Glu Ser Gly Val Pro Asp
50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
            115                 120                 125

```
Gly Gly Ser Gln Ile Gln Leu Val Gln Ser Gly Ser Glu Leu Lys Lys
        130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
                195                 200                 205

Thr Ala Tyr Leu Gln Ile Asn Ala Leu Lys Ala Glu Asp Thr Ala Val
        210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245
```

<210> SEQ ID NO 133
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 133

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Ser Gly Gly Gly Ser Gly Gly
        115                 120                 125

Gly Gly Ser Gln Ile Gln Leu Val Gln Ser Gly Ala Glu Val Lys Lys
        130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Val Thr Ile Thr Leu Asp Thr Ser Ala Ser
                195                 200                 205

Thr Ala Tyr Met Glu Leu Ser Ser Leu Arg Ser Glu Asp Thr Ala Val
        210                 215                 220

Tyr Tyr Cys Ala Arg Ser Gly Gly Tyr Asp Pro Met Asp Tyr Trp Gly
```

```
                225                 230                 235                 240

Gln Gly Thr Thr Val Thr Val Ser Ser
                245

<210> SEQ ID NO 134
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Ser Gly Gly
        115                 120                 125

Gly Gly Ser Gln Ile Gln Leu Val Gln Ser Gly Ser Glu Leu Lys Lys
    130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
        195                 200                 205

Thr Ala Tyr Leu Gln Ile Asn Ala Leu Lys Ala Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 135
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
            35                  40                  45

Arg Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Ser
 65                  70                  75                  80

Ser Leu Glu Pro Glu Asp Val Ala Val Tyr Tyr Cys Gln Gln Ser Asn
                 85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
            115                 120                 125

Gly Gly Ser Gln Ile Gln Leu Val Gln Ser Gly Ala Glu Val Lys Lys
            130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Val Thr Ile Thr Leu Asp Thr Ser Ala Ser
            195                 200                 205

Thr Ala Tyr Met Glu Leu Ser Ser Leu Arg Ser Glu Asp Thr Ala Val
            210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 136
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Ser Thr Tyr Ser Ala Asp Phe
 50                  55                  60

Lys Gly Arg Phe Val Phe Ser Leu Asp Thr Ser Val Ser Thr Ala Tyr
 65                  70                  75                  80

Leu Gln Ile Asn Ala Leu Lys Ala Glu Asp Thr Ala Val Tyr Tyr Cys
                 85                  90                  95

Ala Arg Ser Gly Gly Tyr Asp Pro Met Asp Tyr Trp Gly Gln Gly Thr
            100                 105                 110

```
Thr Val Thr Val Ser Ser Gly Gly Gly Ser Gly Gly Gly Ser
            115                 120                 125

Gly Gly Gly Gly Ser Gly Gly Gly Ser Asp Ile Val Leu Thr Gln
            130                 135                 140

Ser Pro Asp Ser Leu Ala Val Ser Leu Gly Glu Arg Ala Thr Ile Asn
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Pro Pro Lys Leu Leu Ile Tyr Arg
                180                 185                 190

Ala Ser Asn Leu Glu Ser Gly Val Pro Asp Arg Phe Ser Gly Ser Gly
                195                 200                 205

Ser Arg Thr Asp Phe Thr Leu Thr Ile Ser Ser Leu Gln Ala Glu Asp
210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245

<210> SEQ ID NO 137
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Ser Thr Tyr Ser Ala Asp Phe
50                  55                  60

Lys Gly Arg Phe Val Phe Ser Leu Asp Thr Ser Val Ser Thr Ala Tyr
65                  70                  75                  80

Leu Gln Ile Asn Ala Leu Lys Ala Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Ser Gly Gly Gly Gly Ser
            115                 120                 125

Gly Gly Gly Gly Ser Gly Gly Gly Ser Glu Ile Val Leu Thr Gln
            130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Ala Pro Arg Leu Leu Ile Tyr Arg
                180                 185                 190

Ala Ser Asn Leu Glu Ser Gly Ile Pro Ala Arg Phe Ser Gly Ser Gly
                195                 200                 205

Ser Arg Thr Asp Phe Thr Leu Thr Ile Ser Ser Leu Glu Pro Glu Asp
```

```
                      210                 215                 220
Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245

<210> SEQ ID NO 138
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Gly Met Asn Trp Val Arg Gln Ala Pro Gly Gln Arg Leu Glu Trp Met
            35                  40                  45

Gly Trp Ile Asn Thr Tyr Thr Gly Glu Ser Thr Tyr Ser Ala Asp Phe
        50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Asp Pro Met Asp Tyr Trp Gly Gln Gly Thr
                100                 105                 110

Thr Val Thr Val Ser Ser Gly Gly Gly Ser Gly Gly Gly Gly Ser
                115                 120                 125

Gly Gly Gly Gly Ser Gly Gly Gly Ser Asp Ile Val Leu Thr Gln
            130                 135                 140

Ser Pro Asp Ser Leu Ala Val Ser Leu Gly Glu Arg Ala Thr Ile Asn
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Pro Pro Lys Leu Leu Ile Tyr Arg
            180                 185                 190

Ala Ser Asn Leu Glu Ser Gly Val Pro Asp Arg Phe Ser Gly Ser Gly
        195                 200                 205

Ser Arg Thr Asp Phe Thr Leu Thr Ile Ser Ser Leu Gln Ala Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245

<210> SEQ ID NO 139
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139
```

Gln Ile Gln Leu Val Gln Ser Gly Ala Glu Val Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
            35                  40                  45

Gly Trp Ile Asn Thr Tyr Thr Gly Glu Ser Thr Tyr Ser Ala Asp Phe
50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Gly Gly Gly Gly Ser Glu Ile Val Leu Thr Gln
            130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
            165                 170                 175

Trp Tyr Gln Gln Lys Pro Gly Gln Ala Pro Arg Leu Leu Ile Tyr Arg
            180                 185                 190

Ala Ser Asn Leu Glu Ser Gly Ile Pro Ala Arg Phe Ser Gly Ser Gly
            195                 200                 205

Ser Arg Thr Asp Phe Thr Leu Thr Ile Ser Ser Leu Glu Pro Glu Asp
            210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
            245

<210> SEQ ID NO 140
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
            20                  25                  30

Tyr Ile His Trp Val Gln Gln Ala Pro Gly Lys Gly Leu Glu Trp Met
            35                  40                  45

Gly Arg Ile Asp Pro Glu Asn Asp Glu Thr Lys Tyr Gly Pro Ile Phe
50                  55                  60

Gln Gly Arg Val Thr Ile Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
            85                  90                  95

Ala Phe Arg Gly Gly Val Tyr Trp Gly Gln Gly Thr Thr Val Thr Val
                100                 105                 110

Ser Ser Gly Gly Gly Gly Ser Gly Gly Gly Ser Gly Gly Gly
        115                 120                 125

Ser Gly Gly Gly Ser Asp Val Val Met Thr Gln Ser Pro Asp Ser
130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
                180                 185                 190

Leu Asp Ser Gly Val Pro Asp Arg Phe Ser Gly Ser Gly Ser Gly Thr
                195                 200                 205

Asp Phe Thr Leu Thr Ile Ser Ser Leu Gln Ala Glu Asp Val Ala Val
                210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 141
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
                20                  25                  30

Asp Gly Lys Thr Tyr Leu Asn Trp Leu Gln Gln Lys Pro Gly Gln Pro
            35                  40                  45

Pro Lys Arg Leu Ile Ser Leu Val Ser Lys Leu Asp Ser Gly Val Pro
        50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
                100                 105                 110

Gly Gly Gly Gly Ser Gly Gly Gly Gly Ser Gly Gly Gly Gly Ser Gly
            115                 120                 125

Gly Gly Gly Ser Glu Ile Gln Leu Val Gln Ser Gly Ala Glu Val Lys
        130                 135                 140

Lys Pro Gly Ala Thr Val Lys Ile Ser Cys Lys Gly Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
                180                 185                 190

Gly Pro Ile Phe Gln Gly Arg Val Thr Ile Thr Ala Asp Thr Ser Thr

-continued

```
                195                 200                 205
Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 142
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Leu Ser
    130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
                165                 170                 175

Gln Arg Pro Gly Gln Ser Pro Arg Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 143
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 143

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Ser Gly Gly Gly Gly Ser Gly
            115                 120                 125

Gly Gly Gly Ser Glu Ile Gln Leu Val Gln Ser Gly Ala Glu Val Lys
    130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 144
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
            20                  25                  30

Tyr Ile His Trp Val Gln Gln Ala Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly Arg Val Thr Ile Thr Ala Asp Thr Ser Thr Asn Thr Val Tyr
65                  70                  75                  80

```
Met Glu Leu Ser Ser Leu Arg Ser Glu Asp Thr Ala Val Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Ser Gly Gly Gly Gly
        115                 120                 125

Ser Gly Gly Gly Gly Ser Asp Val Val Met Thr Gln Ser Pro Leu Ser
    130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
                165                 170                 175

Gln Arg Pro Gly Gln Ser Pro Arg Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 145
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
                20                  25                  30

Tyr Ile His Trp Val Arg Gln Met Pro Gly Lys Gly Leu Glu Trp Met
            35                  40                  45

Gly Arg Ile Asp Pro Glu Asn Asp Glu Thr Lys Tyr Gly Pro Ile Phe
        50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
```

```
                      180                 185                 190
Leu Asp Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
            210                 215                 220

Tyr Tyr Cys Trp Gln Gly Thr His Phe Pro Gly Thr Phe Gly Gly Gly
225                 230                 235                 240

Thr Lys Val Glu Ile Lys
            245

<210> SEQ ID NO 146
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Asp Gly Lys Thr Tyr Leu Asn Trp Leu Gln Gln Lys Pro Gly Gln Pro
        35                  40                  45

Pro Lys Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Ser Gly Gly Gly Gly Ser Gly
        115                 120                 125

Gly Gly Ser Glu Ile Gln Leu Val Gln Ser Gly Ala Glu Val Lys
    130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
            245

<210> SEQ ID NO 147
<211> LENGTH: 246
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 147

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Ser Gly Gly Gly Gly Ser
            115                 120                 125

Gly Gly Gly Ser Glu Ile Gln Leu Val Gln Ser Gly Ala Glu Val Lys
130                 135                 140

Lys Pro Gly Ala Thr Val Lys Ile Ser Cys Lys Gly Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly Arg Val Thr Ile Thr Ala Asp Thr Ser Thr
        195                 200                 205

Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245

<210> SEQ ID NO 148
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asn Asp Glu Thr Lys Tyr Gly Pro Ile Phe
    50                  55                  60
```

Gln Gly Arg Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
            85                  90                  95

Ala Phe Arg Gly Gly Val Tyr Trp Gly Pro Gly Thr Thr Leu Thr Val
        100                 105                 110

Ser Ser Gly Gly Gly Gly Ser Gly Gly Gly Ser Gly Gly Gly Gly
        115                 120                 125

Ser His Met Asp Val Val Met Thr Gln Ser Pro Leu Thr Leu Ser Val
    130                 135                 140

Ala Ile Gly Gln Ser Ala Ser Ile Ser Cys Lys Ser Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Ser Leu Val Ser Lys Leu Asp Ser
                180                 185                 190

Gly Val Pro Asp Arg Phe Thr Gly Ser Gly Ser Gly Thr Asp Phe Thr
            195                 200                 205

Leu Arg Ile Ser Arg Val Glu Ala Glu Asp Leu Gly Ile Tyr Tyr Cys
        210                 215                 220

Trp Gln Gly Thr His Phe Pro Gly Thr Phe Gly Gly Gly Thr Lys Leu
225                 230                 235                 240

Glu Ile Lys

<210> SEQ ID NO 149
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 149

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Glu Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
        195                 200                 205

Ser Ser Val Glu Ala Glu Asp Ala Thr Tyr Tyr Cys Gln Gln Trp
210                 215                 220

Ser Gly Tyr Pro Leu Thr Phe Gly Ala Gly Thr Lys Leu Glu Ile
225                 230                 235

<210> SEQ ID NO 150
<211> LENGTH: 244
<212> TYPE: PRT
<213> ORGANISM: Homo sapiens

<400> SEQUENCE: 150

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Arg Tyr Tyr Gly Met Asp Val Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Ala Thr Leu Ser Leu Ser Pro Gly Glu Arg Ala Thr Ile Ser Cys
145                 150                 155                 160

Arg Ala Ser Gln Ser Val Ser Ser Asn Phe Ala Trp Tyr Gln Gln Arg
                165                 170                 175

Pro Gly Gln Ala Pro Arg Leu Leu Ile Tyr Asp Ala Ser Asn Arg Ala
            180                 185                 190

Thr Gly Ile Pro Pro Arg Phe Ser Gly Ser Gly Ser Gly Thr Asp Phe
        195                 200                 205

Thr Leu Thr Ile Ser Ser Leu Glu Pro Glu Asp Phe Ala Ala Tyr Tyr
    210                 215                 220

Cys His Gln Arg Ser Asn Trp Leu Tyr Thr Phe Gly Gln Gly Thr Lys
225                 230                 235                 240

Val Asp Ile Lys

<210> SEQ ID NO 151
<211> LENGTH: 253
<212> TYPE: PRT
<213> ORGANISM: Homo sapiens

<400> SEQUENCE: 151

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Arg Arg Thr Val Val Thr Pro Arg Ala Tyr Tyr Gly
                100                 105                 110

Met Asp Val Trp Gly Gln Gly Thr Thr Val Thr Val Ser Ser Gly Gly
            115                 120                 125

Gly Gly Ser Gly Gly Gly Gly Ser Gly Gly Gly Gly Ser Gly Gly Gly
        130                 135                 140

Gly Ser Asp Ile Gln Leu Thr Gln Ser Pro Ser Thr Leu Ser Ala Ser
145                 150                 155                 160

Val Gly Asp Arg Val Thr Ile Thr Cys Gln Ala Ser Gln Asp Ile Ser
                165                 170                 175

Asn Ser Leu Asn Trp Tyr Gln Gln Lys Ala Gly Lys Ala Pro Lys Leu
            180                 185                 190

Leu Ile Tyr Asp Ala Ser Thr Leu Glu Thr Gly Val Pro Ser Arg Phe
        195                 200                 205

Ser Gly Ser Gly Ser Gly Thr Asp Phe Ser Phe Thr Ile Ser Ser Leu
    210                 215                 220

Gln Pro Glu Asp Ile Ala Thr Tyr Tyr Cys Gln Gln His Asp Asn Leu
225                 230                 235                 240

Pro Leu Thr Phe Gly Gln Gly Thr Lys Val Glu Ile Lys
                245                 250

<210> SEQ ID NO 152
<211> LENGTH: 246
<212> TYPE: PRT
<213> ORGANISM: Homo sapiens

<400> SEQUENCE: 152

Gln Val Gln Leu Val Gln Ser Gly Ala Glu Val Lys Lys Pro Gly Ala
1               5                   10                  15

Pro Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Trp Asp Gly Ser Tyr Tyr Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Asp Ile Val Leu
        130                 135                 140
```

```
Thr Gln Thr Pro Ser Ser Leu Ser Ala Ser Val Gly Asp Arg Val Thr
145                 150                 155                 160

Ile Thr Cys Arg Ala Ser Gln Ser Ile Asn Thr Tyr Leu Asn Trp Tyr
            165                 170                 175

Gln His Lys Pro Gly Lys Ala Pro Lys Leu Leu Ile Tyr Ala Ala Ser
        180                 185                 190

Ser Leu Gln Ser Gly Val Pro Ser Arg Phe Ser Gly Ser Gly Ser Gly
            195                 200                 205

Thr Asp Phe Thr Leu Thr Ile Ser Ser Leu Gln Pro Glu Asp Phe Ala
210                 215                 220

Thr Tyr Tyr Cys Gln Gln Ser Phe Ser Pro Leu Thr Phe Gly Gly Gly
225                 230                 235                 240

Thr Lys Leu Glu Ile Lys
                245

<210> SEQ ID NO 153
<211> LENGTH: 242
<212> TYPE: PRT
<213> ORGANISM: Homo sapiens

<400> SEQUENCE: 153

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Val Pro Gly Lys Gly Leu Val Trp Val
        35                  40                  45

Ser Arg Ile Asn Thr Asp Gly Ser Thr Thr Tyr Ala Asp Ser Val
50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Asp Asp Thr Ala Val Tyr Tyr Cys
                85                  90                  95

Val Gly Gly His Trp Ala Val Trp Gly Gln Gly Thr Thr Val Thr Val
            100                 105                 110

Ser Ser Gly Gly Gly Gly Ser Gly Gly Gly Gly Ser Gly Gly Gly Gly
            115                 120                 125

Ser Gly Gly Gly Gly Ser Asp Ile Gln Met Thr Gln Ser Pro Ser Thr
        130                 135                 140

Leu Ser Ala Ser Val Gly Asp Arg Val Thr Ile Thr Cys Arg Ala Ser
145                 150                 155                 160

Gln Ser Ile Ser Asp Arg Leu Ala Trp Tyr Gln Gln Lys Pro Gly Lys
            165                 170                 175

Ala Pro Lys Leu Leu Ile Tyr Lys Ala Ser Ser Leu Glu Ser Gly Val
        180                 185                 190

Pro Ser Arg Phe Ser Gly Ser Gly Ser Gly Thr Glu Phe Thr Leu Thr
    195                 200                 205

Ile Ser Ser Leu Gln Pro Asp Asp Phe Ala Val Tyr Tyr Cys Gln Gln
210                 215                 220

Tyr Gly His Leu Pro Met Tyr Thr Phe Gly Gln Gly Thr Lys Val Glu
225                 230                 235                 240

Ile Lys

<210> SEQ ID NO 154
```

```
<211> LENGTH: 241
<212> TYPE: PRT
<213> ORGANISM: Homo sapiens

<400> SEQUENCE: 154

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Ser Asp Ile Val Met Thr Gln Ser Pro Ser
        130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
        210                 215                 220

Gln Thr Tyr Thr Thr Pro Asp Phe Gly Pro Gly Thr Lys Val Glu Ile
225                 230                 235                 240

Lys

<210> SEQ ID NO 155
<211> LENGTH: 253
<212> TYPE: PRT
<213> ORGANISM: Homo sapiens

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Tyr Arg Leu Ile Ala Val Ala Gly Asp Tyr Tyr Tyr Gly
            100                 105                 110

Met Asp Val Trp Gly Gln Gly Thr Met Val Thr Val Ser Ser Gly Gly
        115                 120                 125

Gly Gly Ser Gly Gly Gly Gly Ser Gly Gly Gly Gly Ser Gly Gly Gly
        130                 135                 140

Gly Ser Asp Ile Gln Met Thr Gln Ser Pro Ser Ser Val Ser Ala Ser
145                 150                 155                 160

Val Gly Asp Arg Val Thr Ile Thr Cys Arg Ala Ser Gln Gly Val Gly
                165                 170                 175

Arg Trp Leu Ala Trp Tyr Gln Gln Lys Pro Gly Thr Ala Pro Lys Leu
        180                 185                 190

Leu Ile Tyr Ala Ala Ser Thr Leu Gln Ser Gly Val Pro Ser Arg Phe
        195                 200                 205

Ser Gly Ser Gly Ser Gly Thr Asp Phe Thr Leu Thr Ile Asn Asn Leu
        210                 215                 220

Gln Pro Glu Asp Phe Ala Thr Tyr Tyr Cys Gln Gln Ala Asn Ser Phe
225                 230                 235                 240

Pro Leu Thr Phe Gly Gly Gly Thr Arg Leu Glu Ile Lys
                245                 250

<210> SEQ ID NO 156
<211> LENGTH: 250
<212> TYPE: PRT
<213> ORGANISM: Homo sapiens

<400> SEQUENCE: 156

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Lys Val Ser Ser Ser Pro Ala Phe Asp Tyr Trp Gly
            100                 105                 110        Gly

Gln Gly Thr Leu Val Thr Val Ser Ser Gly Gly Gly Ser Gly Gly
        115                 120                 125

Gly Gly Ser Gly Gly Gly Gly Ser Gly Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
        180                 185                 190

Ala Ser Thr Arg Ala Thr Gly Ile Pro Asp Arg Phe Ser Gly Ser Gly
        195                 200                 205

Ser Gly Thr Asp Phe Thr Leu Thr Ile Asn Arg Leu Glu Pro Glu Asp
        210                 215                 220
```

```
Phe Ala Val Tyr Tyr Cys Gln His Tyr Gly Gly Ser Pro Leu Ile Thr
225                 230                 235                 240

Phe Gly Gln Gly Thr Arg Leu Glu Ile Lys
                245                 250

<210> SEQ ID NO 157
<211> LENGTH: 246
<212> TYPE: PRT
<213> ORGANISM: Homo sapiens

<400> SEQUENCE: 157

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Pro Phe Thr Gly Tyr
                20                  25                  30

Ser Leu His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Tyr Gly Gly Asn Ser Leu Phe Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Ile Ser Ala Ser Val Gly Asp Thr Val Ser Ile
145                 150                 155                 160

Thr Cys Arg Ala Ser Gln Asp Ser Gly Thr Trp Leu Ala Trp Tyr Gln
                165                 170                 175

Gln Lys Pro Gly Lys Ala Pro Asn Leu Leu Met Tyr Asp Ala Ser Thr
            180                 185                 190

Leu Glu Asp Gly Val Pro Ser Arg Phe Ser Gly Ser Ala Ser Gly Thr
        195                 200                 205

Glu Phe Thr Leu Thr Val Asn Arg Leu Gln Pro Glu Asp Ser Ala Thr
    210                 215                 220

Tyr Tyr Cys Gln Gln Tyr Asn Ser Tyr Pro Leu Thr Phe Gly Gly Gly
225                 230                 235                 240

Thr Lys Val Asp Ile Lys
                245

<210> SEQ ID NO 158
<211> LENGTH: 248
<212> TYPE: PRT
<213> ORGANISM: Homo sapiens

<400> SEQUENCE: 158

Gln Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45
```

```
Gly Ile Ile Asn Pro Ser Gly Ser Thr Gly Tyr Ala Gln Lys Phe
            50                  55                  60

Gln Gly Arg Val Thr Met Thr Arg Asp Thr Ser Thr Ser Thr Val His
 65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Ser Asp Ala Phe Asp Ile Trp Gly
            100                 105                 110

Gln Gly Thr Met Val Thr Val Ser Ser Gly Gly Gly Ser Gly Gly
            115                 120                 125

Gly Gly Ser Gly Gly Gly Ser Gly Gly Gly Ser Asp Ile Gln
            130                 135                 140

Met Thr Gln Ser Pro Pro Ser Leu Ser Ala Ser Val Gly Asp Arg Val
145                 150                 155                 160

Thr Ile Thr Cys Arg Ala Ser Gln Asp Ile Ser Ser Ala Leu Ala Trp
                165                 170                 175

Tyr Gln Gln Lys Pro Gly Thr Pro Pro Lys Leu Leu Ile Tyr Asp Ala
                180                 185                 190

Ser Ser Leu Glu Ser Gly Val Pro Ser Arg Phe Ser Gly Ser Gly Ser
                195                 200                 205

Gly Thr Asp Phe Thr Leu Thr Ile Ser Ser Leu Gln Pro Glu Asp Phe
            210                 215                 220

Ala Thr Tyr Tyr Cys Gln Gln Phe Ser Ser Tyr Pro Leu Thr Phe Gly
225                 230                 235                 240

Gly Gly Thr Arg Leu Glu Ile Lys
                245

<210> SEQ ID NO 159
<211> LENGTH: 255
<212> TYPE: PRT
<213> ORGANISM: Homo sapiens

<400> SEQUENCE: 159

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Val Ala Gly Ile Tyr Tyr Tyr Gly Met Asp Val Trp
            100                 105                 110

Gly Gln Gly Thr Thr Ile Thr Val Ser Ser Gly Gly Gly Ser Gly
            115                 120                 125

Gly Gly Gly Ser Gly Gly Gly Gly Ser Gly Gly Gly Ser Asp Ile
            130                 135                 140

Val Met Thr Gln Thr Pro Asp Ser Leu Ala Val Ser Leu Gly Glu Arg
145                 150                 155                 160

Ala Thr Ile Ser Cys Lys Ser Ser His Ser Val Leu Tyr Asn Arg Asn
```

```
                165                 170                 175
Asn Lys Asn Tyr Leu Ala Trp Tyr Gln Gln Lys Pro Gly Gln Pro Pro
            180                 185                 190

Lys Leu Leu Phe Tyr Trp Ala Ser Thr Arg Lys Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Pro Glu Asp Phe Ala Thr Tyr Phe Cys Gln Gln Thr Gln
225                 230                 235                 240

Thr Phe Pro Leu Thr Phe Gly Gln Gly Thr Arg Leu Glu Ile Asn
                245                 250                 255

<210> SEQ ID NO 160
<211> LENGTH: 241
<212> TYPE: PRT
<213> ORGANISM: Homo sapiens

<400> SEQUENCE: 160

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Arg Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys

<210> SEQ ID NO 161
<211> LENGTH: 246
<212> TYPE: PRT
<213> ORGANISM: Homo sapiens

<400> SEQUENCE: 161
```

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Thr Thr Ser Tyr Ala Phe Asp Ile Trp Gly Gln Gly Thr
            100                 105                 110

Met Val Thr Val Ser Ser Gly Gly Gly Gly Ser Gly Gly Gly Gly Ser
            115                 120                 125

Gly Gly Gly Gly Ser Gly Gly Gly Ser Asp Ile Gln Leu Thr Gln
        130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Thr Trp Leu Ala Trp Tyr Gln Gln
                165                 170                 175

Lys Pro Gly Lys Ala Pro Asn Leu Leu Ile Tyr Lys Ala Ser Thr Leu
            180                 185                 190

Glu Ser Gly Val Pro Ser Arg Phe Ser Gly Ser Gly Ser Gly Thr Glu
            195                 200                 205

Phe Thr Leu Thr Ile Ser Ser Leu Gln Pro Asp Asp Phe Ala Thr Tyr
        210                 215                 220

Tyr Cys Gln Gln Tyr Asn Thr Tyr Ser Pro Tyr Thr Phe Gly Gln Gly
225                 230                 235                 240

Thr Lys Leu Glu Ile Lys
            245

<210> SEQ ID NO 162
<211> LENGTH: 249
<212> TYPE: PRT
<213> ORGANISM: Homo sapiens

<400> SEQUENCE: 162

Gln Val Gln Leu Val Gln Ser Gly Gly Gly Leu Val Lys Pro Gly Gly
1               5                   10                  15

Ser Leu Arg Leu Ser Cys Glu Ala Ser Gly Phe Ile Phe Ser Asp Tyr
            20                  25                  30

Tyr Met Gly Trp Ile Arg Gln Ala Pro Gly Lys Gly Leu Glu Trp Val
            35                  40                  45

Ser Tyr Ile Gly Arg Ser Gly Ser Met Tyr Tyr Ala Asp Ser Val
        50                  55                  60

Lys Gly Arg Phe Thr Phe Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Ser Pro Val Val Ala Thr Glu Asp Phe Gln His Trp Gly
            100                 105                 110

Gln Gly Thr Leu Val Thr Val Ser Ser Gly Gly Gly Gly Ser Gly Gly

```
                115                 120                 125
Gly Gly Ser Gly Gly Gly Ser Gly Gly Gly Ser Asp Ile Val
    130                 135                 140

Met Thr Gln Thr Pro Ala Thr Leu Ser Leu Ser Pro Gly Glu Arg Ala
145                 150                 155                 160

Thr Leu Ser Cys Arg Ala Ser Gln Ser Val Thr Ser Asn Tyr Leu Ala
                165                 170                 175

Trp Tyr Gln Gln Lys Pro Gly Gln Ala Pro Arg Leu Leu Phe Gly
                180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
    210                 215                 220

Phe Ala Met Tyr Tyr Cys Gln Gln Tyr Gly Ser Ala Pro Val Thr Phe
225                 230                 235                 240

Gly Gln Gly Thr Lys Leu Glu Ile Lys
                245

<210> SEQ ID NO 163
<211> LENGTH: 249
<212> TYPE: PRT
<213> ORGANISM: Homo sapiens

<400> SEQUENCE: 163

Gln Val Gln Leu Val Gln Ser Gly Ala Glu Val Arg Ala Pro Gly Ala
1               5                   10                  15

Ser Val Lys Ile Ser Cys Lys Ala Ser Gly Phe Thr Phe Arg Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Arg Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Met Tyr Tyr Cys
                85                  90                  95

Ala Arg Thr Ala Ser Cys Gly Gly Asp Cys Tyr Tyr Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Pro Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
        195                 200                 205

Ser Gly Ala Glu Phe Thr Leu Thr Ile Ser Ser Leu Gln Pro Asp Asp
    210                 215                 220

Phe Ala Thr Tyr Tyr Cys Gln Gln Tyr Gln Ser Tyr Pro Leu Thr Phe
225                 230                 235                 240
```

-continued

```
Gly Gly Gly Thr Lys Val Asp Ile Lys
            245
```

<210> SEQ ID NO 164
<211> LENGTH: 244
<212> TYPE: PRT
<213> ORGANISM: Homo sapiens

<400> SEQUENCE: 164

```
Gln Val Gln Leu Val Gln Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ser Ser Ser Trp Ser Trp Gly Tyr Phe Asp Tyr Trp
            100                 105                 110

Gly Gln Gly Thr Leu Val Thr Val Ser Gly Gly Gly Gly Ser Gly
            115                 120                 125

Gly Gly Gly Ser Gly Gly Gly Ser Ser Glu Leu Thr Gln Asp
            130                 135                 140

Pro Ala Val Ser Val Ala Leu Gly Gln Thr Val Arg Thr Thr Cys Gln
145                 150                 155                 160

Gly Asp Ala Leu Arg Ser Tyr Tyr Ala Ser Trp Tyr Gln Gln Lys Pro
                165                 170                 175

Gly Gln Ala Pro Met Leu Val Ile Tyr Gly Lys Asn Asn Arg Pro Ser
            180                 185                 190

Gly Ile Pro Asp Arg Phe Ser Gly Ser Asp Ser Gly Asp Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Tyr Pro Val Phe Gly Thr Gly Thr Lys
225                 230                 235                 240

Val Thr Val Leu
```

<210> SEQ ID NO 165
<211> LENGTH: 246
<212> TYPE: PRT
<213> ORGANISM: Homo sapiens

<400> SEQUENCE: 165

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Thr Gly Tyr Ala Asp Ser Val
        50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr Tyr Cys
                    85                  90                  95

Ala Lys Asp Ser Ser Trp Tyr Gly Gly Gly Ser Ala Phe Asp Ile
                100                 105                 110

Trp Gly Gln Gly Thr Met Val Thr Val Ser Ser Gly Gly Gly Ser
                115                 120                 125

Gly Gly Gly Gly Ser Gly Gly Gly Ser Ser Glu Leu Thr Gln
            130                 135                 140

Glu Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Phe Gly Arg Ser Arg Arg Pro
                180                 185                 190

Ser Gly Ile Pro Asp Arg Phe Ser Gly Ser Ser Ser Gly Asn Thr Ala
                195                 200                 205

Ser Leu Ile Ile Thr Gly Ala Gln Ala Glu Asp Glu Ala Asp Tyr Tyr
                210                 215                 220

Cys Asn Ser Arg Asp Asn Thr Ala Asn His Tyr Val Phe Gly Thr Gly
225                 230                 235                 240

Thr Lys Leu Thr Val Leu
                245

<210> SEQ ID NO 166
<211> LENGTH: 246
<212> TYPE: PRT
<213> ORGANISM: Homo sapiens

<400> SEQUENCE: 166

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Ser Trp Tyr Gly Gly Gly Ser Ala Phe Asp Ile
                100                 105                 110

Trp Gly Gln Gly Thr Met Val Thr Val Ser Ser Gly Gly Gly Ser
                115                 120                 125

Gly Gly Gly Gly Ser Gly Gly Gly Ser Ser Glu Leu Thr Gln
            130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Tyr Gly Lys Asn Asn Arg Pro
                180                 185                 190
```

```
Ser Gly Ile Pro Asp Arg Phe Ser Gly Ser Ser Gly Asn Thr Ala
            195                 200                 205

Ser Leu Thr Ile Thr Gly Ala Gln Ala Glu Asp Glu Ala Asp Tyr Tyr
210                 215                 220

Cys Asn Ser Arg Gly Ser Ser Gly Asn His Tyr Val Phe Gly Thr Gly
225                 230                 235                 240

Thr Lys Val Thr Val Leu
                245

<210> SEQ ID NO 167
<211> LENGTH: 251
<212> TYPE: PRT
<213> ORGANISM: Homo sapiens

<400> SEQUENCE: 167

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Thr Gly Trp Val Gly Ser Tyr Tyr Tyr Met Asp Val Trp
            100                 105                 110

Gly Lys Gly Thr Thr Val Thr Val Ser Ser Gly Gly Gly Gly Ser Gly
        115                 120                 125

Gly Gly Gly Ser Gly Gly Gly Ser Gly Gly Gly Ser Glu Ile
    130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Ser Val Ser Ser Asn Tyr Leu
                165                 170                 175

Ala Trp Tyr Gln Gln Lys Pro Gly Gln Pro Pro Arg Leu Leu Ile Tyr
            180                 185                 190

Asp Val Ser Thr Arg Ala Thr Gly Ile Pro Ala Arg Phe Ser Gly Gly
        195                 200                 205

Gly Ser Gly Thr Asp Phe Thr Leu Thr Ile Ser Ser Leu Glu Pro Glu
    210                 215                 220

Asp Phe Ala Val Tyr Tyr Cys Gln Gln Arg Ser Asn Trp Pro Pro Trp
225                 230                 235                 240

Thr Phe Gly Gln Gly Thr Lys Val Glu Ile Lys
                245                 250

<210> SEQ ID NO 168
<211> LENGTH: 250
<212> TYPE: PRT
<213> ORGANISM: Homo sapiens

<400> SEQUENCE: 168

Gln Val Gln Leu Val Gln Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Tyr Ser Arg Tyr Tyr Tyr Gly Met Asp Val Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Gly Gly Gly Ser Glu Ile Val
        130                 135                 140

Met Thr Gln Ser Pro Ala Thr Leu Ser Leu Ser Pro Gly Glu Arg Ala
145                 150                 155                 160

Ile Leu Ser Cys Arg Ala Ser Gln Ser Val Tyr Thr Lys Tyr Leu Gly
                165                 170                 175

Trp Tyr Gln Gln Lys Pro Gly Gln Ala Pro Arg Leu Leu Ile Tyr Asp
            180                 185                 190

Ala Ser Thr Arg Ala Thr Gly Ile Pro Asp Arg Phe Ser Gly Ser Gly
            195                 200                 205

Ser Gly Thr Asp Phe Thr Leu Thr Ile Asn Arg Leu Glu Pro Glu Asp
    210                 215                 220

Phe Ala Val Tyr Tyr Cys Gln His Tyr Gly Gly Ser Pro Leu Ile Thr
225                 230                 235                 240

Phe Gly Gln Gly Thr Lys Val Asp Ile Lys
                245                 250

<210> SEQ ID NO 169
<211> LENGTH: 249
<212> TYPE: PRT
<213> ORGANISM: Homo sapiens

<400> SEQUENCE: 169

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Glu Ala Ala Gly His Asp Trp Tyr Phe Asp Leu Trp
            100                 105                 110

Gly Arg Gly Thr Leu Val Thr Val Ser Ser Gly Gly Gly Ser Gly
        115                 120                 125

Gly Gly Gly Ser Gly Gly Gly Ser Gly Gly Gly Ser Asp Ile
        130                 135                 140
```

```
Arg Val Thr Gln Ser Pro Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
                195                 200                 205

Ser Gly Thr Asp Phe Thr Leu Thr Ile Ser Ser Leu Gln Pro Glu Asp
        210                 215                 220

Phe Ala Thr Tyr Tyr Cys Gln Gln Ser Tyr Ser Ile Pro Leu Thr Phe
225                 230                 235                 240

Gly Gln Gly Thr Lys Val Glu Ile Lys
                245

<210> SEQ ID NO 170
<211> LENGTH: 247
<212> TYPE: PRT
<213> ORGANISM: Homo sapiens

<400> SEQUENCE: 170

Gln Val Gln Leu Val Gln Ser Trp Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Ser Pro Arg Val Thr Thr Gly Tyr Phe Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Asp Ile Gln Leu
        130                 135                 140

Thr Gln Ser Pro Ser Thr Leu Ser Ala Ser Val Gly Asp Arg Val Thr
145                 150                 155                 160

Ile Thr Cys Arg Ala Ser Gln Ser Ile Ser Ser Trp Leu Ala Trp Tyr
                165                 170                 175

Gln Gln Lys Pro Gly Lys Ala Pro Lys Leu Leu Ile Tyr Lys Ala Ser
            180                 185                 190

Ser Leu Glu Ser Gly Val Pro Ser Arg Phe Ser Gly Ser Gly Ser Gly
        195                 200                 205

Thr Glu Phe Thr Leu Thr Ile Ser Ser Leu Gln Pro Asp Asp Phe Ala
    210                 215                 220

Thr Tyr Tyr Cys Gln Gln Tyr Ser Ser Tyr Pro Leu Thr Phe Gly Gly
225                 230                 235                 240

Gly Thr Arg Leu Glu Ile Lys
                245
```

<210> SEQ ID NO 171
<211> LENGTH: 253
<212> TYPE: PRT
<213> ORGANISM: Homo sapiens

<400> SEQUENCE: 171

Gln Val Gln Leu Val Gln Ser Gly Ala Glu Val Arg Arg Pro Gly Ala
1               5                   10                  15

Ser Val Lys Ile Ser Cys Arg Ala Ser Gly Asp Thr Ser Thr Arg His
            20                  25                  30

Tyr Ile His Trp Leu Arg Gln Ala Pro Gly Gln Gly Pro Glu Trp Met
        35                  40                  45

Gly Val Ile Asn Pro Thr Thr Gly Pro Ala Thr Gly Ser Pro Ala Tyr
    50                  55                  60

Ala Gln Met Leu Gln Gly Arg Val Thr Met Thr Arg Asp Thr Ser Thr
65                  70                  75                  80

Arg Thr Val Tyr Met Glu Leu Arg Ser Leu Arg Phe Glu Asp Thr Ala
                85                  90                  95

Val Tyr Tyr Cys Ala Arg Ser Val Val Gly Arg Ser Ala Pro Tyr Tyr
            100                 105                 110

Phe Asp Tyr Trp Gly Gln Gly Thr Leu Val Thr Val Ser Ser Gly Gly
        115                 120                 125

Gly Gly Ser Gly Gly Gly Ser Gly Gly Gly Ser Gly Gly Gly
    130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Gly Ile Ser
                165                 170                 175

Asp Tyr Ser Ala Trp Tyr Gln Gln Lys Pro Gly Lys Ala Pro Lys Leu
            180                 185                 190

Leu Ile Tyr Ala Ala Ser Thr Leu Gln Ser Gly Val Pro Ser Arg Phe
        195                 200                 205

Ser Gly Ser Gly Ser Gly Thr Asp Phe Thr Leu Thr Ile Ser Tyr Leu
    210                 215                 220

Gln Ser Glu Asp Phe Ala Thr Tyr Tyr Cys Gln Gln Tyr Tyr Ser Tyr
225                 230                 235                 240

Pro Leu Thr Phe Gly Gly Gly Thr Lys Val Asp Ile Lys
                245                 250

<210> SEQ ID NO 172
<211> LENGTH: 249
<212> TYPE: PRT
<213> ORGANISM: Homo sapiens

<400> SEQUENCE: 172

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Tyr Thr Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

-continued

```
                85                  90                  95
Ala Arg Ile Arg Ser Cys Gly Gly Asp Cys Tyr Tyr Phe Asp Asn Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser Gly Gly Gly Ser Asp Ile
            130                 135                 140

Gln Leu Thr Gln Ser Pro Ser Thr Leu Ser Ala Ser Val Gly Asp Arg
145                 150                 155                 160

Val Thr Ile Thr Cys Arg Ala Ser Glu Asn Val Asn Ile Trp Leu Ala
                165                 170                 175

Trp Tyr Gln Gln Lys Pro Gly Lys Ala Pro Lys Leu Leu Ile Tyr Lys
            180                 185                 190

Ser Ser Ser Leu Ala Ser Gly Val Pro Ser Arg Phe Ser Gly Ser Gly
            195                 200                 205

Ser Gly Ala Glu Phe Thr Leu Thr Ile Ser Ser Leu Gln Pro Asp Asp
            210                 215                 220

Phe Ala Thr Tyr Tyr Cys Gln Gln Tyr Gln Ser Tyr Pro Leu Thr Phe
225                 230                 235                 240

Gly Gly Gly Thr Lys Val Asp Ile Lys
            245
```

<210> SEQ ID NO 173
<211> LENGTH: 246
<212> TYPE: PRT
<213> ORGANISM: Homo sapiens

<400> SEQUENCE: 173

```
Gln Ile Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Val His Val Gly Trp Ile Arg Gln Pro Pro Gly Lys Ala Leu Glu
        35                  40                  45

Trp Leu Ala Leu Ile Ser Trp Ala Asp Asp Lys Arg Tyr Arg Pro Ser
    50                  55                  60

Leu Arg Ser Arg Leu Asp Ile Thr Arg Val Thr Ser Lys Asp Gln Val
65                  70                  75                  80

Val Leu Ser Met Thr Asn Met Gln Pro Glu Asp Thr Ala Thr Tyr Tyr
                85                  90                  95

Cys Ala Leu Gln Gly Phe Asp Gly Tyr Glu Ala Asn Trp Gly Pro Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Gly Ser Asp Ile Val Met Thr
130                 135                 140

Gln Ser Pro Ser Ser Leu Ser Ala Ser Ala Gly Asp Arg Val Thr Ile
145                 150                 155                 160

Thr Cys Arg Ala Ser Arg Gly Ile Ser Ser Ala Leu Ala Trp Tyr Gln
                165                 170                 175

Gln Lys Pro Gly Lys Pro Pro Lys Leu Leu Ile Tyr Asp Ala Ser Ser
            180                 185                 190

Leu Glu Ser Gly Val Pro Ser Arg Phe Ser Gly Ser Gly Ser Gly Thr
            195                 200                 205
```

```
Asp Phe Thr Leu Thr Ile Asp Ser Leu Glu Pro Glu Asp Phe Ala Thr
    210                 215                 220

Tyr Tyr Cys Gln Gln Ser Tyr Ser Thr Pro Trp Thr Phe Gly Gln Gly
225                 230                 235                 240

Thr Lys Val Asp Ile Lys
            245
```

<210> SEQ ID NO 174
<211> LENGTH: 247
<212> TYPE: PRT
<213> ORGANISM: Homo sapiens

<400> SEQUENCE: 174

```
Glu Val Gln Leu Gln Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Glu Met Ala Thr Ile Met Gly Gly Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Leu Met Ile Tyr Asp Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Ser Ser Thr Leu Asp Val Val Phe Gly Gly
225                 230                 235                 240

Gly Thr Lys Leu Thr Val Leu
                245
```

<210> SEQ ID NO 175
<211> LENGTH: 245
<212> TYPE: PRT
<213> ORGANISM: Homo sapiens

<400> SEQUENCE: 175

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ser Leu Ile Ser Gly Asp Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Arg Val Phe Asp Ser Tyr Tyr Met Asp Val Trp Gly Lys Gly Thr
                100                 105                 110

Thr Val Thr Val Ser Ser Gly Gly Gly Gly Ser Gly Gly Gly Gly Ser
            115                 120                 125

Gly Ser Gly Gly Ser Glu Ile Val Leu Thr Gln Ser Pro Leu Ser Leu
130                 135                 140

Pro Val Thr Pro Gly Gln Pro Ala Ser Ile Ser Cys Arg Ser Ser Gln
145                 150                 155                 160

Ser Leu Val Tyr Thr Asp Gly Asn Thr Tyr Leu Asn Trp Phe Gln Gln
                165                 170                 175

Arg Pro Gly Gln Ser Pro Arg Arg Leu Ile Tyr Lys Val Ser Asn Arg
                180                 185                 190

Asp Ser Gly Val Pro Asp Arg Phe Ser Gly Ser Gly Ser Asp Thr Asp
            195                 200                 205

Phe Thr Leu Lys Ile Ser Arg Val Glu Ala Glu Asp Val Gly Ile Tyr
210                 215                 220

Tyr Cys Met Gln Gly Thr His Trp Ser Phe Thr Phe Gly Gln Gly Thr
225                 230                 235                 240

Arg Leu Glu Ile Lys
                245

<210> SEQ ID NO 176
<211> LENGTH: 247
<212> TYPE: PRT
<213> ORGANISM: Homo sapiens

<400> SEQUENCE: 176

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Ser Ile Ser Val Asp Thr Ser Lys Asn Gln Phe
 65                  70                  75                  80

Ser Leu Lys Leu Lys Tyr Val Thr Ala Ala Asp Thr Ala Val Tyr Tyr
                 85                  90                  95

Cys Ala Thr Pro Gly Thr Tyr Tyr Asp Phe Leu Ser Gly Tyr Tyr Pro
                100                 105                 110

Phe Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Asp Ile Val Met
130                 135                 140

Thr Gln Ser Pro Ser Ser Leu Ser Ala Ser Val Gly Asp Arg Val Thr
145                 150                 155                 160

Ile Thr Cys Arg Ala Ser Gln Gly Ile Ser Ser Tyr Leu Ala Trp Tyr
            165                 170                 175

Gln Gln Lys Pro Gly Lys Ala Pro Lys Leu Leu Ile Tyr Ala Ala Ser
        180                 185                 190

Thr Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
210                 215                 220

Thr Tyr Tyr Cys Gln Gln Leu Asn Ser Tyr Pro Tyr Thr Phe Gly Gln
225                 230                 235                 240

Gly Thr Lys Leu Glu Ile Lys
                245

<210> SEQ ID NO 177
<211> LENGTH: 239
<212> TYPE: PRT
<213> ORGANISM: Homo sapiens

<400> SEQUENCE: 177

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Ala Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Leu Arg Ser Gly Arg Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Ile Val Leu Thr Gln Ser Pro Gly Thr Leu Ser Leu
    130                 135                 140

Ser Pro Gly Gly Arg Ala Thr Leu Ser Cys Arg Ala Ser Gln Ser Ile
145                 150                 155                 160

Ser Gly Ser Phe Leu Ala Trp Tyr Gln Gln Lys Pro Gly Gln Ala Pro
                165                 170                 175

Arg Leu Leu Ile Tyr Gly Ala Ser Ser Arg Ala Thr Gly Ile Pro Asp
            180                 185                 190

Arg Phe Ser Gly Ser Gly Ser Gly Thr Asp Phe Thr Leu Thr Ile Ser
        195                 200                 205

Arg Leu Glu Pro Glu Asp Phe Ala Val Tyr Tyr Cys Gln Gln Tyr Gly
    210                 215                 220

Ser Ser Pro Pro Thr Phe Gly Leu Gly Thr Lys Leu Glu Ile Lys
225                 230                 235

<210> SEQ ID NO 178
<211> LENGTH: 245
<212> TYPE: PRT
<213> ORGANISM: Homo sapiens

<400> SEQUENCE: 178

Glu Val Gln Leu Gln Gln Ser Gly Pro Gly Leu Val Arg Pro Ser Glu
1               5                   10                  15

Thr Leu Ser Leu Thr Cys Thr Val Ser Gly Gly Pro Val Arg Ser Gly
            20                  25                  30

Ser His Tyr Trp Asn Trp Ile Arg Gln Pro Pro Gly Arg Gly Leu Glu
        35                  40                  45

Trp Ile Gly Tyr Ile Tyr Tyr Ser Gly Ser Thr Asn Tyr Asn Pro Ser
    50                  55                  60

Leu Glu Asn Arg Val Thr Ile Ser Ile Asp Thr Ser Asn Asn His Phe
65                  70                  75                  80

Ser Leu Lys Leu Ser Ser Val Thr Ala Ala Asp Thr Ala Leu Tyr Phe
                85                  90                  95

Cys Ala Arg Gly Thr Ala Thr Phe Asp Trp Asn Phe Pro Phe Asp Ser
            100                 105                 110

Trp Gly Gln Gly Thr Leu Val Thr Val Ser Gly Gly Gly Gly Ser
        115                 120                 125

Gly Gly Gly Gly Ser Gly Ser Gly Gly Ser Asp Ile Gln Met Thr Gln
    130                 135                 140

Ser Pro Ser Ser Leu Ser Ala Ser Ile Gly Asp Arg Val Thr Ile Thr
145                 150                 155                 160

Cys Arg Ala Ser Gln Ser Ile Ser Ser Tyr Leu Asn Trp Tyr Gln Gln
            165                 170                 175

Lys Pro Gly Lys Ala Pro Lys Leu Leu Ile Tyr Ala Ala Ser Ser Leu
        180                 185                 190

Gln Ser Gly Val Pro Ser Arg Phe Ser Gly Ser Gly Ser Gly Thr Asp
    195                 200                 205

Phe Thr Leu Thr Ile Ser Ser Leu Gln Pro Glu Asp Phe Ala Thr Tyr
    210                 215                 220

Tyr Cys Gln Gln Ser Tyr Ser Thr Pro Trp Thr Phe Gly Gln Gly Thr
225                 230                 235                 240

Lys Leu Glu Ile Lys
            245

<210> SEQ ID NO 179
<211> LENGTH: 249
<212> TYPE: PRT
<213> ORGANISM: Homo sapiens

<400> SEQUENCE: 179

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Val
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Gly Leu Val Val Tyr Ala Ile Arg Val Gly Ser Gly Trp
            100                 105                 110

Phe Asp Tyr Trp Gly Gln Gly Thr Leu Val Thr Val Ser Ser Gly Gly

```
            115                 120                 125
Gly Gly Ser Gly Gly Asp Ser Gly Gly Gly Ser Asp Ile Gln
130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Met Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
210                 215                 220

Ala Thr Tyr Tyr Cys Gln Gln Ser Tyr Ser Thr Pro Pro Trp Thr Phe
225                 230                 235                 240

Gly Gln Gly Thr Lys Val Asp Ile Lys
                245

<210> SEQ ID NO 180
<211> LENGTH: 255
<212> TYPE: PRT
<213> ORGANISM: Homo sapiens

<400> SEQUENCE: 180

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Ser Gly Ser Tyr Tyr Met Glu Asp Ser Tyr
            100                 105                 110

Tyr Tyr Gly Met Asp Val Trp Gly Gln Gly Thr Thr Val Thr Val Ser
        115                 120                 125

Ser Gly Gly Gly Gly Ser Gly Gly Gly Gly Ser Gly Gly Gly Gly Ser
    130                 135                 140

Asn Phe Met Leu Thr Gln Pro His Ser Val Ser Glu Ser Pro Gly Lys
145                 150                 155                 160

Thr Val Thr Ile Ser Cys Thr Gly Ser Gly Ser Ile Ala Ser Asn
                165                 170                 175

Tyr Val Gln Trp Tyr Gln Gln Arg Pro Gly Ser Ala Pro Thr Thr Val
            180                 185                 190

Ile Tyr Glu Asp Asn Gln Arg Pro Ser Gly Val Pro Asp Arg Phe Ser
        195                 200                 205

Gly Ser Ile Asp Ser Ser Ser Asn Ser Ala Ser Leu Thr Ile Ser Gly
    210                 215                 220

Leu Lys Thr Glu Asp Glu Ala Asp Tyr Tyr Cys Gln Ser Tyr Asp Ser
225                 230                 235                 240
```

```
Ser Asn Gln Val Val Phe Gly Gly Gly Thr Lys Leu Thr Val Leu
            245                 250                 255

<210> SEQ ID NO 181
<211> LENGTH: 239
<212> TYPE: PRT
<213> ORGANISM: Homo sapiens

<400> SEQUENCE: 181

Gln Val Asn Leu Arg Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Ala Leu Gly Ser Ser Trp Glu Trp Gly Gln Gly Thr Thr
            100                 105                 110

Val Thr Val Ser Ser Gly Gly Gly Gly Ser Gly Gly Gly Gly Ser Gly
            115                 120                 125

Gly Gly Gly Ser Asp Ile Gln Met Thr Gln Ser Pro Ser Ser Leu Ser
        130                 135                 140

Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Thr Phe Thr Ile Ser
        195                 200                 205

Ser Leu Gln Pro Glu Asp Ile Ala Thr Tyr Tyr Cys Gln Gln Tyr Asp
    210                 215                 220

Asn Leu Pro Leu Thr Phe Gly Gly Gly Thr Lys Leu Glu Ile Lys
225                 230                 235

<210> SEQ ID NO 182
<211> LENGTH: 246
<212> TYPE: PRT
<213> ORGANISM: Homo sapiens

<400> SEQUENCE: 182

Gln Val Gln Leu Val Gln Ser Gly Ala Glu Val Lys Glu Pro Gly Ala
1               5                   10                  15

Ser Val Lys Val Ser Cys Lys Ala Pro Ala Asn Thr Phe Ser Asp His
            20                  25                  30

Val Met His Trp Val Arg Gln Ala Pro Gly Gln Arg Phe Glu Trp Met
            35                  40                  45

Gly Tyr Ile His Ala Ala Asn Gly Gly Thr His Tyr Ser Gln Lys Phe
50                  55                  60

Gln Asp Arg Val Thr Ile Thr Arg Asp Thr Ser Ala Asn Thr Val Tyr
65                  70                  75                  80
```

```
Met Asp Leu Ser Ser Leu Arg Ser Glu Asp Thr Ala Val Tyr Tyr Cys
                85                  90                  95

Ala Arg Gly Gly Tyr Asn Ser Asp Ala Phe Asp Ile Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Gly Gly Gly Ser Asp Ile Val Met Thr
    130                 135                 140

Gln Ser Pro Ser Ser Val Ser Ala Ser Val Gly Asp Arg Val Thr Ile
145                 150                 155                 160

Thr Cys Arg Ala Ser Gln Asp Ile Ser Ser Trp Leu Ala Trp Tyr Gln
                165                 170                 175

Gln Lys Pro Gly Lys Ala Pro Lys Leu Leu Ile Tyr Ala Ala Ser Ser
            180                 185                 190

Leu Gln Ser Gly Val Pro Ser Arg Phe Asn Gly Ser Gly Ser Gly Thr
            195                 200                 205

Asp Phe Thr Leu Thr Ile Ser Ser Leu Gln Pro Glu Asp Phe Ala Thr
            210                 215                 220

Tyr Tyr Cys Gln Gln Ser Tyr Ser Thr Pro Leu Thr Phe Gly Gly Gly
225                 230                 235                 240

Thr Lys Val Glu Ile Lys
                245

<210> SEQ ID NO 183
<211> LENGTH: 248
<212> TYPE: PRT
<213> ORGANISM: Homo sapiens

<400> SEQUENCE: 183

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Val Arg Ala Ile Asp Ala Phe Asp Ile Trp Gly
            100                 105                 110

Gln Gly Thr Met Val Thr Val Ser Ser Gly Gly Gly Ser Gly Gly
            115                 120                 125

Gly Gly Ser Gly Gly Gly Gly Ser Gly Gly Gly Ser Asp Ile Val
        130                 135                 140

Leu Thr Gln Ser Pro Ser Ser Leu Ser Ala Ser Val Gly Asp Arg Val
145                 150                 155                 160

Thr Ile Thr Cys Gln Ala Ser Gln Asp Ile Ser Asn Tyr Leu Asn Trp
                165                 170                 175

Tyr Gln Gln Lys Pro Gly Lys Ala Pro Lys Leu Leu Ile Tyr Asp Ala
            180                 185                 190

Ser Asn Leu Glu Thr Gly Val Pro Ser Arg Phe Ser Gly Ser Gly Ser
            195                 200                 205
```

Gly Thr Asp Phe Thr Phe Thr Ile Ser Ser Leu Gln Pro Glu Asp Phe
    210                 215                 220
Ala Thr Tyr Tyr Cys Gln Gln Ala Tyr Ser Thr Pro Phe Thr Phe Gly
225                 230                 235                 240
Pro Gly Thr Lys Val Glu Ile Lys
            245

<210> SEQ ID NO 184
<211> LENGTH: 246
<212> TYPE: PRT
<213> ORGANISM: Homo sapiens

<400> SEQUENCE: 184

Glu Val Gln Leu Val Gln Ser Gly Gly Gly Val Val Arg Ser Gly Arg
1               5                   10                  15

Ser Leu Arg Leu Ser Cys Ala Ala Ser Gly Phe Thr Phe Asn Ser Tyr
            20                  25                  30

Gly Leu His Trp Val Arg Gln Ala Pro Gly Lys Gly Leu Glu Trp Val
        35                  40                  45

Ala Leu Ile Glu Tyr Asp Gly Ser Asn Lys Tyr Tyr Gly Asp Ser Val
    50                  55                  60

Lys Gly Arg Phe Thr Ile Ser Arg Asp Lys Ser Lys Ser Thr Leu Tyr
65                  70                  75                  80

Leu Gln Met Asp Asn Leu Arg Ala Glu Asp Thr Ala Val Tyr Tyr Cys
                85                  90                  95

Ala Arg Glu Gly Asn Glu Asp Leu Ala Phe Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Ser Glu Ile Val Leu Thr
    130                 135                 140

Gln Ser Pro Ser Ser Leu Ser Ala Ser Val Gly Asp Arg Val Thr Ile
145                 150                 155                 160

Thr Cys Gln Ala Ser Gln Phe Ile Lys Lys Asn Leu Asn Trp Tyr Gln
                165                 170                 175

His Lys Pro Gly Lys Ala Pro Lys Leu Leu Ile Tyr Asp Ala Ser Ser
            180                 185                 190

Leu Gln Thr Gly Val Pro Ser Arg Phe Ser Gly Asn Arg Ser Gly Thr
        195                 200                 205

Thr Phe Ser Phe Thr Ile Ser Ser Leu Gln Pro Glu Asp Val Ala Thr
    210                 215                 220

Tyr Tyr Cys Gln Gln His Asp Asn Leu Pro Leu Thr Phe Gly Gly Gly
225                 230                 235                 240

Thr Lys Val Glu Ile Lys
            245

<210> SEQ ID NO 185
<211> LENGTH: 255
<212> TYPE: PRT
<213> ORGANISM: Homo sapiens

<400> SEQUENCE: 185

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Ser Ser Asn
            20                  25                  30

Tyr Met Thr Trp Val Arg Gln Ala Pro Gly Lys Gly Leu Glu Trp Val
         35                  40                  45

Ser Val Ile Tyr Ser Gly Gly Ala Thr Tyr Tyr Gly Asp Ser Val Lys
     50                  55                  60

Gly Arg Phe Thr Val Ser Arg Asp Asn Ser Lys Asn Thr Val Tyr Leu
 65                  70                  75                  80

Gln Met Asn Arg Leu Thr Ala Glu Asp Thr Ala Val Tyr Tyr Cys Ala
                 85                  90                  95

Arg Asp Arg Leu Tyr Cys Gly Asn Asn Cys Tyr Leu Tyr Tyr Tyr Tyr
             100                 105                 110

Gly Met Asp Val Trp Gly Gln Gly Thr Leu Val Thr Val Ser Ser Gly
         115                 120                 125

Gly Gly Gly Ser Gly Gly Gly Ser Gly Gly Gly Ser Gly Gly
     130                 135                 140

Gly Gly Ser Asp Ile Gln Val Thr Gln Ser Pro Ser Ser Leu Ser Ala
145                 150                 155                 160

Ser Val Gly Asp Arg Val Thr Ile Thr Cys Arg Ala Ser Gln Ser Ile
                165                 170                 175

Ser Ser Tyr Leu Asn Trp Tyr Gln Gln Lys Pro Gly Lys Ala Pro Lys
            180                 185                 190

Leu Leu Ile Tyr Ala Ala Ser Ser Leu Gln Ser Gly Val Pro Ser Arg
        195                 200                 205

Phe Ser Gly Ser Gly Ser Gly Thr Asp Phe Thr Leu Thr Ile Ser Ser
210                 215                 220

Leu Gln Pro Glu Asp Phe Ala Thr Tyr Tyr Cys Gln Gln Ser Tyr Ser
225                 230                 235                 240

Thr Pro Pro Leu Thr Phe Gly Gln Gly Thr Lys Val Glu Ile Lys
                245                 250                 255

<210> SEQ ID NO 186
<211> LENGTH: 247
<212> TYPE: PRT
<213> ORGANISM: Homo sapiens

<400> SEQUENCE: 186

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Pro Phe Thr Gly Tyr
            20                  25                  30

Tyr Ile Gln Trp Val Arg Gln Ala Pro Gly Gln Gly Leu Glu Trp Met
         35                  40                  45

Gly Trp Ile Asp Pro Asn Ser Gly Asn Thr Gly Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Asp Ser Tyr Gly Tyr Tyr Tyr Gly Met Asp Val Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr

```
                145                 150                 155                 160
        Phe Thr Cys Arg Ala Ser Gln Gly Ile Ser Ser Ala Leu Ala Trp Tyr
                        165                 170                 175
        Gln Gln Lys Pro Gly Lys Pro Pro Lys Leu Leu Ile Tyr Asp Ala Ser
                        180                 185                 190
        Ser Leu Glu Ser Gly Val Pro Ser Arg Phe Ser Gly Ser Gly Ser Gly
                        195                 200                 205
        Thr Asp Phe Thr Leu Thr Ile Ser Ser Leu Gln Pro Glu Asp Phe Ala
                210                 215                 220
        Thr Tyr Tyr Cys Gln Gln Phe Asn Asn Tyr Pro Leu Thr Phe Gly Gly
        225                 230                 235                 240
        Gly Thr Lys Val Glu Ile Lys
                        245

<210> SEQ ID NO 187
<211> LENGTH: 245
<212> TYPE: PRT
<213> ORGANISM: Homo sapiens

<400> SEQUENCE: 187

Glu Val Gln Leu Val Glu Ser Gly Gly Gly Leu Val Gln Pro Gly Gly
        1               5                   10                  15
        Ser Leu Arg Leu Ser Cys Ala Ala Ser Gly Phe Thr Phe Ser Ser Tyr
                        20                  25                  30
        Glu Met Asn Trp Val Arg Gln Ala Pro Gly Lys Gly Leu Glu Trp Val
                        35                  40                  45
        Ser Tyr Ile Ser Ser Ser Gly Ser Thr Ile Tyr Tyr Ala Asp Ser Val
                50                  55                  60
        Lys Gly Arg Phe Thr Ile Ser Arg Asp Asn Ala Lys Asn Ser Leu Tyr
        65                  70                  75                  80
        Leu Gln Met Asn Ser Leu Arg Ala Glu Asp Thr Ala Val Tyr Tyr Cys
                        85                  90                  95
        Ala Arg Asp Pro Tyr Ser Ser Trp His Asp Ala Phe Asp Ile Trp
                        100                 105                 110
        Gly Gln Gly Thr Met Val Thr Val Ser Ser Gly Gly Gly Gly Ser Gly
                        115                 120                 125
        Gly Gly Gly Ser Gly Gly Gly Ser Glu Ile Val Leu Thr Gln Ser
                    130                 135                 140
        Pro Gly Thr Leu Ser Leu Ser Pro Gly Glu Arg Ala Thr Leu Ser Cys
        145                 150                 155                 160
        Arg Ala Ser Gln Ser Val Ser Ser Ser Tyr Leu Ala Trp Tyr Gln Gln
                        165                 170                 175
        Lys Pro Gly Gln Ala Pro Arg Leu Leu Ile Tyr Gly Ala Ser Ser Arg
                        180                 185                 190
        Ala Thr Gly Ile Pro Asp Arg Phe Ser Gly Ser Gly Ser Gly Thr Asp
                        195                 200                 205
        Phe Thr Leu Thr Ile Ser Arg Leu Glu Pro Glu Asp Phe Ala Val Tyr
                        210                 215                 220
        Tyr Cys Gln Gln Tyr Gly Ser Ser Pro Leu Thr Phe Gly Gly Gly Thr
        225                 230                 235                 240
        Lys Val Asp Ile Lys
                        245

<210> SEQ ID NO 188
<211> LENGTH: 246
```

```
<212> TYPE: PRT
<213> ORGANISM: Homo sapiens

<400> SEQUENCE: 188

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Gly Trp Val
        35                  40                  45

Ser Gly Ile Ser Arg Ser Gly Glu Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Ser Pro Ala His Tyr Tyr Gly Gly Met Asp Val Trp Gly Gln
            100                 105                 110

Gly Thr Thr Val Thr Val Ser Ser Ala Ser Gly Gly Gly Gly Ser Gly
        115                 120                 125

Gly Arg Ala Ser Gly Gly Gly Ser Asp Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Ile Ser Ser Ser Phe Leu Ala Trp Tyr Gln Gln
                165                 170                 175

Lys Pro Gly Gln Ala Pro Arg Leu Leu Ile Tyr Gly Ala Ser Arg Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Ser Ala Val Tyr
    210                 215                 220

Tyr Cys Gln Gln Tyr His Ser Ser Pro Ser Trp Thr Phe Gly Gln Gly
225                 230                 235                 240

Thr Lys Leu Glu Ile Lys
                245

<210> SEQ ID NO 189
<211> LENGTH: 244
<212> TYPE: PRT
<213> ORGANISM: Homo sapiens

<400> SEQUENCE: 189

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

Ser Val His Ser Phe Leu Ala Tyr Trp Gly Gln Gly Thr Leu Val Thr
            100                 105                 110

Val Ser Ser Ala Ser Gly Gly Gly Gly Ser Gly Arg Ala Ser Gly
        115                 120                 125

Gly Gly Gly Ser Asp Ile Val Met Thr Gln Thr Pro Leu Ser Leu Pro
        130                 135                 140

Val Thr Pro Gly Glu Pro Ala Ser Ile Ser Cys Arg Ser Ser Gln Ser
145                 150                 155                 160

Leu Leu His Ser Asn Gly Tyr Asn Tyr Leu Asp Trp Tyr Leu Gln Lys
            165                 170                 175

Pro Gly Gln Ser Pro Gln Leu Leu Ile Tyr Leu Gly Ser Asn Arg Ala
            180                 185                 190

Ser Gly Val Pro Asp Arg Phe Ser Gly Ser Gly Ser Gly Thr Asp Phe
            195                 200                 205

Thr Leu Lys Ile Ser Arg Val Glu Ala Glu Asp Val Gly Val Tyr Tyr
210                 215                 220

Cys Met Gln Ala Leu Gln Thr Pro Tyr Thr Phe Gly Gly Gly Thr Lys
225                 230                 235                 240

Val Glu Ile Lys

<210> SEQ ID NO 190
<211> LENGTH: 243
<212> TYPE: PRT
<213> ORGANISM: Homo sapiens

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
            85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Arg Ala Ser Gly
        115                 120                 125

Gly Gly Gly Ser Asp Ile Val Met Thr Gln Thr Pro Leu Ser Leu Ser
        130                 135                 140

Val Thr Pro Gly Gln Pro Ala Ser Ile Ser Cys Lys Ser Ser Gln Ser
145                 150                 155                 160

Leu Leu Arg Asn Asp Gly Lys Thr Pro Leu Tyr Trp Tyr Leu Gln Lys
            165                 170                 175

Ala Gly Gln Pro Pro Gln Leu Leu Ile Tyr Glu Val Ser Asn Arg Phe
            180                 185                 190

Ser Gly Val Pro Asp Arg Phe Ser Gly Ser Gly Ser Gly Thr Asp Phe
            195                 200                 205

Thr Leu Lys Ile Ser Arg Val Glu Ala Glu Asp Val Gly Ala Tyr Tyr
210                 215                 220

Cys Met Gln Asn Ile Gln Phe Pro Ser Phe Gly Gly Gly Thr Lys Leu
225                 230                 235                 240

Glu Ile Lys

<210> SEQ ID NO 191
<211> LENGTH: 249
<212> TYPE: PRT
<213> ORGANISM: Homo sapiens

<400> SEQUENCE: 191

Gln Val Gln Leu Val Gln Ser Gly Ala Glu Val Arg Lys Thr Gly Ala
1               5                   10                  15

Ser Val Lys Val Ser Cys Lys Ala Ser Gly Tyr Ile Phe Asp Asn Phe
                20                  25                  30

Gly Ile Asn Trp Val Arg Gln Ala Pro Gly Gln Gly Leu Glu Trp Met
            35                  40                  45

Gly Trp Ile Asn Pro Lys Asn Asn Thr Asn Tyr Ala Gln Lys Phe
    50                  55                  60

Gln Gly Arg Val Thr Ile Thr Ala Asp Glu Ser Thr Asn Thr Ala Tyr
65              70                  75                  80

Met Glu Val Ser Ser Leu Arg Ser Glu Asp Thr Ala Val Tyr Tyr Cys
                85                  90                  95

Ala Arg Gly Pro Tyr Tyr Tyr Gln Ser Tyr Met Asp Val Trp Gly Gln
                100                 105                 110

Gly Thr Met Val Thr Val Ser Ser Ala Ser Gly Gly Gly Gly Ser Gly
            115                 120                 125

Gly Arg Ala Ser Gly Gly Gly Ser Asp Ile Val Met Thr Gln Thr
    130                 135                 140

Pro Leu Ser Leu Pro Val Thr Pro Gly Glu Pro Ala Ser Ile Ser Cys
145                 150                 155                 160

Arg Ser Ser Gln Ser Leu Leu His Ser Asn Gly Tyr Asn Tyr Leu Asn
                165                 170                 175

Trp Tyr Leu Gln Lys Pro Gly Gln Ser Pro Gln Leu Leu Ile Tyr Leu
            180                 185                 190

Gly Ser Lys Arg Ala Ser Gly Val Pro Asp Arg Phe Ser Gly Ser Gly
        195                 200                 205

Ser Gly Thr Asp Phe Thr Leu His Ile Thr Arg Val Gly Ala Glu Asp
    210                 215                 220

Val Gly Val Tyr Tyr Cys Met Gln Ala Leu Gln Thr Pro Tyr Thr Phe
225                 230                 235                 240

Gly Gln Gly Thr Lys Leu Glu Ile Lys
                245

<210> SEQ ID NO 192
<211> LENGTH: 246
<212> TYPE: PRT
<213> ORGANISM: Homo sapiens

<400> SEQUENCE: 192

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
                20                  25                  30

Ala Met Thr Trp Val Arg Gln Ala Pro Gly Lys Gly Leu Glu Trp Val
            35                  40                  45

Ser Val Ile Ser Gly Ser Gly Gly Thr Thr Tyr Tyr Ala Asp Ser Val

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asp Ser Ser Gly Tyr Tyr Tyr Ala Arg Gly Pro Arg Tyr
            100                 105                 110

Trp Gly Gln Gly Thr Leu Val Thr Val Ser Ser Ala Ser Gly Gly Gly
        115                 120                 125

Gly Ser Gly Gly Arg Ala Ser Gly Gly Gly Ser Asp Ile Gln Leu
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Ser Ile Ser Ser Tyr Leu Asn Trp Tyr
            165                 170                 175

Gln Gln Lys Pro Gly Lys Ala Pro Lys Leu Leu Ile Tyr Gly Ala Ser
            180                 185                 190

Thr Leu Ala Ser Gly Val Pro Ala Arg Phe Ser Gly Ser Gly Ser Gly
        195                 200                 205

Thr His Phe Thr Leu Thr Ile Asn Ser Leu Gln Ser Glu Asp Ser Ala
        210                 215                 220

Thr Tyr Tyr Cys Gln Gln Ser Tyr Lys Arg Ala Ser Phe Gly Gln Gly
225                 230                 235                 240

Thr Lys Val Glu Ile Lys
            245

<210> SEQ ID NO 193
<211> LENGTH: 247
<212> TYPE: PRT
<213> ORGANISM: Homo sapiens

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Tyr Tyr Tyr Tyr Met Asp Val Trp Gly Lys Gly Thr
            100                 105                 110

Met Val Thr Val Ser Ser Ala Ser Gly Gly Gly Gly Ser Gly Gly Arg
        115                 120                 125

Ala Ser Gly Gly Gly Gly Ser Glu Ile Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu Tyr Ser Asn Gly Tyr Asn Tyr Val Asp Trp Tyr
                165                 170                 175

Leu Gln Lys Pro Gly Gln Ser Pro Gln Leu Ile Tyr Leu Gly Ser
            180                 185                 190

Asn Arg Ala Ser Gly Val Pro Asp Arg Phe Ser Gly Ser Gly Ser Gly
        195                 200                 205

Thr Asp Phe Lys Leu Gln Ile Ser Arg Val Glu Ala Glu Asp Val Gly
210                 215                 220

Ile Tyr Tyr Cys Met Gln Gly Arg Gln Phe Pro Tyr Ser Phe Gly Gln
225                 230                 235                 240

Gly Thr Lys Val Glu Ile Lys
            245

<210> SEQ ID NO 194
<211> LENGTH: 238
<212> TYPE: PRT
<213> ORGANISM: Homo sapiens

<400> SEQUENCE: 194

Glu Val Gln Leu Leu Glu Thr Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Ala Pro Gly Lys Gly Leu Glu Trp Val
        35                  40                  45

Ser Gly Ile Val Tyr Ser Gly Ser Thr Tyr Tyr Ala Ala Ser Val Lys
50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
            85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
            115                 120                 125

Gly Gly Gly Ser Glu Ile Val Leu Thr Gln Ser Pro Ala Thr Leu Ser
130                 135                 140

Val Ser Pro Gly Glu Ser Ala Thr Leu Ser Cys Arg Ala Ser Gln Ser
145                 150                 155                 160

Val Ser Ser Asn Leu Ala Trp Tyr Gln Gln Lys Pro Gly Gln Ala Pro
            165                 170                 175

Arg Leu Leu Ile Tyr Gly Ala Ser Thr Arg Ala Ser Gly Ile Pro Asp
            180                 185                 190

Arg Phe Ser Gly Ser Gly Ser Gly Thr Asp Phe Thr Leu Thr Ile Ser
        195                 200                 205

Ser Leu Gln Ala Glu Asp Val Ala Val Tyr Tyr Cys Gln Gln Tyr Gly
210                 215                 220

Ser Ser Leu Thr Phe Gly Gly Gly Thr Lys Val Glu Ile Lys
225                 230                 235

<210> SEQ ID NO 195
<211> LENGTH: 239
<212> TYPE: PRT
<213> ORGANISM: Homo sapiens

<400> SEQUENCE: 195

Glu Val Gln Leu Val Glu Thr Gly Gly Gly Leu Val Gln Pro Gly Gly
1               5                   10                  15

```
Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
 50                  55                  60

Gly Arg Phe Thr Ile Ser Arg Asp Asn Ser Arg Asn Thr Leu Tyr Leu
 65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Glu Ile Val Met Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Ser Ser Lys Leu Ala Trp Tyr Gln Gln Lys Pro Gly Gln Ala Pro
                165                 170                 175

Arg Leu Leu Met Tyr Gly Ala Ser Ile Arg Ala Thr Gly Ile Pro Asp
            180                 185                 190

Arg Phe Ser Gly Ser Gly Ser Gly Thr Glu Phe Thr Leu Thr Ile Ser
        195                 200                 205

Ser Leu Glu Pro Glu Asp Phe Ala Val Tyr Tyr Cys Gln Gln Tyr Gly
    210                 215                 220

Ser Ser Ser Trp Thr Phe Gly Gln Gly Thr Lys Val Glu Ile Lys
225                 230                 235

<210> SEQ ID NO 196
<211> LENGTH: 241
<212> TYPE: PRT
<213> ORGANISM: Homo sapiens

<400> SEQUENCE: 196

Glu Val Gln Leu Val Glu Thr Gly Gly Gly Val Val Gln Pro Gly Gly
 1               5                  10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
 50                  55                  60

Gly Arg Phe Thr Ile Ser Arg Asp Asn Ser Arg Asn Thr Leu Tyr Leu
 65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160
```

-continued

Val Gly Ser Thr Asn Leu Ala Trp Tyr Gln Gln Lys Pro Gly Gln Ala
            165                 170                 175

Pro Arg Leu Leu Ile Tyr Asp Ala Ser Asn Arg Ala Thr Gly Ile Pro
            180                 185                 190

Asp Arg Phe Ser Gly Gly Ser Gly Thr Asp Phe Thr Leu Thr Ile
            195                 200                 205

Ser Arg Leu Glu Pro Glu Asp Phe Ala Val Tyr Tyr Cys Gln Gln Tyr
210                 215                 220

Gly Ser Ser Pro Pro Trp Thr Phe Gly Gln Gly Thr Lys Val Glu Ile
225                 230                 235                 240

Lys

<210> SEQ ID NO 197
<211> LENGTH: 239
<212> TYPE: PRT
<213> ORGANISM: Homo sapiens

<400> SEQUENCE: 197

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Gly Asp Gly Met Asp Val Trp Gly Gln Gly Thr Thr
            100                 105                 110

Val Thr Val Ser Ser Ala Ser Gly Gly Gly Gly Ser Gly Arg Ala
            115                 120                 125

Ser Gly Gly Gly Gly Ser Asp Ile Gln Met Thr Gln Ser Pro Ser Ser
130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
            165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
            210                 215                 220

Ser Tyr Thr Leu Ala Phe Gly Gln Gly Thr Lys Val Asp Ile Lys
225                 230                 235

<210> SEQ ID NO 198
<211> LENGTH: 239
<212> TYPE: PRT
<213> ORGANISM: Homo sapiens

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
            85                  90                  95

Ala His Gly Gly Glu Ser Asp Val Trp Gly Gln Gly Thr Thr Val Thr
        100                 105                 110

Val Ser Ser Ala Ser Gly Gly Gly Ser Gly Gly Arg Ala Ser Gly
            115                 120                 125

Gly Gly Gly Ser Asp Ile Gln Leu Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
            165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
        210                 215                 220

Ser Thr Pro Tyr Thr Phe Gly Gln Gly Thr Lys Val Glu Ile Lys
225                 230                 235

<210> SEQ ID NO 199
<211> LENGTH: 246
<212> TYPE: PRT
<213> ORGANISM: Homo sapiens

<400> SEQUENCE: 199

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Ser Thr Met Val Arg Glu Asp Tyr Trp Gly Gln Gly Thr Leu
        100                 105                 110

Val Thr Val Ser Ser Ala Ser Gly Gly Gly Ser Gly Gly Arg Ala
            115                 120                 125

Ser Gly Gly Gly Gly Ser Asp Ile Val Leu Thr Gln Ser Pro Leu Ser
        130                 135                 140

```
Leu Pro Val Thr Leu Gly Gln Pro Ala Ser Ile Ser Cys Lys Ser Ser
145                 150                 155                 160

Glu Ser Leu Val His Asn Ser Gly Lys Thr Tyr Leu Asn Trp Phe His
            165                 170                 175

Gln Arg Pro Gly Gln Ser Pro Arg Arg Leu Ile Tyr Glu Val Ser Asn
        180                 185                 190

Arg Asp Ser Gly Val Pro Asp Arg Phe Thr Gly Ser Gly Ser Gly Thr
        195                 200                 205

Asp Phe Thr Leu Lys Ile Ser Arg Val Glu Ala Glu Asp Val Gly Val
        210                 215                 220

Tyr Tyr Cys Met Gln Gly Thr His Trp Pro Gly Thr Phe Gly Gln Gly
225                 230                 235                 240

Thr Lys Leu Glu Ile Lys
            245

<210> SEQ ID NO 200
<211> LENGTH: 239
<212> TYPE: PRT
<213> ORGANISM: Homo sapiens

<400> SEQUENCE: 200

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Asp Ile Arg Leu Thr Gln Ser Pro Ser Pro Leu Ser
    130                 135                 140

Ala Ser Val Gly Asp Arg Val Thr Ile Thr Cys Gln Ala Ser Glu Asp
145                 150                 155                 160

Ile Asn Lys Phe Leu Asn Trp Tyr His Gln Thr Pro Gly Lys Ala Pro
                165                 170                 175

Lys Leu Leu Ile Tyr Asp Ala Ser Thr Leu Gln Thr Gly Val Pro Ser
            180                 185                 190

Arg Phe Ser Gly Ser Gly Ser Gly Thr Asp Phe Thr Leu Thr Ile Asn
        195                 200                 205

Ser Leu Gln Pro Glu Asp Ile Gly Thr Tyr Tyr Cys Gln Gln Tyr Glu
    210                 215                 220

Ser Leu Pro Leu Thr Phe Gly Gly Gly Thr Lys Val Glu Ile Lys
225                 230                 235

<210> SEQ ID NO 201
<211> LENGTH: 240
<212> TYPE: PRT
```

<213> ORGANISM: Homo sapiens

<400> SEQUENCE: 201

Glu Val Gln Leu Val Glu Thr Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Ser Gly Gly Arg Ala Ser Gly
        115                 120                 125

Gly Gly Gly Ser Glu Thr Thr Leu Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Gly Ser Asn Leu Ala Trp Tyr Gln Gln Lys Pro Gly Gln Gly Pro
                165                 170                 175

Arg Leu Leu Ile Tyr Gly Ala Ser Thr Arg Ala Thr Gly Ile Pro Ala
            180                 185                 190

Arg Phe Ser Gly Ser Gly Ser Gly Thr Glu Phe Thr Leu Thr Ile Ser
        195                 200                 205

Ser Leu Gln Pro Glu Asp Phe Ala Val Tyr Tyr Cys Gln Gln Tyr Asn
    210                 215                 220

Asp Trp Leu Pro Val Thr Phe Gly Gln Gly Thr Lys Val Glu Ile Lys
225                 230                 235                 240

<210> SEQ ID NO 202
<211> LENGTH: 241
<212> TYPE: PRT
<213> ORGANISM: Homo sapiens

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly

```
            115                 120                 125
Gly Gly Gly Ser Glu Ile Val Leu Thr Gln Ser Pro Gly Thr Leu Ser
        130                 135                 140

Leu Ser Pro Gly Glu Arg Ala Thr Leu Ser Cys Arg Ala Ser Gln Ser
145                 150                 155                 160

Ile Gly Ser Ser Leu Ala Trp Tyr Gln Gln Lys Pro Gly Gln Ala
            165                 170                 175

Pro Arg Leu Leu Met Tyr Gly Ala Ser Ser Arg Ala Ser Gly Ile Pro
        180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Val Tyr Tyr Cys Gln Gln Tyr
        210                 215                 220

Ala Gly Ser Pro Pro Phe Thr Phe Gly Gln Gly Thr Lys Val Glu Ile
225                 230                 235                 240

Lys

<210> SEQ ID NO 203
<211> LENGTH: 243
<212> TYPE: PRT
<213> ORGANISM: Homo sapiens

<400> SEQUENCE: 203

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Ala Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
            85                  90                  95

Cys Ala Arg His Trp Gln Glu Trp Pro Asp Ala Phe Asp Ile Trp Gly
        100                 105                 110

Gln Gly Thr Met Val Thr Val Ser Ser Gly Gly Gly Gly Ser Gly Gly
            115                 120                 125

Gly Gly Ser Gly Gly Gly Gly Ser Glu Thr Thr Leu Thr Gln Ser Pro
        130                 135                 140

Ala Phe Met Ser Ala Thr Pro Gly Asp Lys Val Ile Ile Ser Cys Lys
145                 150                 155                 160

Ala Ser Gln Asp Ile Asp Asp Ala Met Asn Trp Tyr Gln Gln Lys Pro
            165                 170                 175

Gly Glu Ala Pro Leu Phe Ile Ile Gln Ser Ala Thr Ser Pro Val Pro
        180                 185                 190

Gly Ile Pro Pro Arg Phe Ser Gly Ser Gly Phe Gly Thr Asp Phe Ser
            195                 200                 205

Leu Thr Ile Asn Asn Ile Glu Ser Glu Asp Ala Ala Tyr Tyr Phe Cys
        210                 215                 220

Leu Gln His Asp Asn Phe Pro Leu Thr Phe Gly Gln Gly Thr Lys Leu
225                 230                 235                 240

Glu Ile Lys
```

<210> SEQ ID NO 204
<211> LENGTH: 244
<212> TYPE: PRT
<213> ORGANISM: Homo sapiens

<400> SEQUENCE: 204

Val Asn Leu Arg Glu Ser Gly Pro Ala Leu Val Lys Pro Thr Gln Thr
1               5                   10                  15

Leu Thr Leu Thr Cys Thr Phe Ser Gly Phe Ser Leu Arg Thr Ser Gly
                20                  25                  30

Met Cys Val Ser Trp Ile Arg Gln Pro Pro Gly Lys Ala Leu Glu Trp
            35                  40                  45

Leu Ala Arg Ile Asp Trp Asp Glu Asp Lys Phe Tyr Ser Thr Ser Leu
        50                  55                  60

Lys Thr Arg Leu Thr Ile Ser Lys Asp Thr Ser Asp Asn Gln Val Val
65                  70                  75                  80

Leu Arg Met Thr Asn Met Asp Pro Ala Asp Thr Ala Thr Tyr Tyr Cys
                85                  90                  95

Ala Arg Ser Gly Ala Gly Gly Thr Ser Ala Thr Ala Phe Asp Ile Trp
            100                 105                 110

Gly Pro Gly Thr Met Val Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Ile Tyr Asn Asn Leu Ala Trp Phe Gln Leu Lys
                165                 170                 175

Pro Gly Ser Ala Pro Arg Ser Leu Met Tyr Ala Ala Asn Lys Ser Gln
            180                 185                 190

Ser Gly Val Pro Ser Arg Phe Ser Gly Ser Ala Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln His Tyr Tyr Arg Phe Pro Tyr Ser Phe Gly Gln Gly Thr Lys
225                 230                 235                 240

Leu Glu Ile Lys

<210> SEQ ID NO 205
<211> LENGTH: 246
<212> TYPE: PRT
<213> ORGANISM: Homo sapiens

<400> SEQUENCE: 205

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                    85                  90                  95

Ala Lys Thr Ile Ala Ala Val Tyr Ala Phe Asp Ile Trp Gly Gln Gly
            100                 105                 110

Thr Thr Val Thr Val Ser Ser Gly Gly Gly Gly Ser Gly Gly Gly Gly
            115                 120                 125

Ser Gly Gly Gly Gly Ser Glu Ile Val Leu Thr Gln Ser Pro Leu Ser
130                 135                 140

Leu Pro Val Thr Pro Glu Glu Pro Ala Ser Ile Ser Cys Arg Ser Ser
145                 150                 155                 160

Gln Ser Leu Leu His Ser Asn Gly Tyr Asn Tyr Leu Asp Trp Tyr Leu
                165                 170                 175

Gln Lys Pro Gly Gln Ser Pro Gln Leu Leu Ile Tyr Leu Gly Ser Asn
            180                 185                 190

Arg Ala Ser Gly Val Pro Asp Arg Phe Ser Gly Ser Gly Ser Gly Thr
                195                 200                 205

Asp Phe Thr Leu Lys Ile Ser Arg Val Glu Ala Glu Asp Val Gly Val
210                 215                 220

Tyr Tyr Cys Met Gln Ala Leu Gln Thr Pro Tyr Thr Phe Gly Gln Gly
225                 230                 235                 240

Thr Lys Leu Glu Ile Lys
                245

<210> SEQ ID NO 206
<211> LENGTH: 240
<212> TYPE: PRT
<213> ORGANISM: Homo sapiens

<400> SEQUENCE: 206

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Gly Ala Phe Asp Ile Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Ser Ser Tyr Val Leu Thr Gln Ser Pro Ser Val Ser Ala
130                 135                 140

Ala Pro Gly Tyr Thr Ala Thr Ile Ser Cys Gly Gly Asn Asn Ile Gly
145                 150                 155                 160

Thr Lys Ser Val His Trp Tyr Gln Gln Lys Pro Gly Gln Ala Pro Leu
                165                 170                 175

Leu Val Ile Arg Asp Asp Ser Val Arg Pro Ser Lys Ile Pro Gly Arg
            180                 185                 190

Phe Ser Gly Ser Asn Ser Gly Asn Met Ala Thr Leu Thr Ile Ser Gly
        195                 200                 205
```

-continued

Val Gln Ala Gly Asp Glu Ala Asp Phe Tyr Cys Gln Val Trp Asp Ser
    210                 215                 220

Asp Ser Glu His Val Val Phe Gly Gly Gly Thr Lys Leu Thr Val Leu
225                 230                 235                 240

<210> SEQ ID NO 207
<211> LENGTH: 241
<212> TYPE: PRT
<213> ORGANISM: Homo sapiens

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Pro Ser Gly Tyr Thr Val Thr Ser His
            20                  25                  30

Tyr Ile His Trp Val Arg Arg Ala Pro Gly Gln Gly Leu Glu Trp Met
        35                  40                  45

Gly Met Ile Asn Pro Ser Gly Val Thr Ala Tyr Ser Gln Thr Leu
    50                  55                  60

Gln Gly Arg Val Thr Met Thr Ser Asp Thr Ser Ser Ser Thr Val Tyr
65                  70                  75                  80

Met Glu Leu Ser Ser Leu Arg Ser Glu Asp Thr Ala Met Tyr Tyr Cys
                85                  90                  95

Ala Arg Glu Gly Ser Gly Ser Gly Trp Tyr Phe Asp Phe Trp Gly Arg
            100                 105                 110

Gly Thr Leu Val Thr Val Ser Gly Gly Gly Gly Ser Gly Gly Gly
        115                 120                 125

Gly Ser Gly Gly Gly Gly Ser Ser Tyr Val Leu Thr Gln Pro Pro Ser
    130                 135                 140

Val Ser Val Ser Pro Gly Gln Thr Ala Ser Ile Thr Cys Ser Gly Asp
145                 150                 155                 160

Gly Leu Ser Lys Lys Tyr Val Ser Trp Tyr Gln Gln Lys Ala Gly Gln
                165                 170                 175

Ser Pro Val Val Leu Ile Ser Arg Asp Lys Glu Arg Pro Ser Gly Ile
            180                 185                 190

Pro Asp Arg Phe Ser Gly Ser Asn Ser Ala Asp Thr Ala Thr Leu Thr
        195                 200                 205

Ile Ser Gly Thr Gln Ala Met Asp Glu Ala Asp Tyr Tyr Cys Gln Ala
    210                 215                 220

Trp Asp Asp Thr Thr Val Val Phe Gly Gly Gly Thr Lys Leu Thr Val
225                 230                 235                 240

Leu

<210> SEQ ID NO 208
<211> LENGTH: 245
<212> TYPE: PRT
<213> ORGANISM: Homo sapiens

<400> SEQUENCE: 208

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

```
Trp Ile Gly Tyr Ile Tyr Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Gly Ile Ala Ala Arg Leu Arg Gly Ala Phe Asp Ile
            100                 105                 110

Trp Gly Gln Gly Thr Met Val Thr Val Ser Ser Gly Gly Gly Gly Ser
            115                 120                 125

Gly Gly Gly Gly Ser Gly Gly Gly Ser Asp Ile Val Met Thr Gln
    130                 135                 140

Ser Pro Ser Ser Val Ser Ala Ser Val Gly Asp Arg Val Ile Ile Thr
145                 150                 155                 160

Cys Arg Ala Ser Gln Gly Ile Arg Asn Trp Leu Ala Trp Tyr Gln Gln
                165                 170                 175

Lys Pro Gly Lys Ala Pro Asn Leu Leu Ile Tyr Ala Ala Ser Asn Leu
            180                 185                 190

Gln Ser Gly Val Pro Ser Arg Phe Ser Gly Ser Gly Ser Gly Ala Asp
            195                 200                 205

Phe Thr Leu Thr Ile Ser Ser Leu Gln Pro Glu Asp Val Ala Thr Tyr
            210                 215                 220

Tyr Cys Gln Lys Tyr Asn Ser Ala Pro Phe Thr Phe Gly Pro Gly Thr
225                 230                 235                 240

Lys Val Asp Ile Lys
                245

<210> SEQ ID NO 209
<211> LENGTH: 253
<212> TYPE: PRT
<213> ORGANISM: Homo sapiens

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

Ala Arg Arg Gly Gly Tyr Gln Leu Leu Arg Trp Asp Val Gly Leu Leu
            100                 105                 110

Arg Ser Ala Phe Asp Ile Trp Gly Gln Gly Thr Met Val Thr Val Ser
            115                 120                 125

Ser Gly Gly Gly Gly Ser Gly Gly Gly Gly Ser Gly Gly Gly Gly Ser
            130                 135                 140

Ser Tyr Val Leu Thr Gln Pro Pro Ser Val Ser Val Ala Pro Gly Gln
145                 150                 155                 160

Thr Ala Arg Ile Thr Cys Gly Gly Asn Asn Ile Gly Ser Lys Ser Val
                165                 170                 175
```

-continued

His Trp Tyr Gln Gln Lys Pro Gly Gln Ala Pro Val Leu Val Leu Tyr
            180                 185                 190

Gly Lys Asn Asn Arg Pro Ser Gly Val Pro Asp Arg Phe Ser Gly Ser
        195                 200                 205

Arg Ser Gly Thr Thr Ala Ser Leu Thr Ile Thr Gly Ala Gln Ala Glu
210                 215                 220

Asp Glu Ala Asp Tyr Tyr Cys Ser Ser Arg Asp Ser Ser Gly Asp His
225                 230                 235                 240

Leu Arg Val Phe Gly Thr Gly Thr Lys Val Thr Val Leu
                245                 250

<210> SEQ ID NO 210
<211> LENGTH: 248
<212> TYPE: PRT
<213> ORGANISM: Homo sapiens

<400> SEQUENCE: 210

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Ser Phe Tyr Ala
    50                  55                  60

Ile Ser Leu Lys Ser Arg Ile Ile Ile Asn Pro Asp Thr Ser Lys Asn
65                  70                  75                  80

Gln Phe Ser Leu Gln Leu Lys Ser Val Thr Pro Glu Asp Thr Ala Val
                85                  90                  95

Tyr Tyr Cys Ala Arg Ser Ser Pro Glu Gly Leu Phe Leu Tyr Trp Phe
            100                 105                 110

Asp Pro Trp Gly Gln Gly Thr Leu Val Thr Val Ser Ser Gly Gly Asp
        115                 120                 125

Gly Ser Gly Gly Gly Gly Ser Gly Gly Gly Ser Ser Ser Glu Leu
    130                 135                 140

Thr Gln Asp Pro Ala Val Ser Val Ala Leu Gly Gln Thr Ile Arg Ile
145                 150                 155                 160

Thr Cys Gln Gly Asp Ser Leu Gly Asn Tyr Tyr Ala Thr Trp Tyr Gln
                165                 170                 175

Gln Lys Pro Gly Gln Ala Pro Val Leu Val Ile Tyr Gly Thr Asn Asn
            180                 185                 190

Arg Pro Ser Gly Ile Pro Asp Arg Phe Ser Ala Ser Ser Ser Gly Asn
        195                 200                 205

Thr Ala Ser Leu Thr Ile Thr Gly Ala Gln Ala Glu Asp Glu Ala Asp
    210                 215                 220

Tyr Tyr Cys Asn Ser Arg Asp Ser Ser Gly His His Leu Leu Phe Gly
225                 230                 235                 240

Thr Gly Thr Lys Val Thr Val Leu
                245

<210> SEQ ID NO 211
<211> LENGTH: 246
<212> TYPE: PRT
<213> ORGANISM: Homo sapiens

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Glu Gly Ser Gly Ser Leu Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Met Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Ser Ser Ala Tyr Leu Ala Trp Tyr Gln Gln Lys Pro Gly Gln
                165                 170                 175

Pro Pro Arg Leu Leu Ile Ser Gly Ala Ser Thr Arg Ala Thr Gly Ile
            180                 185                 190

Pro Asp Arg Phe Gly Gly Ser Gly Ser Gly Thr Asp Phe Thr Leu Thr
            195                 200                 205

Ile Ser Arg Leu Glu Pro Glu Asp Phe Ala Val Tyr Tyr Cys Gln His
        210                 215                 220

Tyr Gly Ser Ser Phe Asn Gly Ser Ser Leu Phe Thr Phe Gly Gln Gly
225                 230                 235                 240

Thr Arg Leu Glu Ile Lys
            245

<210> SEQ ID NO 212
<211> LENGTH: 241
<212> TYPE: PRT
<213> ORGANISM: Homo sapiens

<400> SEQUENCE: 212

Glu Val Gln Leu Val Glu Thr Gly Gly Gly Leu Val Gln Pro Gly Gly
1               5                   10                  15

Ser Leu Arg Leu Ser Cys Ala Ala Ser Gly Ile Thr Phe Ser Arg Tyr
            20                  25                  30

Pro Met Ser Trp Val Arg Gln Ala Pro Gly Lys Gly Leu Glu Trp Val
        35                  40                  45

Ser Gly Ile Ser Asp Ser Gly Val Ser Thr Tyr Tyr Ala Asp Ser Ala
    50                  55                  60

Lys Gly Arg Phe Thr Ile Ser Arg Asp Asn Ser Lys Asn Thr Leu Phe
65                  70                  75                  80

Leu Gln Met Ser Ser Leu Arg Asp Glu Asp Thr Ala Val Tyr Tyr Cys
                85                  90                  95

Val Thr Arg Ala Gly Ser Glu Ala Ser Asp Ile Trp Gly Gln Gly Thr
            100                 105                 110

Met Val Thr Val Ser Ser Gly Gly Gly Gly Ser Gly Gly Gly Gly Ser

```
                    115                 120                 125
Gly Gly Gly Gly Ser Glu Ile Val Leu Thr Gln Ser Pro Ala Thr Leu
                130                 135                 140

Ser Leu Ser Pro Gly Glu Arg Ala Thr Leu Ser Cys Arg Ala Ser Gln
145                 150                 155                 160

Ser Val Ser Asn Ser Leu Ala Trp Tyr Gln Gln Lys Pro Gly Gln Ala
                165                 170                 175

Pro Arg Leu Leu Ile Tyr Asp Ala Ser Ser Arg Ala Thr Gly Ile Pro
                180                 185                 190

Asp Arg Phe Ser Gly Ser Gly Ser Gly Thr Asp Phe Thr Leu Thr Ile
                195                 200                 205

Ser Arg Leu Glu Pro Glu Asp Phe Ala Ile Tyr Tyr Cys Gln Gln Phe
        210                 215                 220

Gly Thr Ser Ser Gly Leu Thr Phe Gly Gly Gly Thr Lys Leu Glu Ile
225                 230                 235                 240

Lys

<210> SEQ ID NO 213
<211> LENGTH: 248
<212> TYPE: PRT
<213> ORGANISM: Homo sapiens

<400> SEQUENCE: 213

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Ala Thr Tyr Lys Arg Glu Leu Arg Tyr Tyr Gly Met Asp
            100                 105                 110

Val Trp Gly Gln Gly Thr Met Val Thr Val Ser Ser Gly Gly Gly Gly
        115                 120                 125

Ser Gly Gly Gly Gly Ser Gly Gly Gly Ser Glu Ile Val Met Thr
    130                 135                 140

Gln Ser Pro Gly Thr Val Ser Leu Ser Pro Gly Glu Arg Ala Thr Leu
145                 150                 155                 160

Ser Cys Arg Ala Ser Gln Ser Val Ser Ser Ser Phe Leu Ala Trp Tyr
                165                 170                 175

Gln Gln Lys Pro Gly Gln Ala Pro Arg Leu Leu Ile Tyr Gly Ala Ser
            180                 185                 190

Ser Arg Ala Thr Gly Ile Pro Asp Arg Phe Ser Gly Ser Gly Ser Gly
        195                 200                 205

Thr Asp Phe Thr Leu Thr Ile Ser Arg Leu Glu Pro Glu Asp Ser Ala
    210                 215                 220

Val Tyr Tyr Cys Gln Gln Tyr His Ser Ser Pro Ser Trp Thr Phe Gly
225                 230                 235                 240

Gln Gly Thr Arg Leu Glu Ile Lys
```

```
<210> SEQ ID NO 214
<211> LENGTH: 248
<212> TYPE: PRT
<213> ORGANISM: Homo sapiens

<400> SEQUENCE: 214
```

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Lys Ala Glu Asp Thr Ala Val Tyr Tyr Cys
                85                  90                  95

Ala Arg Ala Thr Tyr Lys Arg Glu Leu Arg Tyr Tyr Gly Met Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Ser Thr Leu Ser Leu Ser Pro Gly Glu Ser Ala Thr Leu
145                 150                 155                 160

Ser Cys Arg Ala Ser Gln Ser Val Ser Thr Thr Phe Leu Ala Trp Tyr
                165                 170                 175

Gln Gln Lys Pro Gly Gln Ala Pro Arg Leu Leu Ile Tyr Gly Ser Ser
            180                 185                 190

Asn Arg Ala Thr Gly Ile Pro Asp Arg Phe Ser Gly Ser Gly Ser Gly
        195                 200                 205

Thr Asp Phe Thr Leu Thr Ile Arg Arg Leu Glu Pro Glu Asp Phe Ala
    210                 215                 220

Val Tyr Tyr Cys Gln Gln Tyr His Ser Ser Pro Ser Trp Thr Phe Gly
225                 230                 235                 240

Gln Gly Thr Lys Val Glu Ile Lys
                245

```
<210> SEQ ID NO 215
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 215
```

Glu Val Gln Leu Val Glu Thr Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Gly Lys Ala Val Pro Asp Val Trp Gly Gln Gly Thr Thr
            100                 105                 110

Val Thr Val Ser Ser Gly Gly Gly Ser Gly Gly Gly Ser Gly
        115                 120                 125

Gly Gly Gly Ser Asp Ile Val Met Thr Gln Thr Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Ser Phe Gly Gln Gly Thr Arg Leu Glu Ile Lys
225                 230                 235

<210> SEQ ID NO 216
<211> LENGTH: 246
<212> TYPE: PRT
<213> ORGANISM: Homo sapiens

<400> SEQUENCE: 216

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Arg Pro Gly Lys Gly Leu Glu Trp Val
        35                  40                  45

Ala Ser Ile Asn Trp Lys Gly Asn Ser Leu Ala Tyr Gly Asp Ser Val
    50                  55                  60

Lys Gly Arg Phe Ala Ile Ser Arg Asp Asn Ala Lys Asn Thr Val Phe
65                  70                  75                  80

Leu Gln Met Asn Ser Leu Arg Thr Glu Asp Thr Ala Val Tyr Tyr Cys
                85                  90                  95

Ala Ser His Gln Gly Val Ala Tyr Tyr Asn Tyr Ala Met Asp Val Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
130                 135                 140

Pro Gly Thr Leu Ser Leu Ser Pro Gly Glu Arg Ala Thr Leu Ser Cys
145                 150                 155                 160

Arg Ala Thr Gln Ser Ile Gly Ser Ser Phe Leu Ala Trp Tyr Gln Gln
                165                 170                 175

Arg Pro Gly Gln Ala Pro Arg Leu Leu Ile Tyr Gly Ala Ser Gln Arg
            180                 185                 190

-continued

```
Ala Thr Gly Ile Pro Asp Arg Phe Ser Gly Arg Gly Ser Gly Thr Asp
            195                 200                 205

Phe Thr Leu Thr Ile Ser Arg Val Glu Pro Glu Asp Ser Ala Val Tyr
    210                 215                 220

Tyr Cys Gln His Tyr Glu Ser Ser Pro Ser Trp Thr Phe Gly Gln Gly
225                 230                 235                 240

Thr Lys Val Glu Ile Lys
                245

<210> SEQ ID NO 217
<211> LENGTH: 241
<212> TYPE: PRT
<213> ORGANISM: Homo sapiens

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Val Arg Asp Gly Met Asp Val Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ala Thr Leu Ser
    130                 135                 140

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Asn Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Ser Pro Pro Arg Phe Thr Phe Gly Pro Gly Thr Lys Val Asp Ile
225                 230                 235                 240

Lys

<210> SEQ ID NO 218
<211> LENGTH: 242
<212> TYPE: PRT
<213> ORGANISM: Homo sapiens

<400> SEQUENCE: 218

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Pro Gln Thr Gly Thr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln His
210                 215                 220

Tyr Gly Ser Ser Pro Ser Trp Thr Phe Gly Gln Gly Thr Arg Leu Glu
225                 230                 235                 240

Ile Lys

<210> SEQ ID NO 219
<211> LENGTH: 248
<212> TYPE: PRT
<213> ORGANISM: Homo sapiens

<400> SEQUENCE: 219

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Met Ser Arg Glu Asn Asp Lys Asn Ser Val Phe
65                  70                  75                  80

Leu Gln Met Asn Ser Leu Arg Val Glu Asp Thr Gly Val Tyr Tyr Cys
                85                  90                  95

Ala Arg Ala Asn Tyr Lys Arg Glu Leu Arg Tyr Tyr Tyr Gly Met Asp
            100                 105                 110

Val Trp Gly Gln Gly Thr Met Val Thr Val Ser Ser Gly Gly Gly Gly
        115                 120                 125

Ser Gly Gly Gly Gly Ser Gly Gly Gly Gly Ser Glu Ile Val Met Thr
    130                 135                 140

Gln Ser Pro Gly Thr Leu Ser Leu Ser Pro Gly Glu Ser Ala Thr Leu
145                 150                 155                 160

Ser Cys Arg Ala Ser Gln Arg Val Ala Ser Asn Tyr Leu Ala Trp Tyr
                165                 170                 175

Gln His Lys Pro Gly Gln Ala Pro Ser Leu Leu Ile Ser Gly Ala Ser
            180                 185                 190

Ser Arg Ala Thr Gly Val Pro Asp Arg Phe Ser Gly Ser Gly Ser Gly
        195                 200                 205

Thr Asp Phe Thr Leu Ala Ile Ser Arg Leu Glu Pro Glu Asp Ser Ala
    210                 215                 220

Val Tyr Tyr Cys Gln His Tyr Asp Ser Ser Pro Ser Trp Thr Phe Gly
225                 230                 235                 240

Gln Gly Thr Lys Val Glu Ile Lys
                245

<210> SEQ ID NO 220
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 220

Glu Val Gln Leu Leu Glu Thr Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Val Gly Ala Thr Gly Ala Phe Asp Ile Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Gly
    130                 135                 140

Thr Leu Ser Leu Ser Pro Gly Glu Arg Ala Thr Leu Ser Cys Arg Ala
145                 150                 155                 160

Ser Gln Ser Leu Ser Ser Asn Phe Leu Ala Trp Tyr Gln Gln Lys Pro
                165                 170                 175

Gly Gln Ala Pro Gly Leu Leu Ile Tyr Gly Ala Ser Asn Trp Ala Thr
            180                 185                 190

Gly Thr Pro Asp Arg Phe Ser Gly Ser Gly Ser Gly Thr Asp Phe Thr
        195                 200                 205

Leu Thr Ile Thr Arg Leu Glu Pro Glu Asp Phe Ala Val Tyr Tyr Cys
    210                 215                 220

Gln Tyr Tyr Gly Thr Ser Pro Met Tyr Thr Phe Gly Gln Gly Thr Lys
225                 230                 235                 240

Val Glu Ile Lys

<210> SEQ ID NO 221
<211> LENGTH: 244
<212> TYPE: PRT
<213> ORGANISM: Homo sapiens

<400> SEQUENCE: 221

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Trp Phe Gly Glu Gly Phe Asp Pro Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Leu Leu His Ser Asn Gly Tyr Asn Tyr Leu Asp Trp Tyr Leu Gln Lys
                165                 170                 175

Pro Gly Gln Ser Pro Gln Leu Leu Ile Tyr Leu Gly Ser Asn Arg Ala
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Met Gln Ala Leu Gln Thr Pro Leu Thr Phe Gly Gly Gly Thr Lys
225                 230                 235                 240

Val Asp Ile Lys

<210> SEQ ID NO 222
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Gly Tyr Asp Ser Ser Gly Tyr Tyr Arg Asp Tyr Tyr Gly
            100                 105                 110

Met Asp Val Trp Gly Gln Gly Thr Thr Val Thr Val Ser Ser Gly Gly
            115                 120                 125

Gly Gly Ser Gly Gly Gly Ser Gly Gly Gly Ser Glu Ile Val
        130                 135                 140

Leu Thr Gln Ser Pro Gly Thr Leu Ser Leu Ser Pro Gly Glu Arg Ala
145                 150                 155                 160

Thr Leu Ser Cys Arg Ala Ser Gln Ser Val Ser Ser Ser Tyr Leu Ala
                165                 170                 175

Trp Tyr Gln Gln Lys Pro Gly Gln Ala Pro Arg Leu Leu Ile Tyr Gly
            180                 185                 190

Thr Ser Ser Arg Ala Thr Gly Ile Ser Asp Arg Phe Ser Gly Ser Gly
            195                 200                 205

Ser Gly Thr Asp Phe Thr Leu Thr Ile Ser Arg Leu Glu Pro Glu Asp
        210                 215                 220

Phe Ala Val Tyr Tyr Cys Gln His Tyr Gly Asn Ser Pro Pro Lys Phe
225                 230                 235                 240

Thr Phe Gly Pro Gly Thr Lys Leu Glu Ile Lys
                245                 250

<210> SEQ ID NO 223
<211> LENGTH: 246
<212> TYPE: PRT
<213> ORGANISM: Homo sapiens

<400> SEQUENCE: 223

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Met Gly Trp Ser Ser Gly Tyr Leu Gly Ala Phe Asp Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Glu Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Val Ala Ser Ser Phe Leu Ala Trp Tyr Gln Gln
                165                 170                 175

Lys Pro Gly Gln Ala Pro Arg Leu Leu Ile Tyr Gly Ala Ser Gly Arg
```

```
                180                 185                 190
Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Phe Ala Val Tyr
    210                 215                 220

Tyr Cys Gln His Tyr Gly Gly Ser Pro Arg Leu Thr Phe Gly Gly Gly
225                 230                 235                 240

Thr Lys Val Asp Ile Lys
                245

<210> SEQ ID NO 224
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Ser Ala Ser Gln Asp Ile Ser Asn Tyr Leu Asn Trp
                165                 170                 175

Tyr Gln Gln Lys Pro Gly Lys Ala Pro Lys Leu Leu Ile Tyr Tyr Thr
            180                 185                 190

Ser Asn Leu His Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Arg Lys Leu Pro Trp Thr Phe Gly
225                 230                 235                 240

Gln Gly Thr Lys Leu Glu Ile Lys Arg
                245

<210> SEQ ID NO 225
<211> LENGTH: 249
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Gln Val Gln Leu Val Gln Ser Gly Ala Glu Val Lys Lys Pro Gly Ser
130                 135                 140

Ser Val Lys Val Ser Cys Lys Ala Ser Gly Gly Thr Phe Ser Asn Tyr
145                 150                 155                 160

Trp Met His Trp Val Arg Gln Ala Pro Gly Gln Gly Leu Glu Trp Met
            165                 170                 175

Gly Ala Thr Tyr Arg Gly His Ser Asp Thr Tyr Tyr Asn Gln Lys Phe
        180                 185                 190

Lys Gly Arg Val Thr Ile Thr Ala Asp Lys Ser Thr Ser Thr Ala Tyr
    195                 200                 205

Met Glu Leu Ser Ser Leu Arg Ser Glu Asp Thr Ala Val Tyr Tyr Cys
210                 215                 220

Ala Arg Gly Ala Ile Tyr Asn Gly Tyr Asp Val Leu Asp Asn Trp Gly
225                 230                 235                 240

Gln Gly Thr Leu Val Thr Val Ser Ser
                245

<210> SEQ ID NO 226
<211> LENGTH: 250
<212> TYPE: PRT
<213> ORGANISM: Homo sapiens

<400> SEQUENCE: 226

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

```
                85                  90                  95
Ala Arg Leu Gly Gly Ser Leu Pro Asp Tyr Gly Met Asp Val Trp Gly
                100                 105                 110

Gln Gly Thr Met Val Thr Val Ser Ser Ala Ser Gly Gly Gly Gly Ser
            115                 120                 125

Gly Gly Gly Gly Ser Gly Gly Gly Ser Glu Ile Val Leu Thr Gln
        130                 135                 140

Ser Pro Leu Ser Leu Pro Val Thr Pro Gly Glu Pro Ala Ser Ile Ser
145                 150                 155                 160

Cys Arg Ser Ser Gln Ser Leu Leu His Ser Asn Gly Tyr Asn Tyr Leu
                165                 170                 175

Asp Trp Tyr Leu Gln Lys Pro Gly Gln Ser Pro Gln Leu Leu Ile Tyr
            180                 185                 190

Leu Gly Ser Asn Arg Ala Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ala Leu Gln Thr Leu Ile Thr
225                 230                 235                 240

Phe Gly Gln Gly Thr Lys Val Asp Ile Lys
                245                 250

<210> SEQ ID NO 227
<211> LENGTH: 251
<212> TYPE: PRT
<213> ORGANISM: Homo sapiens

<400> SEQUENCE: 227

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Ile Phe Thr Asn Tyr
                20                  25                  30

Tyr Val His Trp Val Arg Gln Ala Pro Gly Gln Gly Leu Glu Trp Met
            35                  40                  45

Gly Ile Ile Ser Pro Ser Gly Ser Pro Thr Tyr Ala Gln Arg Leu
        50                  55                  60

Gln Gly Arg Val Thr Met Thr Arg Asp Leu Ser Thr Ser Thr Val Tyr
65                  70                  75                  80

Met Glu Leu Ser Ser Leu Thr Ser Glu Asp Thr Ala Val Tyr Phe Cys
                85                  90                  95

Ala Arg Glu Ser Arg Leu Arg Gly Asn Arg Leu Gly Leu Gln Ser Ser
                100                 105                 110

Ile Phe Asp His Trp Gly Gln Gly Thr Leu Val Thr Val Ser Ser Ala
            115                 120                 125

Ser Gly Gly Gly Gly Ser Gly Gly Gly Ser Gly Gly Gly Gly Ser
        130                 135                 140

Asp Ile Arg Met Thr Gln Ser Pro Pro Ser Leu Ser Ala Ser Val Gly
145                 150                 155                 160

Asp Arg Val Thr Ile Pro Cys Gln Ala Ser Gln Asp Ile Asn Asn His
                165                 170                 175

Leu Asn Trp Tyr Gln Gln Lys Pro Gly Lys Ala Pro Gln Leu Leu Ile
            180                 185                 190

Tyr Asp Thr Ser Asn Leu Glu Ile Gly Val Pro Ser Arg Phe Ser Gly
        195                 200                 205
```

```
Ser Gly Ser Gly Thr Asp Phe Thr Leu Thr Ile Ser Ser Leu Gln Pro
    210                 215                 220

Glu Asp Ile Ala Thr Tyr Tyr Cys Gln Gln Tyr Glu Asn Leu Pro Leu
225                 230                 235                 240

Thr Phe Gly Gly Gly Thr Lys Val Glu Ile Lys
                245                 250

<210> SEQ ID NO 228
<211> LENGTH: 249
<212> TYPE: PRT
<213> ORGANISM: Homo sapiens

<400> SEQUENCE: 228

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asp Thr Ile Arg Gly Pro Asn Tyr Tyr Tyr Gly Met
            100                 105                 110

Asp Val Trp Gly Gln Gly Thr Thr Val Thr Val Ser Ser Ala Ser Gly
        115                 120                 125

Gly Gly Gly Ser Gly Gly Gly Ser Gly Gly Gly Ser Glu Thr
    130                 135                 140

Thr Leu Thr Gln Ser Pro Ser Ser Val Ser Ala Ser Val Gly Asp Arg
145                 150                 155                 160

Val Ser Ile Thr Cys Arg Ala Ser Gln Asp Ile Asp Thr Trp Leu Ala
                165                 170                 175

Trp Tyr Gln Leu Lys Pro Gly Lys Ala Pro Lys Leu Leu Met Tyr Ala
            180                 185                 190

Ala Ser Asn Leu Gln Gly Val Pro Ser Arg Phe Ser Gly Ser Gly
        195                 200                 205

Ser Gly Thr Asp Phe Ile Leu Thr Ile Ser Ser Leu Gln Pro Glu Asp
    210                 215                 220

Phe Ala Thr Tyr Tyr Cys Gln Gln Ala Ser Ile Phe Pro Pro Thr Phe
225                 230                 235                 240

Gly Gly Gly Thr Lys Val Asp Ile Lys
                245

<210> SEQ ID NO 229
<211> LENGTH: 250
<212> TYPE: PRT
<213> ORGANISM: Homo sapiens

<400> SEQUENCE: 229

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Thr Thr Ala Tyr
 65                  70                  75                  80

Leu Gln Trp Ser Ser Leu Arg Ala Ser Asp Ser Ala Met Tyr Tyr Cys
                 85                  90                  95

Ala Arg Gly Gly Tyr Ser Asp Tyr Asp Tyr Tyr Phe Asp Phe Trp Gly
            100                 105                 110

Gln Gly Thr Leu Val Thr Val Ser Ser Ala Ser Gly Gly Gly Gly Ser
        115                 120                 125

Gly Gly Gly Gly Ser Gly Gly Gly Ser Glu Ile Val Met Thr Gln
    130                 135                 140

Ser Pro Leu Ser Leu Pro Val Thr Pro Gly Glu Pro Ala Ser Ile Ser
145                 150                 155                 160

Cys Arg Ser Ser Gln Ser Leu Leu His Ser Asn Gly Tyr Asn Tyr Leu
                165                 170                 175

Asp Trp Tyr Leu Gln Lys Pro Gly Gln Ser Pro Gln Leu Leu Ile Tyr
            180                 185                 190

Leu Gly Ser Asn Arg Ala Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ala Leu Gln Thr Pro Phe Thr
225                 230                 235                 240

Phe Gly Gly Gly Thr Lys Val Glu Ile Lys
                245                 250

<210> SEQ ID NO 230
<211> LENGTH: 240
<212> TYPE: PRT
<213> ORGANISM: Homo sapiens

<400> SEQUENCE: 230

Gln Val Gln Leu Val Gln Ser Gly Gly Asp Leu Ala Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Val Ile Trp Pro Asp Gly Gly Gln Lys Tyr Tyr Gly Asp Ser Val
 50                  55                  60

Lys Gly Arg Phe Thr Val Ser Arg Asp Asn Pro Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Val Arg His Phe Asn Ala Trp Asp Tyr Trp Gly Gln Gly Thr Leu Val
            100                 105                 110

Thr Val Ser Ser Ala Ser Gly Gly Gly Gly Ser Gly Gly Gly Gly Ser
        115                 120                 125

Gly Gly Gly Gly Ser Asp Ile Gln Leu Thr Gln Ser Pro Ser Ser Leu
    130                 135                 140

Ser Ala Tyr Val Gly Gly Arg Val Thr Ile Thr Cys Gln Ala Ser Gln
145                 150                 155                 160

-continued

Gly Ile Ser Gln Phe Leu Asn Trp Phe Gln Gln Lys Pro Lys Ala
       165         170         175

Pro Lys Leu Leu Ile Ser Asp Ala Ser Asn Leu Glu Pro Gly Val Pro
       180         185         190

Ser Arg Phe Ser Gly Ser Gly Ser Gly Thr Asp Phe Thr Phe Thr Ile
       195         200         205

Thr Asn Leu Gln Pro Glu Asp Ile Ala Thr Tyr Tyr Cys Gln Gln Tyr
   210         215         220

Asp Asp Leu Pro Leu Thr Phe Gly Gly Gly Thr Lys Val Glu Ile Lys
225         230         235        240

<210> SEQ ID NO 231
<211> LENGTH: 248
<212> TYPE: PRT
<213> ORGANISM: Homo sapiens

<400> SEQUENCE: 231

Gln Val Gln Leu Val Gln Ser Gly Gly Gly Val Val Gln Pro Gly Lys
1         5         10         15

Ser Leu Arg Leu Ser Cys Ala Ala Ser Gly Phe Thr Phe Ser Ile Phe
       20         25         30

Ala Met His Trp Val Arg Gln Ala Pro Gly Lys Gly Leu Glu Trp Val
     35         40         45

Ala Thr Ile Ser Tyr Asp Gly Ser Asn Ala Phe Tyr Ala Asp Ser Val
  50        55         60

Glu Gly Arg Phe Thr Ile Ser Arg Asp Asn Ser Lys Asp Ser Leu Tyr
65         70         75         80

Leu Gln Met Asp Ser Leu Arg Pro Glu Asp Thr Ala Val Tyr Tyr Cys
       85         90         95

Val Lys Ala Gly Asp Gly Gly Tyr Asp Val Phe Asp Ser Trp Gly Gln
      100         105         110

Gly Thr Leu Val Thr Val Ser Ser Ala Ser Gly Gly Gly Gly Ser Gly
     115         120         125

Gly Gly Gly Ser Gly Gly Gly Ser Glu Ile Val Met Thr Gln Ser
130         135         140

Pro Leu Ser Leu Pro Val Thr Pro Gly Glu Pro Ala Ser Ile Ser Cys
145         150         155         160

Arg Ser Ser Gln Ser Leu Leu His Ser Asn Gly Tyr Asn Tyr Leu Asp
       165         170         175

Trp Tyr Leu Gln Lys Pro Gly Gln Ser Pro Gln Leu Leu Ile Tyr Leu
       180         185         190

Gly Ser Asn Arg Ala Ser Gly Val Pro Asp Arg Phe Ser Gly Ser Gly
     195         200         205

Ser Gly Thr Asp Phe Thr Leu Lys Ile Ser Arg Val Glu Ala Glu Asp
  210        215         220

Val Gly Val Tyr Tyr Cys Met Gln Ala Leu Gln Thr Pro Thr Phe Gly
225         230         235         240

Pro Gly Thr Lys Val Asp Ile Lys
       245

<210> SEQ ID NO 232
<211> LENGTH: 245
<212> TYPE: PRT
<213> ORGANISM: Homo sapiens

<400> SEQUENCE: 232

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Glu Thr Asp Tyr Tyr Gly Ser Gly Thr Phe Asp Tyr Trp Gly
            100                 105                 110

Gln Gly Thr Leu Val Thr Val Ser Ser Ala Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Ser
145                 150                 155                 160

Cys Arg Ala Ser Gln Gly Ile Gly Ile Tyr Leu Ala Trp Tyr Gln Gln
                165                 170                 175

Arg Ser Gly Lys Pro Pro Gln Leu Leu Ile His Gly Ala Ser Thr Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Ser Tyr
    210                 215                 220

Trp Cys Gln Gln Ser Asn Asn Phe Pro Pro Thr Phe Gly Gln Gly Thr
225                 230                 235                 240

Lys Val Glu Ile Lys
            245

<210> SEQ ID NO 233
<211> LENGTH: 245
<212> TYPE: PRT
<213> ORGANISM: Homo sapiens

<400> SEQUENCE: 233

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Met Phe Thr Asp Phe
            20                  25                  30

Phe Ile His Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asn Thr Ser Ile Ser Thr Ala Tyr
65              70                  75                  80

Met Glu Leu Ser Ser Leu Arg Ser Glu Asp Thr Ala Val Tyr Tyr Cys
                85                  90                  95

Ala Thr Trp Tyr Ser Ser Gly Trp Tyr Gly Ile Ala Asn Ile Trp Gly
            100                 105                 110

Gln Gly Thr Met Val Thr Val Ser Ser Ala Ser Gly Gly Gly Gly Ser

```
            115                 120                 125
Gly Gly Gly Gly Ser Gly Gly Gly Ser Asp Ile Gln Leu Thr Gln
130                 135                 140

Ser Pro Ser Ser Leu Ser Ala Ser Val Gly Asp Arg Val Thr Ile Thr
145                 150                 155                 160

Cys Gln Ala Ser His Asp Ile Ser Asn Tyr Leu His Trp Tyr Gln Gln
                165                 170                 175

Lys Pro Gly Lys Ala Pro Lys Leu Leu Ile Tyr Asp Ala Ser Asn Leu
            180                 185                 190

Glu Thr Gly Val Pro Ser Arg Phe Thr Gly Ser Gly Ser Gly Thr Asp
        195                 200                 205

Phe Thr Leu Thr Ile Arg Ser Leu Gln Pro Glu Asp Val Ala Ala Tyr
    210                 215                 220

Tyr Cys Gln Gln Ser Asp Asp Leu Pro His Thr Phe Gly Gln Gly Thr
225                 230                 235                 240

Lys Val Asp Ile Lys
            245

<210> SEQ ID NO 234
<211> LENGTH: 244
<212> TYPE: PRT
<213> ORGANISM: Homo sapiens

<400> SEQUENCE: 234

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Pro Ser Ser Trp Gly Glu Phe Asp Tyr Trp Gly Gln
            100                 105                 110

Gly Thr Leu Val Thr Val Ser Ser Ala Ser Gly Gly Gly Gly Ser Gly
        115                 120                 125

Gly Gly Gly Ser Gly Gly Gly Ser Asp Ile Arg Leu Thr Gln Ser
130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Leu Thr Phe Gly Gly Gly Thr Lys
225                 230                 235                 240
```

Val Asp Ile Lys

<210> SEQ ID NO 235
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 235

Asn Ile Met Leu Thr Gln Ser Pro Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
            100                 105                 110

Arg Gly Gly Gly Gly Ser Gly Gly Gly Gly Ser Ser Gly Gly Gly Ser
        115                 120                 125

Gln Val Gln Leu Gln Gln Pro Gly Ala Glu Val Val Lys Pro Gly Ala
    130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
            180                 185                 190

Lys Gly Lys Ala Thr Leu Thr Ala Asp Lys Ser Ser Thr Thr Ala Tyr
        195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Ala Gly Thr
225                 230                 235                 240

Thr Val Thr Val Ser Ser
                245

<210> SEQ ID NO 236
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 236

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Gly Gly Gly Ser Gly Gly Gly Ser Gly Gly Gly Ser
            115                 120                 125

Gln Val Gln Leu Gln Gln Pro Gly Ala Glu Val Val Lys Pro Gly Ala
        130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
            180                 185                 190

Gln Gly Lys Ala Thr Leu Thr Ala Asp Lys Ser Ser Thr Thr Ala Tyr
        195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Gln Gly Thr
225                 230                 235                 240

Thr Val Thr Val Ser Ser
            245

<210> SEQ ID NO 237
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Gly Gly Gly Ser Gln Ile Val Leu Thr Gln Ser
            130             135             140

Pro Ser Ile Met Ser Val Ser Pro Gly Glu Lys Val Thr Ile Thr Cys
145                 150                 155                 160

Ser Ala Ser Ser Val Ser Tyr Met His Trp Phe Gln Gln Lys Pro
                165                 170                 175

Gly Thr Ser Pro Lys Leu Cys Ile Tyr Ser Thr Ser Asn Leu Ala Ser
            180                 185                 190

Gly Val Pro Ala Arg Phe Ser Gly Arg Gly Ser Gly Thr Ser Tyr Ser
                195                 200                 205

Leu Thr Ile Ser Arg Val Ala Ala Glu Asp Ala Ala Thr Tyr Tyr Cys
            210                 215                 220

Gln Gln Arg Ser Asn Tyr Pro Pro Trp Thr Phe Gly Gly Gly Thr Lys
225                 230                 235                 240

Leu Glu Ile Lys

<210> SEQ ID NO 238
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Gly Gly Gly Ser Gln Ile Val Leu Thr Gln Ser
            130             135             140

Pro Ala Ile Met Ser Ala Ser Pro Gly Glu Lys Val Thr Ile Thr Cys
145                 150                 155                 160

Ser Ala Ser Ser Val Ser Tyr Leu His Trp Phe Gln Gln Lys Pro
                165                 170                 175

Gly Thr Ser Pro Lys Leu Trp Val Tyr Ser Thr Ser Asn Leu Pro Ser
            180                 185                 190

Gly Val Pro Ala Arg Phe Gly Ser Gly Ser Gly Thr Ser Tyr Ser
                195                 200                 205

Leu Thr Ile Ser Arg Met Glu Ala Glu Asp Ala Ala Thr Tyr Tyr Cys
            210                 215                 220

Gln Gln Arg Ser Ile Tyr Pro Pro Trp Thr Phe Gly Gly Gly Thr Lys
225                 230                 235                 240

Leu Glu Ile Lys

<210> SEQ ID NO 239
<211> LENGTH: 244
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Ser Gly Gly Gly Gly Ser Gln Ile Val Leu Thr Gln Ser
    130                 135                 140

Pro Ser Ile Met Ser Val Ser Pro Gly Glu Lys Val Thr Ile Thr Cys
145                 150                 155                 160

Ser Ala Ser Ser Ser Val Ser Tyr Met His Trp Phe Gln Gln Lys Pro
                165                 170                 175

Gly Thr Ser Pro Lys Leu Gly Ile Tyr Ser Thr Ser Asn Leu Ala Ser
            180                 185                 190

Gly Val Pro Ala Arg Phe Ser Gly Arg Gly Ser Gly Thr Ser Tyr Ser
        195                 200                 205

Leu Thr Ile Ser Arg Val Ala Ala Glu Asp Ala Ala Thr Tyr Tyr Cys
    210                 215                 220

Gln Gln Arg Ser Asn Tyr Pro Pro Trp Thr Phe Gly Gly Gly Thr Lys
225                 230                 235                 240

Leu Glu Ile Lys

<210> SEQ ID NO 240
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

```
Thr Val Asn Trp Tyr Gln Gln Val Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Thr Lys Leu Thr Val Leu Gly Ser
                100                 105                 110

Arg Gly Gly Gly Gly Ser Gly Gly Gly Ser Gly Gly Gly Gly Ser
                115                 120                 125

Leu Glu Met Ala Gln Met Gln Leu Val Gln Ser Gly Ala Glu Val Lys
130                 135                 140

Glu Pro Gly Glu Ser Leu Arg Ile Ser Cys Lys Gly Ser Gly Tyr Ser
145                 150                 155                 160

Phe Thr Asn Phe Trp Ile Ser Trp Val Arg Gln Met Pro Gly Lys Gly
                165                 170                 175

Leu Glu Trp Met Gly Arg Val Asp Pro Gly Tyr Ser Tyr Ser Thr Tyr
                180                 185                 190

Ser Pro Ser Phe Gln Gly His Val Thr Ile Ser Ala Asp Lys Ser Thr
                195                 200                 205

Ser Thr Ala Tyr Leu Gln Trp Asn Ser Leu Lys Ala Ser Asp Thr Ala
210                 215                 220

Met Tyr Tyr Cys Ala Arg Val Gln Tyr Ser Gly Tyr Tyr Asp Trp Phe
225                 230                 235                 240

Asp Pro Trp Gly Gln Gly Thr Leu Val Thr Val Ser Ser
                245                 250

<210> SEQ ID NO 241
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

Gln Thr Val Val Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Tyr Val Tyr Trp Tyr Gln Gln Leu Pro Gly Thr Ala Pro Lys Leu Leu
            35                  40                  45

Ile Tyr Arg Ser Asn Gln Arg Pro Ser Gly Val Pro Asp Arg Phe Ser
 50                  55                  60

Gly Ser Lys Ser Gly Thr Ser Ala Ser Leu Ala Ile Ser Gly Pro Arg
 65                  70                  75                  80

Ser Val Asp Glu Ala Asp Tyr Tyr Cys Ala Ala Trp Asp Asp Ser Leu
                 85                  90                  95

Asn Gly Val Val Phe Gly Gly Thr Lys Leu Thr Val Leu Gly Ser
                100                 105                 110

Arg Gly Gly Gly Gly Ser Gly Gly Gly Ser Gly Gly Gly Ser Leu
                115                 120                 125
```

```
Glu Met Ala Gln Val Gln Leu Val Gln Ser Gly Ala Glu Val Lys Lys
            130                 135                 140

Pro Gly Ser Ser Val Lys Val Ser Cys Lys Ala Ser Gly Gly Thr Phe
145                 150                 155                 160

Ser Ser Tyr Ala Ile Ser Trp Val Arg Gln Ala Pro Gly Gln Gly Leu
                165                 170                 175

Glu Trp Met Gly Gly Ile Ile Pro Ile Phe Gly Thr Ala Asn Tyr Ala
            180                 185                 190

Gln Lys Phe Gln Gly Arg Val Thr Ile Thr Ala Asp Glu Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Arg Ile Pro Pro Tyr Tyr Gly Met Asp Val Trp
225                 230                 235                 240

Gly Gln Gly Thr Thr Val Thr Val Ser Ser
                245                 250

<210> SEQ ID NO 242
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Asp Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Gln Gln Ser Gly Pro Gly Leu Val Lys Pro Ser
    130                 135                 140

Gln Thr Leu Ser Leu Thr Cys Ala Ile Ser Gly Asp Ser Val Ser Ser
145                 150                 155                 160

Asn Ser Ala Ala Trp Asn Trp Ile Arg Gln Ser Pro Ser Arg Gly Leu
                165                 170                 175

Glu Trp Leu Gly Arg Thr Tyr Tyr Gly Ser Lys Trp Tyr Asn Asp Tyr
            180                 185                 190

Ala Val Ser Val Lys Ser Arg Ile Thr Ile Asn Pro Asp Thr Ser Lys
        195                 200                 205

Asn Gln Phe Ser Leu Gln Leu Asn Ser Val Thr Pro Glu Asp Thr Ala
    210                 215                 220

Val Tyr Tyr Cys Ala Arg Gly Arg Leu Gly Asp Ala Phe Asp Ile Trp
```

Gly Gln Gly Thr Met Val Thr Val Ser Ser
                245                 250

<210> SEQ ID NO 243
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Lys Trp
            20                  25                  30

Leu Ala Trp Tyr Gln Gln Arg Pro Gly Lys Ala Pro Gln Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Asn Ser Tyr Ala Thr
                85                  90                  95

Phe Gly Gln Gly Thr Lys Val Glu Ile Lys Arg Ser Arg Gly Gly Gly
            100                 105                 110

Gly Ser Gly Gly Gly Gly Ser Gly Gly Gly Gly Ser Leu Glu Met Ala
        115                 120                 125

Gln Val Gln Leu Val Gln Ser Gly Ala Glu Val Lys Lys Pro Gly Glu
    130                 135                 140

Ser Leu Lys Ile Ser Cys Lys Gly Ser Gly Tyr Asn Phe Ser Asn Lys
145                 150                 155                 160

Trp Ile Gly Trp Val Arg Gln Leu Pro Gly Arg Gly Leu Glu Trp Ile
                165                 170                 175

Ala Ile Ile Tyr Pro Gly Tyr Ser Asp Ile Thr Tyr Ser Pro Ser Phe
            180                 185                 190

Gln Gly Arg Val Thr Ile Ser Ala Asp Thr Ser Ile Asn Thr Ala Tyr
        195                 200                 205

Leu His Trp His Ser Leu Lys Ala Ser Asp Thr Ala Met Tyr Tyr Cys
    210                 215                 220

Val Arg His Thr Ala Leu Ala Gly Phe Asp Tyr Trp Gly Leu Gly Thr
225                 230                 235                 240

Leu Val Thr Val Ser Ser
                245

<210> SEQ ID NO 244
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Gln Ser Val Val Thr Gln Pro Pro Ser Val Ser Val Ala Pro Gly Lys
1               5                   10                  15

Thr Ala Arg Ile Thr Cys Gly Arg Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Ser Leu Glu Met Ala
        115                 120                 125

Glu Val Gln Leu Val Gln Ser Gly Gly Gly Val Val Arg Pro Gly Gly
        130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Arg Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Leu Tyr Tyr Cys
        210                 215                 220

Ala Arg Glu Arg Gly Tyr Gly Tyr His Asp Pro His Asp Tyr Trp Gly
225                 230                 235                 240

Gln Gly Thr Leu Val Thr Val Ser Ser
                245

<210> SEQ ID NO 245
<211> LENGTH: 251
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 245

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu Gly
            100                 105                 110

```
Ser Arg Gly Gly Gly Ser Gly Gly Gly Ser Gly Gly Gly
    115                 120                 125

Ser Leu Glu Met Ala Glu Val Gln Leu Val Glu Thr Gly Gly Gly Leu
    130                 135                 140

Leu Gln Pro Gly Gly Ser Leu Arg Leu Ser Cys Ala Ala Ser Gly Phe
145                 150                 155                 160

Ser Val Ser Gly Thr Tyr Met Gly Trp Val Arg Gln Ala Pro Gly Lys
                165                 170                 175

Gly Leu Glu Trp Val Ala Leu Leu Tyr Ser Gly Gly Thr Tyr His
                180                 185                 190

Pro Ala Ser Leu Gln Gly Arg Phe Ile Val Ser Arg Asp Ser Ser Lys
                195                 200                 205

Asn Met Val Tyr Leu Gln Met Asn Ser Leu Lys Ala Glu Asp Thr Ala
    210                 215                 220

Val Tyr Tyr Cys Ala Lys Gly Gly Ala Gly Gly His Phe Asp Ser
225                 230                 235                 240

Trp Gly Gln Gly Thr Leu Val Thr Val Ser Ser
                245                 250

<210> SEQ ID NO 246
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gln Ile Asp Pro Trp Gly Gln Glu Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Gln Leu Gln Ser Gly Val Pro Ser
                180                 185                 190

Arg Phe Ser Gly Ser Gly Ser Gly Thr Asp Phe Thr Leu Thr Ile Ser
                195                 200                 205

Ser Leu Gln Pro Glu Asp Phe Ala Thr Tyr Tyr Cys Gln Gln Gly Pro
```

```
                210                 215                 220
Gly Thr Pro Asn Thr Phe Gly Gln Gly Thr Lys Val Glu Ile Lys Arg
225                 230                 235                 240

Ala

<210> SEQ ID NO 247
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Gly Ser Thr Ser Gly Ser Gly Lys Pro Gly Ser Gly Glu Gly Ser Thr
1               5                   10                  15

Lys Gly

<210> SEQ ID NO 248
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr
            115

<210> SEQ ID NO 249
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 249

Glu Leu Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
```

```
                35                  40                  45

Tyr Ser Ala Thr Tyr Arg Asn Ser Gly Val Pro Asp Arg Phe Thr Gly
     50                  55                  60

Ser Gly Ser Gly Thr Asp Phe Thr Leu Thr Ile Thr Asn Val Gln Ser
 65                  70                  75                  80

Lys Asp Leu Ala Asp Tyr Phe Cys Gln Tyr Asn Arg Tyr Pro
                 85                  90                  95

Tyr Thr Ser Gly Gly Gly Thr Lys Leu Glu Ile Lys Arg Arg Ser
            100                 105                 110
```

<210> SEQ ID NO 250
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

```
Leu Pro Glu Thr Gly Gly Gly Lys
 1               5
```

<210> SEQ ID NO 251
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 251

```
Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 252
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

```
Ile Leu Trp His Glu Met Trp His Glu Gly Leu Ile Glu Ala Ser Arg
 1               5                  10                  15

Leu Tyr Phe Gly Glu Arg Asn Val Lys Gly Met Phe Glu Val Leu Glu
             20                  25                  30
```

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 253
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 254
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
            35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 255
<211> LENGTH: 95
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 255

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95

<210> SEQ ID NO 256
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95

<210> SEQ ID NO 257
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30
```

```
Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
            85                  90                  95

<210> SEQ ID NO 258
<211> LENGTH: 1132
<212> TYPE: PRT
<213> ORGANISM: Homo sapiens

<400> SEQUENCE: 258

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
 50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
            85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
```

-continued

```
305                 310                 315                 320
Cys Pro Pro Val Ala Glu Thr Lys His Phe Leu Tyr Ser Ser Gly
                325                 330                 335
Asp Lys Glu Gln Leu Arg Pro Ser Phe Leu Ser Ser Leu Arg Pro
                340                 345                 350
Ser Leu Thr Gly Ala Arg Arg Leu Val Glu Thr Ile Phe Leu Gly Ser
                355                 360                 365
Arg Pro Trp Met Pro Gly Thr Pro Arg Arg Leu Pro Arg Leu Pro Gln
370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
Gly Ser Val Ala Ala Pro Glu Glu Asp Thr Asp Pro Arg Arg Leu
                435                 440                 445
Val Gln Leu Leu Arg Gln His Ser Ser Pro Trp Gln Val Tyr Gly Phe
                450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
                500                 505                 510
Ser Val Arg Gly Cys Ala Trp Leu Arg Arg Ser Pro Gly Val Gly Cys
                515                 520                 525
Val Pro Ala Ala Glu His Arg Leu Arg Glu Glu Ile Leu Ala Lys Phe
                530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
                580                 585                 590
Leu Lys Arg Val Gln Leu Arg Glu Leu Ser Glu Ala Glu Val Arg Gln
                595                 600                 605
His Arg Glu Ala Arg Pro Ala Leu Leu Thr Ser Arg Leu Arg Phe Ile
610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
                660                 665                 670
Pro Gly Leu Leu Gly Ala Ser Val Leu Gly Leu Asp Asp Ile His Arg
                675                 680                 685
Ala Trp Arg Thr Phe Val Leu Arg Val Arg Ala Gln Asp Pro Pro
                690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
```

-continued

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gly Ile Pro
            820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 259
<211> LENGTH: 4027
<212> TYPE: DNA
<213> ORGANISM: Homo sapiens

<400> SEQUENCE: 259

| | |
|---|---|
| caggcagcgt ggtcctgctg cgcacgtggg aagccctggc cccggccacc cccgcgatgc | 60 |
| cgcgcgctcc ccgctgccga gccgtgcgct ccctgctgcg cagccactac cgcgaggtgc | 120 |
| tgccgctggc cacgttcgtg cggcgcctgg ggccccaggg ctggcggctg gtgcagcgcg | 180 |
| gggaccggc ggctttccgc cgcgctggtgg cccagtgcct ggtgtgcgtg ccctgggacg | 240 |
| cacggccgcc ccccgccgcc ccctccttcc gccaggtgtc ctgcctgaag gagctggtgg | 300 |
| cccgagtgct gcagaggctg tgcgagcgcg gcgcgaagaa cgtgctggcc ttcggcttcg | 360 |
| cgctgctgga cggggcccgc gggggccccc ccgaggcctt caccaccagc gtgcgcagct | 420 |
| acctgcccaa cacggtgacc gacgcactgc ggggagcgg ggcgtggggg ctgctgttgc | 480 |
| gccgcgtggg cgacgacgtg ctggttcacc tgctggcacg ctgcgcgctc tttgtgctgg | 540 |
| tggctcccag ctgcgcctac caggtgtgcg ggccgccgct gtaccagctc ggcgctgcca | 600 |
| ctcaggcccg gcccccgcca cacgctagtg daccccgaag cgtctggga tgcgaacggg | 660 |
| cctggaacca tagcgtcagg gaggccgggg tcccctggg cctgccagcc ccgggtgcga | 720 |
| ggaggcgcg gggcagtgcc agccgaagtc tgccgttgcc caagaggccc aggcgtggcg | 780 |
| ctgcccctga gccggagcgg acgcccgttg ggcaggggtc ctgggcccac ccgggcagga | 840 |
| cgcgtggacc gagtgaccgt ggtttctgtg tggtgtcacc tgccagaccc gccgaagaag | 900 |
| ccacctcttt ggagggtgcg ctctctggca cgcgccactc ccacccatcc gtgggccgcc | 960 |
| agcaccacgc gggcccccca tccacatcgc ggccaccacg tccctgggac acgccttgtc | 1020 |
| ccccggtgta cgccgagacc aagcacttcc tctactcctc aggcgacaag gagcagctgc | 1080 |
| ggccctcctt cctactcagc tctctgaggc ccagcctgac tggcgctcgg aggctcgtgg | 1140 |
| agaccatctt tctgggttcc aggccctgga tgccagggac tccccgcagg ttgccccgcc | 1200 |
| tgccccagcg ctactggcaa atgcggcccc tgtttctgga gctgcttggg aaccacgcgc | 1260 |
| agtgcccta cggggtgctc ctcaagacgc actgcccgct gcgagctgcg gtcacccag | 1320 |
| cagccggtgt ctgtgcccgg gagaagcccc agggctctgt ggcggcccc gaggaggagg | 1380 |
| acacagaccc ccgtcgcctg gtgcagctgc tccgccagca cagcagcccc tggcaggtgt | 1440 |
| acggcttcgt gcgggcctgc ctgcgccggc tggtgccccc aggcctctgg ggctccaggc | 1500 |
| acaacgaacg ccgcttcctc aggaacacca agaagttcat ctccctgggg aagcatgcca | 1560 |
| agctctcgct gcaggagctg acgtggaaga tgagcgtgcg gggctgcgct tggctgcgca | 1620 |
| ggagcccagg ggttggctgt gttccggccg cagagcaccg tctgcgtgag gagatcctgg | 1680 |
| ccaagttcct gcactggctg atgagtgtgt acgtcgtcga gctgctcagg tctttcttt | 1740 |
| atgtcacgga gaccacgttt caaaagaaca ggctcttttt ctaccggaag agtgtctgga | 1800 |
| gcaagttgca aagcattgga atcagacagc acttgaagag ggtgcagctg cgggagctgt | 1860 |
| cggaagcaga ggtcaggcag catcgggaag ccaggcccgc cctgctgacg tccagactcc | 1920 |
| gcttcatccc caagcctgac gggctgcggc cgattgtgaa catggactac gtcgtgggag | 1980 |
| ccagaacgtt ccgcagagaa aagagggccg agcgtctcac ctcgagggtg aaggcactgt | 2040 |
| tcagcgtgct caactacgag cgggcgcggc gccccgcct cctgggcgcc tctgtgctgg | 2100 |
| gcctggacga tatccacagg gcctggcgca ccttcgtgct gcgtgtgcgg gcccaggacc | 2160 |

```
cgccgcctga gctgtacttt gtcaaggtgg atgtgacggg cgcgtacgac accatccccc    2220
aggacaggct cacggaggtc atcgccagca tcatcaaacc ccagaacacg tactgcgtgc    2280
gtcggtatgc cgtggtccag aaggccgccc atgggcacgt ccgcaaggcc ttcaagagcc    2340
acgtctctac cttgacagac ctccagccgt acatgcgaca gttcgtggct cacctgcagg    2400
agaccagccc gctgagggat gccgtcgtca tcgagcagag ctcctccctg aatgaggcca    2460
gcagtggcct cttcgacgtc ttcctacgct tcatgtgcca ccacgccgtg cgcatcaggg    2520
gcaagtccta cgtccagtgc caggggatcc cgcagggctc catcctctcc acgctgctct    2580
gcagcctgtg ctacgcgac atggagaaca agctgtttgc ggggattcgg cgggacgggc     2640
tgctcctgcg tttggtggat gatttcttgt tggtgacacc tcacctcacc cacgcgaaaa    2700
ccttcctcag gaccctggtc cgaggtgtcc ctgagtatgg ctgcgtggtg aacttgcgga    2760
agacagtggt gaacttccct gtagaagacg aggccctggg tggcacggct tttgttcaga    2820
tgccggccca cggcctattc ccctggtgcg gcctgctgct ggatacccgg accctggagg    2880
tgcagagcga ctactccagc tatgcccgga cctccatcag agccagtctc accttcaacc    2940
gcggcttcaa ggctggggagg aacatgcgtc gcaaactctt tggggtcttg cggctgaagt    3000
gtcacagcct gtttctggat ttgcaggtga acagcctcca gacggtgtgc accaacatct    3060
acaagatcct cctgctgcag gcgtacaggt ttcacgcatg tgtgctgcag ctcccatttc    3120
atcagcaagt ttggaagaac cccacatttt tcctgcgcgt catctctgac acggcctccc    3180
tctgctactc catcctgaaa gccaagaacg cagggatgtc gctgggggcc aagggcgccg    3240
ccggccctct gccctccgag gccgtgcagt ggctgtgcca ccaagcattc ctgctcaagc    3300
tgactcgaca ccgtgtcacc tacgtgccac tcctggggtc actcaggaca gcccagacgc    3360
agctgagtcg gaagctcccg gggacgacgc tgactgccct ggaggccgca gccaacccgg    3420
cactgccctc agacttcaag accatcctgg actgatggcc accgcccac agccaggccg     3480 agagcagaca ccagcagccc tgtcacgccg ggctctacgt cccagggagg gaggggcggc    3540
ccacacccag gcccgcaccg ctgggagtct gaggcctgag tgagtgtttg gcgaggcct    3600 gcatgtccgg ctgaaggctg agtgtccggc tgaggcctga gcgagtgtcc agccaagggc    3660
tgagtgtcca gcacacctgc cgtcttcact tccccacagg ctggcgctcg gctccacccc    3720
agggccagct tttcctcacc aggagcccgg cttccactcc ccacatagga atagtccatc    3780
cccagattcg ccattgttca ccctcgccc tgccctcctt tgccttccac ccccaccatc     3840
caggtggaga ccctgagaag gaccctggga gctctgggaa tttggagtga ccaaaggtgt    3900
gccctgtaca caggcgagga ccctgcacct ggatgggggt ccctgtgggt caaattgggg    3960
ggaggtgctg tgggagtaaa atactgaata tatgagtttt tcagttttga aaaaaaaaa    4020 aaaaaaa                                                              4027
```

<210> SEQ ID NO 260
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 260

Met Ala Leu Pro Val Thr Ala Leu Leu Leu Pro Leu Ala Leu Leu Leu
1               5                   10                  15

-continued

```
His Ala Ala Arg Pro Asp Ile Gln Met Thr Gln Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
                405                 410                 415

Pro Glu Met Gly Gly Lys Pro Arg Arg Lys Asn Pro Gln Glu Gly Leu
            420                 425                 430
```

-continued

```
Tyr Asn Glu Leu Gln Lys Asp Lys Met Ala Glu Ala Tyr Ser Glu Ile
            435                 440                 445

Gly Met Lys Gly Glu Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 261
<211> LENGTH: 41
<212> TYPE: PRT
<213> ORGANISM: Homo sapiens

<400> SEQUENCE: 261

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 262
<211> LENGTH: 123
<212> TYPE: DNA
<213> ORGANISM: Homo sapiens

<400> SEQUENCE: 262
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 263
<211> LENGTH: 35
<212> TYPE: PRT
<213> ORGANISM: Homo sapiens

<400> SEQUENCE: 263

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 264
<211> LENGTH: 105
<212> TYPE: DNA
<213> ORGANISM: Homo sapiens

<400> SEQUENCE: 264
acaaaaaaga agtattcatc cagtgtgcac gaccctaacg gtgaatacat gttcatgaga     60
gcagtgaaca cagccaaaaa atccagactc acagatgtga cccta                    105

<210> SEQ ID NO 265
<211> LENGTH: 23
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic peptide"

<400> SEQUENCE: 265

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 266
<211> LENGTH: 521
<212> TYPE: DNA
<213> ORGANISM: Homo sapiens

<400> SEQUENCE: 266

| acccctctct ccagccacta agccagttgc tccctcggct gacggctgca cgcgaggcct | 60 |
| ccgaacgtct tacgccttgt ggcgcgcccg tccttgtccc gggtgtgatg gcggggtgtg | 120 |
| gggcggaggg cgtggcgggg aagggccggc gacgagagcc gcgcgggacg actcgtcggc | 180 |
| gataaccggt gtcgggtagc gccagccgcg cgacggtaac gagggaccgc gacaggcaga | 240 |
| cgctcccatg atcactctgc acgccgaagg caaatagtgc aggccgtgcg gcgcttggcg | 300 |
| ttccttggaa gggctgaatc cccgcctcgt ccttcgcagc ggccccccgg gtgttcccat | 360 |
| cgccgcttct aggcccactg cgacgcttgc ctgcacttct acacgctct gggtcccagc | 420 |
| cgcggcgacg caaagggcct tggtgcgggt ctcgtcggcg cagggacgcg tttgggtccc | 480 |
| gacggaacct tttccgcgtt ggggttgggg caccataagc t | 521 |

<210> SEQ ID NO 267
<211> LENGTH: 118
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 267

| acccctctct ccagccacta agccagttgc tccctcggct gacggctgca cgcgaggcct | 60 |
| ccgaacgtct tacgccttgt ggcgcgcccg tccttgtccc gggtgtgatg gcggggtg | 118 |

<210> SEQ ID NO 268
<211> LENGTH: 221
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 268

| acccctctct ccagccacta agccagttgc tccctcggct gacggctgca cgcgaggcct | 60 |
| ccgaacgtct tacgccttgt ggcgcgcccg tccttgtccc gggtgtgatg gcggggtgtg | 120 |
| gggcggaggg cgtggcgggg aagggccggc gacgagagcc gcgcgggacg actcgtcggc | 180 |
| gataaccggt gtcgggtagc gccagccgcg cgacggtaac g | 221 |

<210> SEQ ID NO 269
<211> LENGTH: 324
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 269
acccctctct ccagccacta agccagttgc tccctcggct gacggctgca cgcgaggcct      60
ccgaacgtct tacgccttgt ggcgcgcccg tccttgtccc gggtgtgatg gcggggtgtg     120
gggcggaggg cgtggcgggg aagggccggc gacgagagcc gcgcgggacg actcgtcggc     180
gataaccggt gtcgggtagc gccagccgcg cgacggtaac gagggaccgc gacaggcaga     240
cgctcccatg atcactctgc acgccgaagg caaatagtgc aggccgtgcg gcgcttggcg     300
ttccttggaa gggctgaatc cccg                                           324

<210> SEQ ID NO 270
<211> LENGTH: 422
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 270
acccctctct ccagccacta agccagttgc tccctcggct gacggctgca cgcgaggcct      60
ccgaacgtct tacgccttgt ggcgcgcccg tccttgtccc gggtgtgatg gcggggtgtg     120
gggcggaggg cgtggcgggg aagggccggc gacgagagcc gcgcgggacg actcgtcggc     180
gataaccggt gtcgggtagc gccagccgcg cgacggtaac gagggaccgc gacaggcaga     240
cgctcccatg atcactctgc acgccgaagg caaatagtgc aggccgtgcg gcgcttggcg     300
ttccttggaa gggctgaatc cccgcctcgt ccttcgcagc ggccccccgg tgttcccat     360 cgccgcttct aggcccactg cgacgcttgc ctgcacttct tacacgctct gggtcccagc     420
cg                                                                   422

<210> SEQ ID NO 271
<211> LENGTH: 48
<212> TYPE: PRT
<213> ORGANISM: Homo sapiens

<400> SEQUENCE: 271

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 272
<211> LENGTH: 123
<212> TYPE: DNA
<213> ORGANISM: Homo sapiens

<400> SEQUENCE: 272
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                  123

<210> SEQ ID NO 273
```

```
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Met Ala Leu Pro Val Thr Ala Leu Leu Leu Pro Leu Ala Leu Leu Leu
1               5                   10                  15

His Ala Ala Arg Pro
            20

<210> SEQ ID NO 274
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
atggccctgc ctgtgacagc cctgctgctg cctctggctc tgctgctgca tgccgctaga    60
ccc                                                                  63

<210> SEQ ID NO 275
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Gly Ser Gly Glu Gly Arg Gly Ser Leu Leu Thr Cys Gly Asp Val Glu
1               5                   10                  15

Glu Asn Pro Gly Pro
            20
```